US012752023B2

(12) United States Patent
Small et al.

(10) Patent No.: US 12,752,023 B2
(45) **Date of Patent: *Oct. 6, 2026**

(54) NEAR-INFRARED DYES AND CONJUGATES FOR TARGETING TUMORS

(71) Applicant: Lahjavida, Inc., Colorado Springs, CO (US)

(72) Inventors: Lyle D. Small, Colorado Springs, CO (US); Ruizheng Wang, Colorado Springs, CO (US)

(73) Assignee: Lahjavida, LLC, Colorado Springs, CO (US)

( * ) Notice: Subject to any disclaimer, the term of this patent is extended or adjusted under 35 U.S.C. 154(b) by 0 days.

This patent is subject to a terminal disclaimer.

(21) Appl. No.: 19/343,829

(22) Filed: Sep. 29, 2025

(65) Prior Publication Data

US 2026/0027241 A1 Jan. 29, 2026

Related U.S. Application Data

(63) Continuation-in-part of application No. 19/035,666, filed on Jan. 23, 2025, which is a continuation-in-part (Continued)

(51) Int. Cl.

| | |
|---|---|
| ***A61K 51/04*** | (2006.01) |
| ***A61K 47/54*** | (2017.01) |
| ***A61P 35/00*** | (2006.01) |

(52) U.S. Cl.

CPC ........ *A61K 51/0446* (2013.01); *A61K 47/545* (2017.08); *A61K 51/0497* (2013.01); *A61P 35/00* (2018.01); *A61K 2121/00* (2013.01)

(58) Field of Classification Search

None

See application file for complete search history.

(56) References Cited

U.S. PATENT DOCUMENTS

| | | | |
|---|---|---|---|
| 4,226,164 | A | 10/1980 | Carter |
| 9,234,078 | B2 | 1/2016 | Sun et al. |

(Continued)

FOREIGN PATENT DOCUMENTS

| | | | |
|---|---|---|---|
| JP | 2014525914 | A | 10/2014 |
| KR | 10-2016-0088830 | | 7/2016 |

(Continued)

OTHER PUBLICATIONS

An et al. Heptamethine carbocyanine DZ-1 dye for near-infrared fluorescence imaging of hepatocellular carcinoma. Oncotarget. May 24, 2017; 8(34):56880.

(Continued)

*Primary Examiner* — Michael G. Hartley

*Assistant Examiner* — Kaila A Craig

(74) *Attorney, Agent, or Firm* — Craig R. Miles; CR MILES P.C.

(57) ABSTRACT

A conjugate including a tumor-targeting NIR dye coupled to a therapeutic agent via a linker, whereby the dye functions to direct the conjugate and correspondingly, the therapeutic agent, to a target tumor cell population. Additionally, a method of killing tumor cells by directing a conjugate including a tumor-targeting NIR dye coupled to a therapeutic agent via a linker to a target tumor cell population.

2 Claims, 22 Drawing Sheets
(2 of 22 Drawing Sheet(s) Filed in Color)

Related U.S. Application Data of application No. 18/869,200, filed as application No. PCT/US2023/023173 on May 23, 2023.

(60) Provisional application No. 63/624,122, filed on Jan. 23, 2024.

(56) References Cited

U.S. PATENT DOCUMENTS

| | | | | |
|---|---|---|---|---|
| 10,030,036 | B2 | 7/2018 | Krutak | |
| 10,307,489 | B2 | 6/2019 | Chung | |
| 12,109,276 | B2 | 10/2024 | Small et al. | |
| 2008/0160090 | A1 | 7/2008 | Oraevsky et al. | |
| 2009/0025977 | A1 | 1/2009 | Anderson et al. | |
| 2010/0022449 | A1 | 1/2010 | Achilefu et al. | |
| 2011/0085974 | A1 | 4/2011 | Chung et al. | |
| 2011/0250146 | A1 | 10/2011 | Zhang et al. | |
| 2012/0251453 | A1 | 10/2012 | Fukuda et al. | |
| 2013/0039858 | A1 | 2/2013 | Brown et al. | |
| 2015/0376209 | A1 | 12/2015 | Krutak et al. | |
| 2016/0281082 | A1 | 9/2016 | Lellouche et al. | |
| 2018/0327427 | A1 | 11/2018 | Krutak et al. | |
| 2018/0353913 | A1 | 12/2018 | Link et al. | |
| 2018/0369422 | A1 | 12/2018 | Haber et al. | |
| 2019/0240342 | A1 | 8/2019 | Chung | |
| 2019/0269801 | A1 | 9/2019 | Chung et al. | |
| 2022/0031855 | A1 | 2/2022 | Chung | |
| 2024/0335570 | A1* | 10/2024 | Low | A61K 51/0497 |

FOREIGN PATENT DOCUMENTS

| | | | | |
|---|---|---|---|---|
| WO | WO 2006/019775 A1 | 2/2006 | | |
| WO | WO 2009/012109 | 1/2009 | | |
| WO | WO 2016/106324 A1 | 6/2016 | | |
| WO | WO 2017/201089 A1 | 11/2017 | | |
| WO | WO-2022093800 A2 * | 5/2022 | | A61K 49/0032 |

OTHER PUBLICATIONS

Choi et al. Novel synthetic approach for accessing drug-dye conjugates for targeted tumour therapy. Results in Chemistry. Jan. 1, 2022; 4:100343.

Choi et al. PARP inhibitor cyanine dye conjugate with enhanced cytotoxic and antiproliferative activity in patient derived glioblastoma cell lines. Bioorganic & Medicinal Chemistry Letters. Jul. 15, 2020; 30(14):127252.

Choi et al. The synthesis of a novel Crizotinib heptamethine cyanine dye conjugate that potentiates the cytostatic and cytotoxic effects of Crizotinib in patient-derived glioblastoma cell lines. Bioorganic & Medicinal Chemistry Letters. Sep. 15, 2019; 29(18):2617-21.

Guan et al. Improving therapeutic potential of farnesylthiosalicylic acid: Tumor specific delivery via conjugation with heptamethine cyanine dye. Molecular pharmaceutics. Jan. 3, 2017; 14(1):1-3.

Guan et al. Synthesis and biological evaluation of genistein-IR783 conjugate: cancer cell targeted delivery in MCF-7 for superior anti-cancer therapy. Molecules. Nov. 14, 2019; 24(22):4120.

Jiang et al. Cyanine-gemcitabine conjugates as targeted theranostic agents for glioblastoma tumor cells. Journal of medicinal chemistry. Aug. 30, 2019; 62(20):9236-45.

Li et al. Targeted methotrexate prodrug conjugated with heptamethine cyanine dye improving chemotherapy and monitoring itself activating by dual-modal imaging. Frontiers in Materials. Jul. 5, 2018; 5:35.

Lv et al. Mitochondria-targeted prostate cancer therapy using a near-infrared fluorescence dye-monoamine oxidase A inhibitor conjugate. Journal of Controlled Release. Jun. 10, 2018; 279:234-42.

Mrdenovic et al. Targeting Burkitt lymphoma with a tumor cell-specific heptamethine carbocyanine-cisplatin conjugate. Cancer. Jul. 1, 2019; 125(13):2222-32.

Usama et al. Conjugation of Dasatinib with MHI-148 Has a Significant Advantageous Effect in Viability Assays for Glioblastoma Cells. ChemMedChem. Sep, 4, 2019; 14(17):1575-9.

Wu et al. Monoamine oxidase A inhibitor-near-infrared dye conjugate reduces prostate tumor growth. Journal of the American Chemical Society. Feb. 18, 2015; 137(6):2366-74.

Wu et al. Near-infrared fluorescence heptamethine carbocyanine dyes mediate imaging and targeted drug delivery for human brain tumor. Biomaterials. Oct. 1, 2015; 67:1-0.

Yang et al. Design, synthesis, and evaluation of monoamine oxidase a inhibitors-indocyanine dyes conjugates as targeted antitumor agents. Molecules. Apr. 10, 2019; 24(7):1400.

Zhao et al. Mediated imaging and improved targeting of farnesylthiosalicylic acid delivery for pancreatic cancer via conjugation with near-infrared fluorescence heptamethine carbocyanine dye. ACS Applied Bio Materials. Jan. 20, 2020; 3(2):1129-38.

Zheng et al. Coupling the near-infrared fluorescent dye IR-780 with cabazitaxel makes renal cell carcinoma chemotherapy possible. Biomedicine & Pharmacotherapy. Aug. 1, 2019; 116:109001.

U.S. Appl. No. 61/178,835, filed May 15, 2009, Henary et al.

U.S. Appl. No. 61/309,282, filed 2010.

PCT International Patent Application No. PCT/US23/23173, International Search Report and Written Opinion of the International Searching Authority dated Oct. 5, 2023, 10 pages.

PCT International Patent Application No. PCT/US20/22668, International Search Report and Written Opinion of the International Searching Authority dated Jul. 6, 2020, 11 pages.

Brazilian Patent Application No. BR1120210182292, Office Action dated May 14, 2024, 7 pages.

Canadian Patent Application No. 3,133,750, Office Action dated Mar. 29, 2023, 4 pages.

Canadian Patent Application No. 3,133,750, Office Action dated Sep. 8, 2023, 5 pages.

Canadian Patent Application No. 3,133,750, Office Action dated Jan. 25, 2024, 3 pages.

European Patent Application No. 20774094.5, Supplementary European search Report dated Feb. 2, 2023, 12 pages.

Japanese Patent Application No. 2021-555580, Office Action dated May 11, 2023, 6 pages.

Japanese Patent Application No. 2021-555580, Office Action dated Jan. 4, 2024, 14 pages (with English translation).

U.S. Appl. No. 12/778,569, Office Action mailed Mar. 4, 2016.

U.S. Appl. No. 12/778,569, Office Action mailed Jul. 19, 2016.

U.S. Appl. No. 12/778,569, Office Action mailed Jun. 9, 2017.

U.S. Appl. No. 12/778,569, Notice of Allowance mailed Jun. 13, 2018.

U.S. Appl. No. 16/816,118, Office Action mailed Aug. 27, 2021.

U.S. Appl. No. 16/816,118, Office Action mailed Apr. 14, 2022.

U.S. Appl. No. 16/816,118, Office Action mailed May 2, 2023.

U.S. Appl. No. 16/816,118, Office Action mailed Oct. 2, 2023.

Ali et al. Efficacy, long-term toxicity, and mechanistic studies of gold nanorods photothermal therapy of cancer in xenograft mice. Proceedings of the National Academy of Sciences, Mar. 2017, 114(15):E3110-E3118.

Alrahili et al. Absorption cross section of gold nanoparticles based on NIR laser heating and thermodynamic calculations. Scientific Reports, Nov. 2020, 10, article No. 18790.

Alrahili et al. Morphology Dependence in Photothermal Heating of Gold Nanomaterials with Near-Infrared Laser. J. Phys. Chem. C, Feb. 2020, 124(8):4755-4763.

Amina et al. A Review of the Synthesis and Functionalization of Gold Nanoparticles as a Drug Delivery Vehicle. Int J Nanomedicine, Dec. 2020, 15:9823-9857.

Beik et al. Nanotechnology in hyperthermia cancer therapy: From fundamental principles to advanced applications. J. Control. Release, Aug. 2016, 235:205-221.

Bevilacqua et al. Antifouling Strategies of Nanoparticles for Diagnostic and Therapeutic Application: A Systematic Review of the Literature. Nanomaterials, Mar. 2021, 11(3):780.

Chichel et al. Hyperthermia—description of a method and a review of clinical applications. Rep Pract Oncol Radiother, Oct. 2007, 12(15):267-275.

Choi et al. Heptamethine Cyanine Dye Mediated Drug Delivery: Hype or Hope. Bioconjug. Chem., Jun. 2020, 31(7):1724-1739.

(56) References Cited

OTHER PUBLICATIONS

Cooper et al. The Use of Heptamethine Cyanine Dyes as Drug-Conjugate Systems in the Treatment of Primary and Metastatic Brain Tumors. Frontiers in Oncology, Jun. 2021, vol. 11, Article 654921, 16 pages.
Fan et al. Nanotechnology for Multimodal Synergistic Cancer Therapy. Chem. Rev., Nov. 2017, 117(22):13566-13638.
Fu et al. Plasmonic Enhancement of Single-Molecule Fluorescence Near a Silver Nanoparticle. J Fluoresc., Nov. 2007, 17(6):811-816.
García et al. Zwitterionic-Coated “Stealth” Nanoparticles for Biomedical Applications: Recent Advances in Countering Biomolecular Corona Formation and Uptake by the Mononuclear Phagocyte System. Small, Jul. 2014 (published online Mar. 2014), 10(13):2516-2529.
HirscH et al. Nanoshell-mediated near-infrared thermal therapy of tumors under magnetic resonance guidance. PNAS, Nov. 2003, 100(23):13549-13554.
Huang et al. Applications of gold nanorods for cancer imaging and photothermal therapy. Cancer nanotechnology. Methods Mol Biol, Jan. 2010, 624:343-357.
Huang et al. Folic acid-conjugated silica-modified gold nanorods for X-ray/CT imaging-guided dual-mode radiation and photo-thermal therapy. Biomaterials Dec. 2011, 32(36):9796-9809.
Huang et al. Plasmonic photothermal therapy (PPTT) using gold nanoparticles. Lasers in medical science, Jul. 2008 (published online Aug. 2007), 23(3):217-228.
Jauffred et al. Plasmonic Heating of Nanostructures. Chem. Rev., May 2019, 119(13):8087-8130.
Jiao et al. A near-infrared heptamethine aminocyanine dye with a lo9ng-lived excited triplet state for photodynamic therapy. Chem. Commun., Jul. 2018, 54(66):9198-9201.
Lee et al. Near-Infrared Heptamethine Cyanine Based Iron Oxide Nanoparticles for Tumor Targeted Multimodal Imaging and Photothermal Therapy. Scientific Reports, May 2017, 7(1):1-14.
Li et al. RGD-conjugated dendrimer-modified gold nanorods for in vivo tumor targeting and photothermal therapy. Molecular pharmaceutics, 2010 (published on Web Nov. 2009), 7(1):94-104.
Luo et al. A review of NIR dyes in cancer targeting and imaging. Biomaterials, Jul. 2011, 32(29):7127-7138.
Luo et al. Multifunctional Photosensitizer Grafted on Polyethylene Glycol and Polyethylenimine Dual-Functionalized Nanographene Oxide for Cancer-Targeted Near-Infrared Imaging and Synergistic Phototherapy. Applied Materials & Interfaces, Jul. 2016, 8(27):17176-17186.
Park et al. Magnetic Iron oxide Nanoworms for Tumor Targeting and Imaging. Adv Mater., May 2008, 20(9):1630-1635.
Pham et al. Synthesis and Application of a Water-Soluble Near-Infrared Dye for Cancer Detection Using Optical Imaging. Bioconjugate Chem., April 2005, 16(3):735-740.
Pubchem. Substance Record for SIDS 135686945. Available Date May 28, 2012 [retrieved on Jun. 15, 2020] from the Internet, https://pubchem.ncbi.nim.nih.gov/substance/135686945.
Raoof et al. Gold Nanoparticles and Radiofrequency in Experimental Models for Hepatocellular Carcinoma. Nanomedicine, Aug. 2014, 10(6):1121-1130.
Rastinehad et al. Gold nanoshell-localized photothermal ablation of prostate tumors in a clinical pilot device study. PNAS, Sep. 2019, 116(37):18590-18596.
Sato et al. Synthesis and spectral properties of polymethine-cyanine dye-nitroxide radical hybrid compounds for use as fluorescence probes to monitor reducing species and radicals. Spectrochimica Acta Part A: Molecular and Biomolecular Spectroscopy, Jan. 2009, 71(5):2030-2039.
Savchuk et al. Size-dependent emission of a dipole coupled to a metal nanoparticle. MRS Advances, Nov. 2020, 5(62):3315-3325.
Shi et al. Heptamethine carbocyanine dye-mediated near-infrared imaging of canine and human cancers through the HIF-1α/OATPs signaling axis. Oncotarget, Oct. 2014, 5(20):10114-26.
Tan et al. A NIR heptamethine dye with intrinsic cancer targeting, imaging and photosensitizing properties. Biomaterials, Mar. 2012, 33(7):2230-2239.
Tong et al. Self-Assembly of Phospholipid-PEG Coating on Nanoparticles through Dual Solvent Exchange. Nano Lett., Sep. 2011, 11(9):3720-3726.
Wang et al. Design of a Multi-Dopamine-Modified Polymer Ligand Optimally Suited for Interfacing Magnetic Nanoparticles with Biological Systems. Langmuir, Jun. 2014, 30(21):6197-6208.
Yang et al. Near IR Heptamethine Cyanine Dye-Mediated Cancer Imaging. Clin. Cancer Res., May 2010, 16(10):2833-2844.
Yeh et al. Tumor targeting and MR imaging with lipophilic cyanine-mediated near-infrared responsive porous Gd silicate nanoparticles. Biomaterials, Jul. 2013, 34(22):5677-88.
Zhang et al. pH- and Enzyme-Sensitive IR820-Paclitaxel Conjugate Self-Assembled Nanovehicles for Near-Infrared Fluorescence Imaging-Guided Chemo-Photothermal Therapy. Applied Materials & Interfaces, Sep. 2018, 10(36):30092-30102.
Zhou et al. Superstable Magnetic Nanoparticles in Conjugation with Near-Infrared Dye as a Multimodal Theranostic Platform. Applied Materials & Interfaces, Feb. 2016, 8(7):4424-33.

* cited by examiner

*azonafide-PEABA*

*doxorubicin*

*exatecan*

*3-aminophenyl hemiasterlin*

*MMAD*

*MMAE*

*MMAF*

*MMAU*

*SGD-1882 PBD dimer*

*SG3199 PBD dimer*

*paclitaxel*

*PNU159682*

*SN-38*

*abemaciclib*

*clindamycin*

*dolastatin 10* duocarmycin gefitinib indibulin retapamulin rifabutin sunitinib tubulysin M vinblastine

*palbociclib*

*ribociclib*

*Val-Ala*

*Val-Cit*

*Val-Gly*

*Val-Lys*

*Gly-Gly*

*Phe-Lys*

*Ala-Ala-Asn*

*Glu-Val-Cit*

*Gly-Gly-Phe-Gly*

*glucuronic acid*

*phosphate*

*pyrophosphate*

*sulfonate*

*Gly-Pro-Leu-Gly-Ile-Ala-Gly-Gln*

PABA

PABC

DMED

PEG

DBCO-amine amine pyridine imidazole arginine lysine histidine triphenylphosphonium guanidine salts rhodamine 123

MKT-077 fatty acid p-iodophenyl butyric acid

DOTA

NOTA

DTPA macropa

*lenalidomide*

*pomalidomide*

*iberdomide*

*24 h post dose*

*4 days post dose*

*9 days post dose*

*24 h post dose*

*4 days post dose*

*9 days post dose*

NEAR-INFRARED DYES AND CONJUGATES FOR TARGETING TUMORS

I. BACKGROUND

There remains a need for targeted cancer therapeutic agents with maximal efficacy in treating or killing tumor cells and minimal toxicity toward non-tumor or "normal" cells.

II. SUMMARY OF THE INVENTION

Generally, the present invention details the use of tumor-targeting near-infrared (NIR) dyes in conjunction with a variety of therapeutic agents.

Following, a broad object of a particular embodiment of the invention can be to provide a conjugate including a tumor-targeting NIR dye coupled to a therapeutic agent via a linker, whereby the dye functions to direct the conjugate and correspondingly, the therapeutic agent, to a target tumor cell population.

Another broad object of a particular embodiment of the invention can be to provide a method of killing tumor cells by directing a conjugate including a tumor-targeting NIR dye coupled to a therapeutic agent via a linker to a target tumor cell population.

Naturally, further objects of the invention are disclosed throughout other areas of the specification, drawings, and claims.

III. A BRIEF DESCRIPTION OF THE DRAWINGS

The patent or application file contains at least one drawing executed in color. Copies of this patent or patent application publication with color drawing(s) will be provided by the Office upon request and payment of the necessary fee.

IV. DETAILED DESCRIPTION OF THE PREFERRED EMBODIMENTS

Figure 1A:
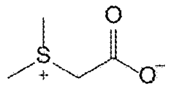
FIG. 1A shows an illustrative example of a zwitterion which may be useful with the present invention when attached to a tumor-targeting NIR dye to form the inventive conjugate.
Figure 1B:
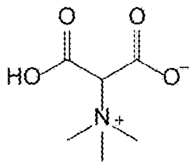
FIG. 1B shows an illustrative example of a zwitterion which may be useful with the present invention when attached to a tumor-targeting NIR dye to form the inventive conjugate.
Figure 1C:
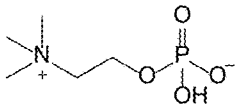
FIG. 1C shows an illustrative example of a zwitterion which may be useful with the present invention when attached to a tumor-targeting NIR dye to form the inventive conjugate.
Figure 1D:
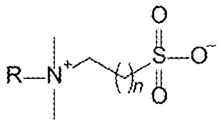
FIG. 1D shows an illustrative example of a zwitterion which may be useful with the present invention when attached to a tumor-targeting NIR dye to form the inventive conjugate.
Figure 1E:
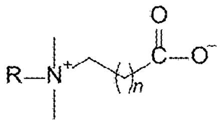
FIG. 1E shows an illustrative example of a zwitterion which may be useful with the present invention when attached to a tumor-targeting NIR dye to form the inventive conjugate.
Figure 1F:
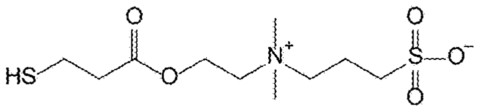
FIG. 1F shows an illustrative example of a zwitterion which may be useful with the present invention when attached to a tumor-targeting NIR dye to form the inventive conjugate.
Figure 1G:
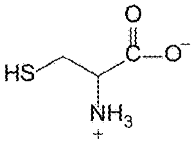
FIG. 1G shows an illustrative example of a zwitterion which may be useful with the present invention when attached to a tumor-targeting NIR dye to form the inventive conjugate.
Figure 1H:
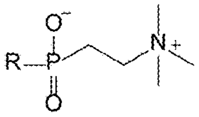
FIG. 1H shows an illustrative example of a zwitterion which may be useful with the present invention when attached to a tumor-targeting NIR dye to form the inventive conjugate.
Figure 1I:
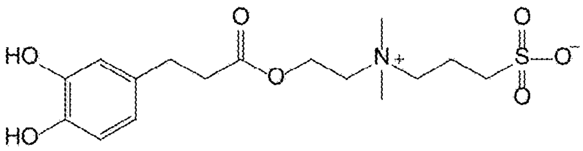
FIG. 1I shows an illustrative example of a zwitterion which may be useful with the present invention when attached to a tumor-targeting NIR dye to form the inventive conjugate.
Figure 1J:
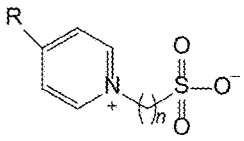
FIG. 1J shows an illustrative example of a zwitterion which may be useful with the present invention when attached to a tumor-targeting NIR dye to form the inventive conjugate.
Figure 1K:
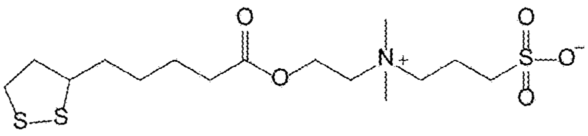
FIG. 1K shows an illustrative example of a zwitterion which may be useful with the present invention when attached to a tumor-targeting NIR dye to form the inventive conjugate.
Figure 2A:
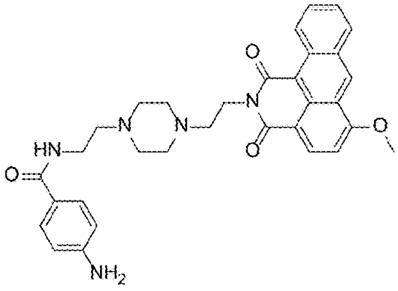
FIG. 2A shows an illustrative example of a chemotherapeutic agent having a linkable amine group which may be useful with the present invention when attached to a tumor-targeting NIR dye to form the inventive conjugate.
Figure 2B:
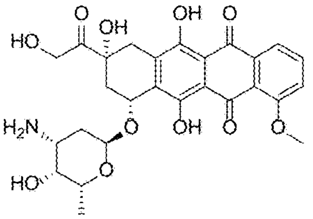
FIG. 2B shows an illustrative example of a chemotherapeutic agent having a linkable amine group which may be useful with the present invention when attached to a tumor-targeting NIR dye to form the inventive conjugate.
Figure 2C:
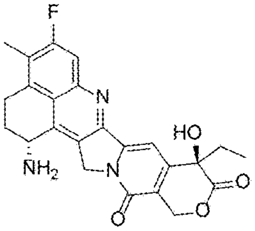
FIG. 2C shows an illustrative example of a chemotherapeutic agent having a linkable amine group which may be useful with the present invention when attached to a tumor-targeting NIR dye to form the inventive conjugate.
Figure 2D:
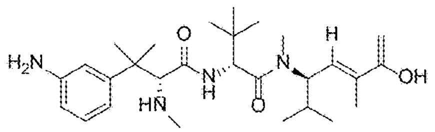
FIG. 2D shows an illustrative example of a chemotherapeutic agent having a linkable amine group which may be useful with the present invention when attached to a tumor-targeting NIR dye to form the inventive conjugate.
Figure 2E:
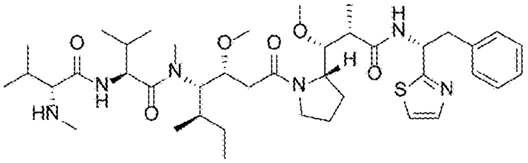
FIG. 2E shows an illustrative example of a chemotherapeutic agent having a linkable amine group which may be useful with the present invention when attached to a tumor-targeting NIR dye to form the inventive conjugate.
Figure 2F:
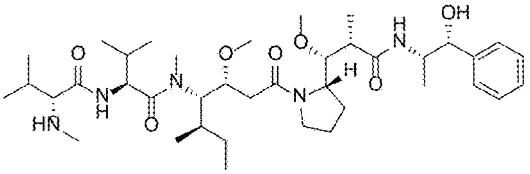
FIG. 2F shows an illustrative example of a chemotherapeutic agent having a linkable amine group which may be useful with the present invention when attached to a tumor-targeting NIR dye to form the inventive conjugate.
Figure 2G:
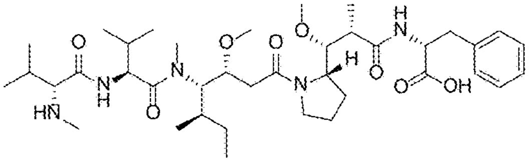
FIG. 2G shows an illustrative example of a chemotherapeutic agent having a linkable amine group which may be useful with the present invention when attached to a tumor-targeting NIR dye to form the inventive conjugate.
Figure 2H:
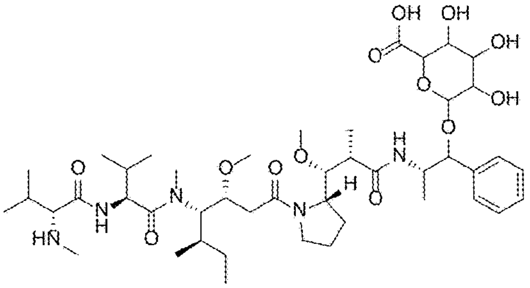
FIG. 2H shows an illustrative example of a chemotherapeutic agent having a linkable amine group which may be useful with the present invention when attached to a tumor-targeting NIR dye to form the inventive conjugate.
Figure 2I:
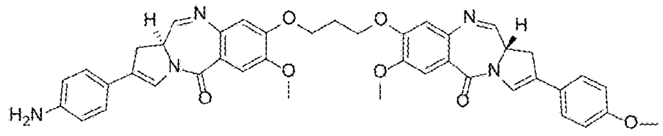
FIG. 2I shows an illustrative example of a chemotherapeutic agent having a linkable amine group which may be useful with the present invention when attached to a tumor-targeting NIR dye to form the inventive conjugate.
Figure 2J:
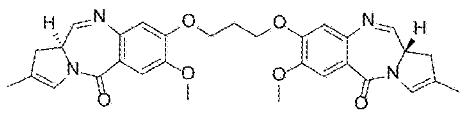
FIG. 2J shows an illustrative example of a chemotherapeutic agent having a linkable amine group which may be useful with the present invention when attached to a tumor-targeting NIR dye to form the inventive conjugate.

The present invention provides an effective and versatile delivery method which combines tumor-targeting NIR dyes with various cancer therapeutic agents to create conjugates for (i) targeting tumor cells and/or (ii) killing tumor cells and/or (iii) imaging tumor cells and/or (iv) theranostics, whereby the dye functions to direct the conjugate and correspondingly, the therapeutic agent, to a target tumor cell population; this can be in contrast to the non-specific delivery of conventional anticancer agents which may cause significant adverse side effects. In addition to targeting tumor cells, the present dye can absorb NIR light and emit in the same region with appreciable brightness for corresponding detection and imaging/visualization of tumor location; thus, the dye can function as an optical reporter which may enable real-time monitoring of the delivery and release of the therapeutic agent. Such a property can be extremely desirable considering the noninvasive nature of NIR light and its tissue penetration, which may be orders of magnitude greater than that for ultraviolet or visible light.

As to particular embodiments, the dye can be a cyanine dye, whereby chemically, cyanine dyes include two nitrogen atoms joined by a polymethine chain.

As to particular embodiments, the dye can be a heptamethine cyanine dye.

As to particular embodiments, the dye can have Formula I as follows:

I

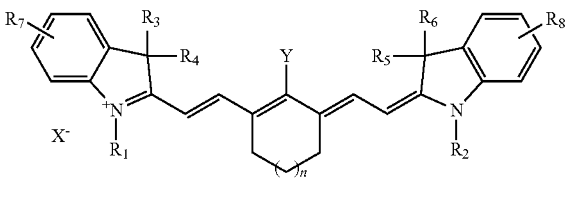

wherein:

$R_1$ to $R_8$ can each be independently an unsubstituted or substituted C1 to C10 alkyl group, an unsubstituted or substituted aryl group, an unsubstituted or substituted C1 to C10 alkoxyl group, an alkylsulfonate, an alkyl carboxylic acid group, or an alkylamino group;

X can be $Br^-$, $Cl^-$, $I^-$, perchlorate ($ClO_4^-$), tosylate (OTs), or absent if another covalently linked anion moiety is present in the dye molecule;

Y can be Cl, or a substituted C, O, S, or N group; and n can be 0 (such as for a five-membered ring) or 1 (such as for a six-membered ring).

Exemplary dyes which may be useful with the present invention are shown in Formulas II through V.

II

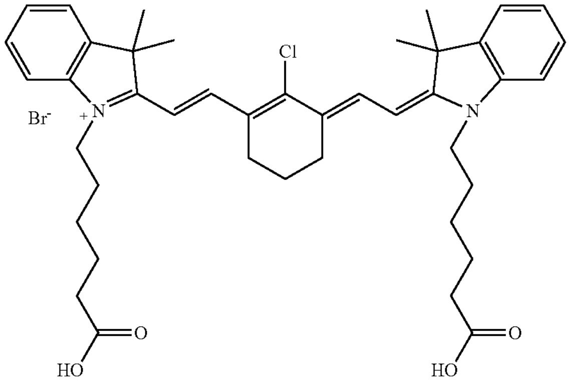

-continued

III

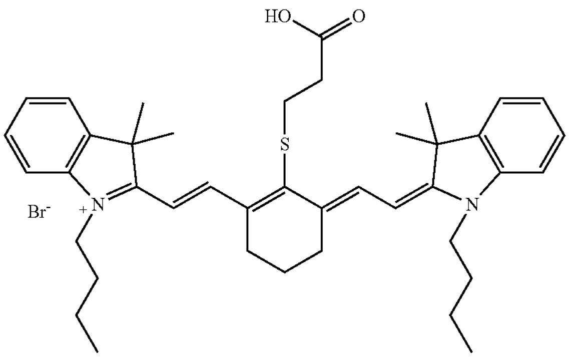

IV

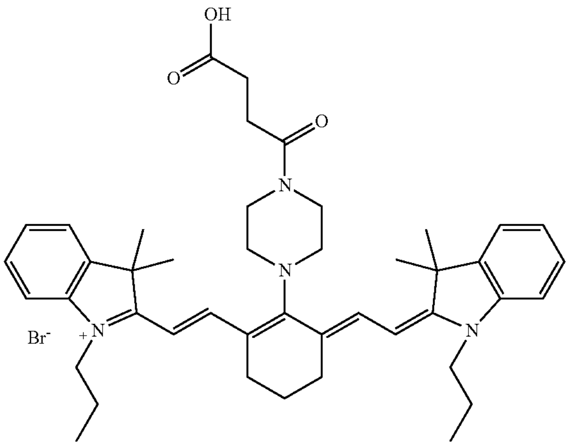

V

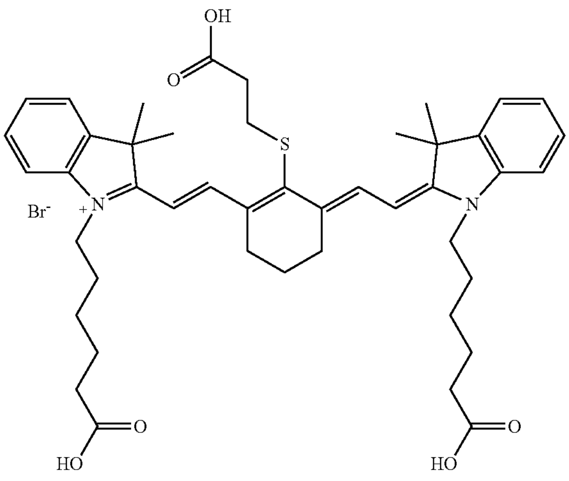

As to particular embodiments, the dye can be modified to have zwitterionic functionality, whereby such a modification may include the attachment of one or more zwitterions to the dye or the incorporation of one or more zwitterions into the dye, each said zwitterion functioning as a polyelectrolyte or dipolar ion which has both positively and negatively charged groups, yet can be overall neutral in charge. Additionally, zwitterions can have a high hydration capacity and correspondingly may be highly hydrated via electrostatic interactions of their positively and negatively charged groups with polar water molecules, whereby the resultant tightly bound water layer forms a dense and stable hydration shell or solvation shell which can provide a physical and energetic barrier that may prevent undesired adsorption, such as but not limited to protein adsorption; thus, zwitterions can have effective antifouling properties.

As to particular embodiments, illustrative examples of zwitterions which may be useful with the present invention when attached to or incorporated into the present dye include those shown in FIGS. 1A through 1K. In line with the above, the zwitterions shown in these figures can be overall neutrally charged and have remarkable hydration capabilities via strong ion-dipole interactions of their positively and negatively charged groups with polar water molecules.

To impart zwitterionic functionality to the dye, a zwitterion can be covalently or electrostatically attached or bound to the dye via the central ring (such as the central cyclopentyl or cyclohexyl ring), via the nitrogen of an indole moiety, via a geminal position, or via an aromatic ring. As to particular embodiments, one or more of $R_1$ to $R_8$ or Y as shown in Formula I can be functionalized with a zwitterion and/or used as a linking site to attach or bind a zwitterion to the dye.

Exemplary dyes having zwitterionic functionality which may be useful with the present invention are shown in Formulas VI through XV.

VI

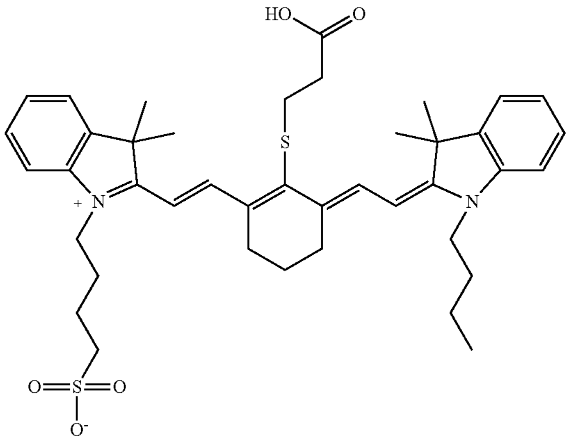

VII

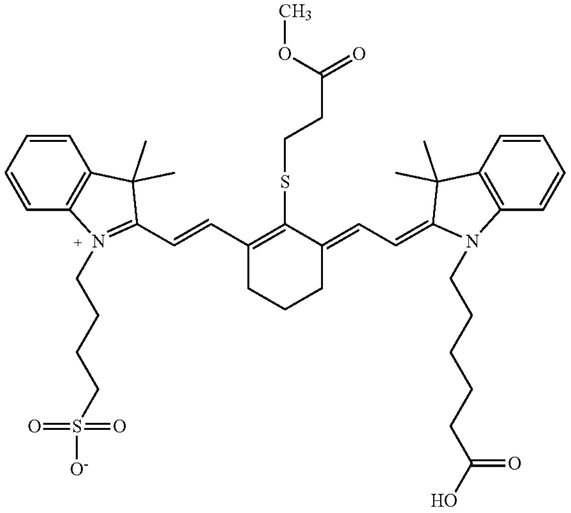

-continued

VIII

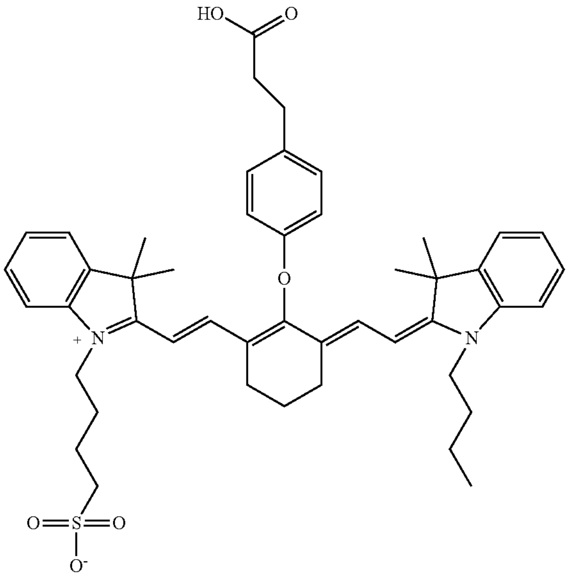

IX

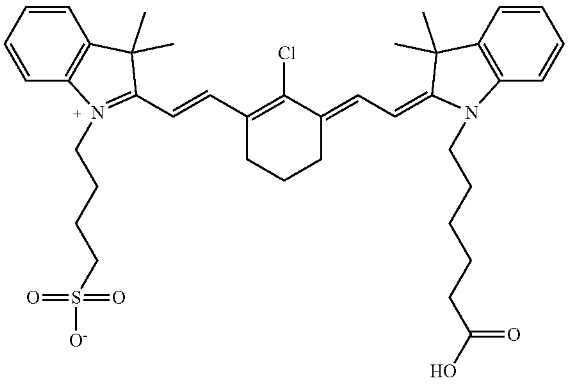

X

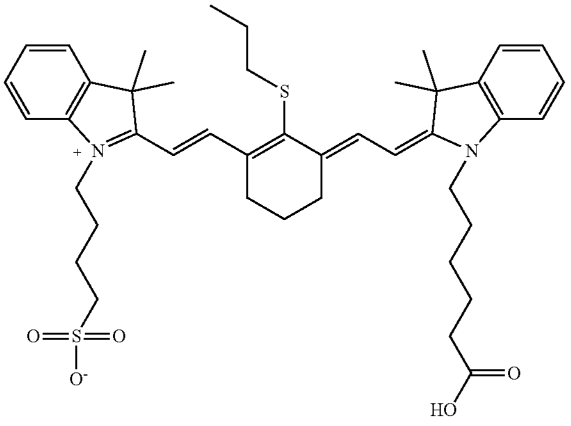

-continued
XI
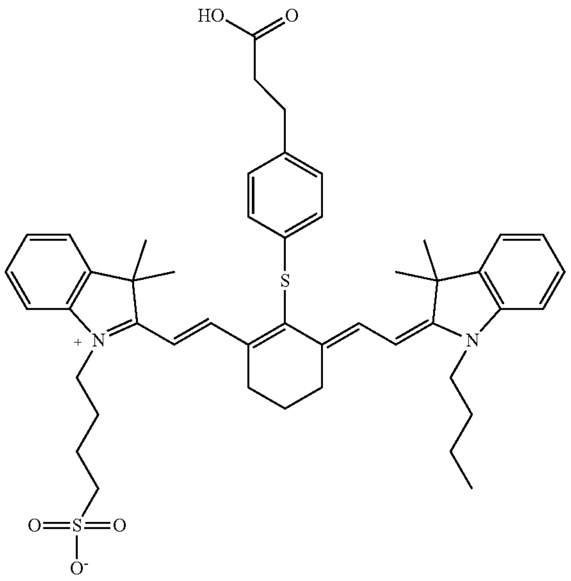
XII
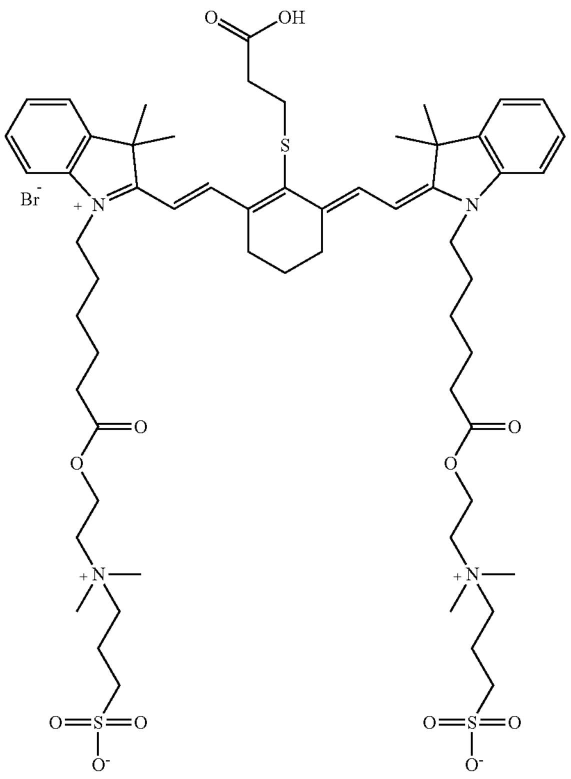
-continued
XIII
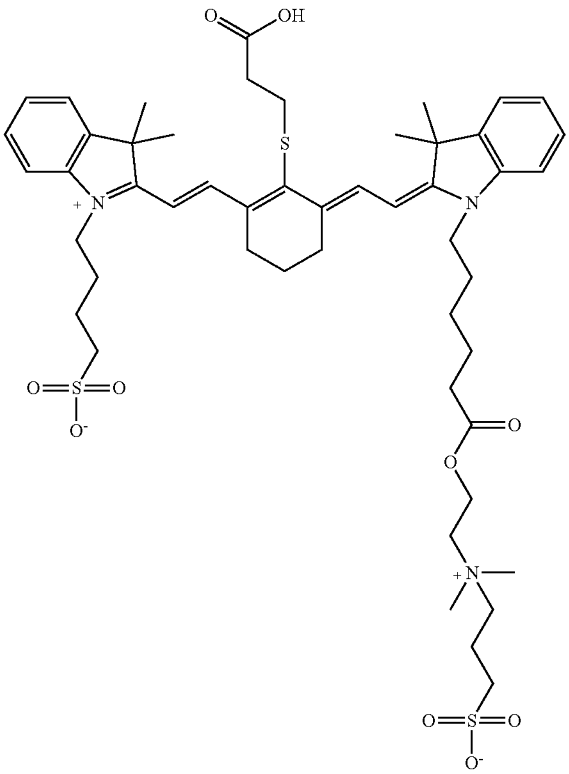
XIV
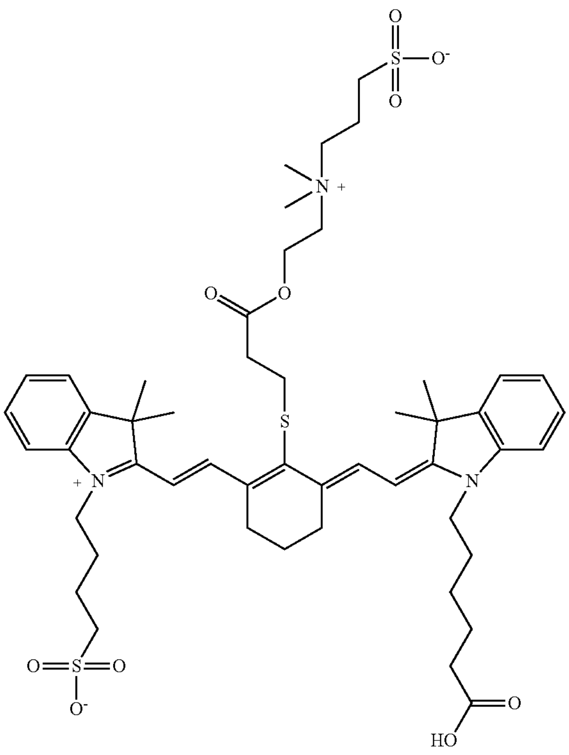

-continued

XV

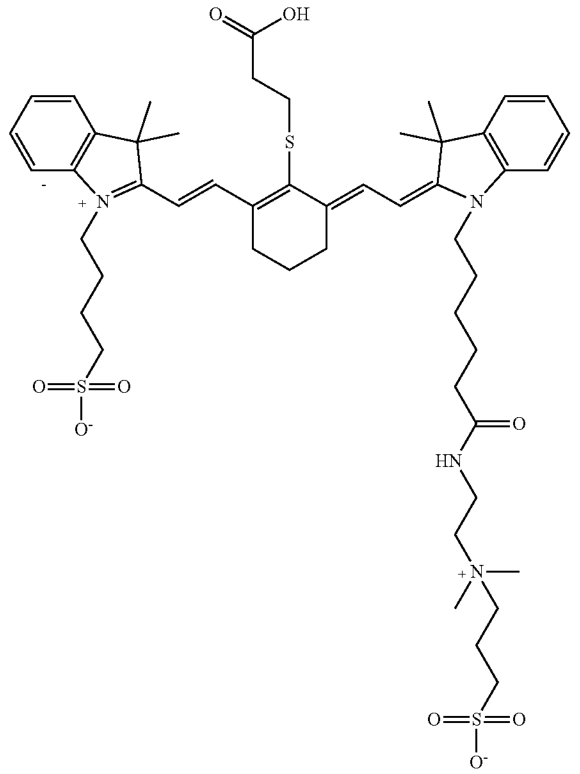

As stated above, the present invention can combine a tumor-targeting NIR dye with various therapeutic agents to create conjugates for the treatment of different cancers, whereby these conjugates may be delivered directly to a target tumor cell population. To form such conjugates, a payload, such as a therapeutic agent, can be covalently or electrostatically attached or bound to the dye, for example via the central ring (such as the central cyclopentyl or cyclohexyl ring), via the nitrogen of an indole moiety, via a geminal position, or via an aromatic ring. As to particular embodiments, one or more of $R_1$ to $R_8$ or Y as shown in Formula I can be used as a linking site to attach or bind the payload to the dye via various linkers to form the present conjugate.

As to particular embodiments, a dye can be coupled to (for example via conjugation) a payload comprising a chemotherapeutic agent via various linkers for use in chemotherapy, as per the present invention. As used herein, the term "chemotherapeutic agent" can mean a chemical agent, and the term "chemotherapy" can mean the therapeutic use of such a chemical agent.

As a first example, chemotherapeutic agents which may be conjugated to a tumor-targeting NIR dye as per the present invention can include, but are not limited to, DNA damaging agents, tubulin inhibitors, and growth factor inhibitors (such as inhibitors of epidermal growth factor (EGF), vascular endothelial growth factor (VEGF), platelet-derived endothelial growth factor (PDGF), fibroblast growth factor (FGF), human epidermal growth factor receptor 2 (HER2), or the like).

As a second example, chemotherapeutic agents including a linkable amine group which may be conjugated to a tumor-targeting NIR dye as per the present invention can include those shown in FIGS. 2A through 2J.

Figure 3A:
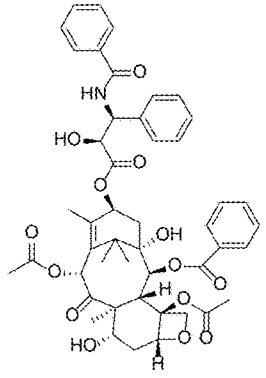
FIG. 3A shows an illustrative example of a chemotherapeutic agent having a linkable hydroxyl group which may be useful with the present invention when attached to a tumor-targeting NIR dye to form the inventive conjugate.
Figure 3B:
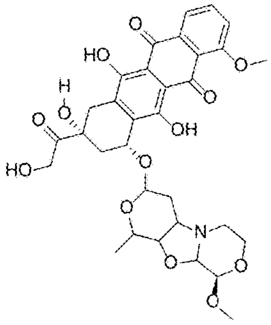
FIG. 3B shows an illustrative example of a chemotherapeutic agent having a linkable hydroxyl group which may be useful with the present invention when attached to a tumor-targeting NIR dye to form the inventive conjugate.
Figure 3C:
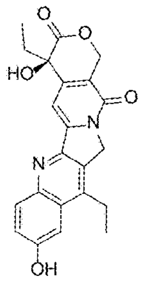
FIG. 3C shows an illustrative example of a chemotherapeutic agent having a linkable hydroxyl group which may be useful with the present invention when attached to a tumor-targeting NIR dye to form the inventive conjugate.

As a third example, chemotherapeutic agents including a linkable hydroxyl group which may be conjugated to a tumor-targeting NIR dye as per the present invention can include those shown in FIGS. 3A through 3C.

As a fourth example, chemotherapeutic agents including a linkable tertiary amine group which may be conjugated to a tumor-targeting NIR dye as per the present invention can include those shown in FIGS. 4A through 4K.

Figure 4A:
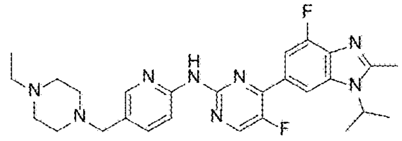
FIG. 4A shows an illustrative example of a chemotherapeutic agent having a linkable tertiary amine group which may be useful with the present invention when attached to a tumor-targeting NIR dye to form the inventive conjugate.
Figure 4B:
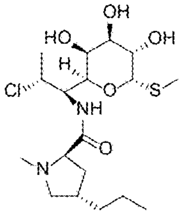
FIG. 4B shows an illustrative example of a chemotherapeutic agent having a linkable tertiary amine group which may be useful with the present invention when attached to a tumor-targeting NIR dye to form the inventive conjugate.
Figure 4C:
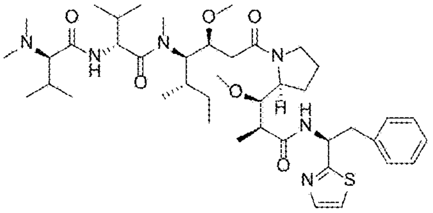
FIG. 4C shows an illustrative example of a chemotherapeutic agent having a linkable tertiary amine group which may be useful with the present invention when attached to a tumor-targeting NIR dye to form the inventive conjugate.
Figure 4D:
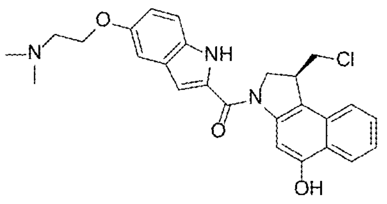
FIG. 4D shows an illustrative example of a chemotherapeutic agent having a linkable tertiary amine group which may be useful with the present invention when attached to a tumor-targeting NIR dye to form the inventive conjugate.
Figure 4E:
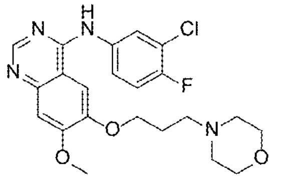
FIG. 4E shows an illustrative example of a chemotherapeutic agent having a linkable tertiary amine group which may be useful with the present invention when attached to a tumor-targeting NIR dye to form the inventive conjugate.
Figure 4F:
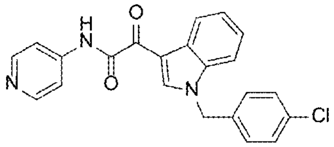
FIG. 4F shows an illustrative example of a chemotherapeutic agent having a linkable tertiary amine group which may be useful with the present invention when attached to a tumor-targeting NIR dye to form the inventive conjugate.
Figure 4G:
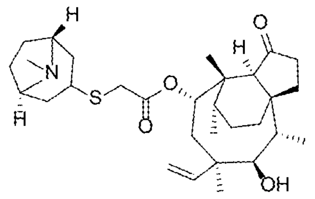
FIG. 4G shows an illustrative example of a chemotherapeutic agent having a linkable tertiary amine group which may be useful with the present invention when attached to a tumor-targeting NIR dye to form the inventive conjugate.
Figure 4H:
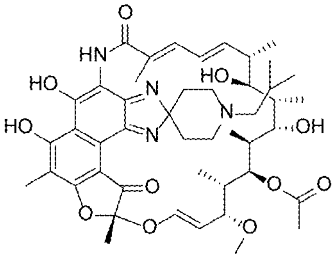
FIG. 4H shows an illustrative example of a chemotherapeutic agent having a linkable tertiary amine group which may be useful with the present invention when attached to a tumor-targeting NIR dye to form the inventive conjugate.
Figure 4I:
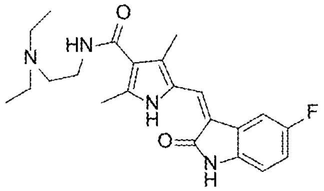
FIG. 4I shows an illustrative example of a chemotherapeutic agent having a linkable tertiary amine group which may be useful with the present invention when attached to a tumor-targeting NIR dye to form the inventive conjugate.
Figure 4J:
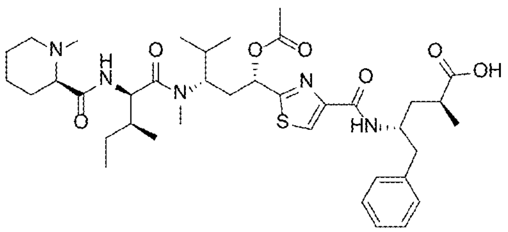
FIG. 4J shows an illustrative example of a chemotherapeutic agent having a linkable tertiary amine group which may be useful with the present invention when attached to a tumor-targeting NIR dye to form the inventive conjugate.
Figure 4K:
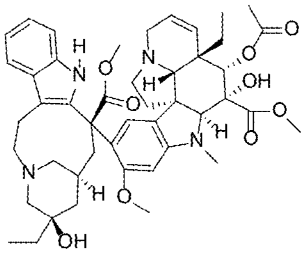
FIG. 4K shows an illustrative example of a chemotherapeutic agent having a linkable tertiary amine group which may be useful with the present invention when attached to a tumor-targeting NIR dye to form the inventive conjugate.
Figure 4L:
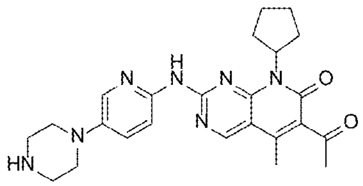
FIG. 4L shows an illustrative example of a chemotherapeutic agent having a linkable secondary amine group which may be useful with the present invention when attached to a tumor-targeting NIR dye to form the inventive conjugate.
Figure 4M:
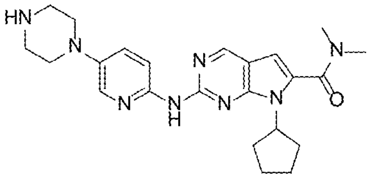
FIG. 4M shows an illustrative example of a chemotherapeutic agent having a linkable secondary amine group which may be useful with the present invention when attached to a tumor-targeting NIR dye to form the inventive conjugate.

As a fifth example, chemotherapeutic agents including a linkable secondary amine group, such as in a piperazine ring, which may be conjugated to a tumor-targeting NIR dye as per the present invention can include those shown in FIGS. 4L and 4M.

As a sixth example, chemotherapeutic agents which may be conjugated to a tumor-targeting NIR dye as per the present invention can include abemaciclib, actinomycin, all-trans retinoic acid, azacitidine, azathioprine, azonafide, azonafide-PEABA, bleomycin, bortezomib, carboplatin, capecitabine, cisplatin, chlorambucil, clindamycin, cyclophosphamide, cytarabine, daunorubicin, dolastatin 10, doxifluridine, doxorubicin, duocarmycin, epirubicin, epothilone, etoposide, exatecan, fluorouracil, gefitinib, gemcitabine, hemiasterlin, 3-aminophenyl hemiasterlin, hydroxyurea, idarubicin, imatinib, indibulin, irinotecan, matrine, monomethyl auristatin E (MMAE), monomethyl auristatin F (MMAF), monomethyl auristatin U (MMAU), mechlorethamine, methotrexate, mitoxantrone, monomethyl dolastatin 10 (MMAD), nitrogen mustard, oxaliplatin, paclitaxel, palbociclib, pemetrexed, PNU159682, pyrrolobenzodiazepines (PBD), PBD dimers, retapamulin, ribociclib, rifabutin, SG3199 PBD dimer, SN-38, sunitinib, teniposide, tioguanine, topotecan, tubulysin A, tubulysin B, tubulysin D, tubulysin M, tubulysin U, tubulysin V, valrubicin, vemurafenib, vinblastine, vincristine, vindesine, or the like.

For use with the present invention, the chemotherapeutic agent can be fully pharmacologically active following conjugation or alternatively, the chemotherapeutic agent may be a prodrug, meaning an inactive or less active derivative of the chemotherapeutic agent which can be transformed into its pharmacologically active form via metabolism, such as by an enzymatic and/or chemical mechanism, whereby the pharmacologically active form may be effective to kill tumor cells.

In contrast to administration in its pharmacologically active form, administering a chemotherapeutic agent in its prodrug form can improve the absorption, distribution, metabolism, and/or excretion (ADME) of said chemotherapeutic agent. For example, a prodrug form can have improved bioavailability relative to its pharmacologically active form, which may be beneficial for chemotherapeutic agents that are poorly absorbed via the gastrointestinal tract. Additionally, the prodrug form can facilitate how selectively the chemotherapeutic agent interacts with cells or processes that are not its intended target, which may reduce unintended, undesirable, and/or adverse side effects of the chemotherapeutic agent.

As stated above, the present dye can be coupled to (for example via conjugation) a chemotherapeutic agent via various linkers for use in chemotherapy, whereby the specific linker which conjugates the two compounds may contribute to a decrease in the adverse side effects of the chemotherapeutic agent, as the linker can affect the pharmacokinetics, pharmacodynamics, stability, toxicity, etc. of the chemotherapeutic agent incorporated into the conjugate. A preferred linker can ensure adequate stability of the chemotherapeutic agent in the circulation, effectively prevent premature release of the chemotherapeutic agent proximate an unintended target, and use the inherent properties of tumor cells and/or the tumor microenvironment to facilitate the release and/or pharmacological activation of the chemotherapeutic agent only proximate a target tumor cell population.

As to particular embodiments, a linker comprising a cleavable portion can be useful to conjugate a tumor-targeting NIR dye and a chemotherapeutic agent as per the present invention.

Figure 5:
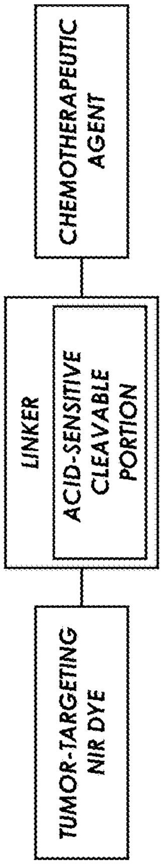
FIG. 5 shows an embodiment of the inventive conjugate.

Now referring primarily to FIG. 5, as to particular embodiments, the linker can comprise a cleavable portion with pH sensitivity, whereby acid-sensitive cleavable portions may exploit the acidic microenvironment of tumors to trigger the hydrolysis of an acid-labile group(s) within the acid-sensitive cleavable portion to facilitate the release of the chemotherapeutic agent only proximate a target tumor cell population.

Figure 6A:
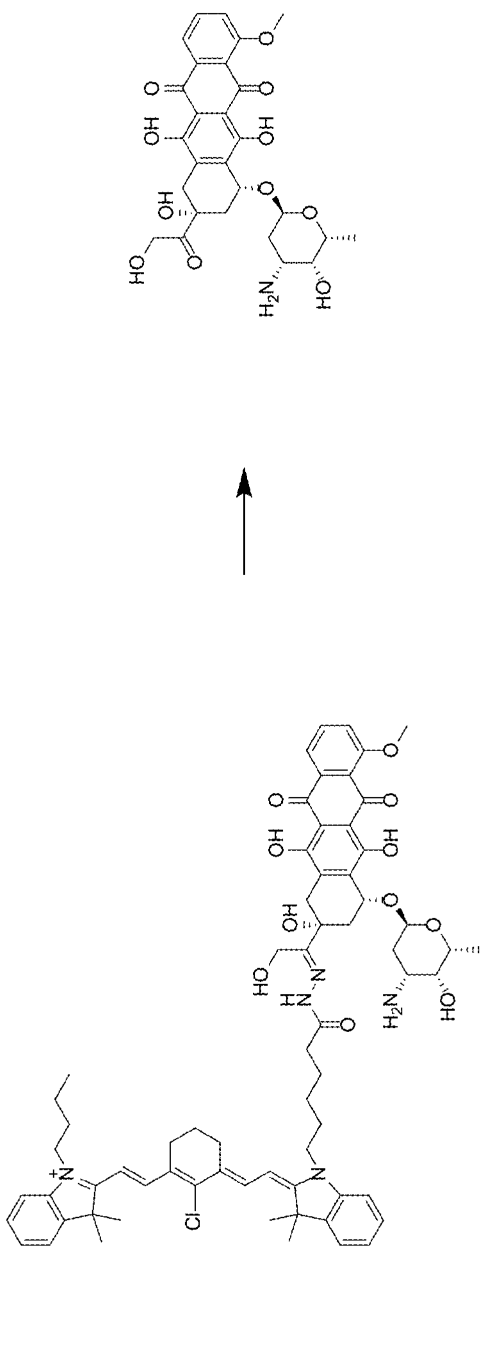
FIG. 6A shows a tumor-targeting NIR dye coupled to a chemotherapeutic agent via a linker including a cleavable portion with acid sensitivity.
Figure 6B:
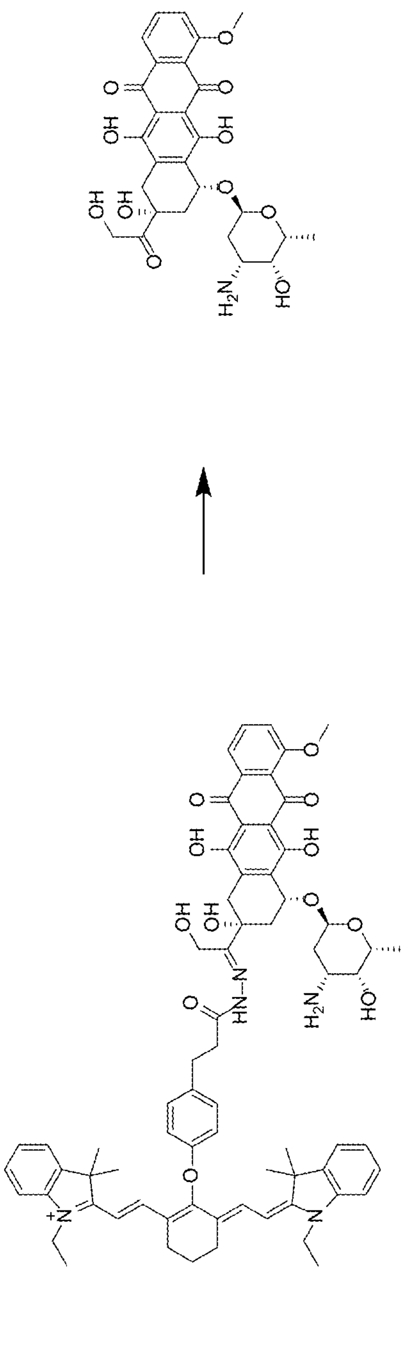
FIG. 6B shows a tumor-targeting NIR dye coupled to a chemotherapeutic agent via a linker including a cleavable portion with acid sensitivity.
Figure 7E:
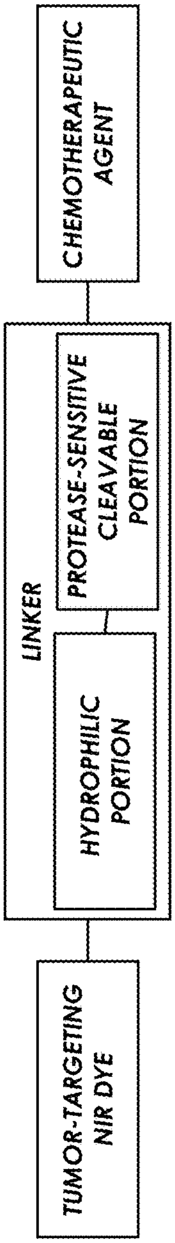
FIG. 7E shows an embodiment of the inventive conjugate.
Figure 7F:
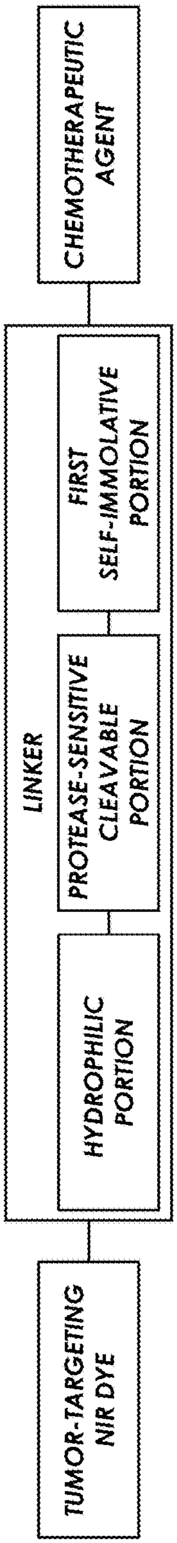
FIG. 7F shows an embodiment of the inventive conjugate.

As to particular embodiments, a cleavable portion with acid sensitivity can comprise an acid-labile hydrazone bond (as shown in FIGS. 6A and 6B).

Now referring primarily to FIGS. 7A through 7F, as to particular embodiments, the linker can comprise a cleavable portion with enzyme sensitivity (i.e., an enzymatically-cleavable portion), such as a cleavable portion with protease sensitivity. In use, a protease found in tumor cells and/or in the tumor microenvironment can recognize and cleave a specific substrate to advantageously release a linked payload only proximate a target tumor cell population. Further, protease-sensitive cleavable portions can be stable in the systemic circulation due to the presence of protease inhibitors in the blood. As to particular embodiments, illustrative examples of protease-sensitive cleavable portions which may be useful with the present invention include those shown in FIGS. 8A through 8N.

As to particular embodiments, the linker can comprise a cleavable peptide portion with protease sensitivity. In use, a protease found in tumor cells and/or in the tumor microenvironment can recognize and cleave a specific peptide sequence in a cleavable peptide portion to advantageously release a linked payload only proximate a target tumor cell population.

Figure 8A:
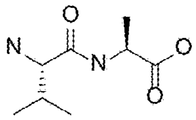
FIG. 8A shows an illustrative example of a protease-sensitive cleavable peptide portion which may be useful with the present invention to link a tumor-targeting NIR dye and a chemotherapeutic agent to form the inventive conjugate.
Figure 8B:
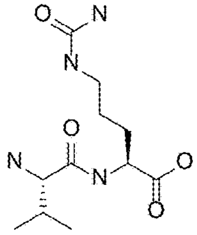
FIG. 8B shows an illustrative example of a protease-sensitive cleavable peptide portion which may be useful with the present invention to link a tumor-targeting NIR dye and a chemotherapeutic agent to form the inventive conjugate.
Figure 8C:
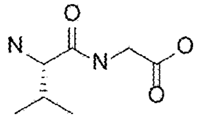
FIG. 8C shows an illustrative example of a protease-sensitive cleavable peptide portion which may be useful with the present invention to link a tumor-targeting NIR dye and a chemotherapeutic agent to form the inventive conjugate.
Figure 8D:
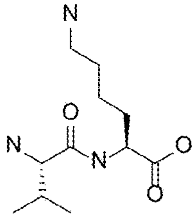
FIG. 8D shows an illustrative example of a protease-sensitive cleavable peptide portion which may be useful with the present invention to link a tumor-targeting NIR dye and a chemotherapeutic agent to form the inventive conjugate.
Figure 8E:
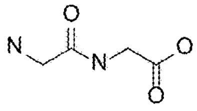
FIG. 8E shows an illustrative example of a protease-sensitive cleavable peptide portion which may be useful with the present invention to link a tumor-targeting NIR dye and a chemotherapeutic agent to form the inventive conjugate.
Figure 8F:
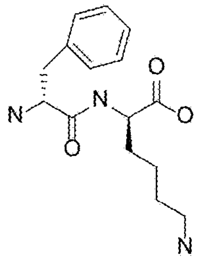
FIG. 8F shows an illustrative example of a protease-sensitive cleavable peptide portion which may be useful with the present invention to link a tumor-targeting NIR dye and a chemotherapeutic agent to form the inventive conjugate.
Figure 8G:
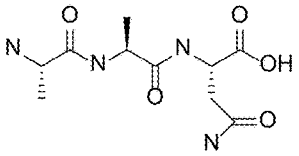
FIG. 8G shows an illustrative example of a protease-sensitive cleavable peptide portion which may be useful with the present invention to link a tumor-targeting NIR dye and a chemotherapeutic agent to form the inventive conjugate.
Figure 8H:
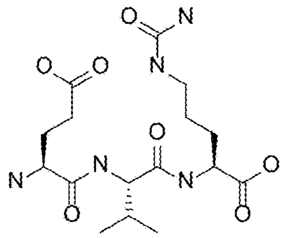
FIG. 8H shows an illustrative example of a protease-sensitive cleavable peptide portion which may be useful with the present invention to link a tumor-targeting NIR dye and a chemotherapeutic agent to form the inventive conjugate.
Figure 8I:
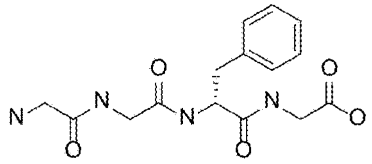
FIG. 8I shows an illustrative example of a protease-sensitive cleavable peptide portion which may be useful with the present invention to link a tumor-targeting NIR dye and a chemotherapeutic agent to form the inventive conjugate.
Figure 8J:
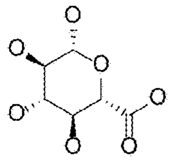
FIG. 8J shows an illustrative example of a protease-sensitive cleavable portion which may be useful with the present invention to link a tumor-targeting NIR dye and a chemotherapeutic agent to form the inventive conjugate.

As to particular embodiments, a cleavable peptide portion with protease sensitivity can comprise a peptide sequence which may be cleaved by cathepsin B, a lysosomal protease which may be overexpressed in and around tumor cells. As illustrative examples, cathepsin B-sensitive peptide sequences can include a valine-citrulline (VC) dipeptide (as shown in FIGS. 8B and 9A through 9D), a valine-alanine (VA) dipeptide (as shown in FIGS. 8A and 9E), a phenylalanine-lysine (FK) dipeptide (as shown in FIG. 8F), and a glycine-glycine-phenylalanine-glycine (GGFG) tetrapeptide (as shown in FIGS. 81 and 9F).

As to particular embodiments, a cleavable peptide portion with protease sensitivity can comprise a peptide sequence which may be cleaved by matrix metalloproteinase 2 (MMP-2), an enzyme which breaks down components of the extracellular matrix and may be overexpressed in and around tumor cells. As an illustrative example, an MMP-2-sensitive peptide sequence can include the synthetic octapeptide glycine-proline-leucine-glycine-isoleucine-alanine-glycine-glutamine (GPLGIAGQ) (as shown in FIG. 8N).

Figure 8K:
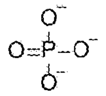
FIG. 8K shows an illustrative example of a protease-sensitive cleavable portion which may be useful with the present invention to link a tumor-targeting NIR dye and a chemotherapeutic agent to form the inventive conjugate.
Figure 8L:
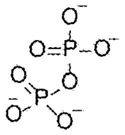
FIG. 8L shows an illustrative example of a protease-sensitive cleavable portion which may be useful with the present invention to link a tumor-targeting NIR dye and a chemotherapeutic agent to form the inventive conjugate.
Figure 8M:
FIG. 8M shows an illustrative example of a protease-sensitive cleavable portion which may be useful with the present invention to link a tumor-targeting NIR dye and a chemotherapeutic agent to form the inventive conjugate.
Figure 8N:
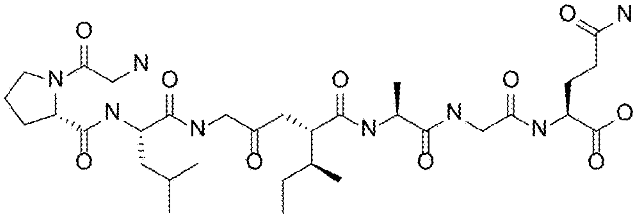
FIG. 8N shows an illustrative example of a protease-sensitive cleavable peptide portion which may be useful with the present invention to link a tumor-targeting NIR dye and a chemotherapeutic agent to form the inventive conjugate.
Figure 10A:
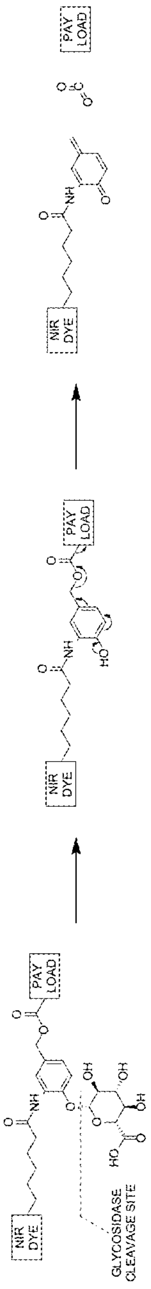
FIG. 10A shows a tumor-targeting NIR dye coupled to a chemotherapeutic agent via a linker including a cleavable portion with enzyme sensitivity.
Figure 10B:
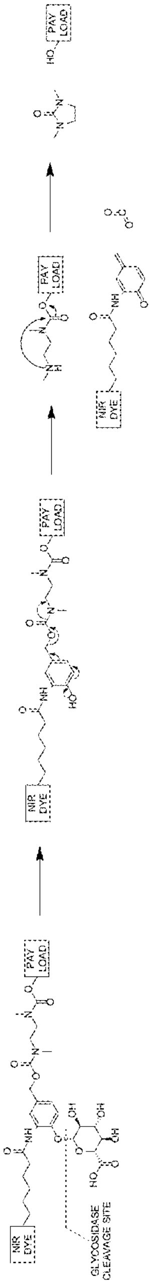
FIG. 10B shows a tumor-targeting NIR dye coupled to a chemotherapeutic agent via a linker including a cleavable portion with enzyme sensitivity.

As to particular embodiments, a cleavable portion with protease sensitivity can comprise glucuronic acid (as shown in FIGS. 8N, 10A, and 10B) which may be cleaved by β-glucuronidase, a glycosidase which breaks down complex carbohydrates and may be overexpressed in and around tumor cells. Of note, glucuronic acid-containing cleavable portions can have relatively high water solubility.

Figure 9A:
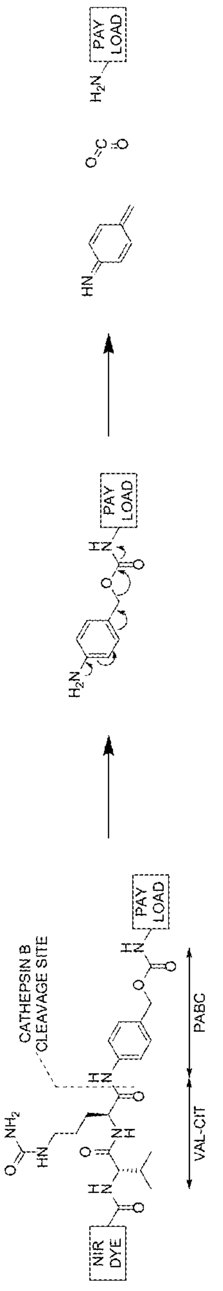
FIG. 9A shows a tumor-targeting NIR dye coupled to a chemotherapeutic agent via a linker including a cleavable portion with enzyme sensitivity.
Figure 9B:
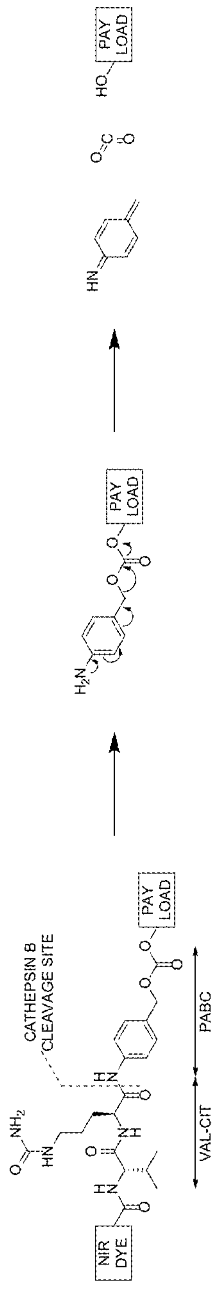
FIG. 9B shows a tumor-targeting NIR dye coupled to a chemotherapeutic agent via a linker including a cleavable portion with enzyme sensitivity.
Figure 9C:
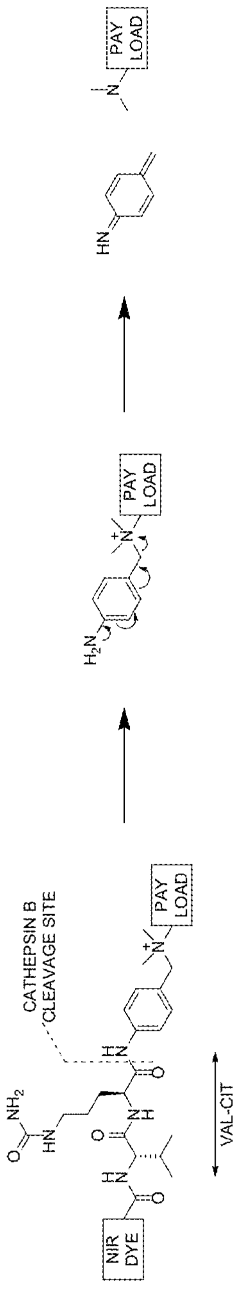
FIG. 9C shows a tumor-targeting NIR dye coupled to a chemotherapeutic agent via a linker including a cleavable portion with enzyme sensitivity.
Figure 9D:
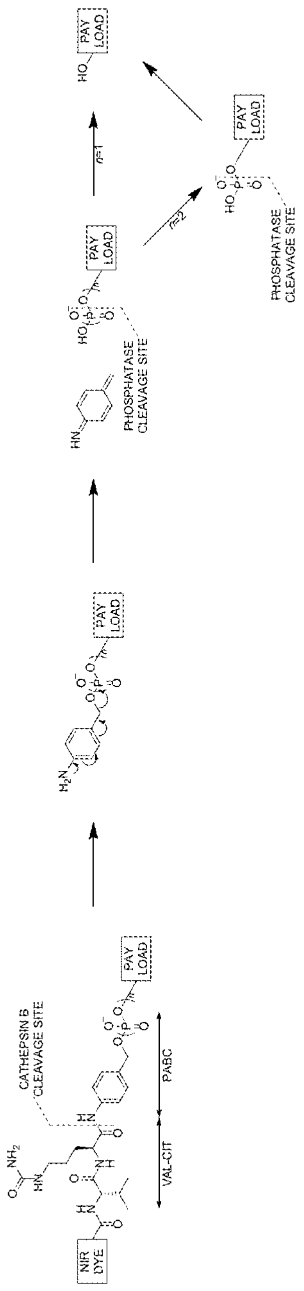
FIG. 9D shows a tumor-targeting NIR dye coupled to a chemotherapeutic agent via a linker including a cleavable portion with enzyme sensitivity.
Figure 9E:
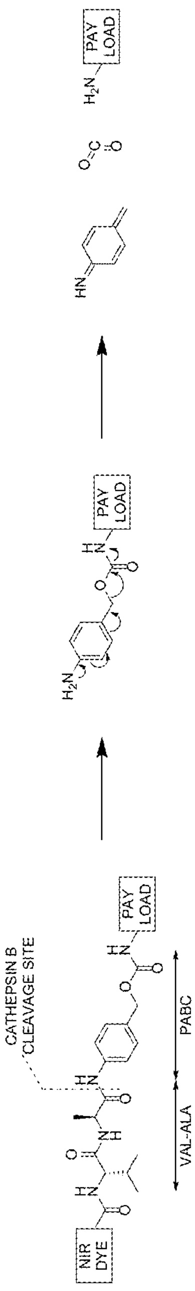
FIG. 9E shows a tumor-targeting NIR dye coupled to a chemotherapeutic agent via a linker including a cleavable portion with enzyme sensitivity.
Figure 9F:
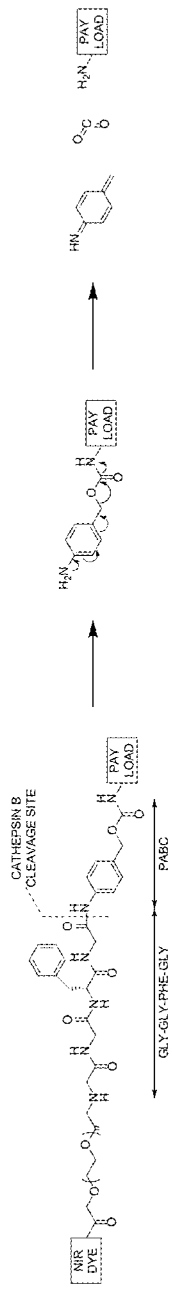
FIG. 9F shows a tumor-targeting NIR dye coupled to a chemotherapeutic agent via a linker including a cleavable portion with enzyme sensitivity.

As to particular embodiments, a cleavable portion with protease sensitivity can comprise a phosphatase-sensitive phosphate (as shown in FIGS. 8K and 9D) or a pyrophosphatase-sensitive pyrophosphate (as shown in FIG. 8L), whereby phosphatase and pyrophosphatase catalyze the hydrolysis of phosphate and pyrophosphate, respectively. Of note, phosphate-containing cleavable portions and pyrophosphate-containing cleavable portions can have relatively high water solubility.

Figure 11:
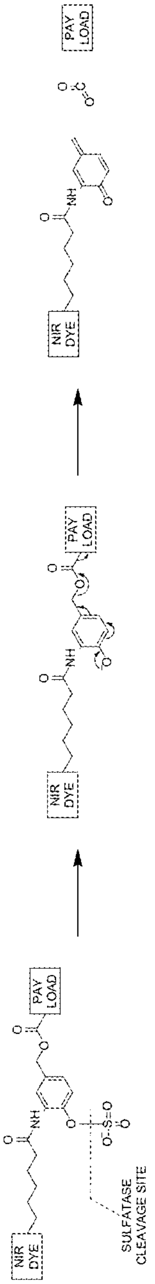
FIG. 11 shows a tumor-targeting NIR dye coupled to a chemotherapeutic agent via a linker including a cleavable portion with enzyme sensitivity.

As to particular embodiments, a cleavable portion with protease sensitivity can comprise a sulphatase-sensitive sulphonate (as shown in FIGS. 8M and 11), whereby a sulphatase catalyzes the hydrolysis of a sulfate ester. Of note, sulphonate-containing cleavable portions can have relatively high water solubility.

Exemplary conjugates comprising a tumor-targeting NIR dye and specifically, the dye shown in Formula VI, coupled to a chemotherapeutic agent via a linker including a cleavable peptide portion which may be useful with the present invention are shown in Formulas XVI through LIII.

XVI
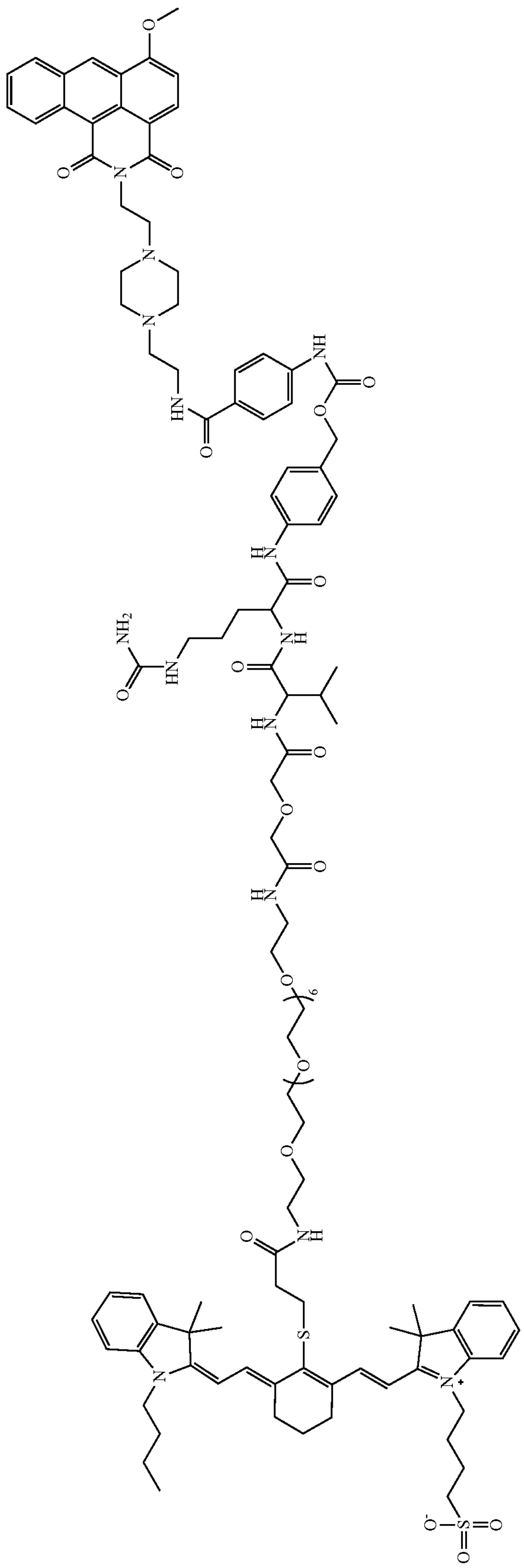

-continued
XVII
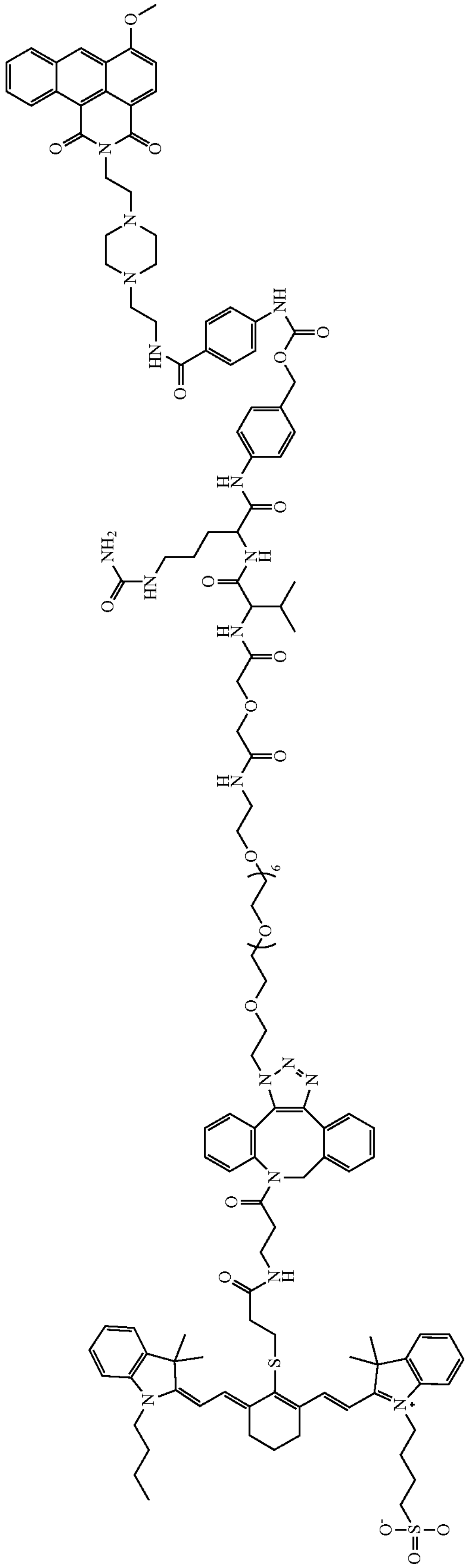
XVIII
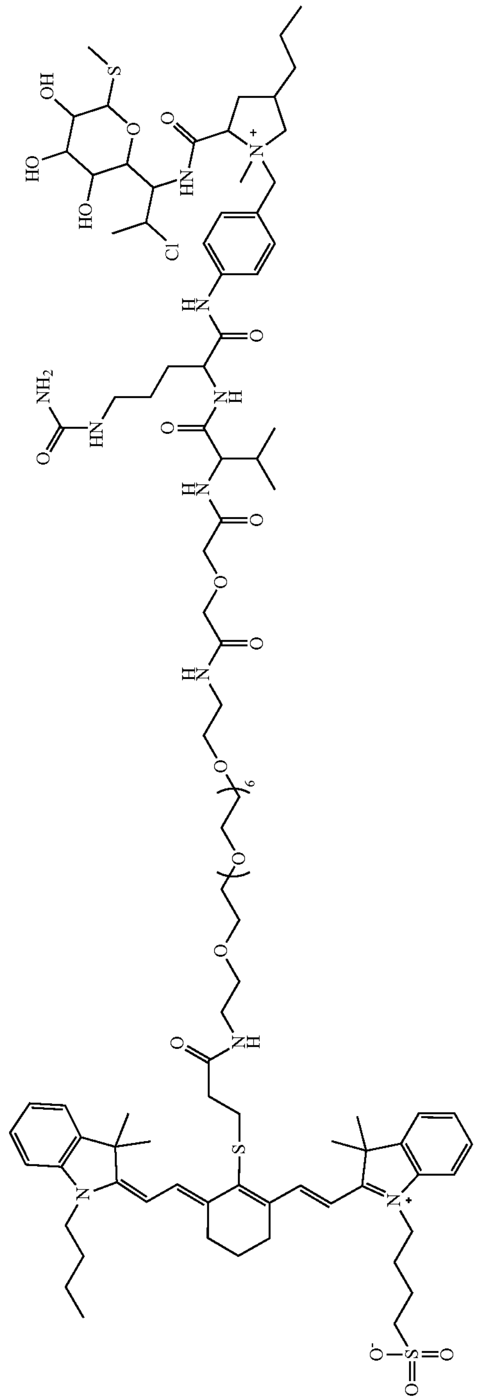

-continued
XIX
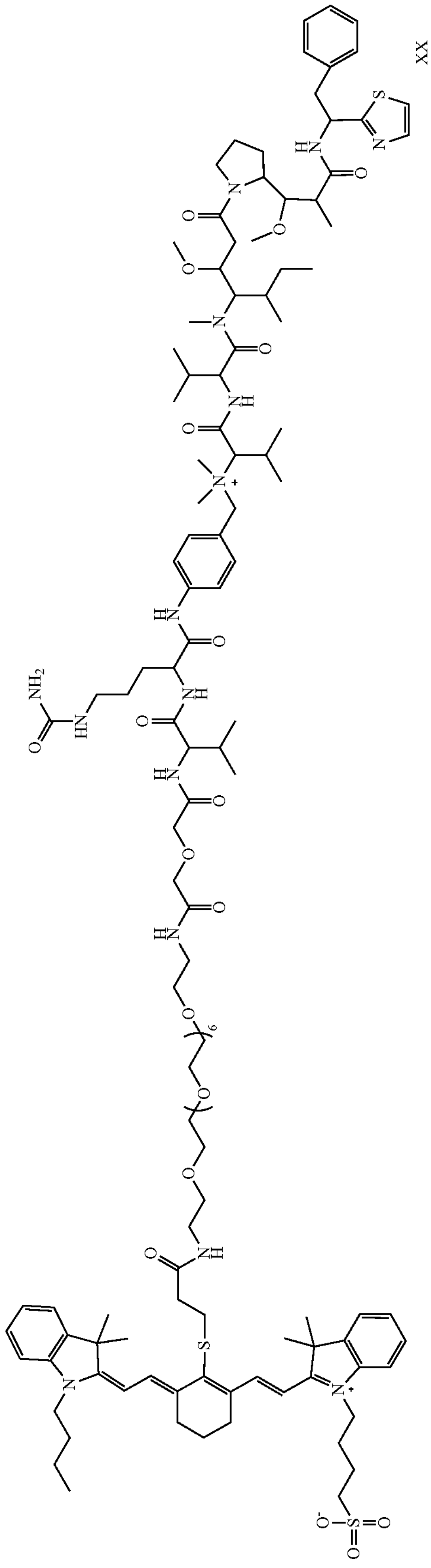
XX
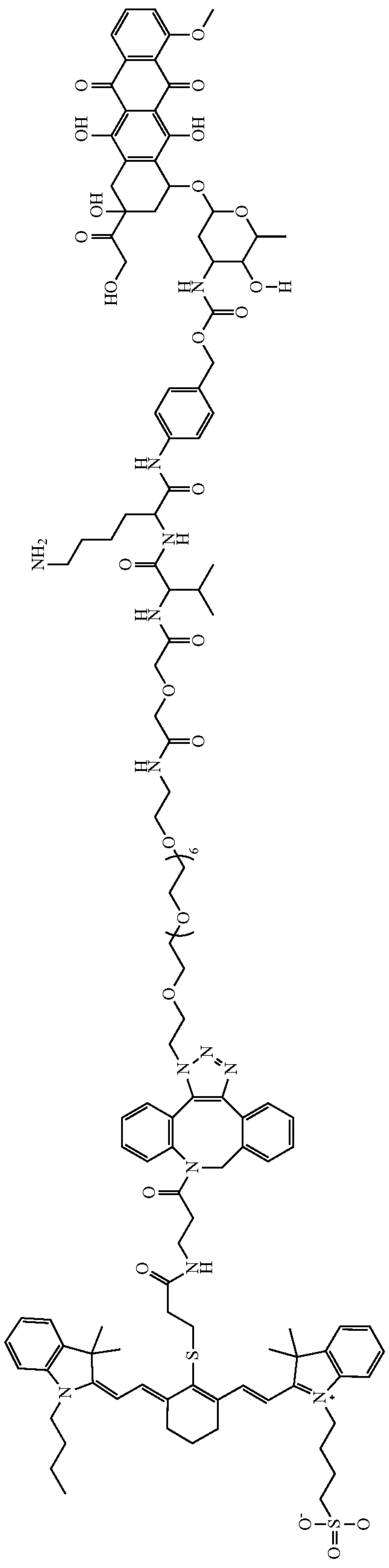

-continued
XXI
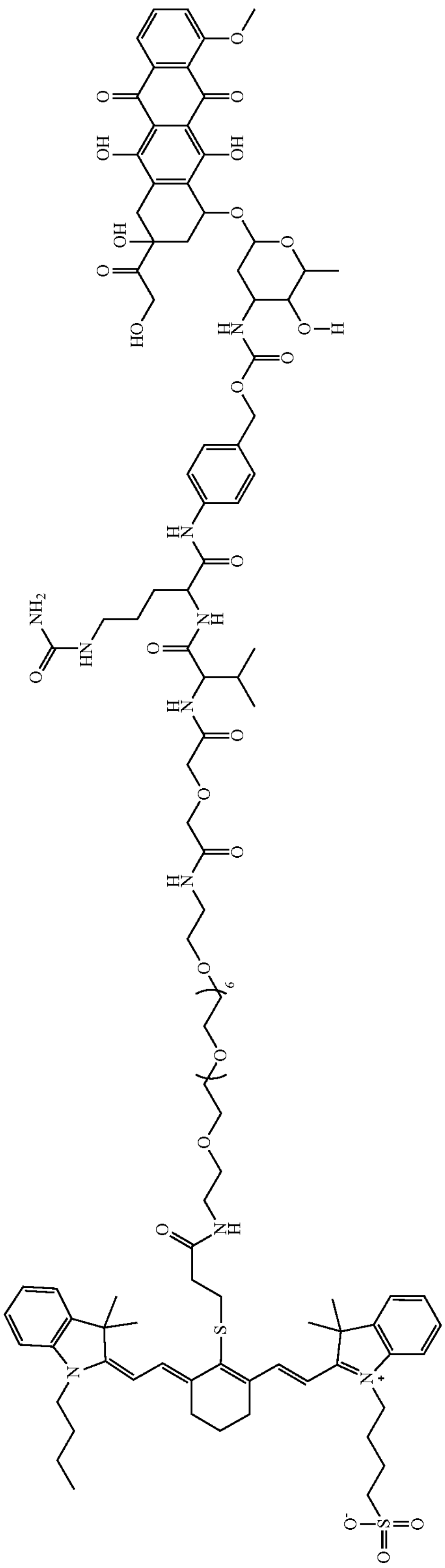
XXII
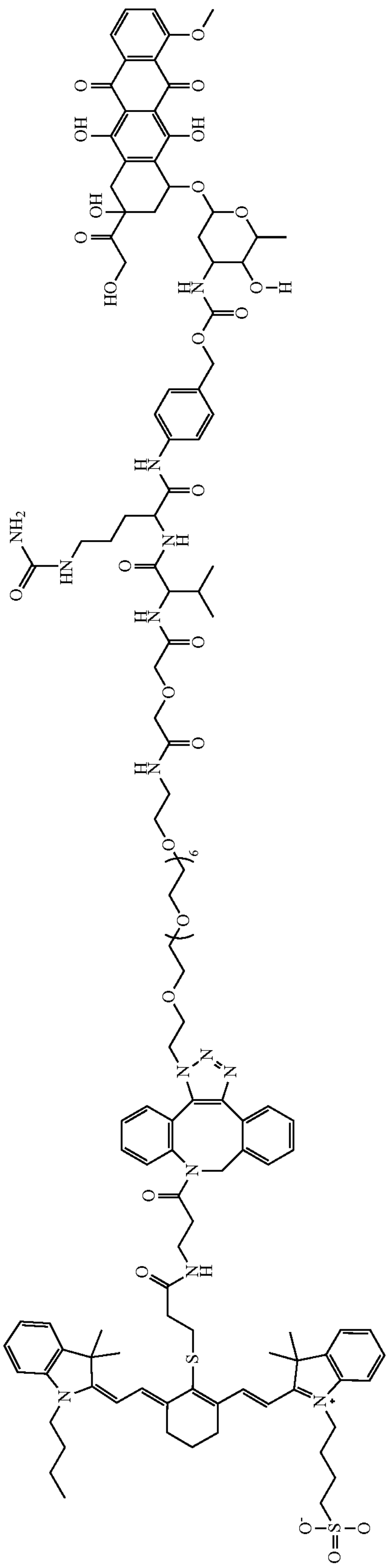

-continued
XXIII
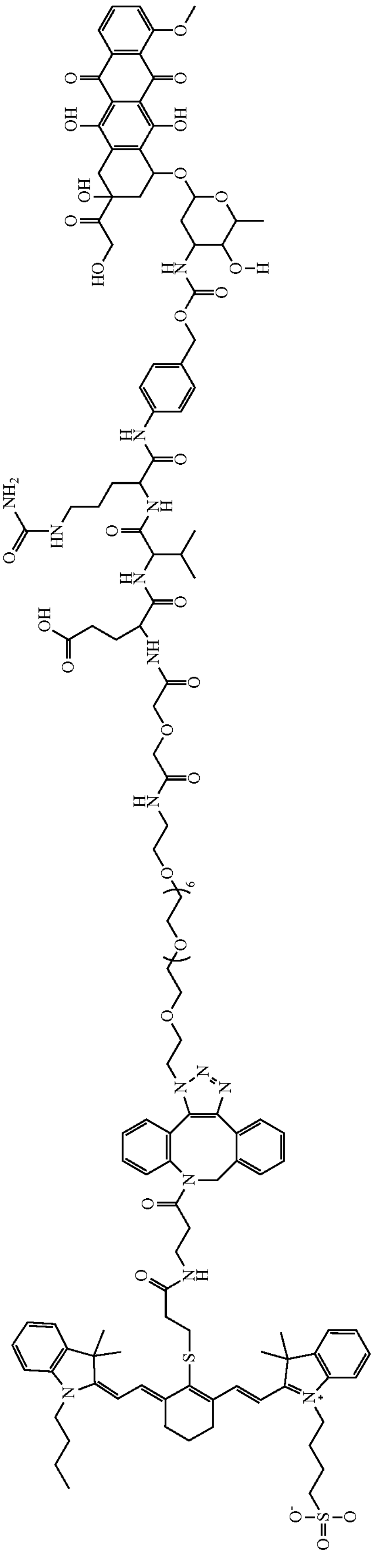
XXIV
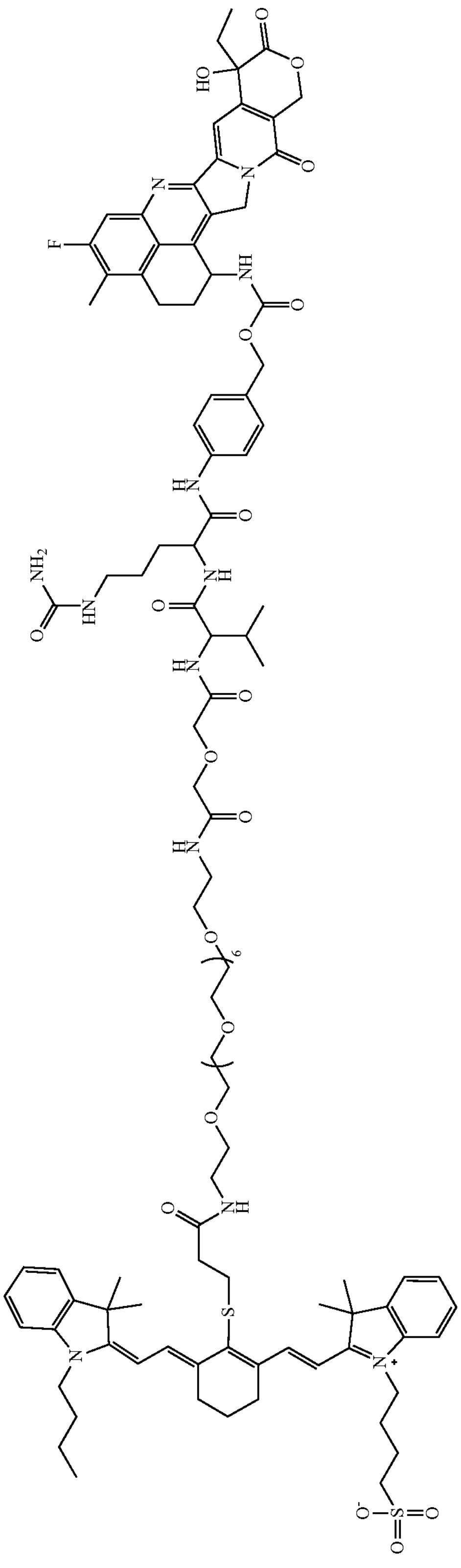

-continued
XXV
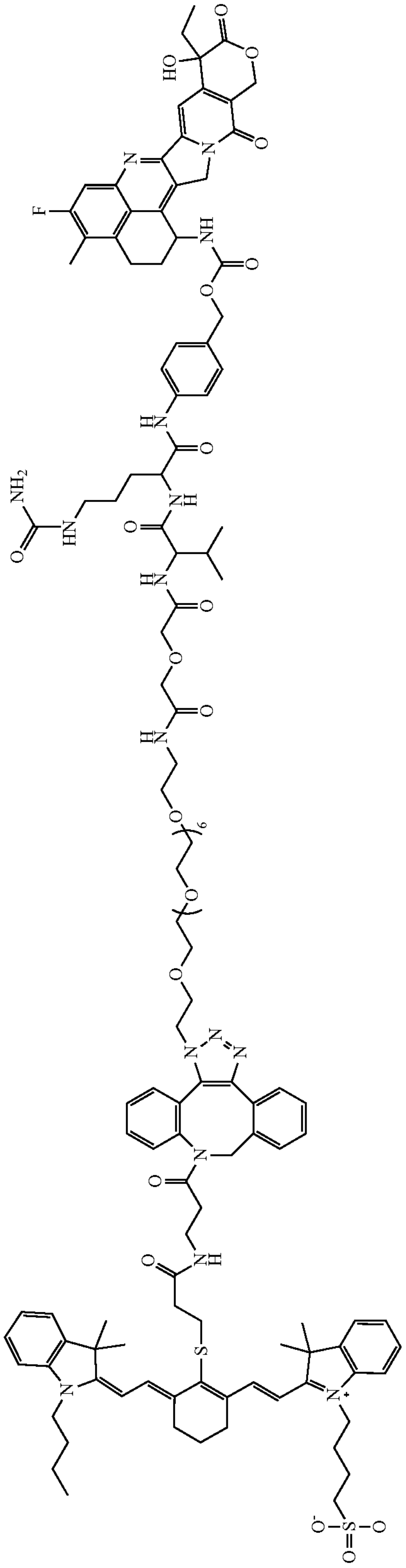
XXVI
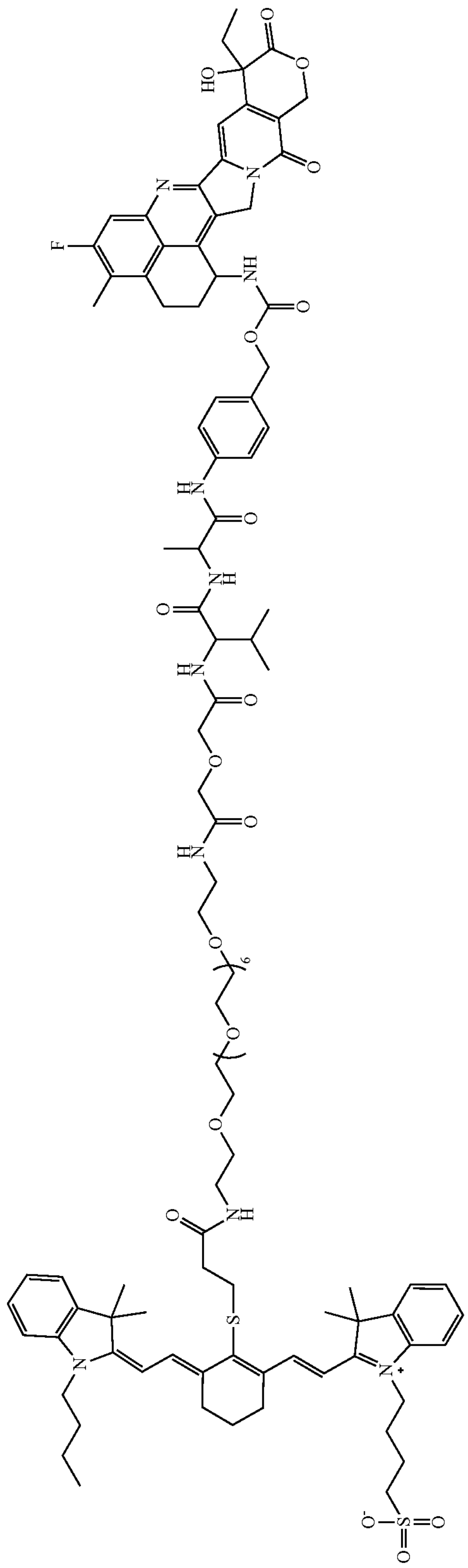

-continued
XXVII
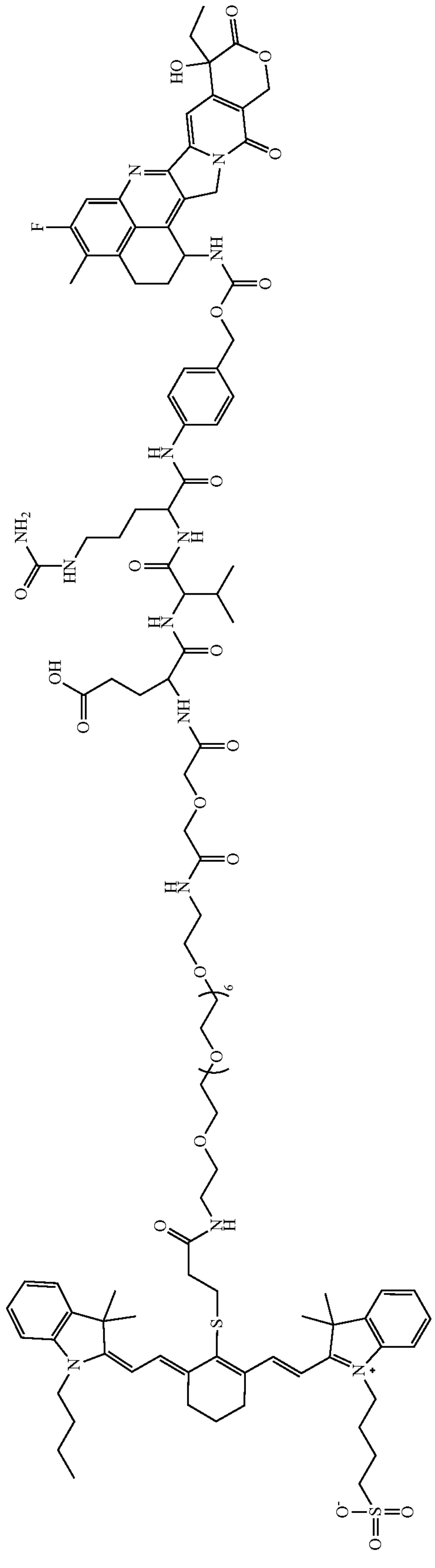
XXVIII
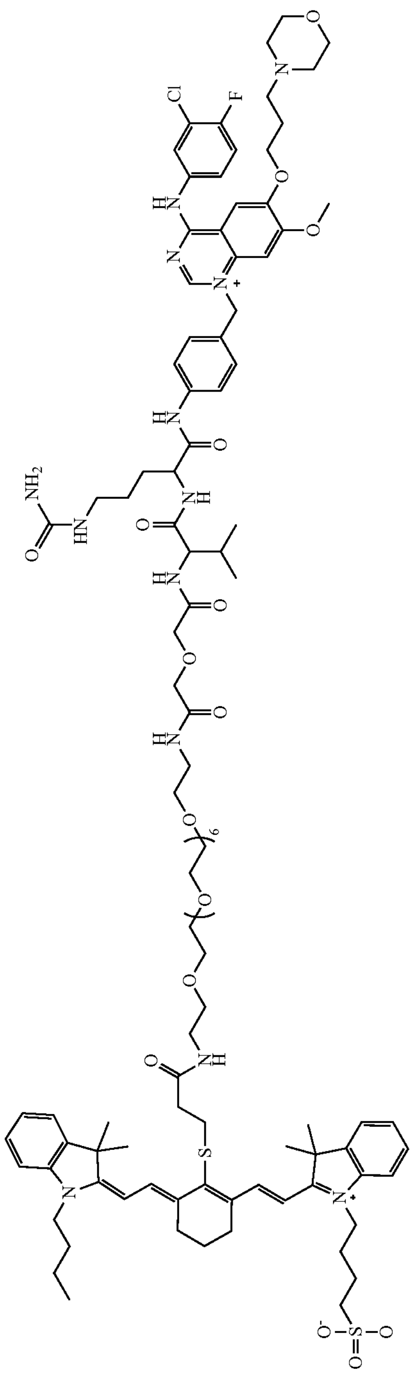

-continued
XXIX
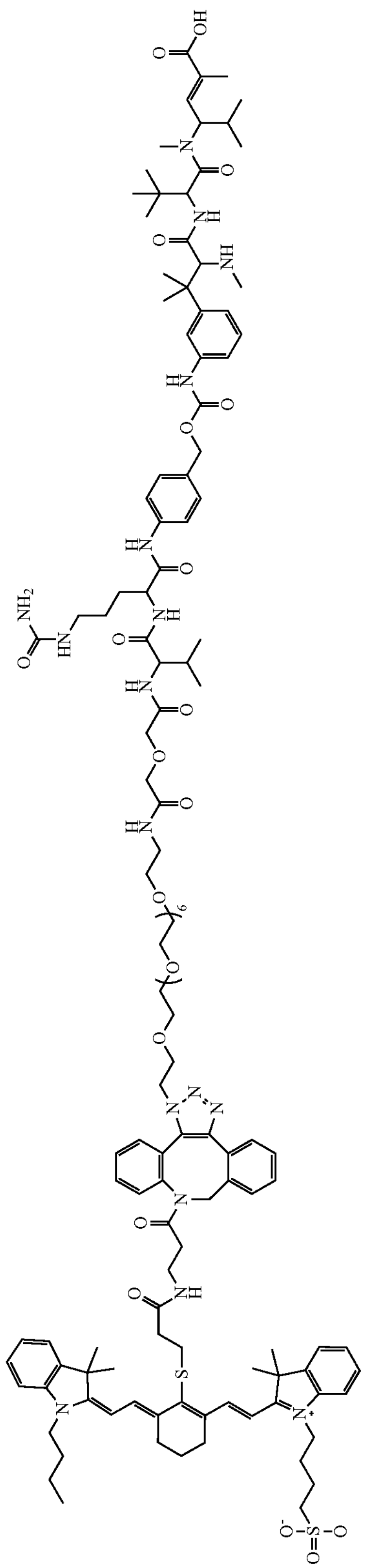
XXX
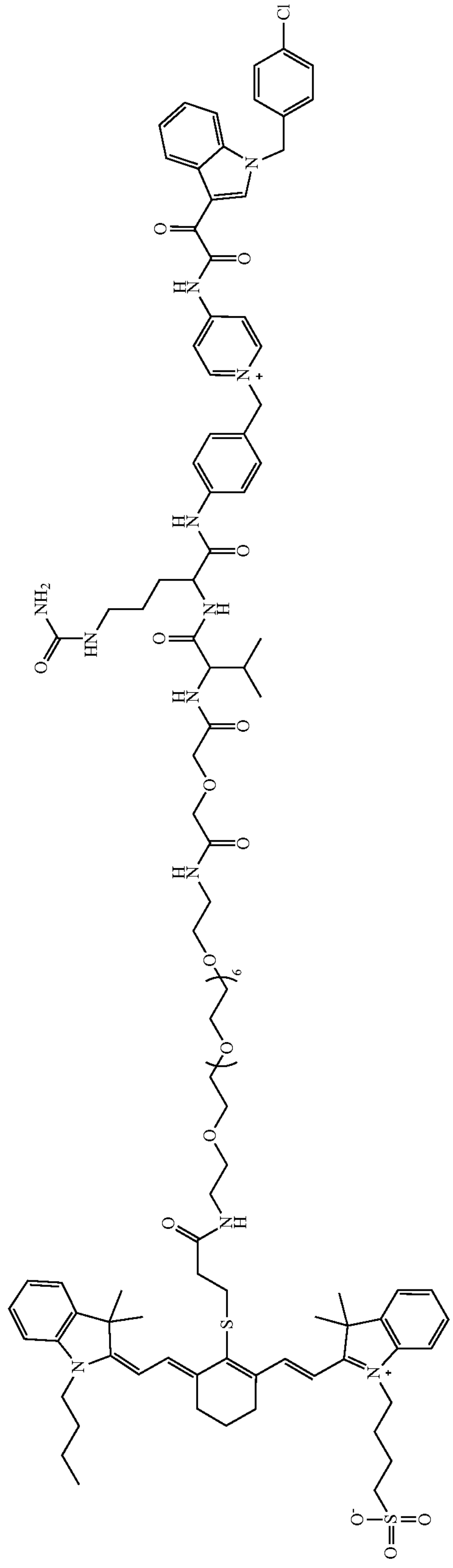

-continued
XXXI
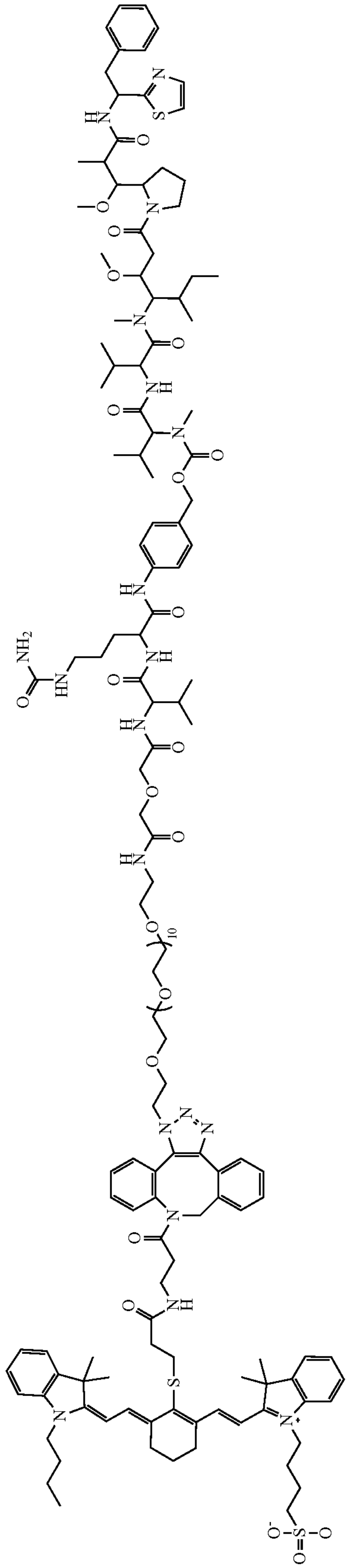
XXXII
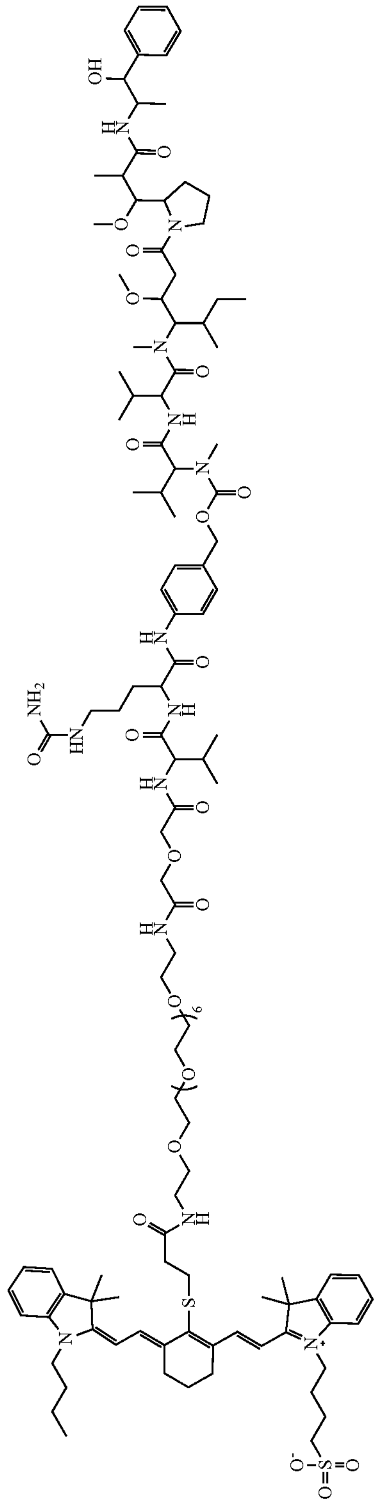

-continued
XXXIII
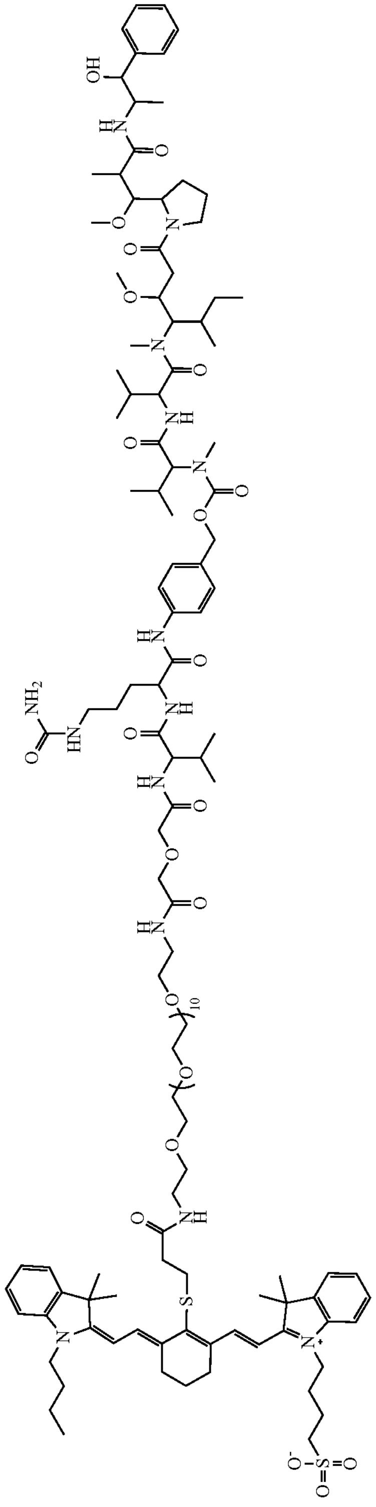
XXXIV
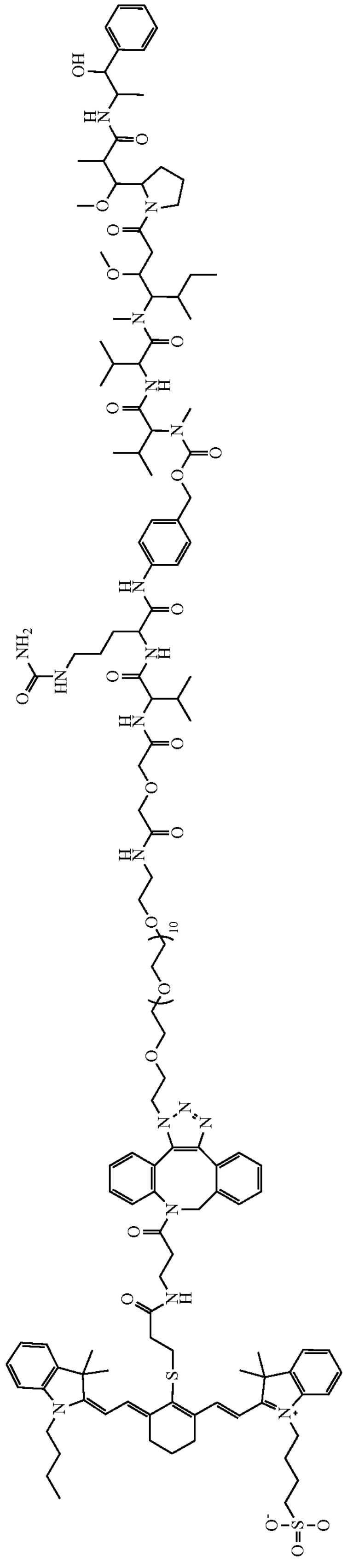

XXXV
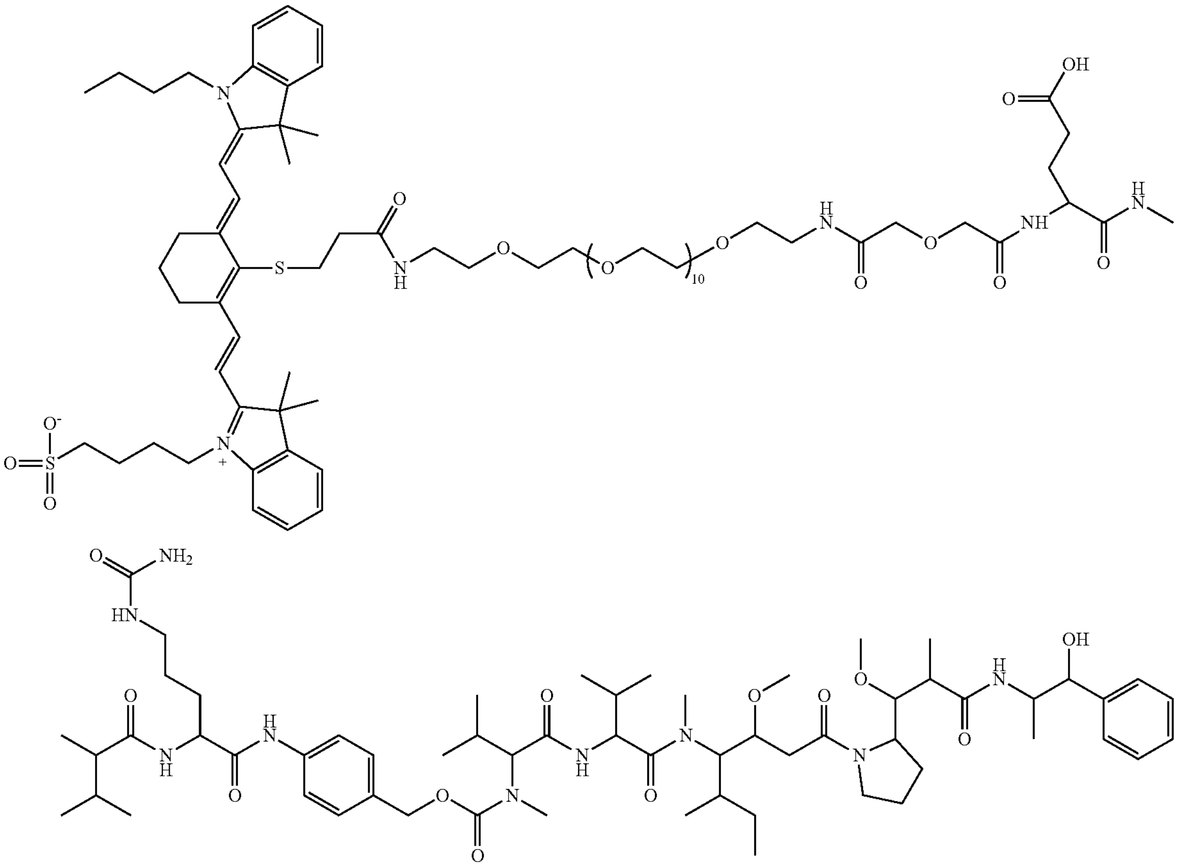
XXXVI
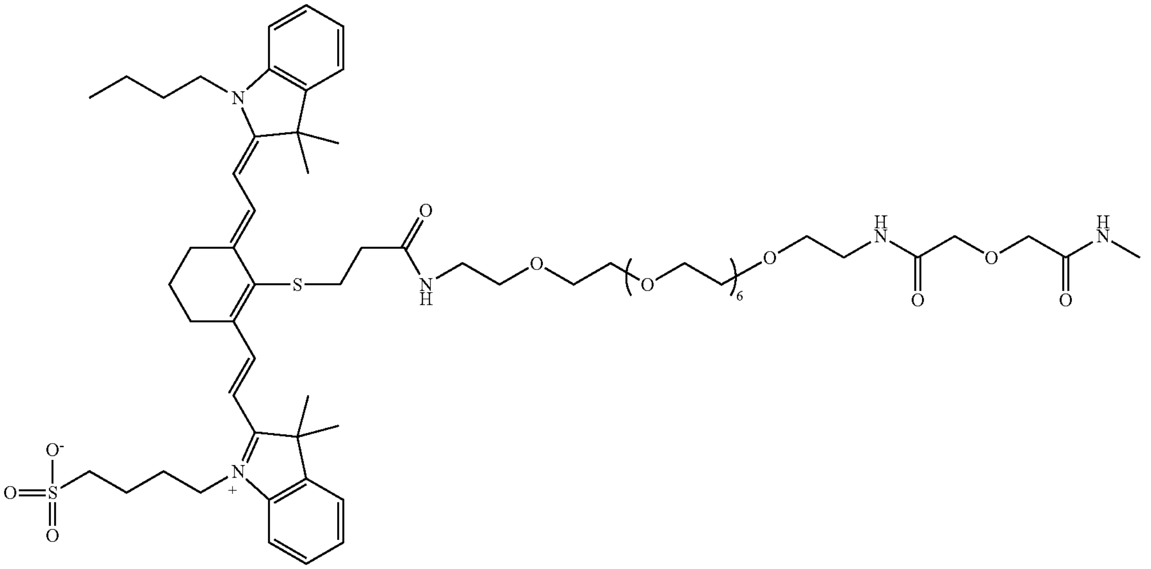

-continued
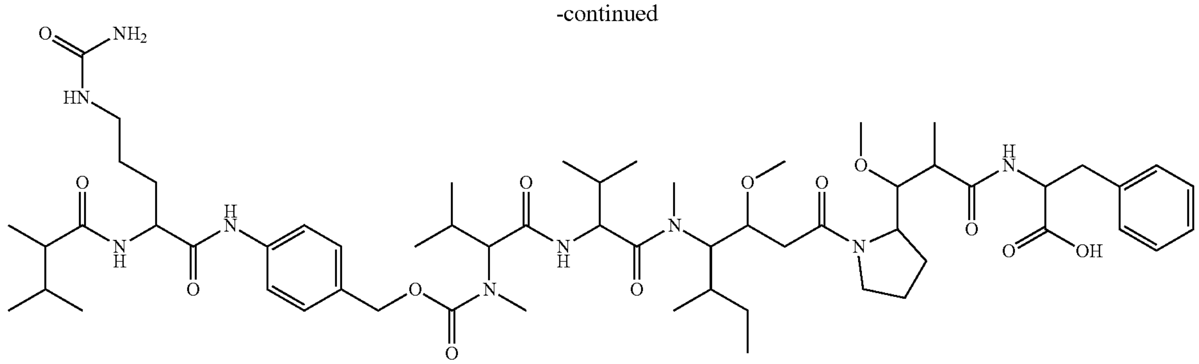
XXXVII
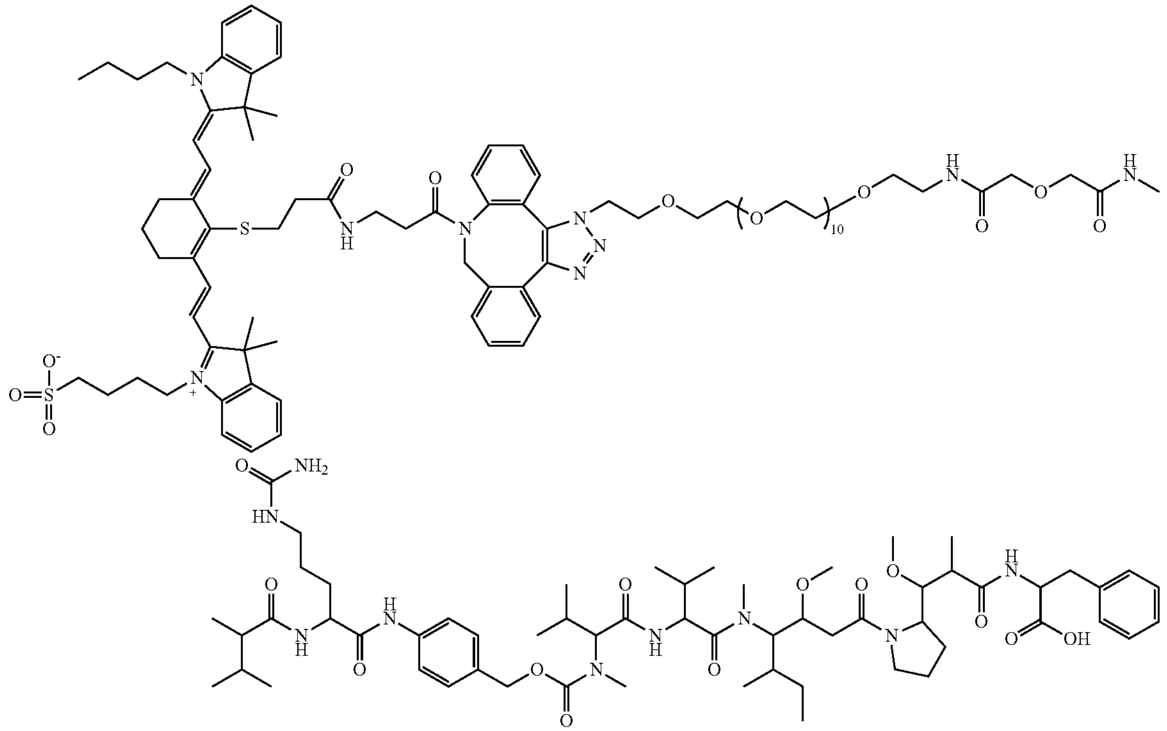
XXXVIII
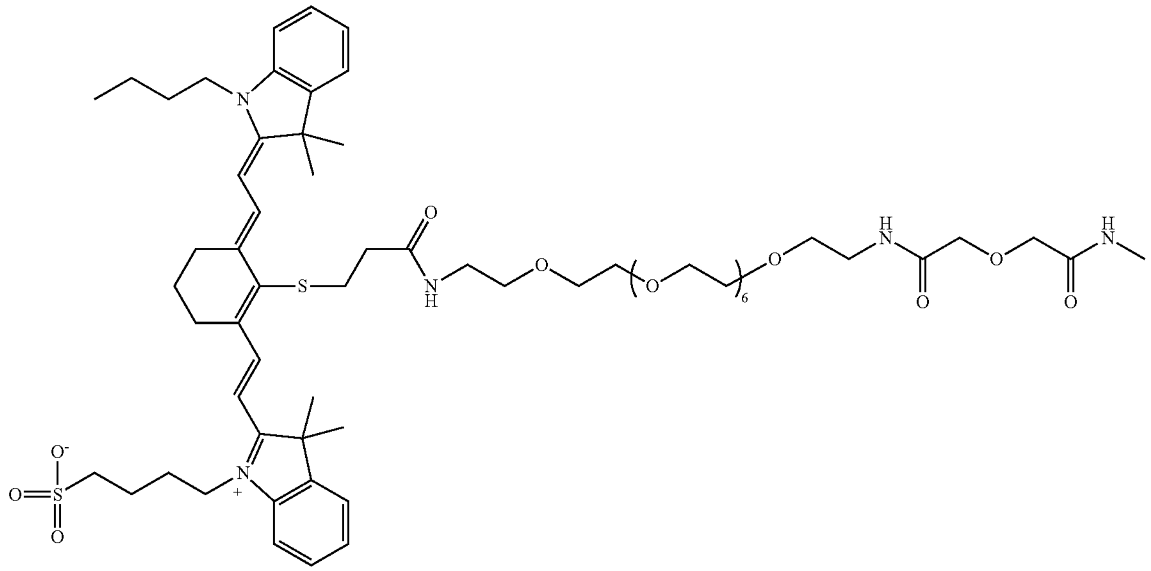

-continued
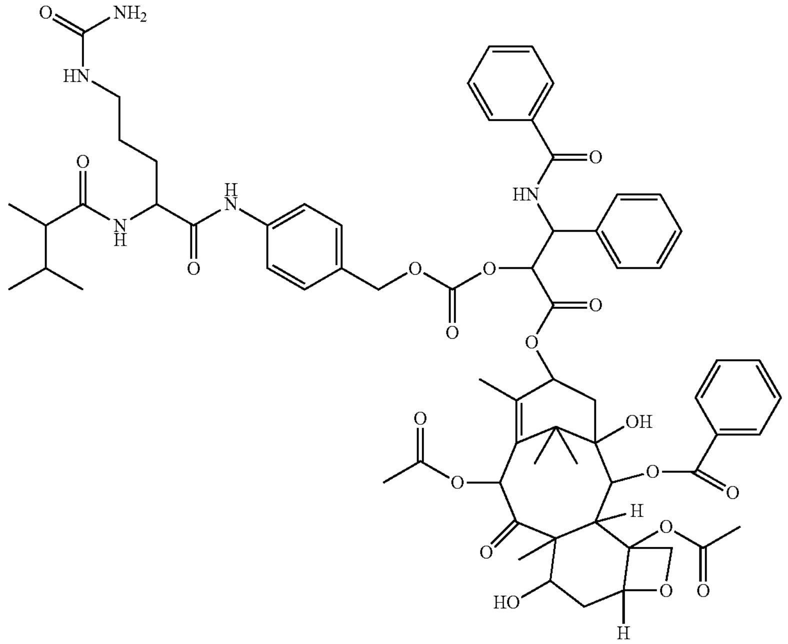
XXXIX
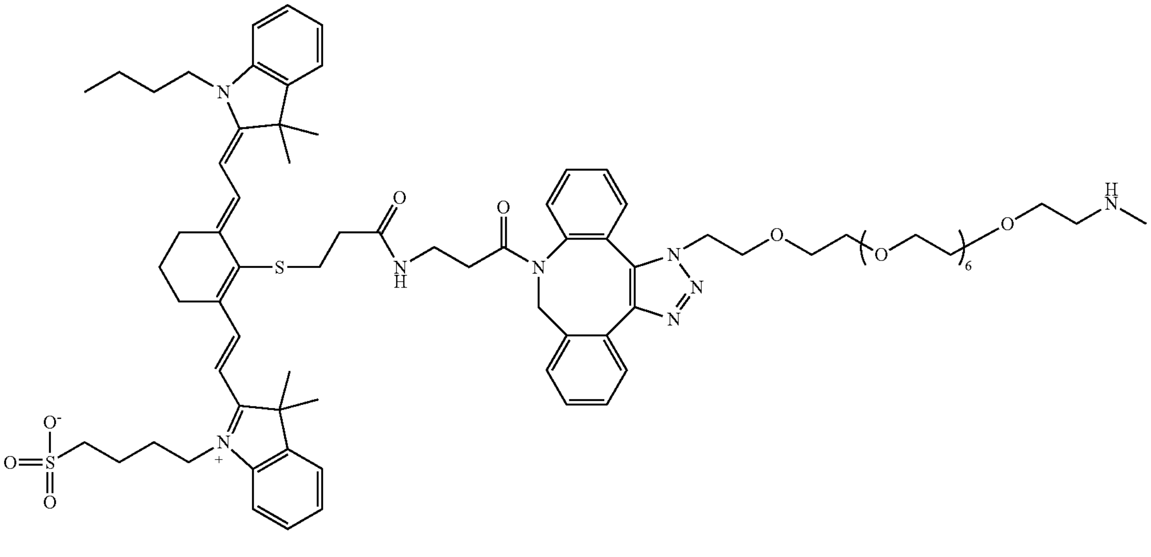

-continued
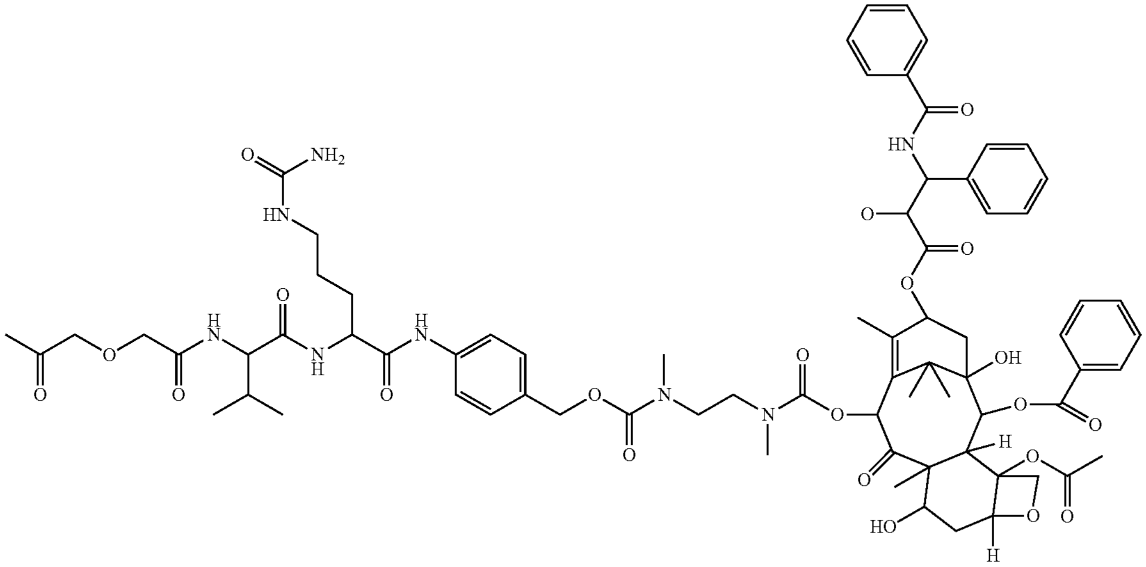
XL
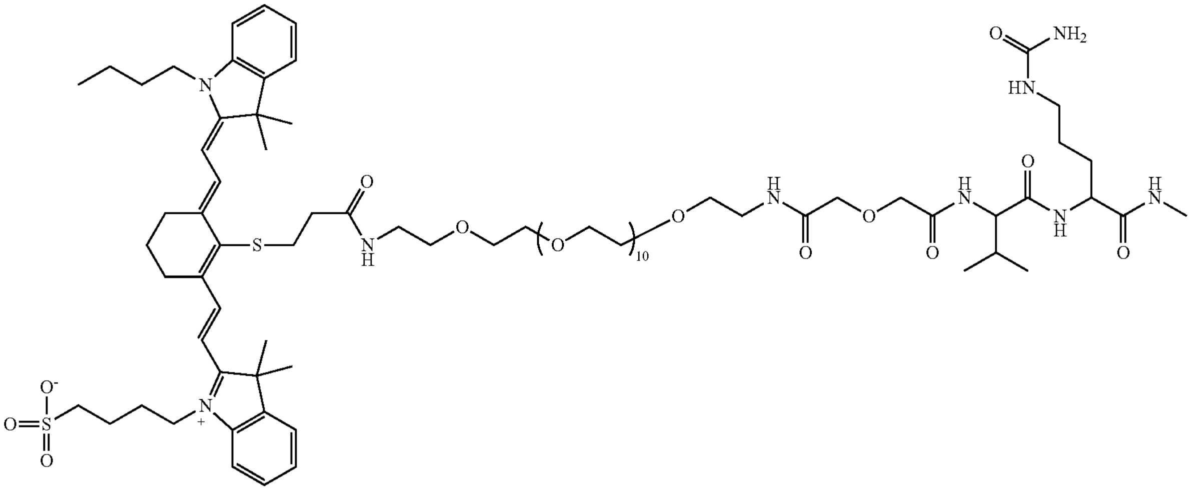
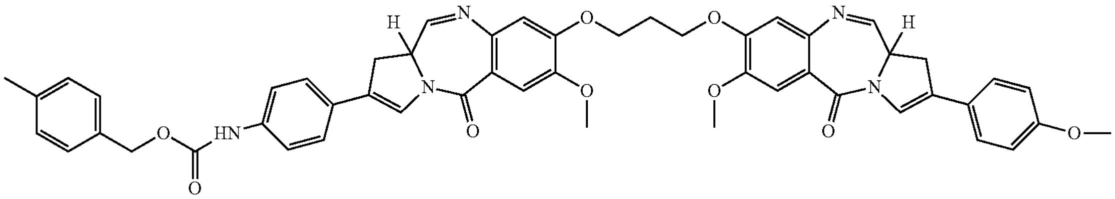

-continued
XLI
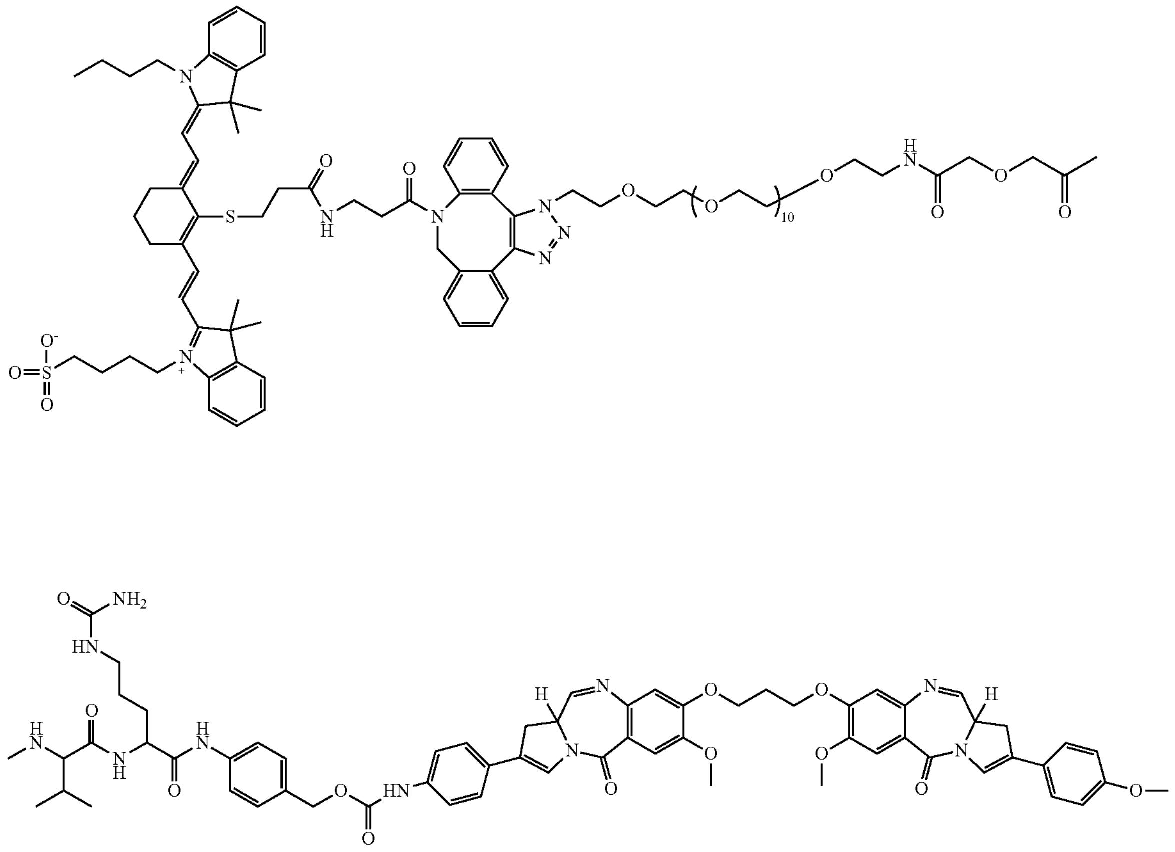
XLII
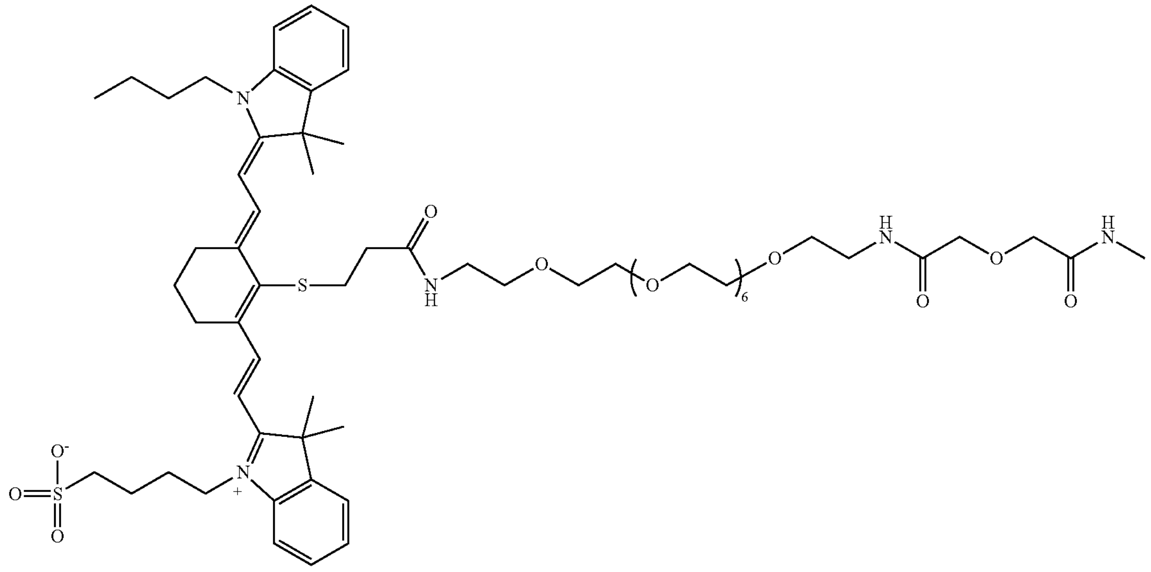

-continued
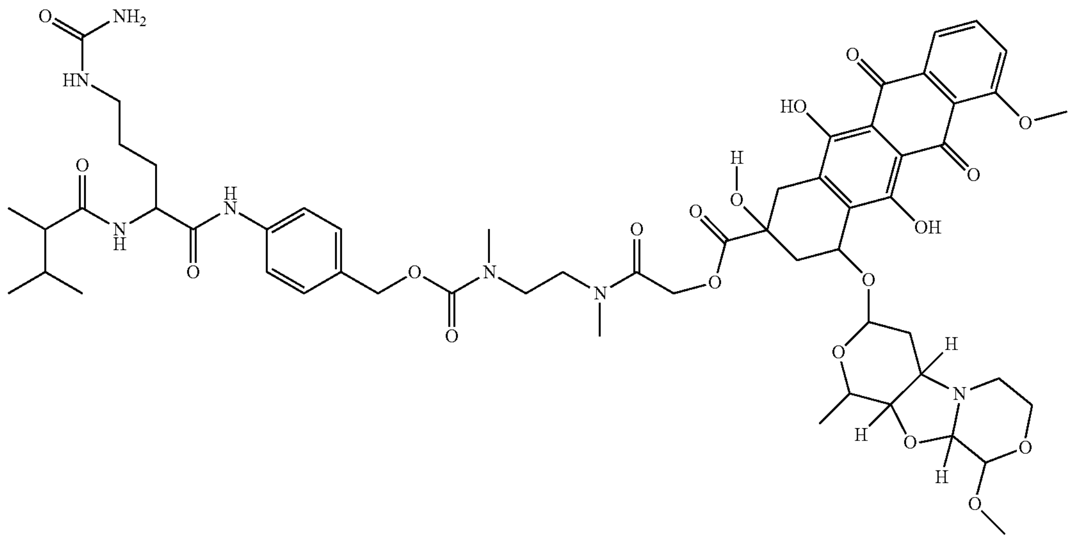
XLIII
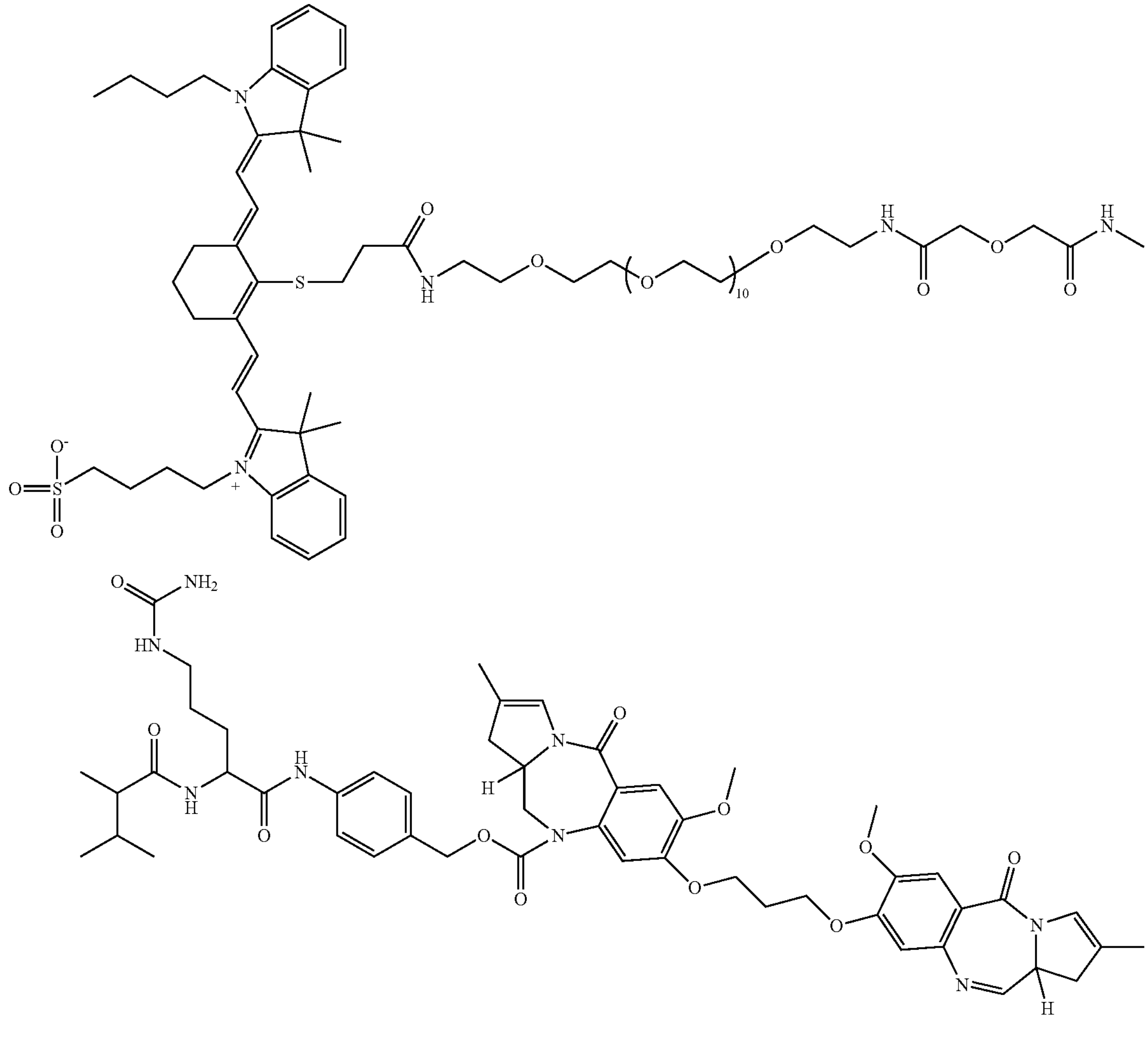

-continued
XLIV
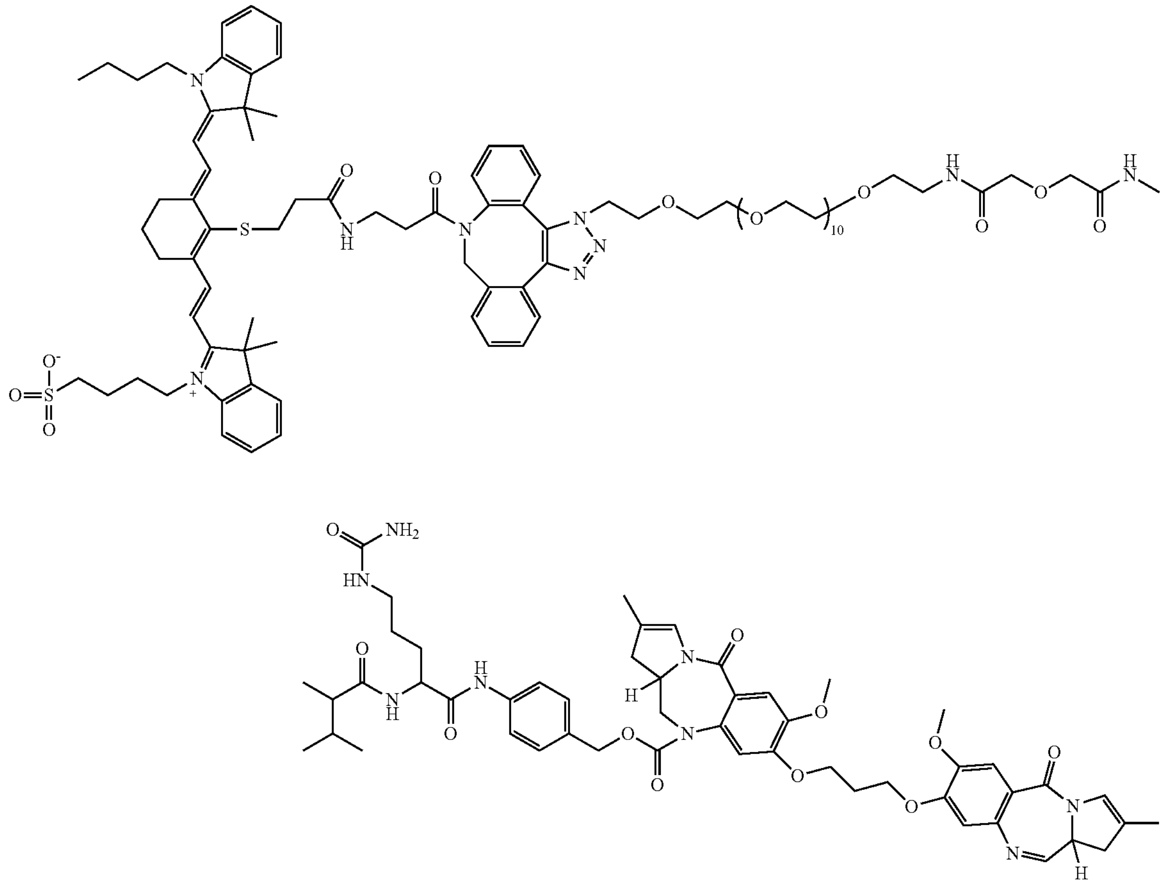
XLV
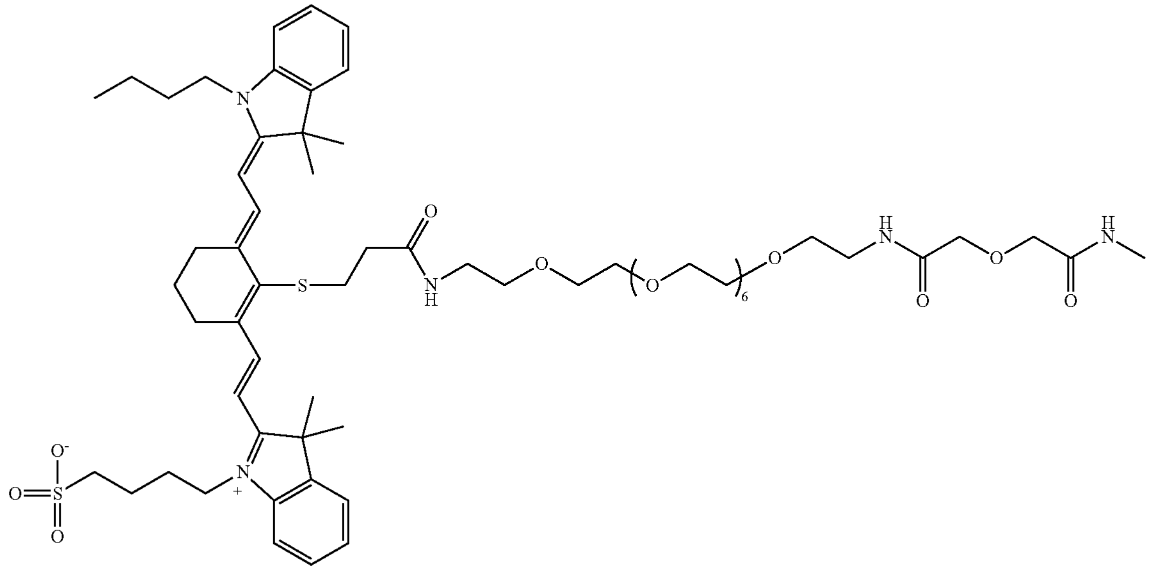

-continued
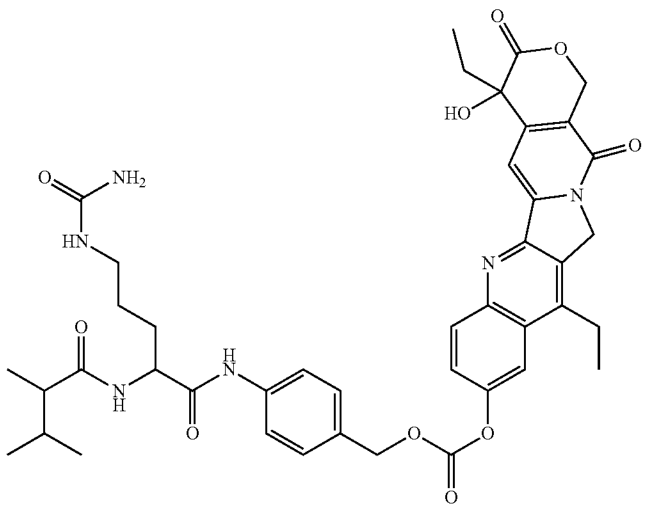
XLVI
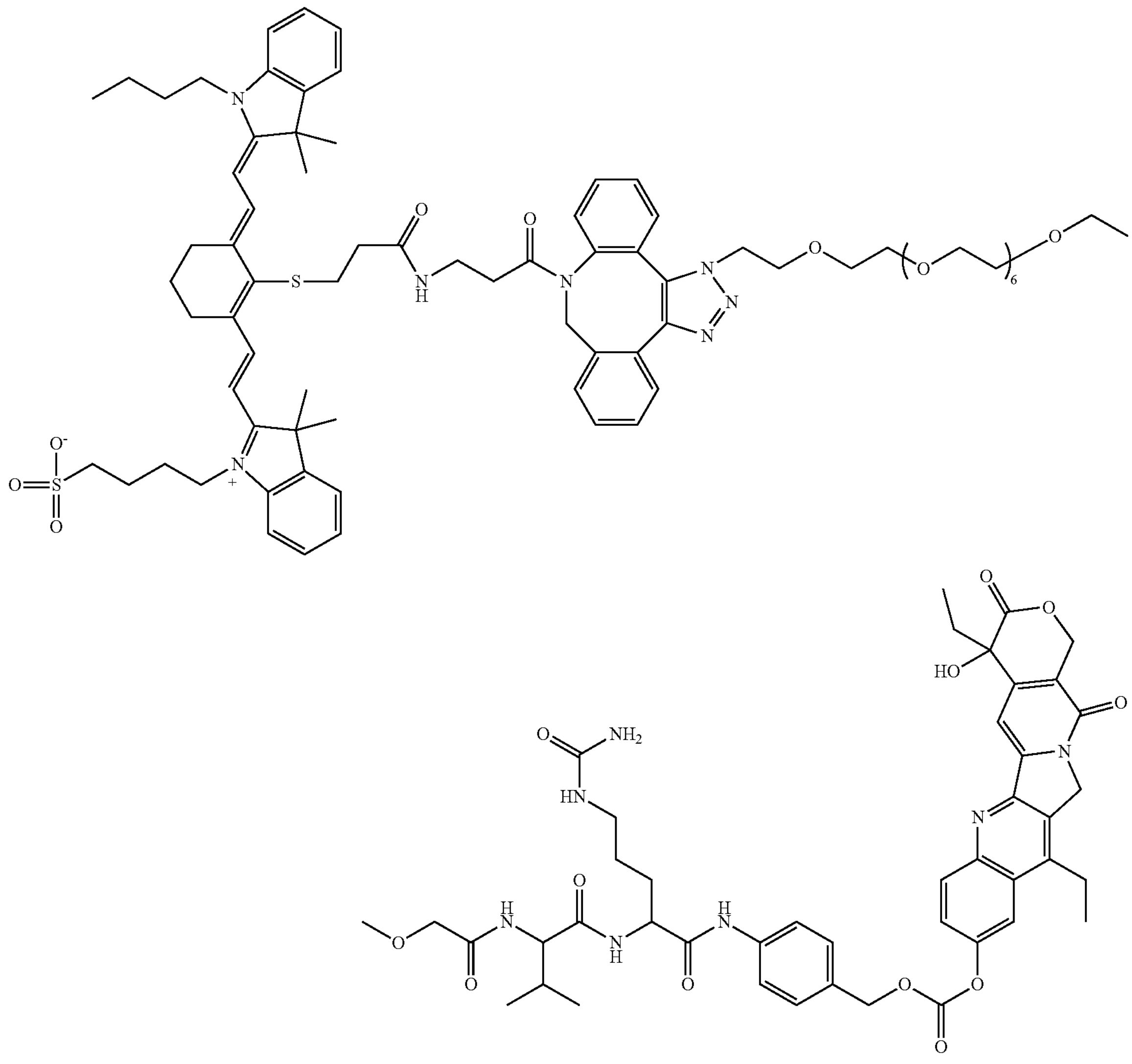

-continued
XLVII
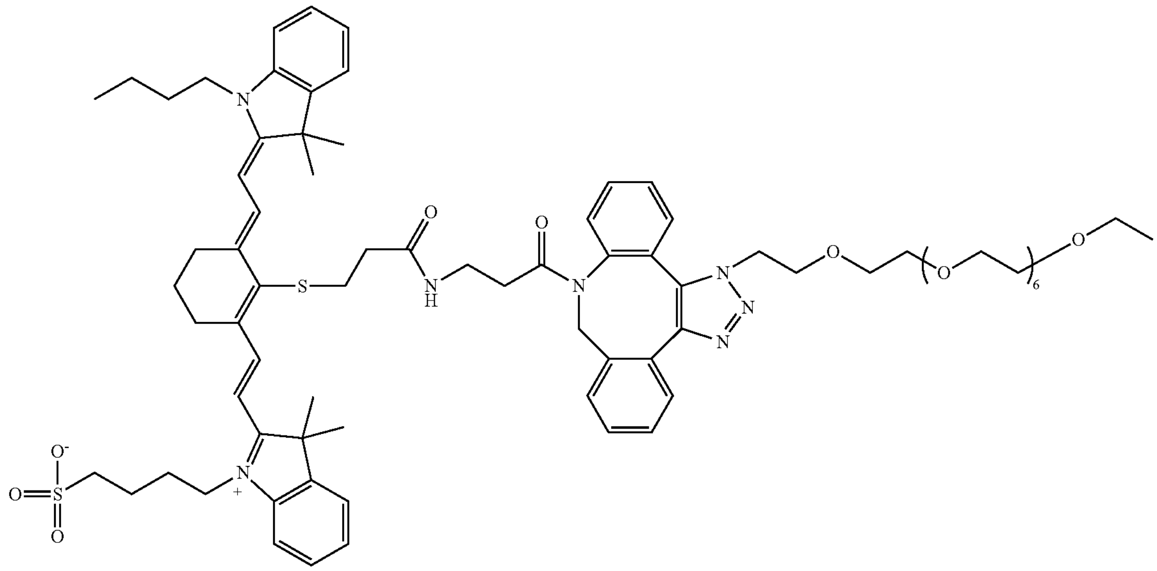
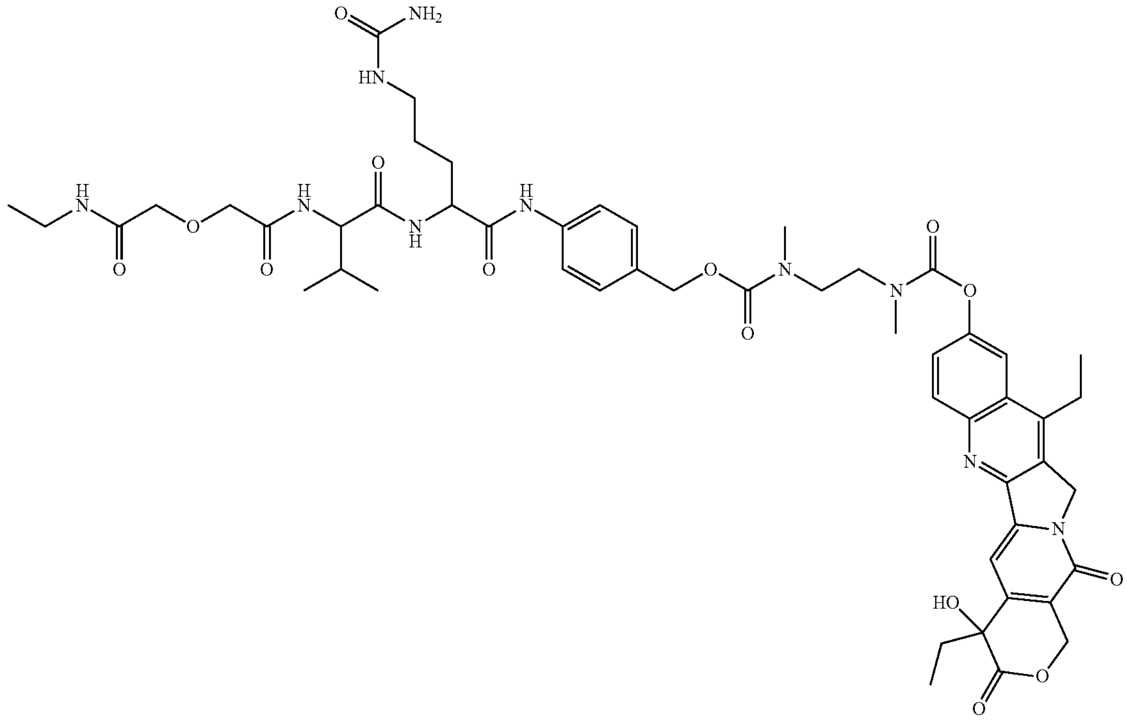

-continued
XLVIII
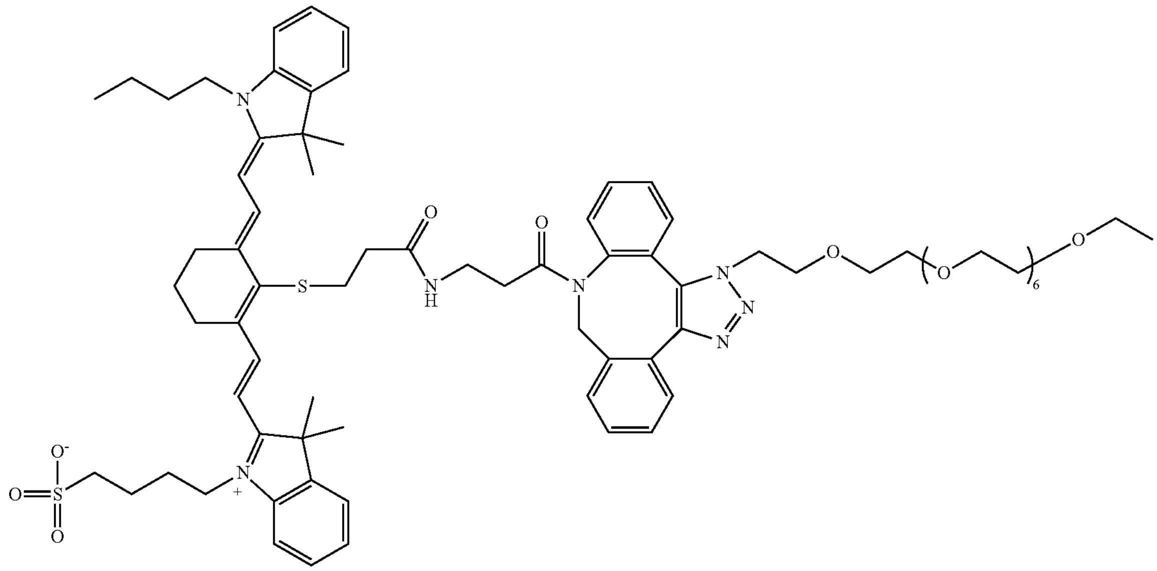
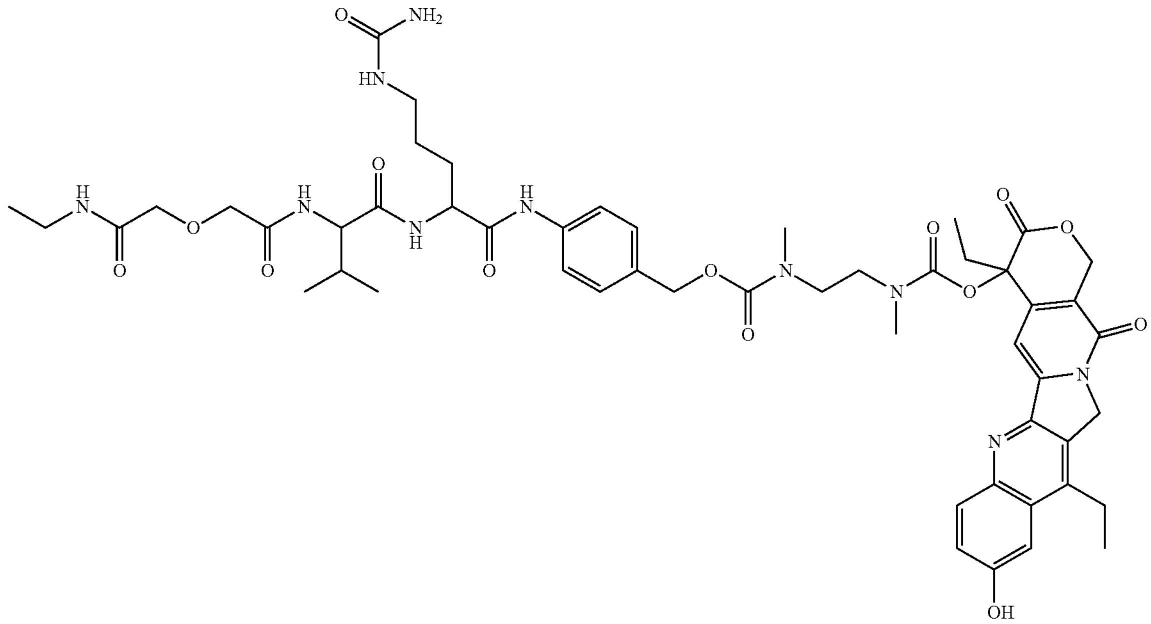

-continued
XLIX
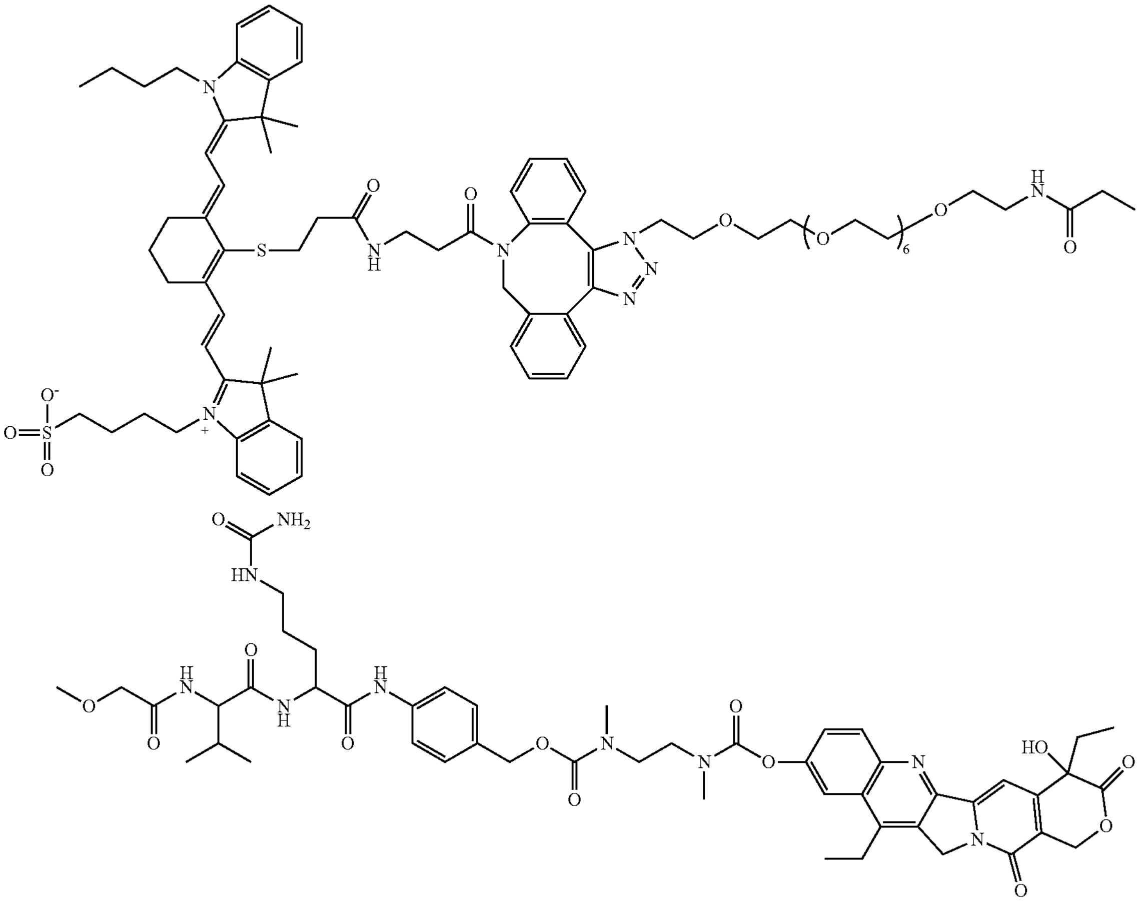
L
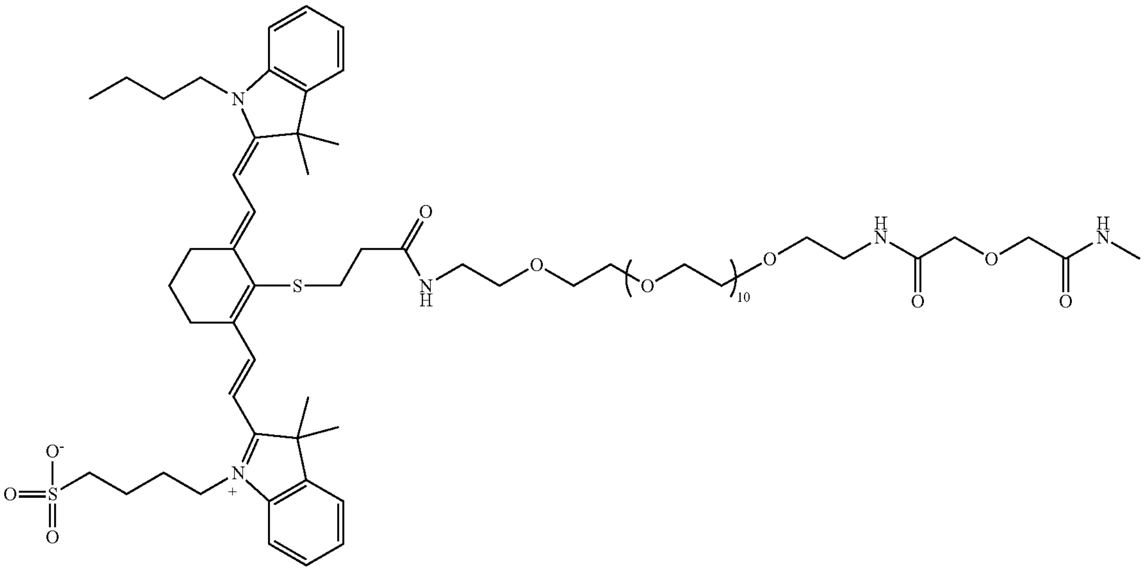

-continued
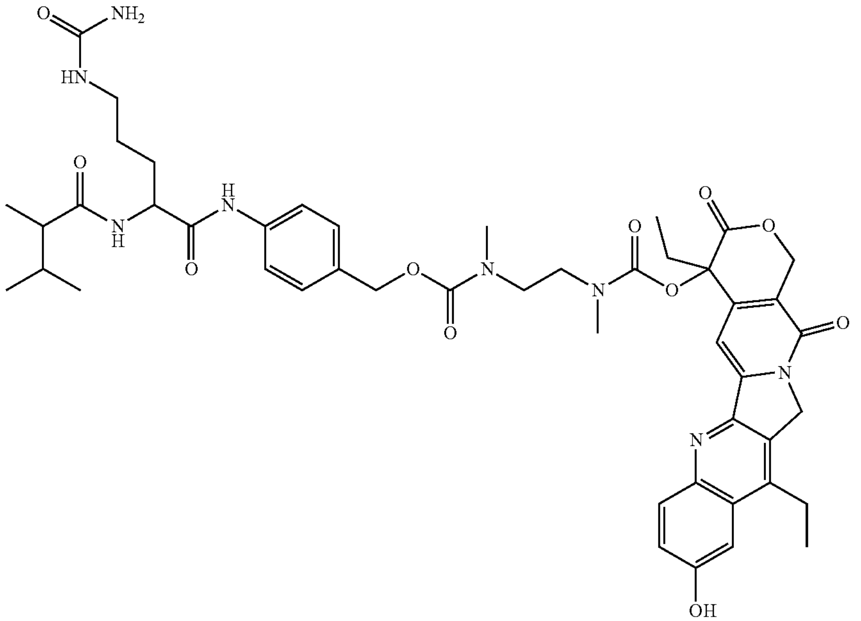
LI
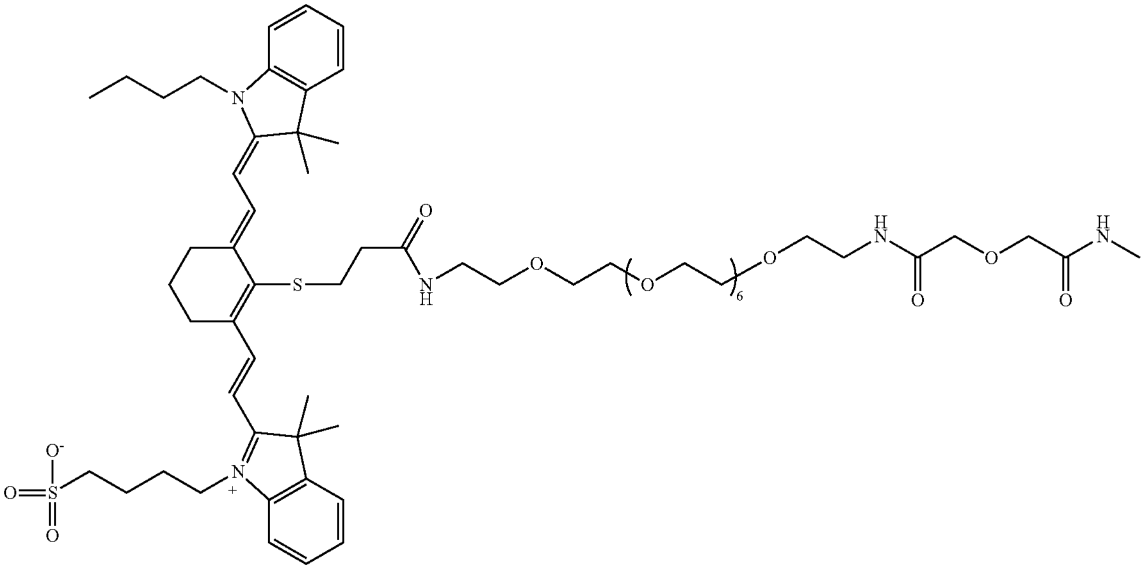
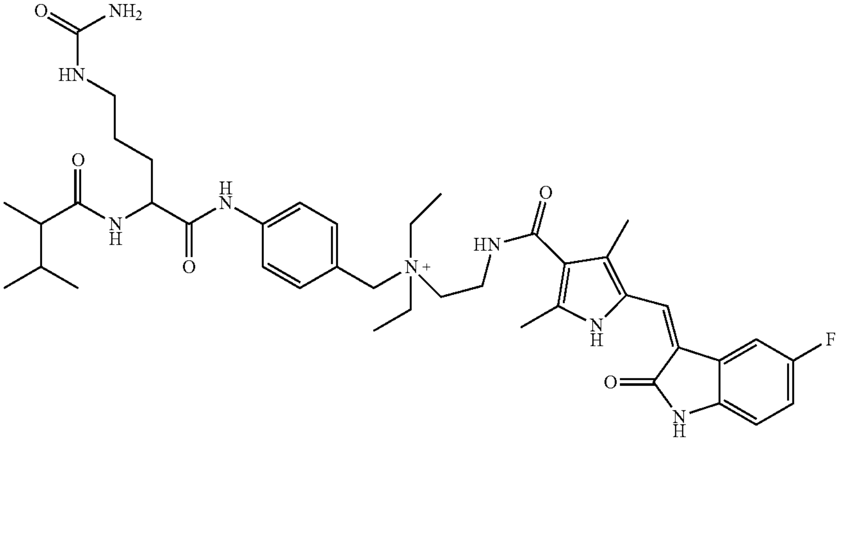

-continued
LII
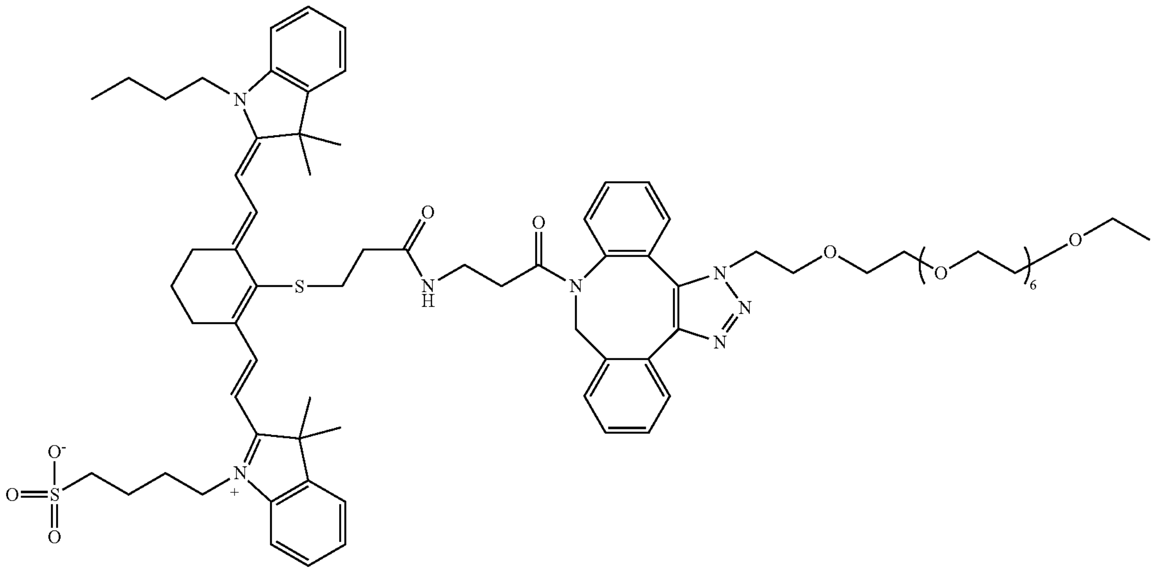
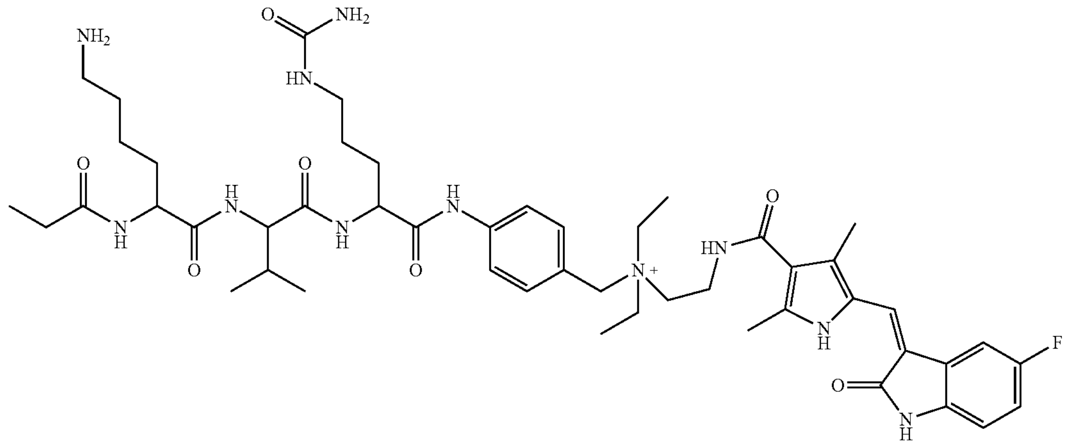
LIII
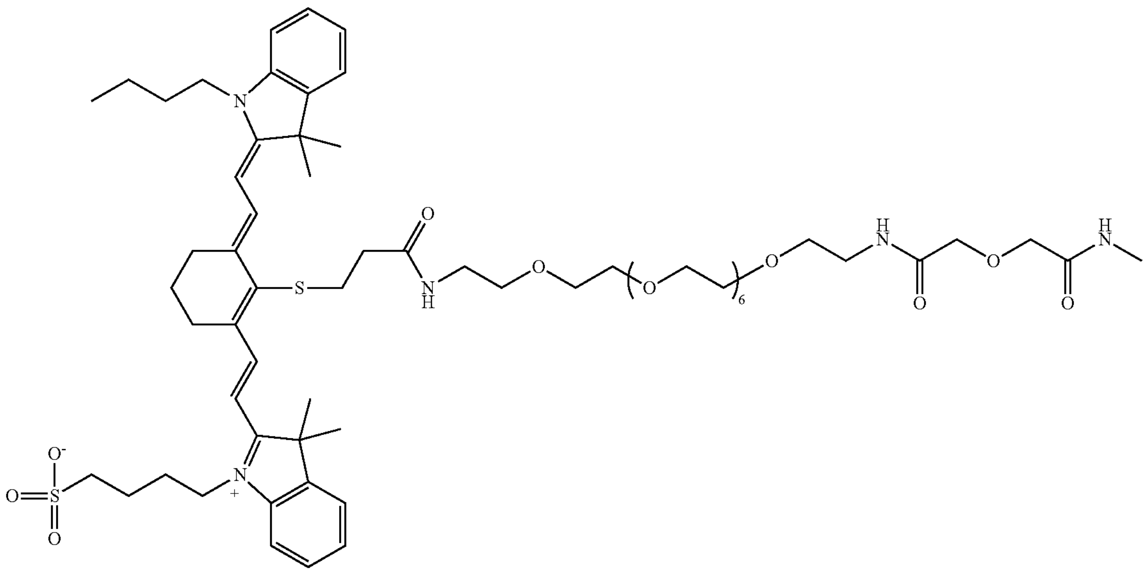

-continued
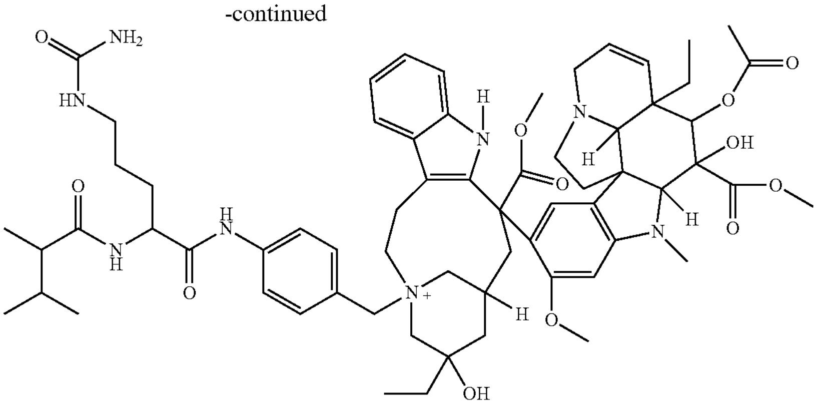
Exemplary conjugates comprising a tumor-targeting NIR dye and specifically, the dye shown in Formula VII, coupled to a chemotherapeutic agent via a linker including a cleavable peptide portion which may be useful with the present invention are shown in Formulas LIV through LXIX.

LIV
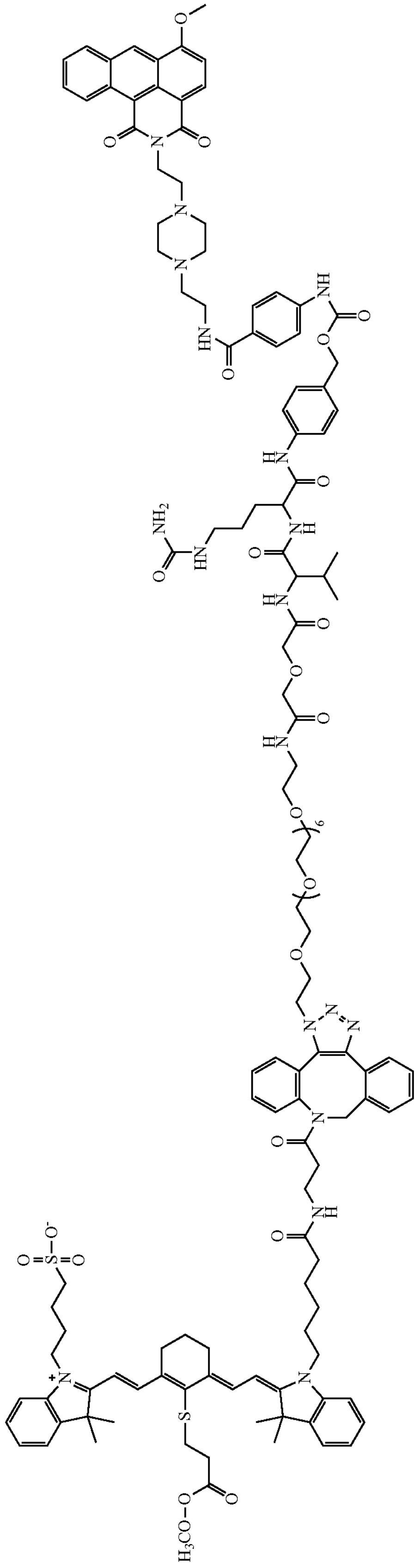
LV
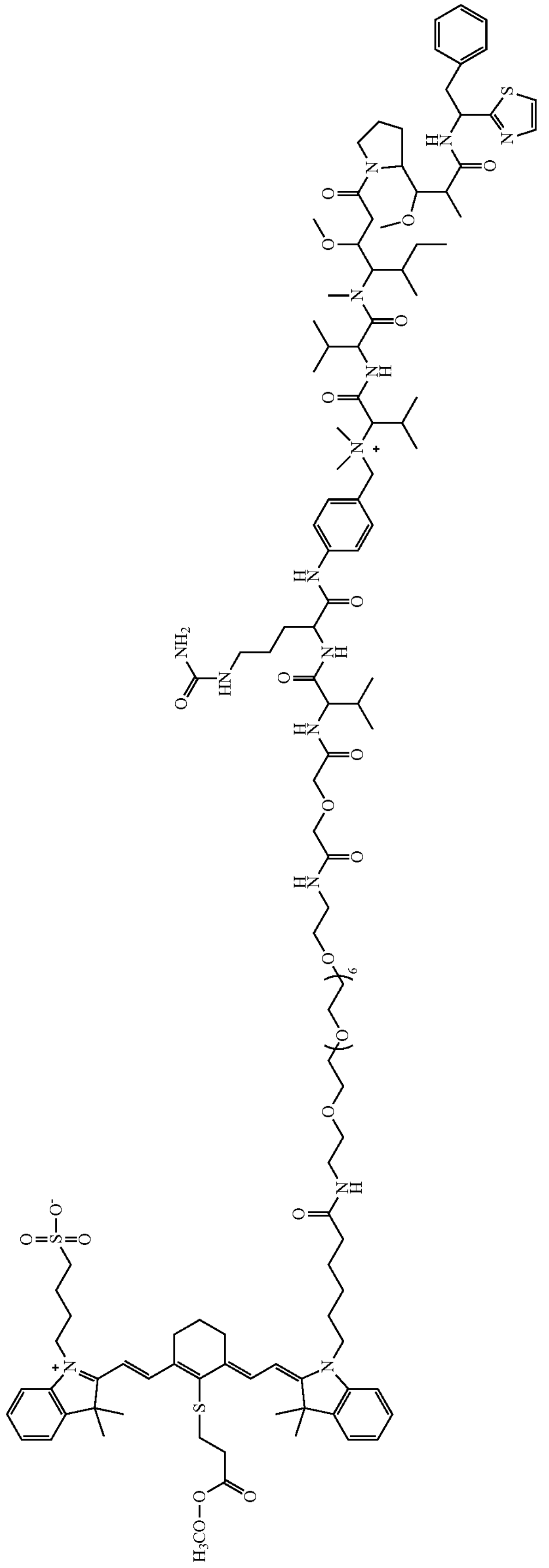

-continued
LVI
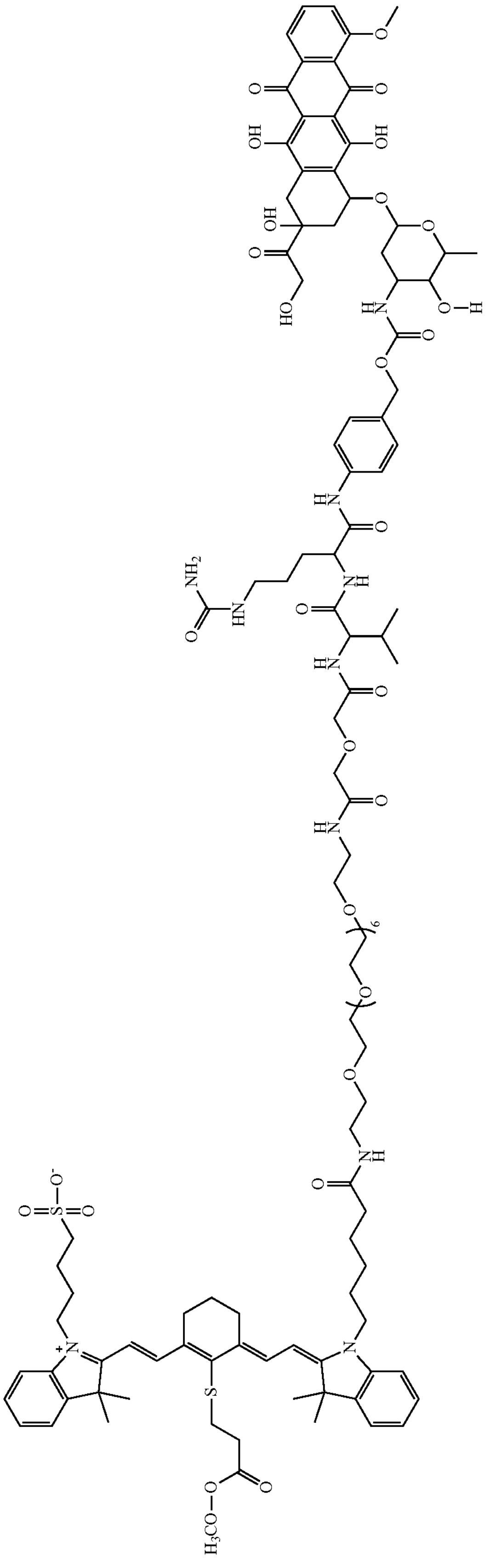
LVII
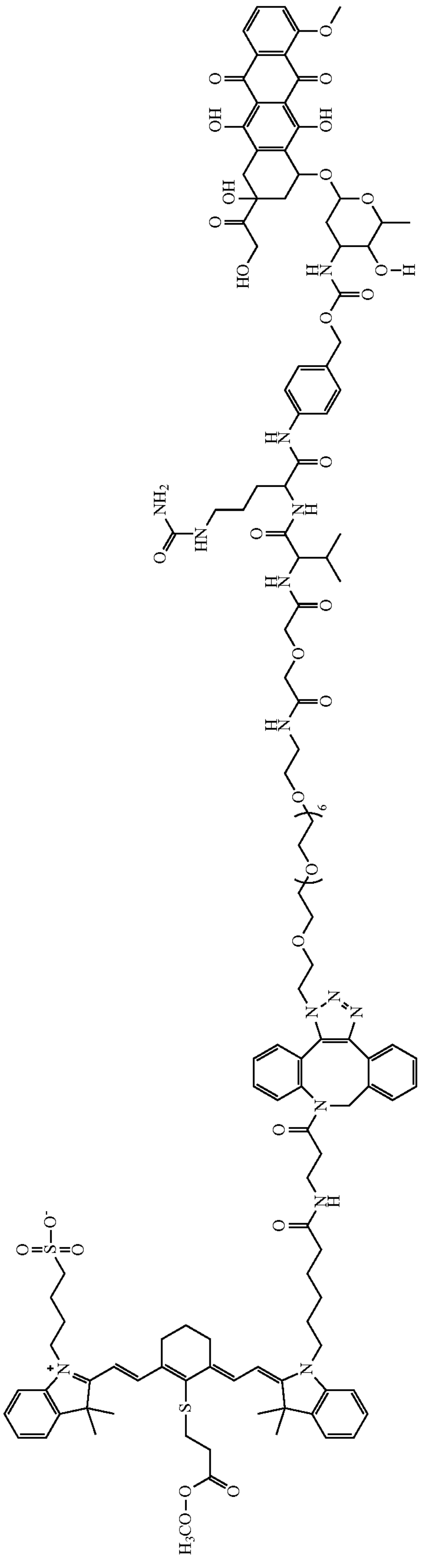

-continued
LVIII
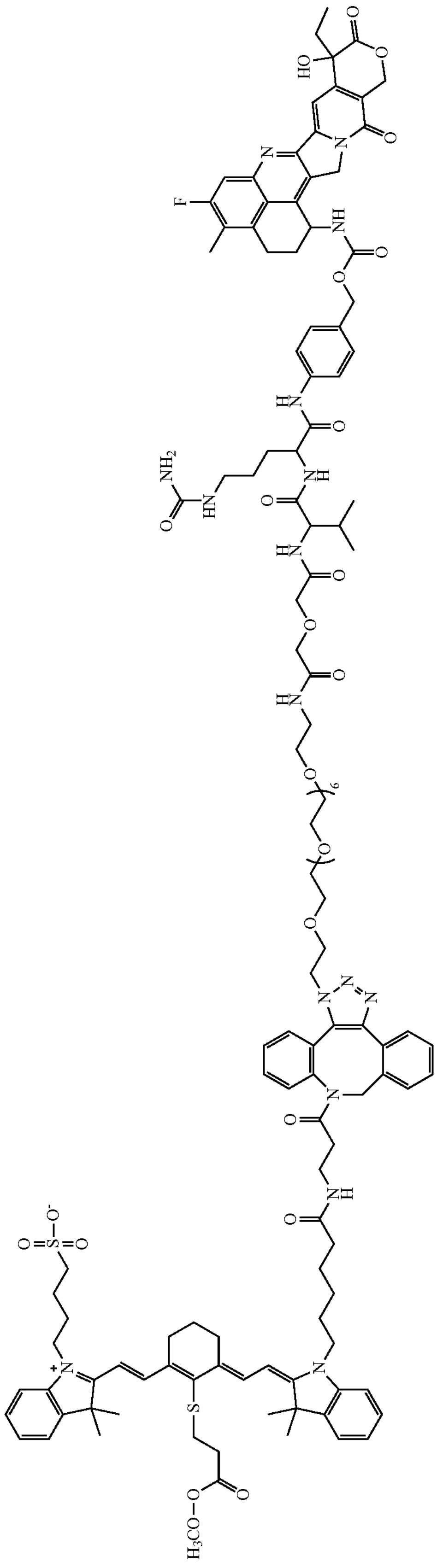
LIX
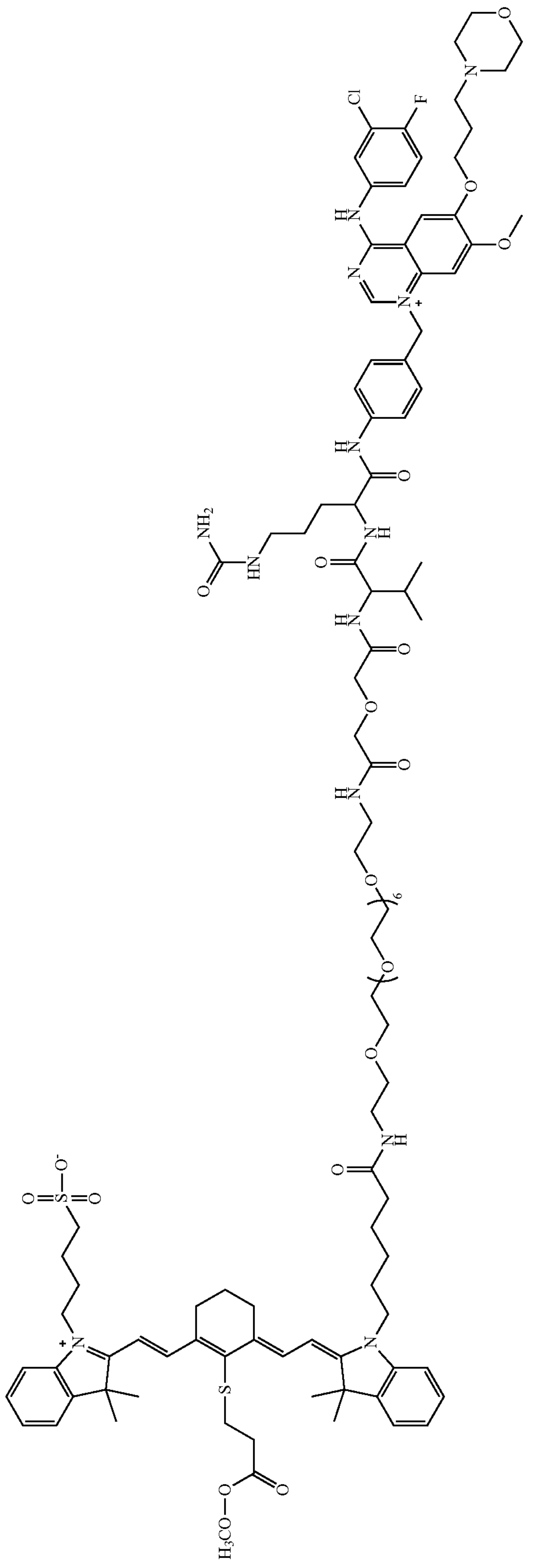

-continued
LX
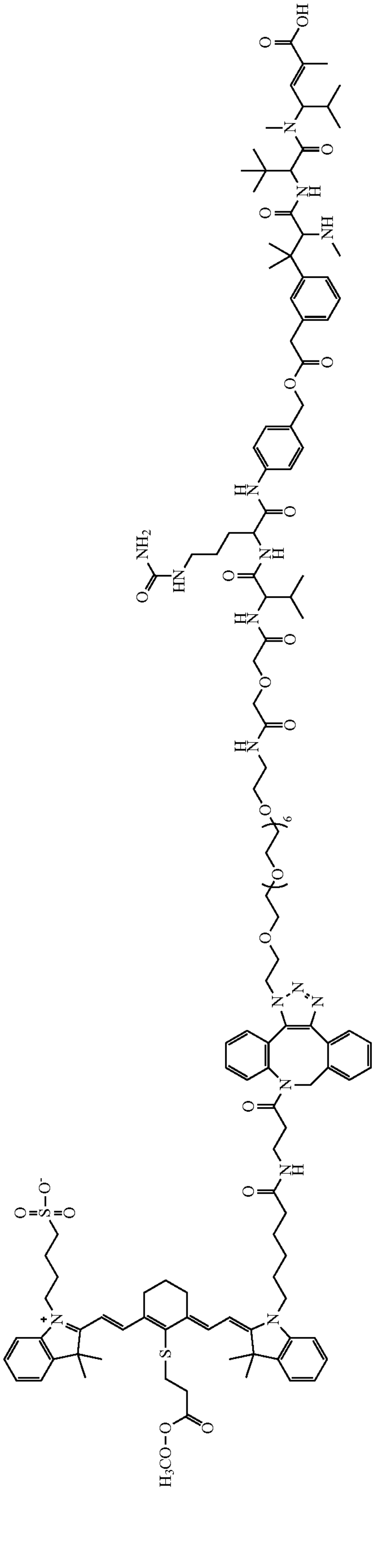
LXI
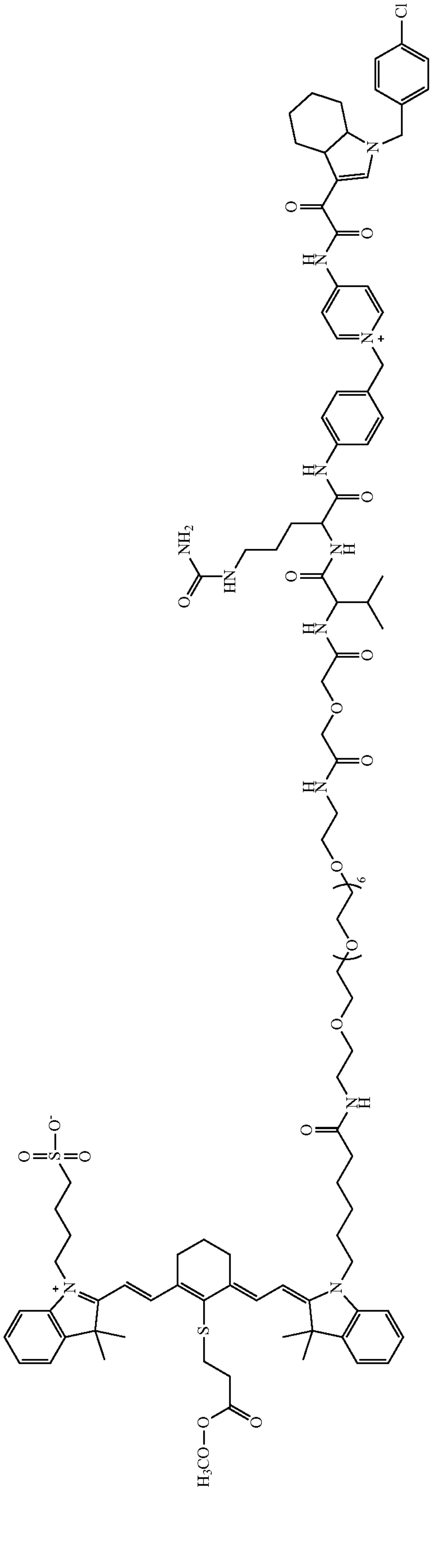

-continued
LXII
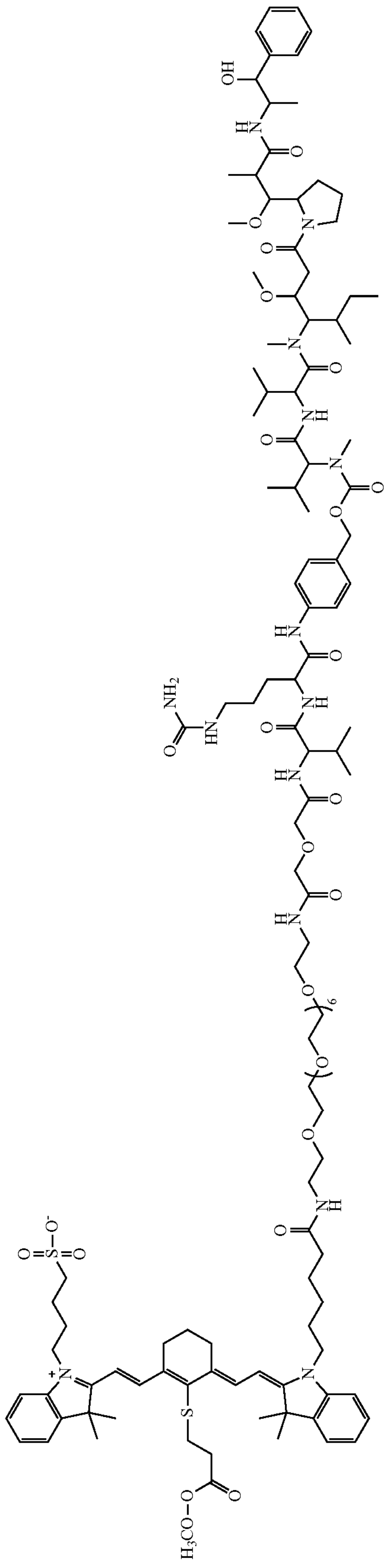

-continued
LXIII
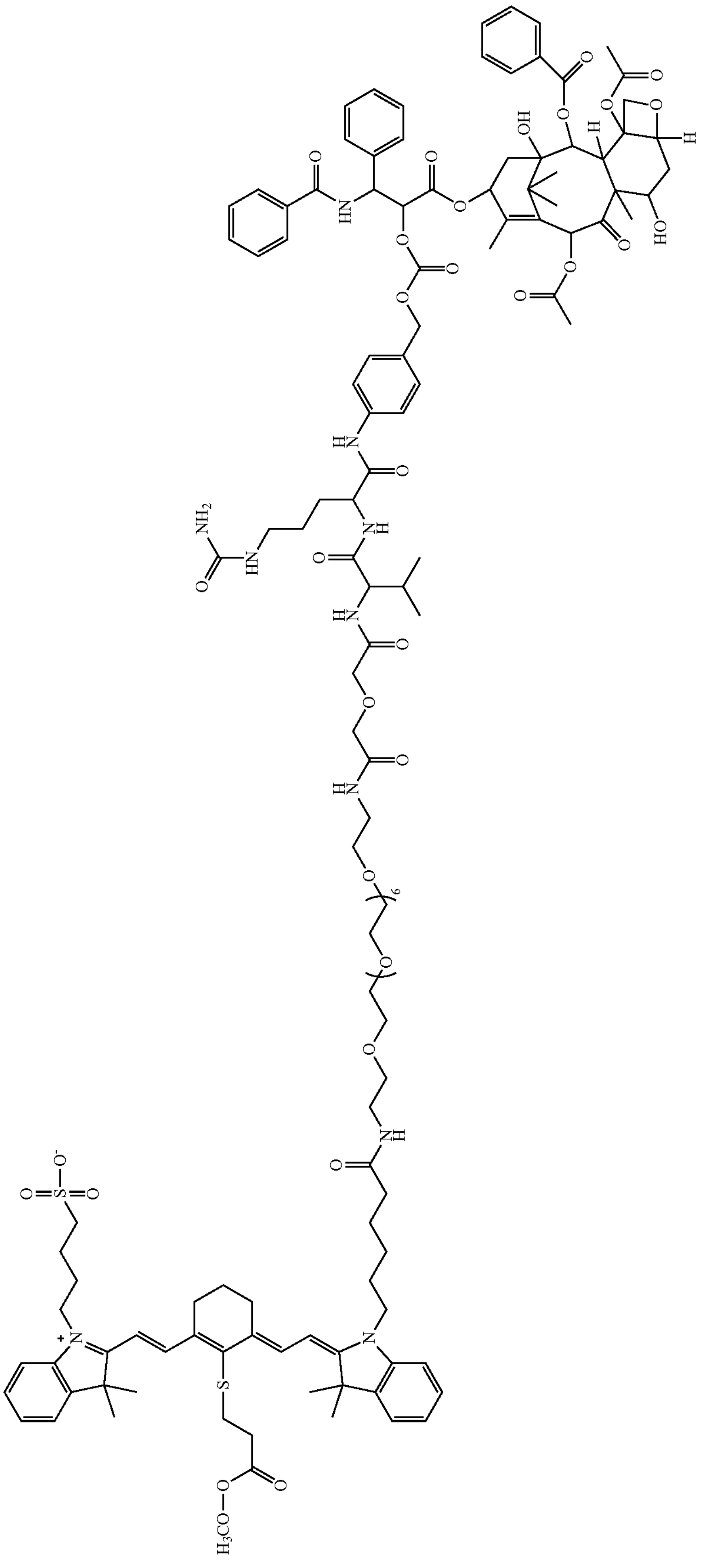

-continued
LXIV
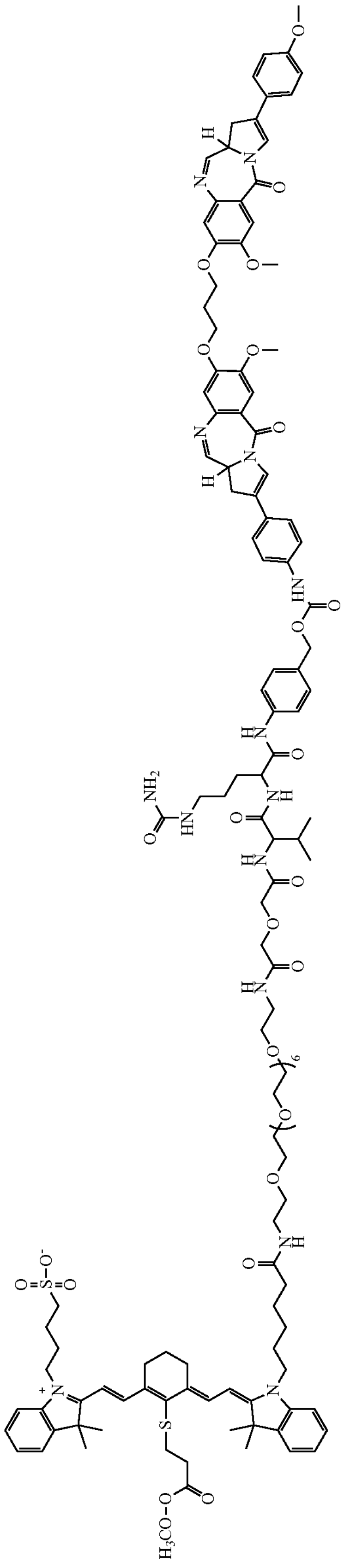
LXV
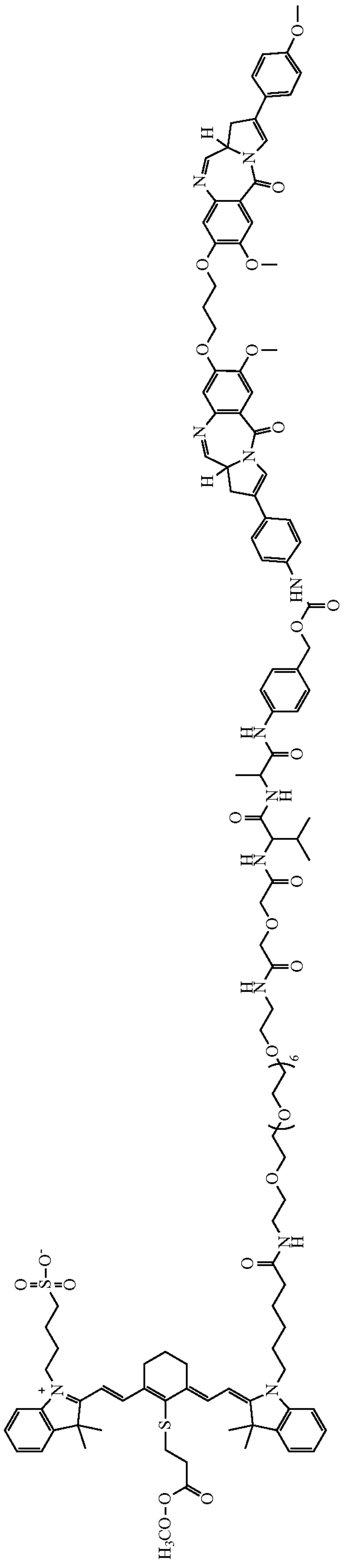

-continued
LXVI
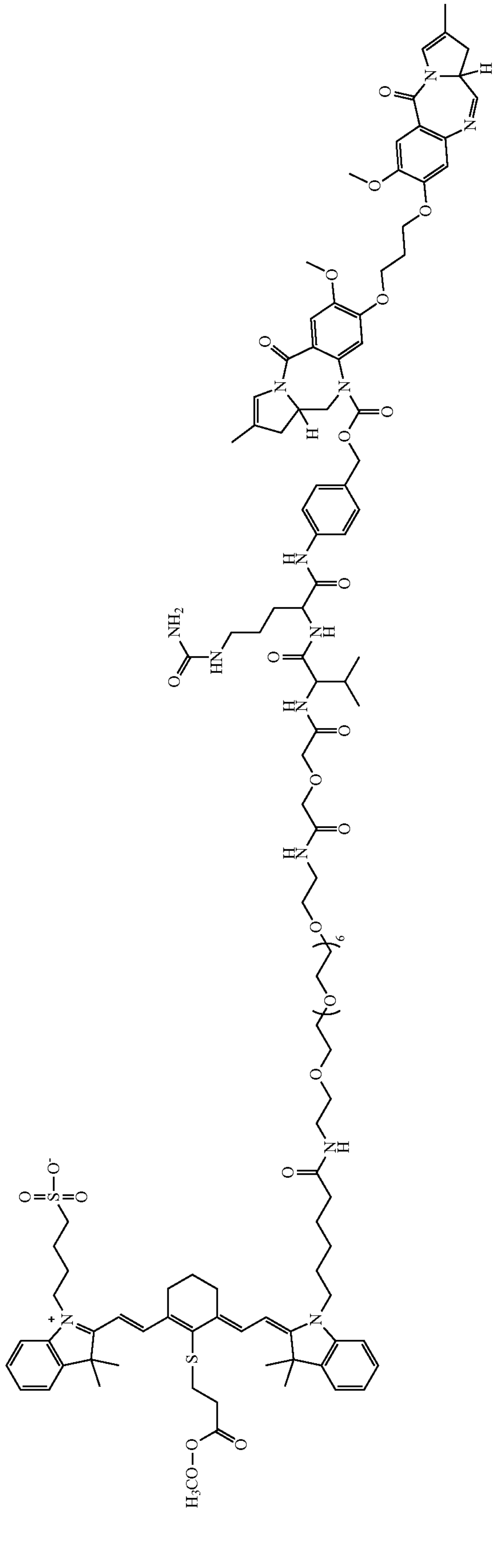
LXVII
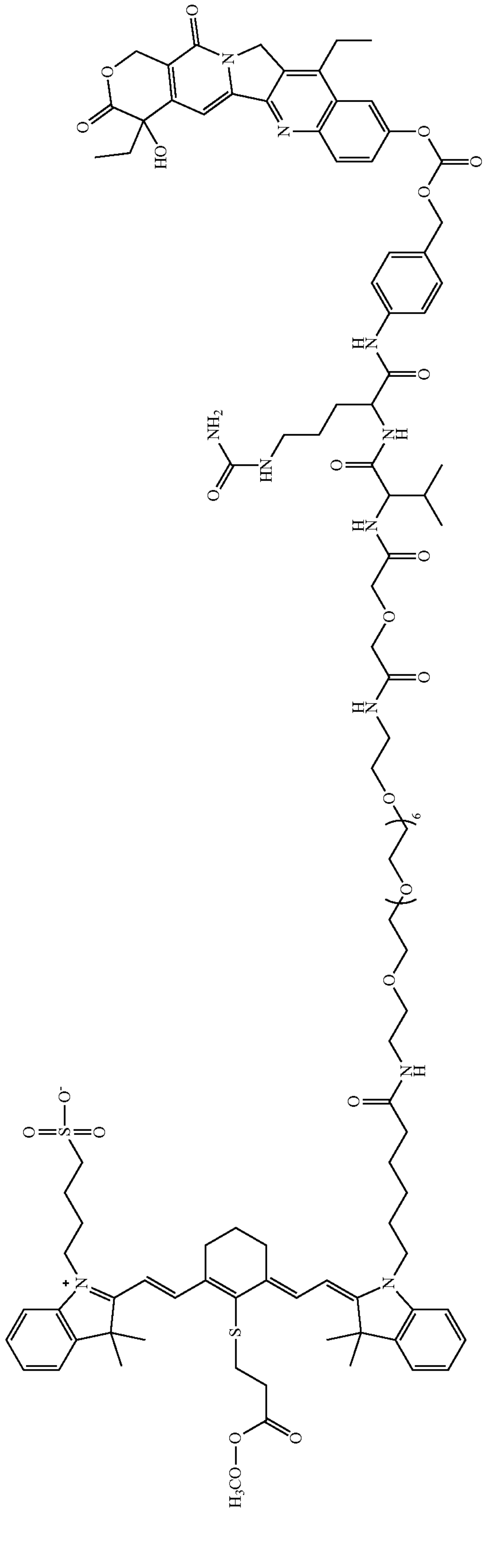

-continued
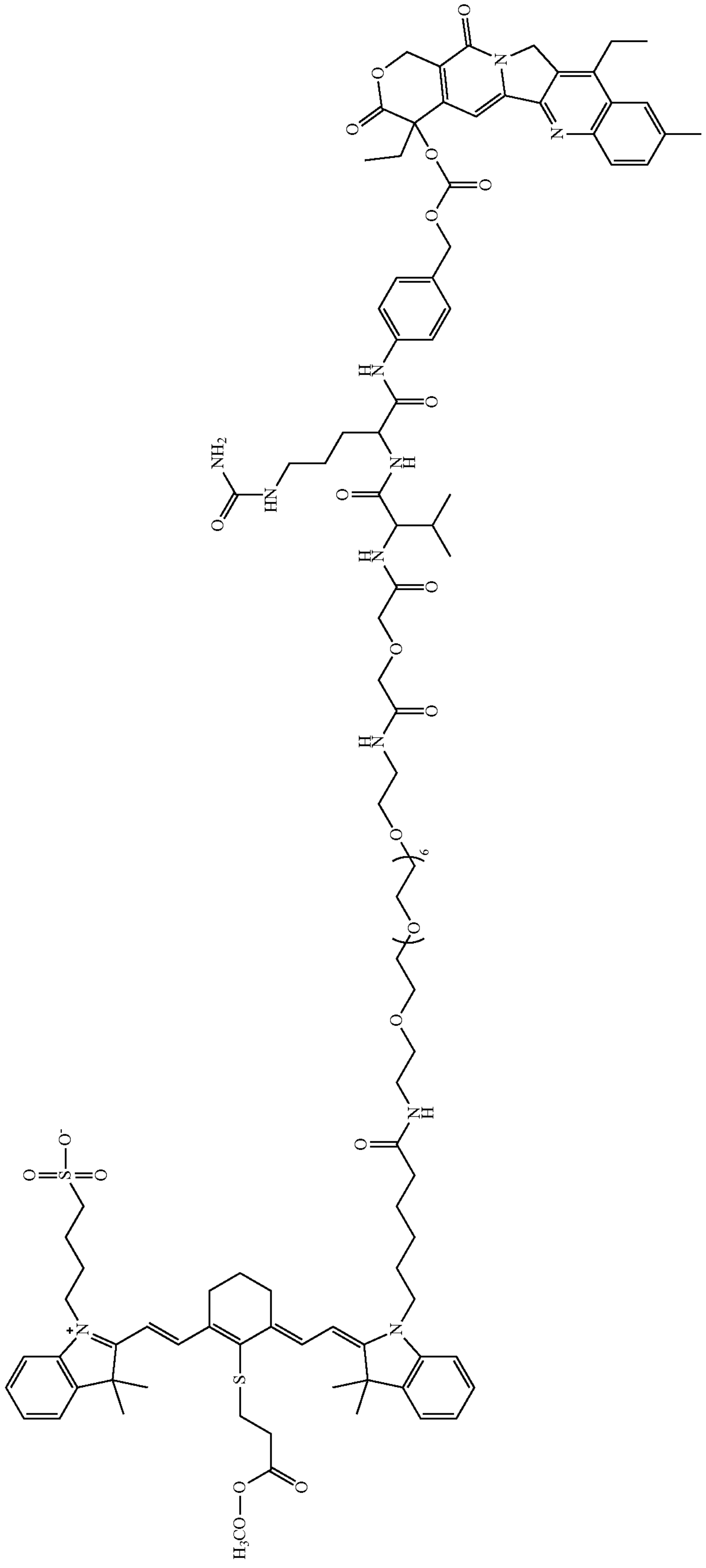
LXVIII

-continued
LXIX
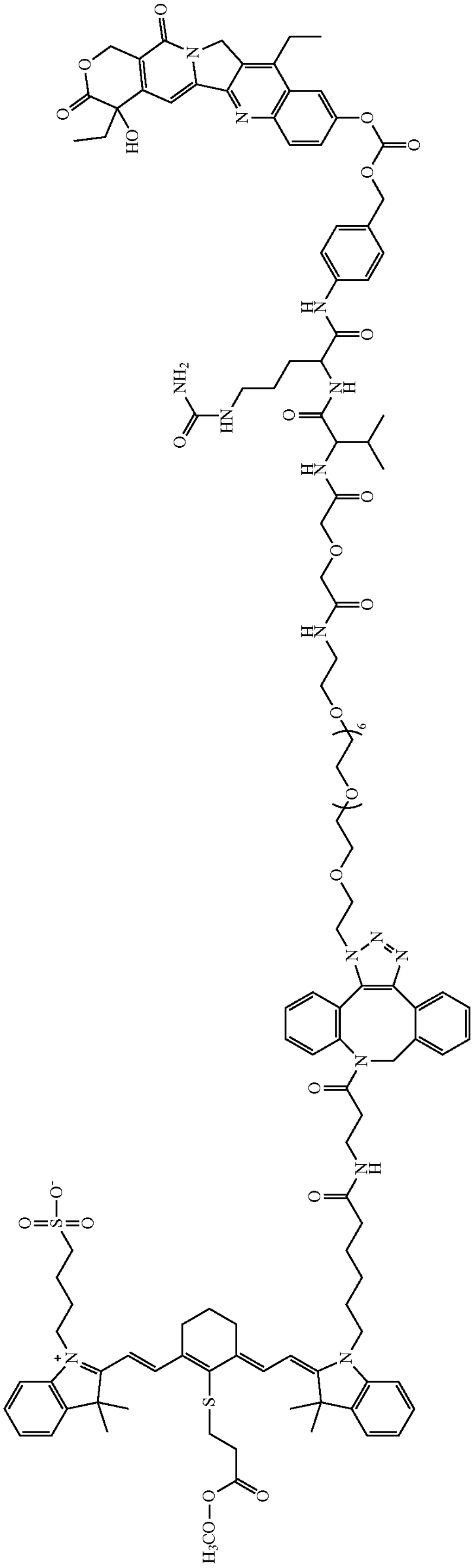

Exemplary conjugates comprising a tumor-targeting NIR dye and specifically, the dye shown in Formula VIII, coupled to a chemotherapeutic agent via a linker including a cleavable peptide portion which may be useful with the present invention are shown in Formulas LXX through LXXIV.
LXX
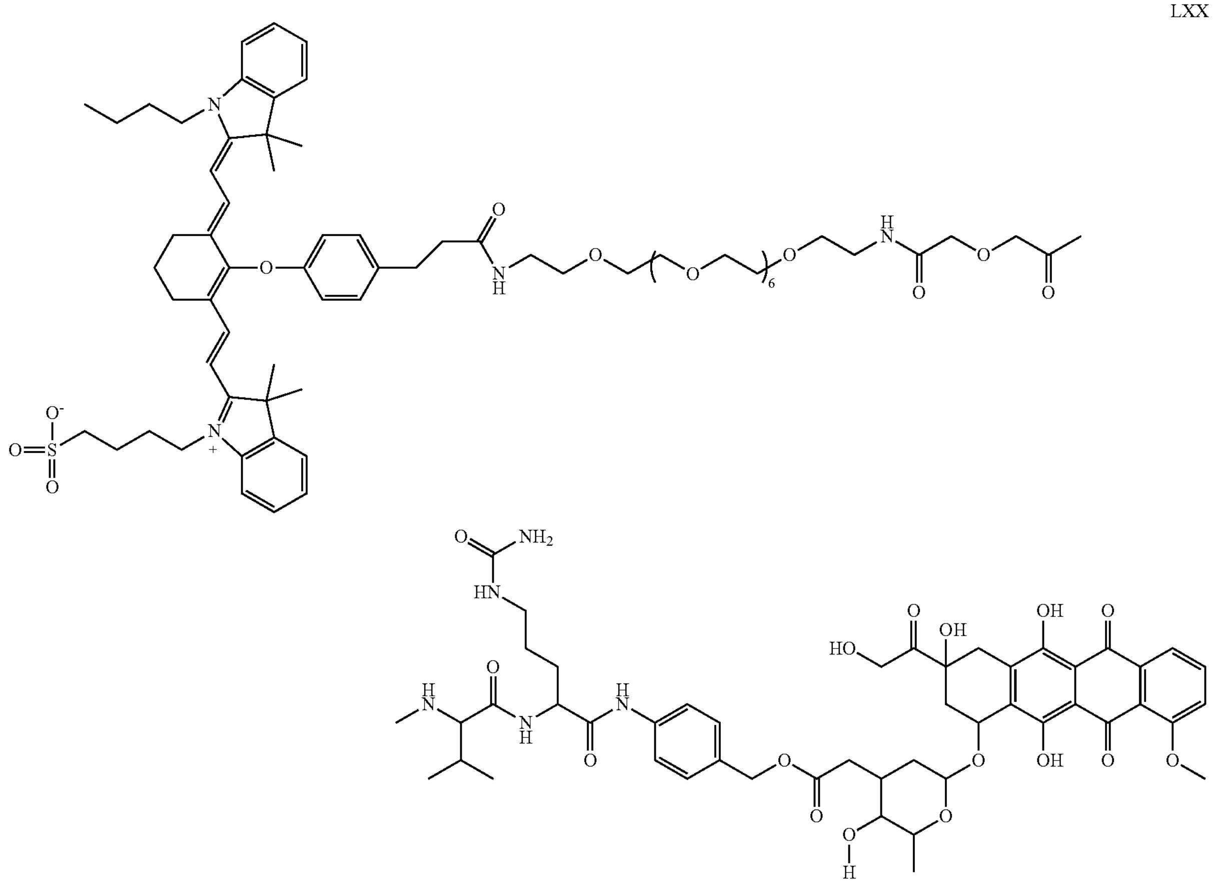
LXXI
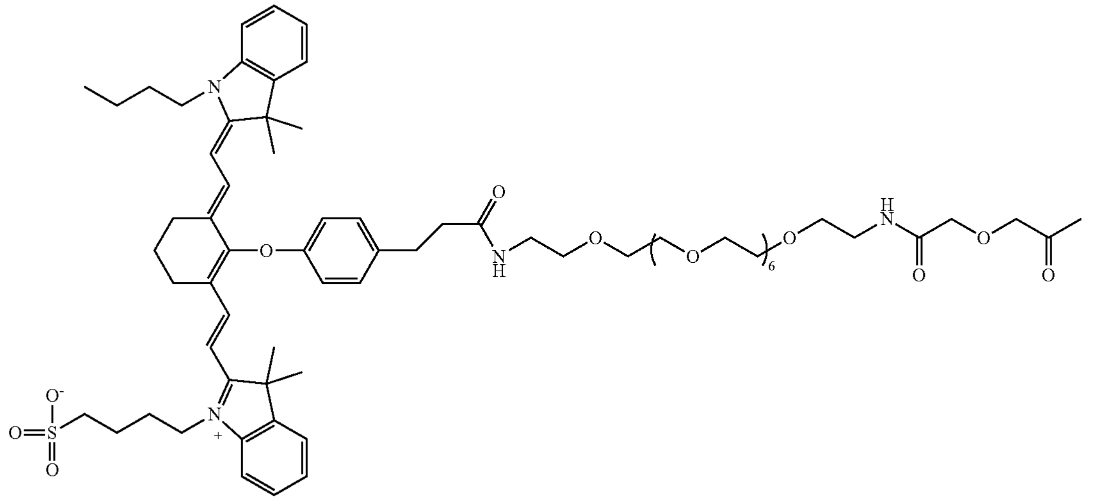

-continued
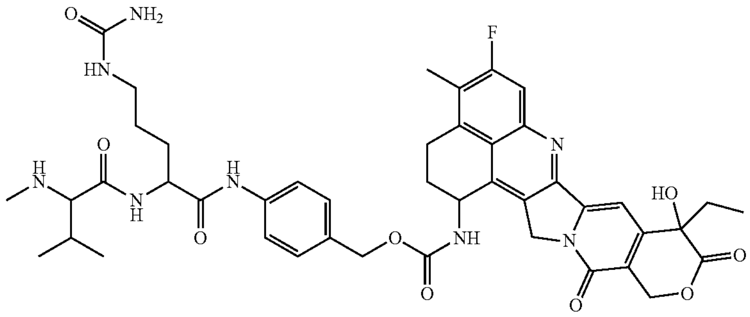
LXXII
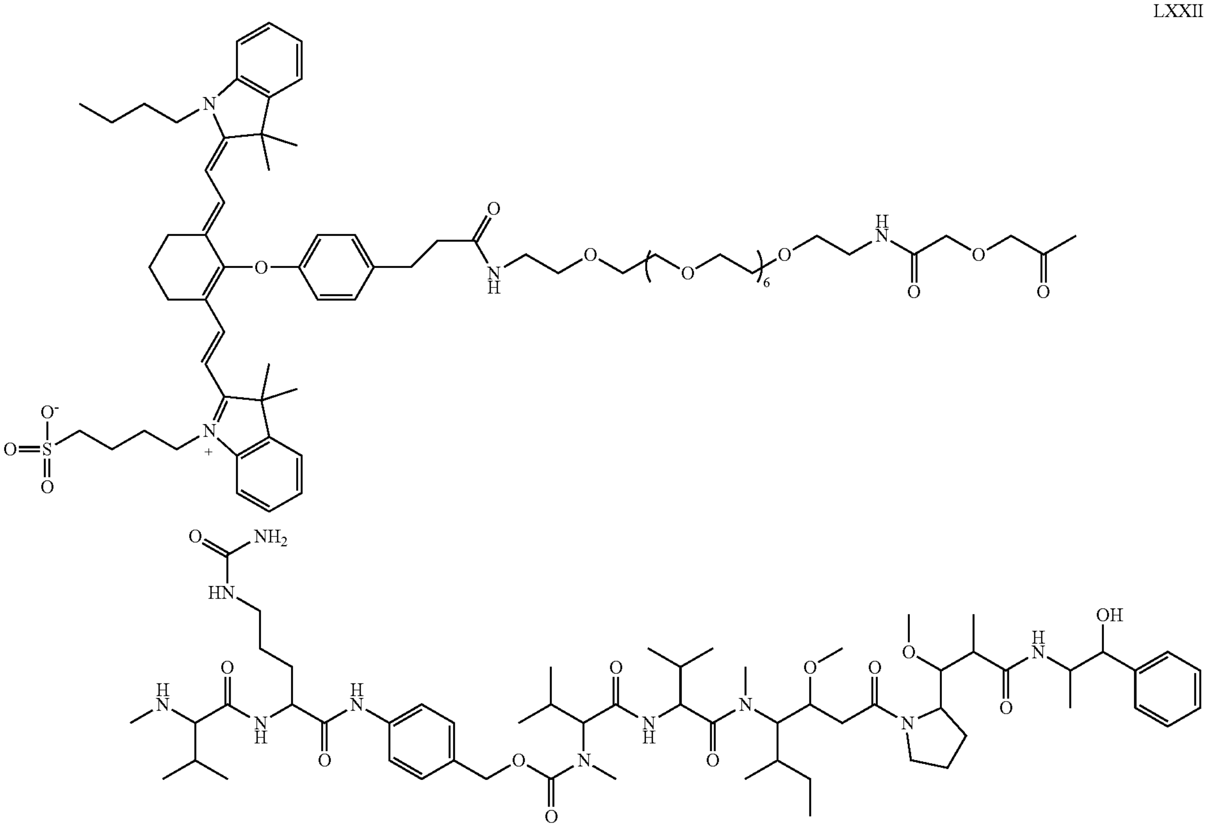
LXXIII
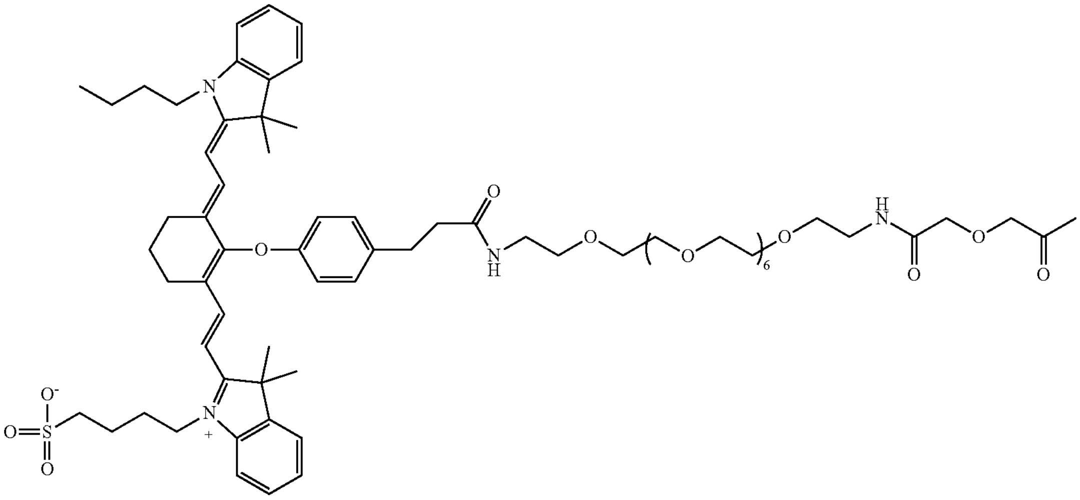

-continued
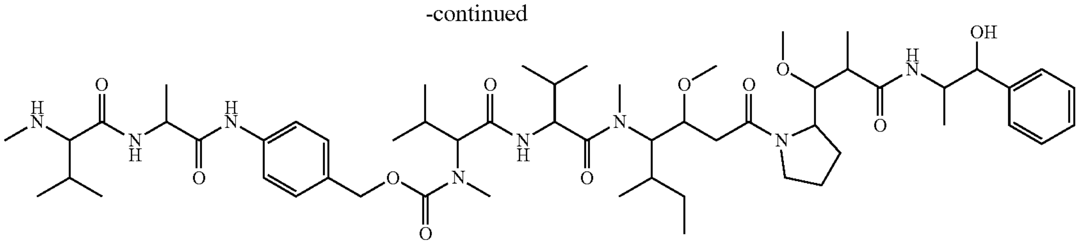
LXXIV
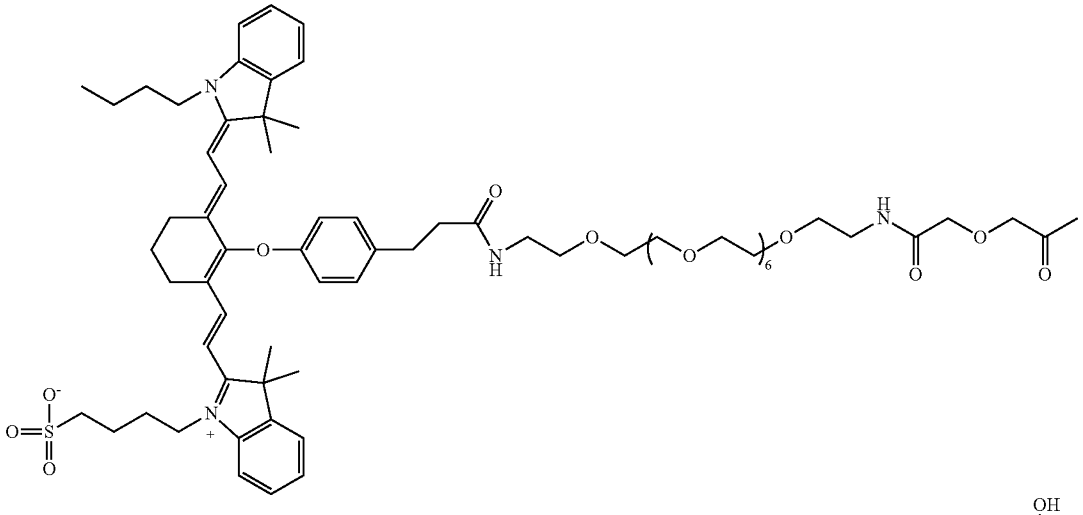
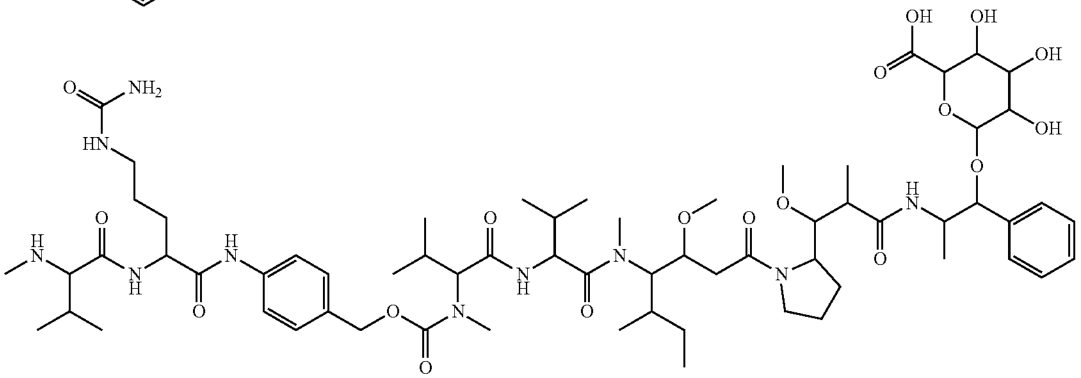
Exemplary conjugates comprising a tumor-targeting NIR dye and specifically, the dye shown in Formula IX, coupled to a chemotherapeutic agent via a linker including a cleavable peptide portion which may be useful with the present invention are shown in Formulas LXXV through LXXVII.
LXXV
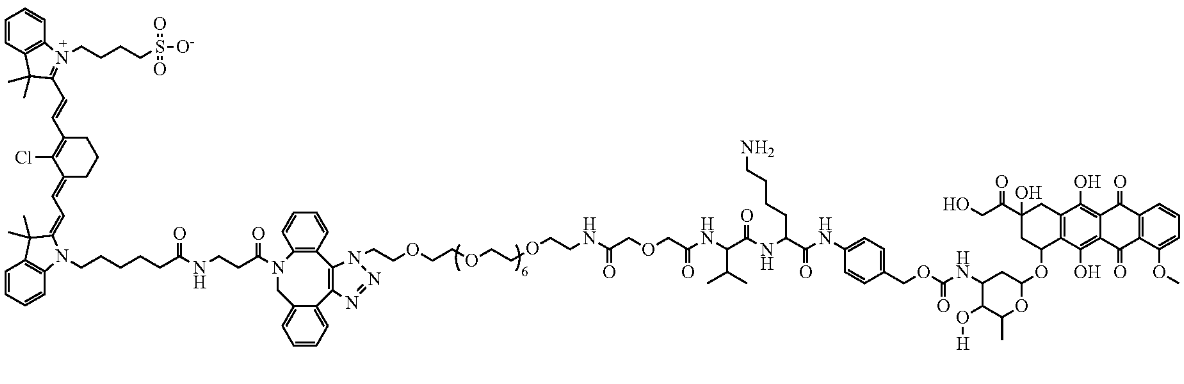

-continued
LXXVI
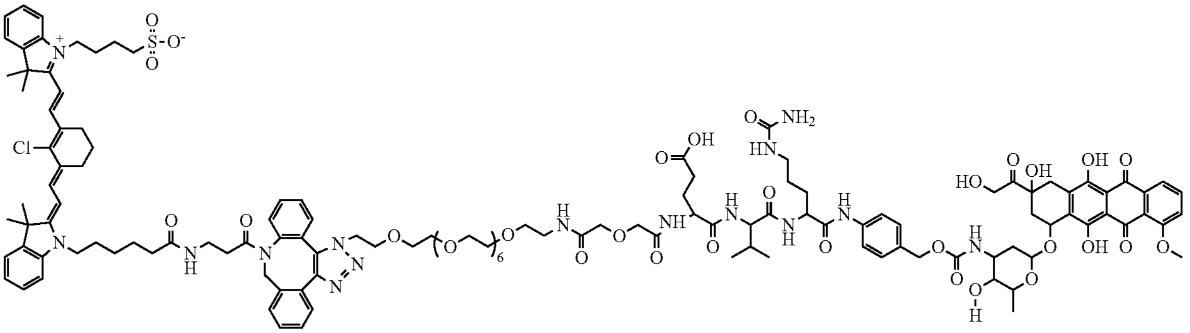
LXXVII
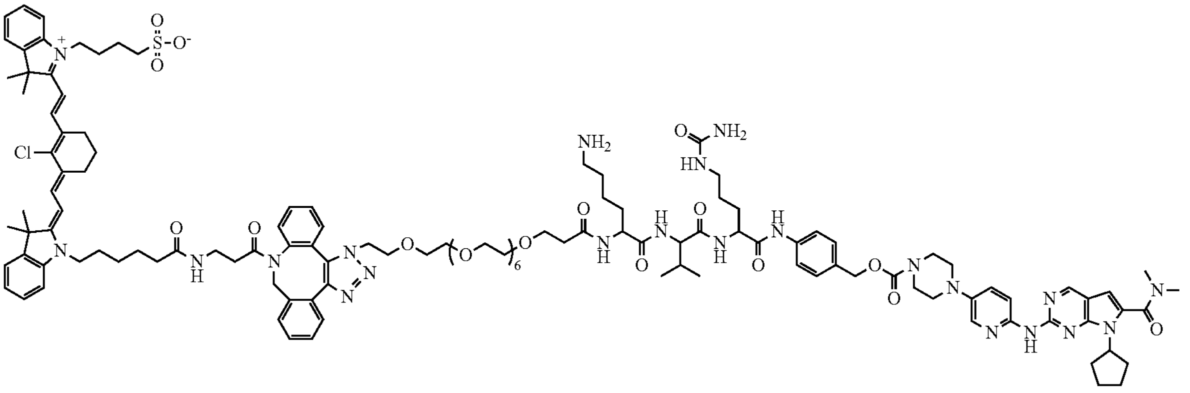
An exemplary conjugate comprising a tumor-targeting NIR dye and specifically, the dye shown in Formula XV, coupled to a chemotherapeutic agent via a linker including a cleavable peptide portion which may be useful with the present invention is shown in Formula LXXVIII.

LXXVIII
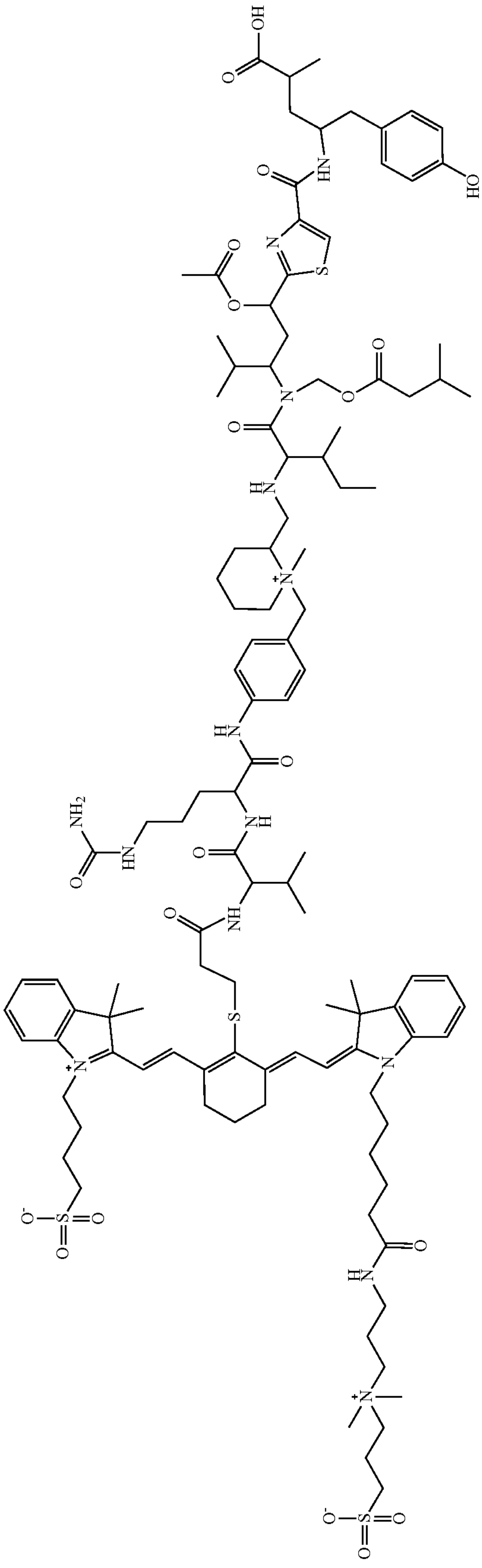

As to particular embodiments, the linker can comprise a self-immolative (or self-eliminating or self-degrading) portion which may be useful to conjugate a tumor-targeting NIR dye and a chemotherapeutic agent as per the present invention.

Now referring primarily to FIGS. 7B, 7C, 7D, and 7F, as to particular embodiments, a first self-immolative portion can be used with the present conjugate to link a dye and a chemotherapeutic agent. As to particular embodiments, a first self-immolative portion can be useful to link a cleavable peptide portion and a chemotherapeutic agent, whereby the first self-immolative portion may function to space the cleavable peptide portion and the chemotherapeutic agent to relieve steric hinderance and thus allow a protease to access the protease-sensitive cleavable peptide portion for cleavage thereof. Following cleavage of the cleavable peptide portion, a specific stimulus (such as an enzyme, pH change, etc.) can trigger the first self-immolative portion to release the chemotherapeutic agent and correspondingly deliver the conjugate's payload proximate a target tumor cell population.

Figure 12A:
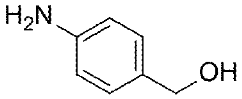
FIG. 12A shows an illustrative example of a first self-immolative portion of a linker which may be useful with the present invention.
Figure 12B:
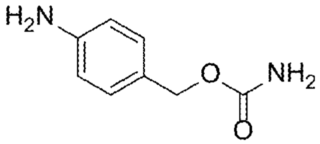
FIG. 12B shows an illustrative example of a first self-immolative portion of a linker which may be useful with the present invention.

As to particular embodiments, illustrative examples of first self-immolative portions which may be useful with the present invention include para-aminobenzyl alcohol (PABA) and para-aminobenzyl carbamate (PABC), as shown in FIGS. 12A and 12B, respectively. Following cleavage of the cleavable peptide portion and exposure to an acidic environment, both PABA and PABC can undergo a 1,6-elimination reaction to release the chemotherapeutic agent.

Figure 7A:
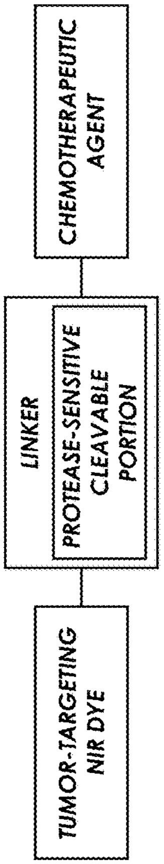
FIG. 7A shows an embodiment of the inventive conjugate.
Figure 7B:
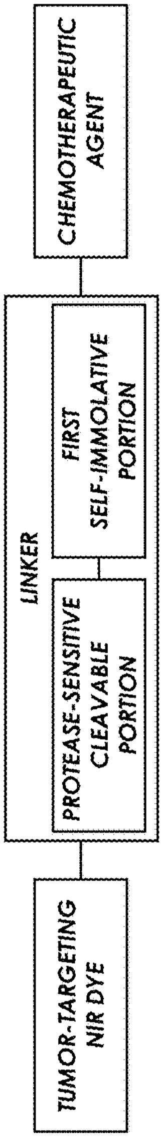
FIG. 7B shows an embodiment of the inventive conjugate.
Figure 7C:
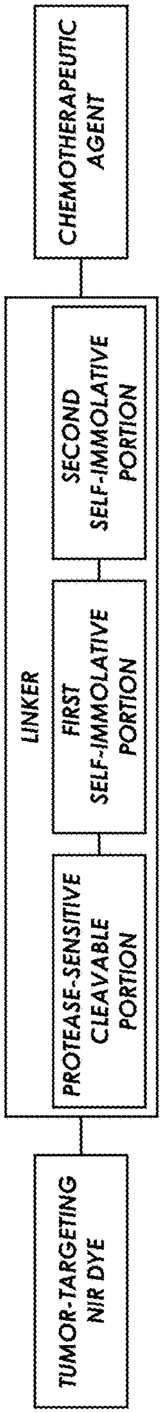
FIG. 7C shows an embodiment of the inventive conjugate.
Figure 7D:
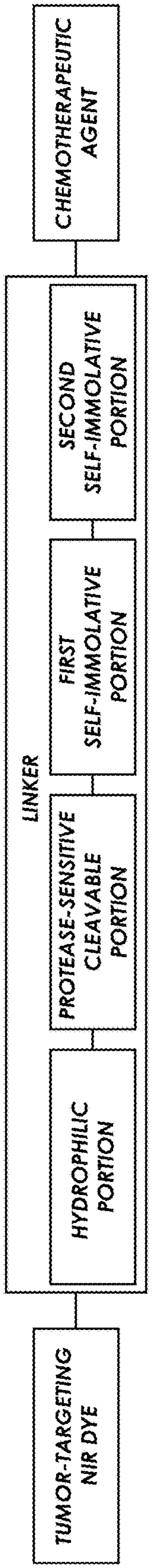
FIG. 7D shows an embodiment of the inventive conjugate.

Now referring primarily to FIGS. 7C and 7D, as to particular embodiments, a second self-immolative portion can be used with the present conjugate to link a dye and a chemotherapeutic agent. As to particular embodiments, a second self-immolative portion can be useful to link a first self-immolative portion and a chemotherapeutic agent. Following self-elimination of the first self-immolative portion, a specific stimulus (such as an enzyme, pH change, etc.) can trigger the second self-immolative portion to release the chemotherapeutic agent and correspondingly deliver the conjugate's payload proximate a target tumor cell population.

Figure 13:
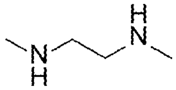
FIG. 13 shows an illustrative example of a second self-immolative portion of a linker which may be useful with the present invention.

As to particular embodiments, an illustrative example of a second self-immolative portion which may be useful with the present invention includes N,N-dimethylethylenediamine (DMED), as shown in FIG. 13. Following self-elimination of the first self-immolative portion, DMED can undergo a cyclization reaction to form 1,3-dimethyl-2-imidazolidinone and release the chemotherapeutic agent. As to particular embodiments, DMED may be particularly useful between cleavable peptide portions comprising glucuronic acid and chemotherapeutic agents having a linkable hydroxyl group.

As to particular embodiments, a solubility-modifying portion can be used with the present conjugate to link a dye and a chemotherapeutic agent to achieve the desired solubility of the conjugate. Now referring primarily to FIGS. 7D through 7F, as to particular embodiments, due to the hydrophobic nature of the dye and/or the chemotherapeutic agent and/or some peptides, the solubility-modifying portion can be a hydrophilic portion which may link the dye and the cleavable linker, whereby the hydrophilic portion does not interfere with the drug release mechanism. As to particular embodiments, an illustrative example of a hydrophilic portion which may be useful with the present invention is shown in Formula LXXIX.

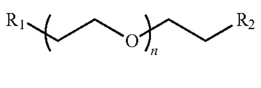

LXXIX wherein:

$R_1$ can be any functional group which can form a stable bond with the dye;

$R_2$ can be any functional group which can form a stable bond with the cleavable portion of the linker; and n can be 0 to 45.

Figure 14:
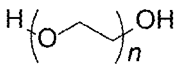
FIG. 14 shows an illustrative example of a hydrophilic portion of a linker which may be useful with the present invention.

As to particular embodiments, an illustrative example of a hydrophilic portion which may be useful with the present invention includes polyethylene glycol (PEG) (as shown in FIG. 14) with various chain lengths, whereby PEG may increase solubility in aqueous mediums and provide the desired drug metabolism and pharmacokinetics (DMPK) of the delivered chemotherapeutic agent. Notably, a longer PEG chain generally leads to greater hydrophilicity.

Figure 15:
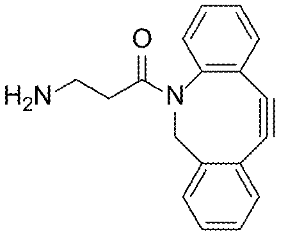
FIG. 15 shows an illustrative example of a click chemistry reagent which may be useful with the present invention.

As to particular embodiments, click chemistry can be used to link the dye and the linker, such as the hydrophilic portion of the linker or the cleavable portion of the linker. As but one illustrative example, dibenzocyclooctyne (DBCO)-containing reagents, as such dibenzocyclooctyne-amine (as shown in FIG. 15), may be useful with the present invention for click chemistry. These reagents include a highly reactive DBCO group which readily reacts with azide-tagged molecules or biomolecules to form a stable triazole ring without the need for a copper catalyst.

As to particular embodiments, the present conjugate can include a dye linked to two chemotherapeutic agents, whether the same or different.

Exemplary conjugates comprising a tumor-targeting NIR dye coupled to two chemotherapeutic agents via respective linkers, each including a cleavable peptide portion, which may be useful with the present invention are shown in Formulas LXXX through LXXXIII.

LXXX
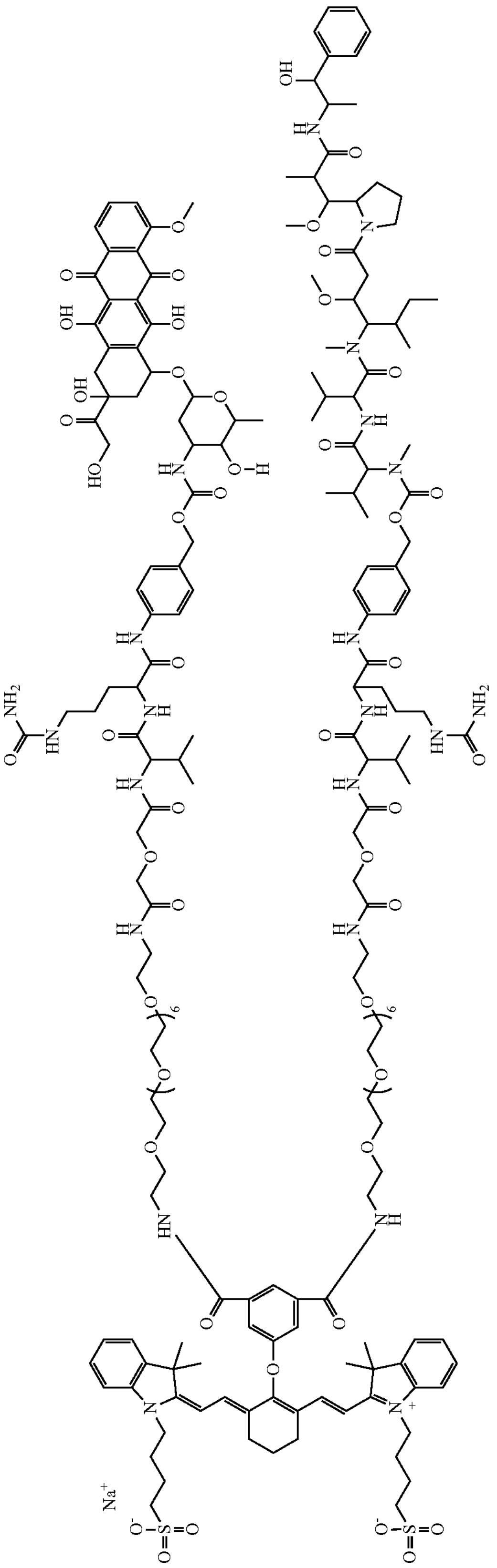

-continued
LXXXI
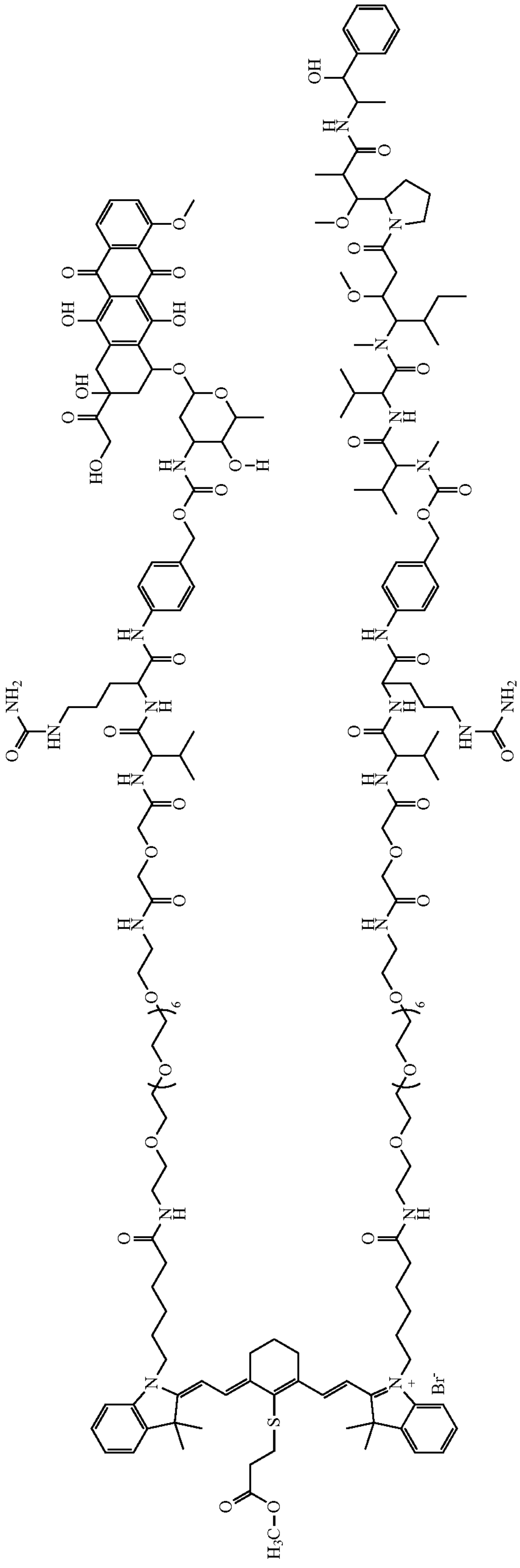
LXXXII
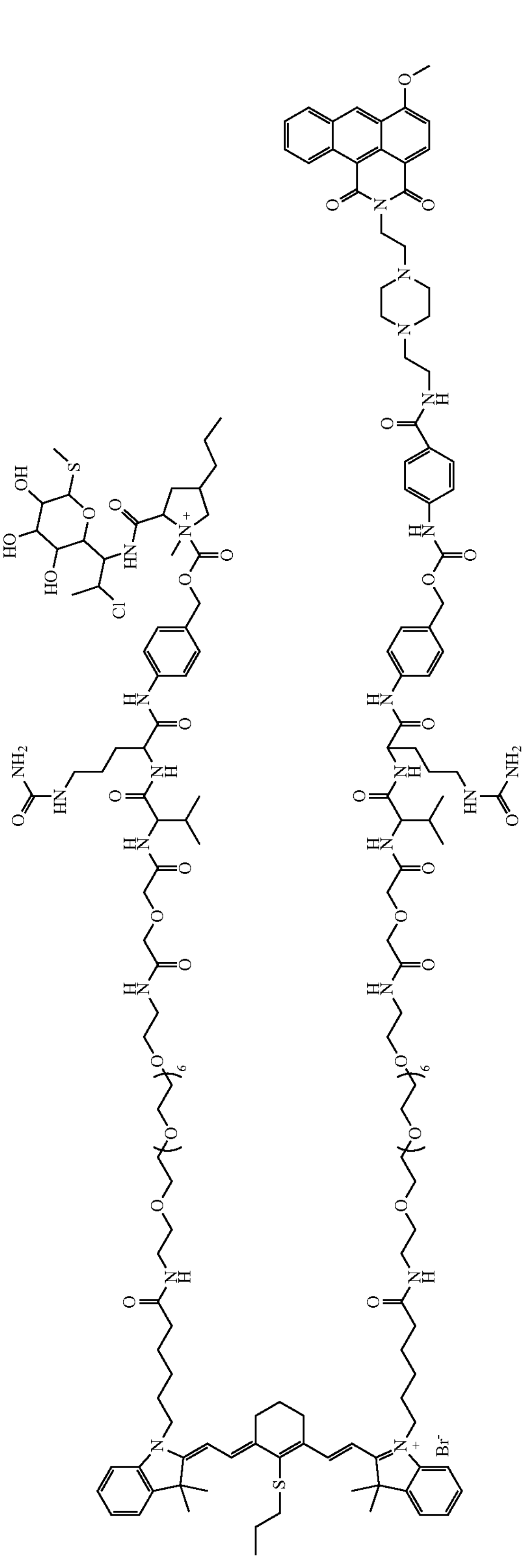

-continued
LXXXIII
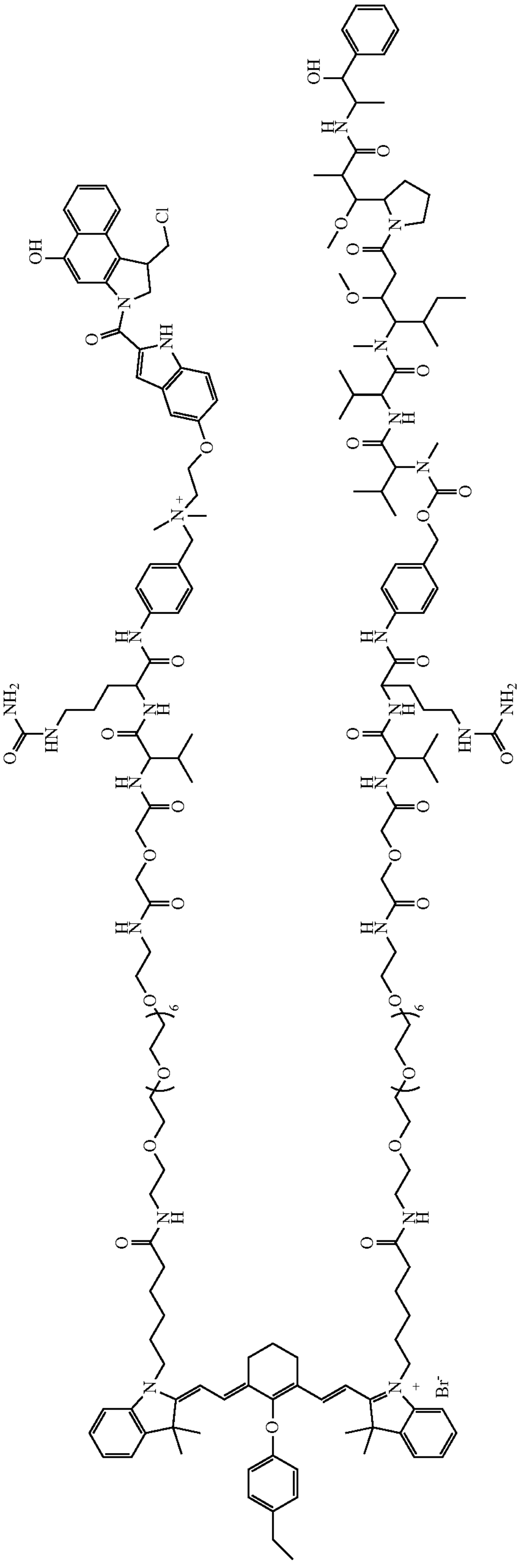

Figure 16:
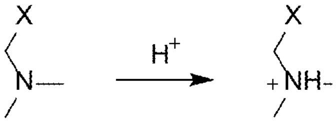
FIG. 16 shows a compound which can function as a base which may accept a proton ($H^+$).
Figure 17A:
FIG. 17A shows an illustrative example of a basic functional group which may be useful with the present invention.
Figure 17B:
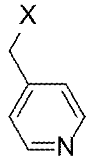
FIG. 17B shows an illustrative example of a basic functional group which may be useful with the present invention.
Figure 17C:
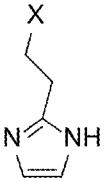
FIG. 17C shows an illustrative example of a basic functional group which may be useful with the present invention.
Figure 17D:
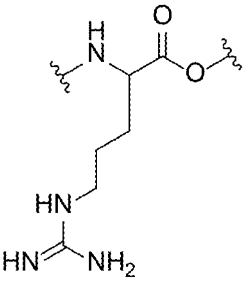
FIG. 17D shows an illustrative example of a basic functional group which may be useful with the present invention.
Figure 17E:
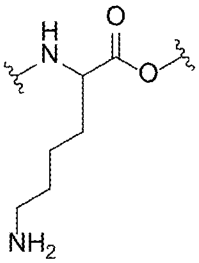
FIG. 17E shows an illustrative example of a basic functional group which may be useful with the present invention.
Figure 17F:
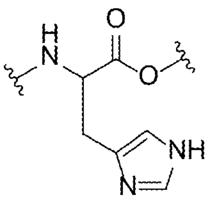
FIG. 17F shows an illustrative example of a basic functional group which may be useful with the present invention.
Figure 18A:
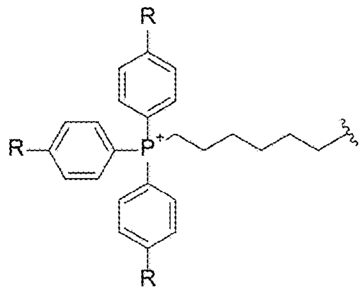
FIG. 18A shows an illustrative example of a mitochondria-targeting functional group which may be useful with the present invention.
Figure 18B:
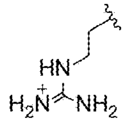
FIG. 18B shows an illustrative example of a mitochondria-targeting functional group which may be useful with the present invention.
Figure 18C:
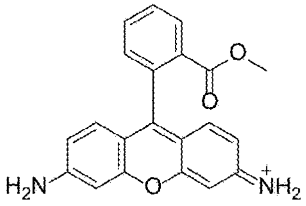
FIG. 18C shows an illustrative example of a mitochondria-targeting functional group which may be useful with the present invention.
Figure 18D:
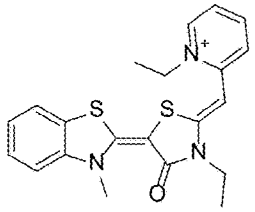
FIG. 18D shows an illustrative example of a mitochondria-targeting functional group which may be useful with the present invention.

As to particular embodiments, the tumor-targeting NIR dye or the linker can be modified to have a basic functionality, whereby such a modification may include the attachment of one or more basic compounds to the dye or the linker or the incorporation of one or more basic compounds into the dye or the linker. Each basic compound can function as a base which may accept a proton ($H^+$) (as shown in FIG. 16) and thus be protonated in an acidic environment, such as a tumor microenvironment which can be acidic as a result of increased glycolytic metabolism and limited oxygen and nutrient availability that may lead to the buildup of lactic acid and other acidic metabolites. Protonation of the basic compound proximate the tumor microenvironment can enhance penetration into the tumor via attraction of its positive charge to the negative charges on tumor cell membranes for uptake and retention. Additionally, in the circulation, the basic functionality can impart a relatively neutral charge to the dye or the linker which may preclude interaction with positively or negatively charged proteins in the blood and subsequent recognition and clearance by the macrophage scavenger system.

As a first example, basic functional groups which may be useful with the present invention include amines, sulfonamides, and imidazoles.

As a second example, basic functional groups which may be useful with the present invention can include those shown in FIGS. 17A through 17F.

Exemplary dyes having a basic functional group which may be useful with the present invention are shown in Formulas LXXXIV through XCII.

LXXXIV

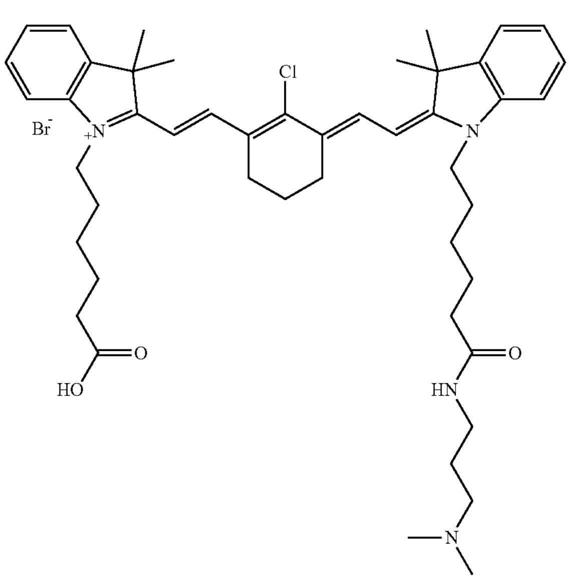

-continued

LXXXV

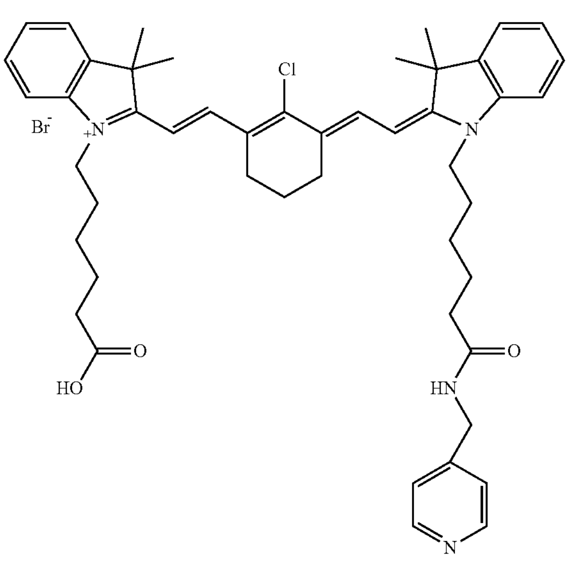

LXXXVI

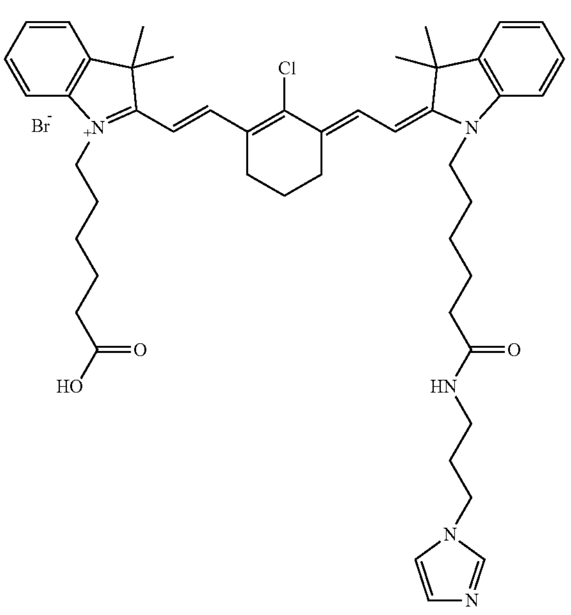

-continued
LXXXVII
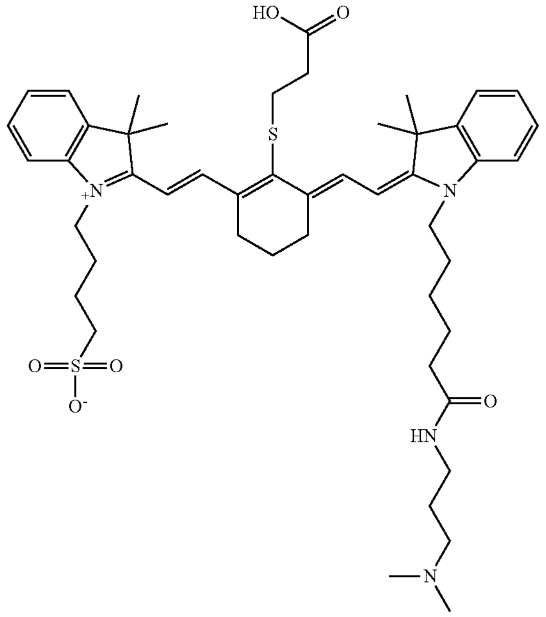
LXXXVIII
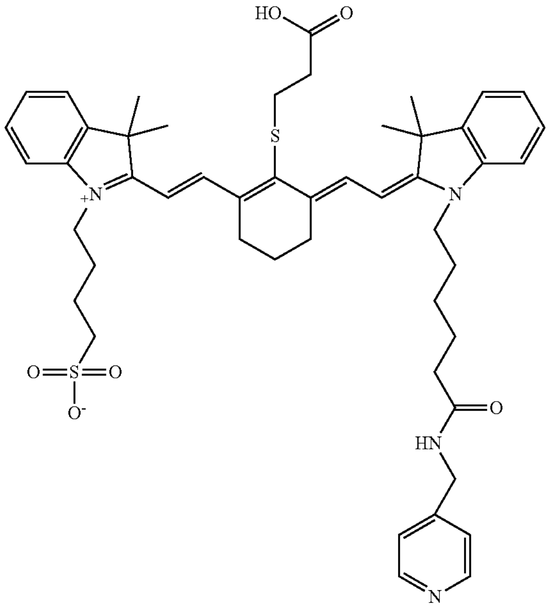
-continued
LXXXIX
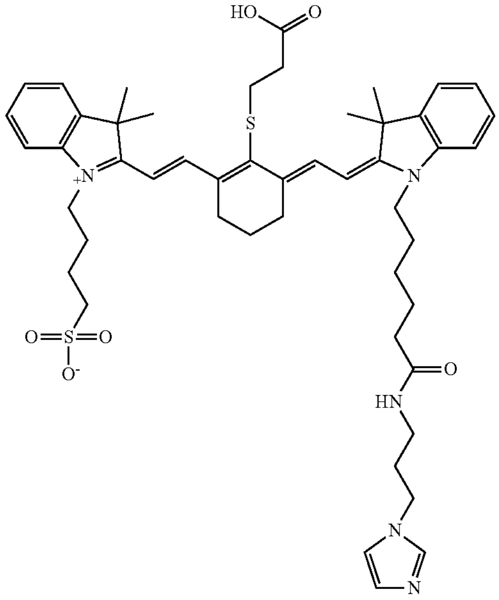
XC
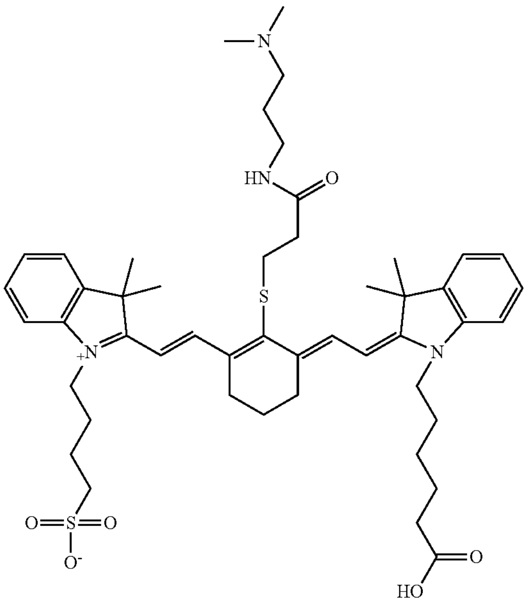

-continued
XCI
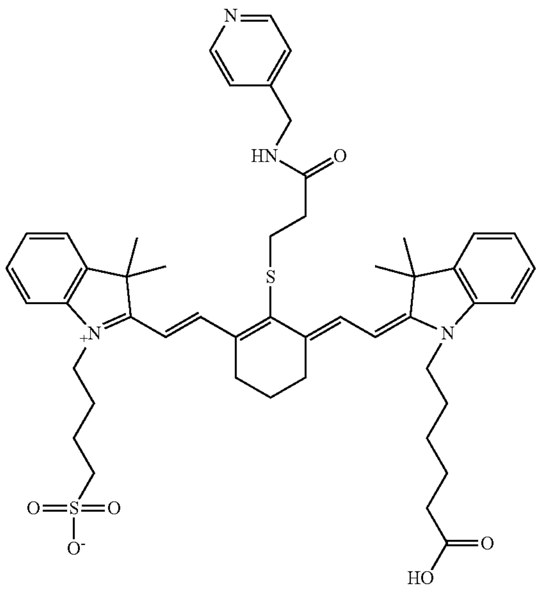
-continued
XCII
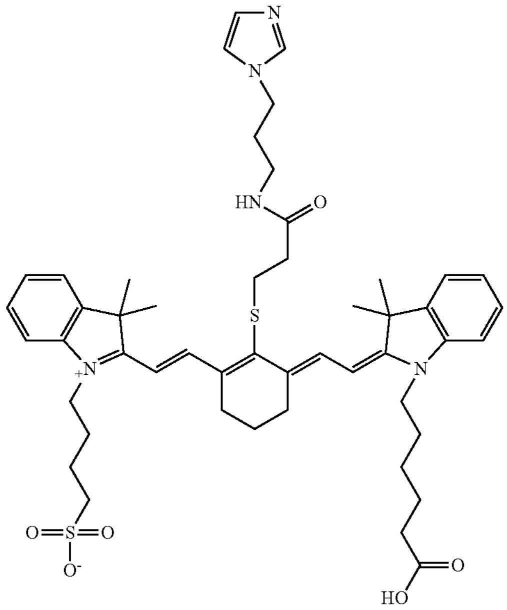
An exemplary conjugate comprising a tumor-targeting NIR dye having a basic functional group and specifically, the dye shown in Formula LXXXIV, coupled to a chemotherapeutic agent via a linker including a cleavable peptide portion which may be useful with the present invention is shown in Formula XCIII.

XCIII
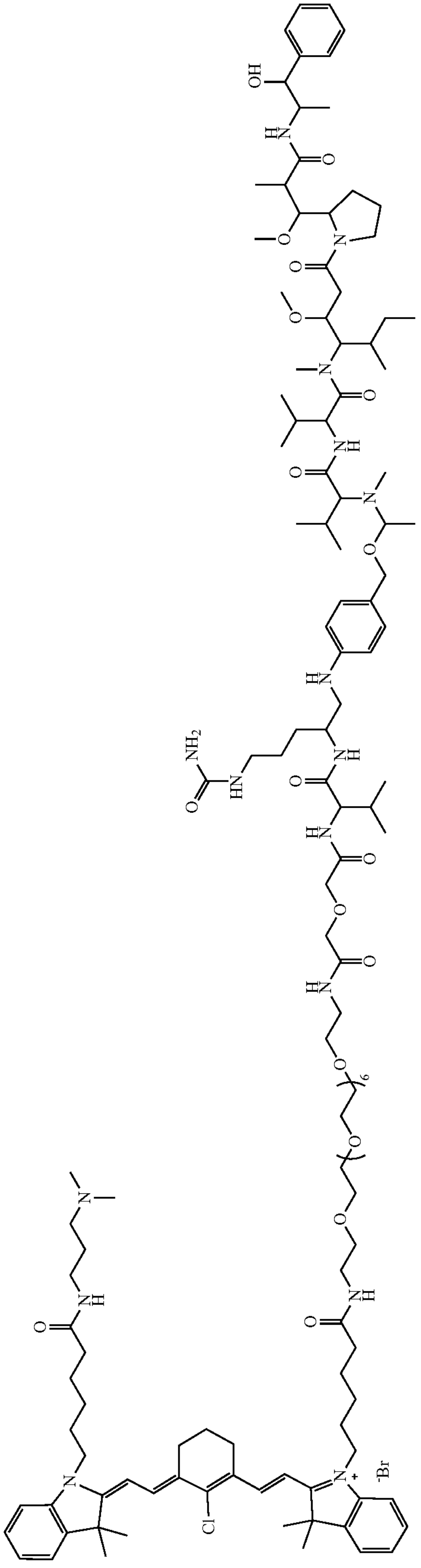

Exemplary conjugates comprising a tumor-targeting NIR dye having a basic functional group and specifically, the dye shown in Formula LXXXVII, coupled to a chemotherapeutic agent via a linker including a cleavable peptide portion which may be useful with the present invention are shown in Formulas XCIV and XCV.

XCIV
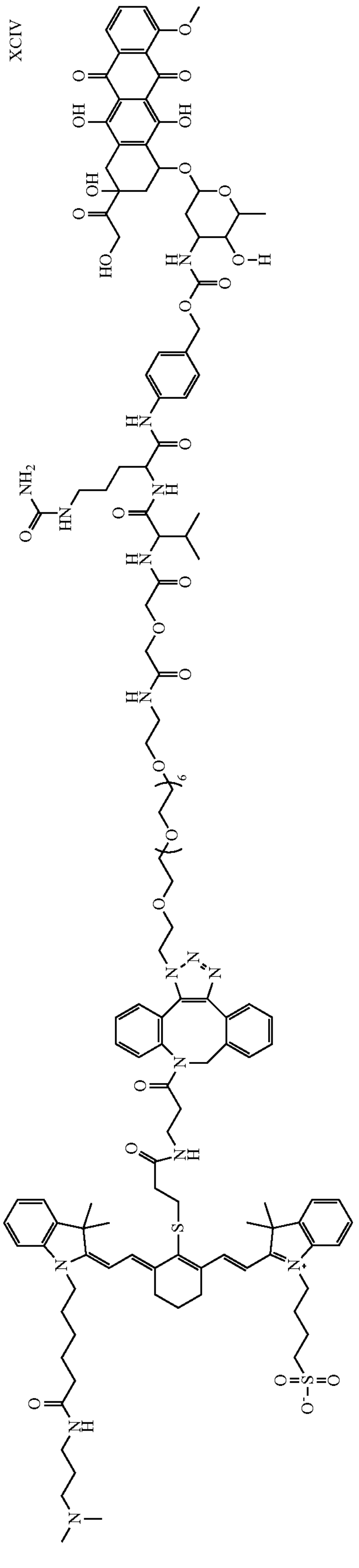
XCV
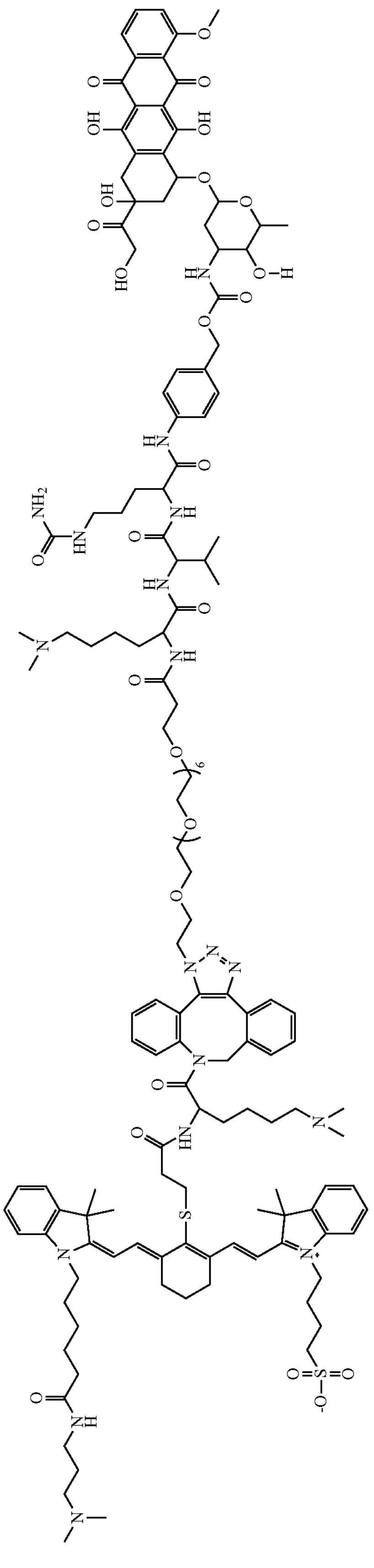

An exemplary conjugate comprising a tumor-targeting NIR dye having a basic functional group and specifically, the dye shown in Formula XC, coupled to a chemotherapeutic agent via a linker including a cleavable peptide portion which may be useful with the present invention is shown in Formula XCVI.

XCVI
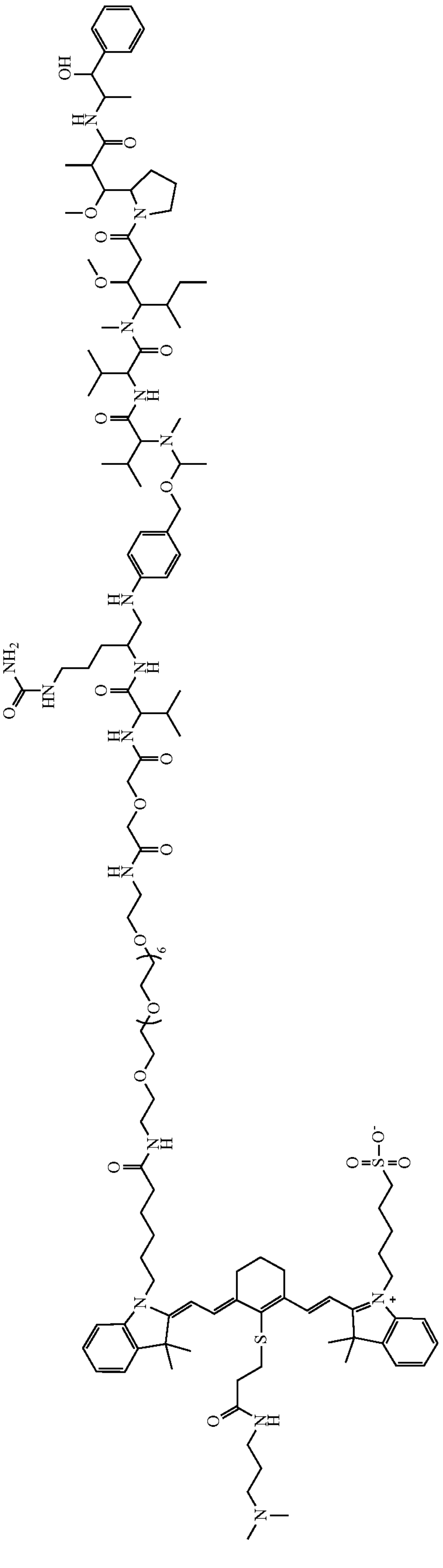

An exemplary conjugate comprising a tumor-targeting NIR dye having a basic functional group and specifically, the dye shown in Formula XCI, coupled to a chemotherapeutic agent via a linker including a cleavable peptide portion which may be useful with the present invention is shown in Formula XCVII.

XCVII

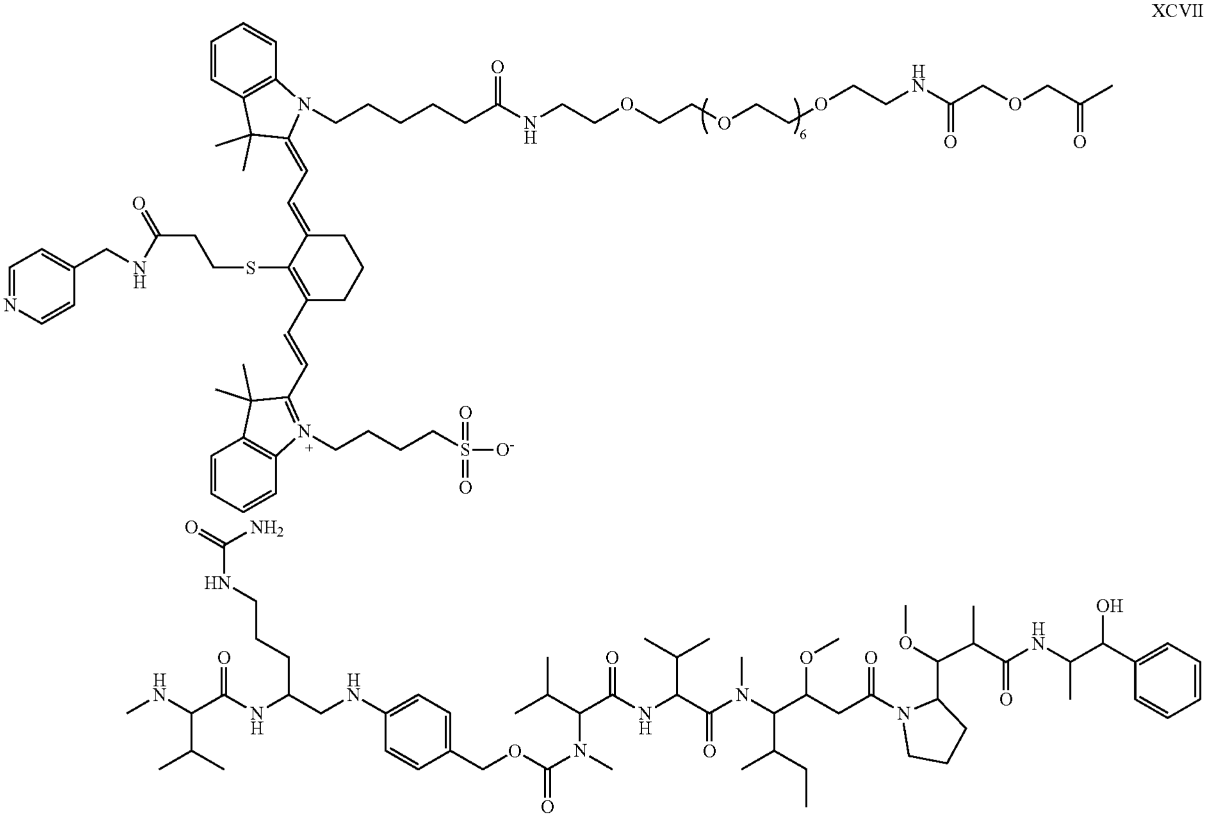

As to particular embodiments, as stated above, the linker can also be modified to have a basic functionality, whereby such a modification may include the attachment of one or more basic compounds to the linker or the incorporation of one or more basic compounds into the linker.

Exemplary linkers having a basic functional group and a cleavable peptide portion which may be useful with the present invention are shown in Formulas XCVIII through CVII.

XCVIII

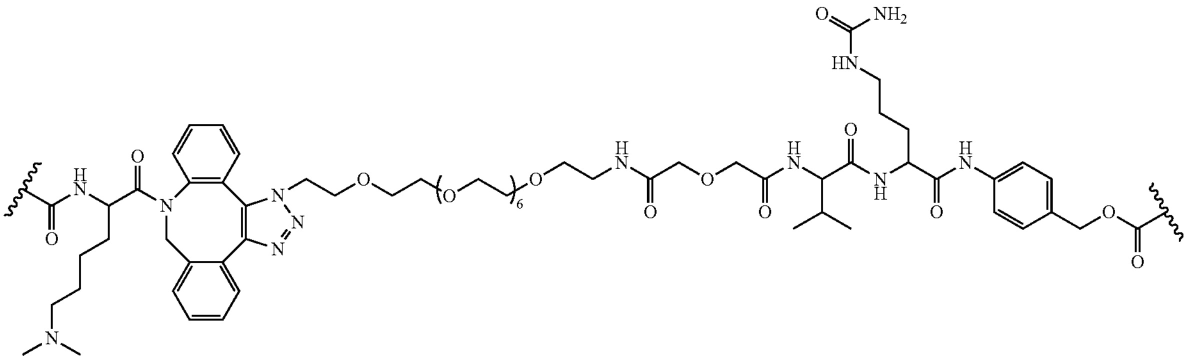

-continued
XCIX
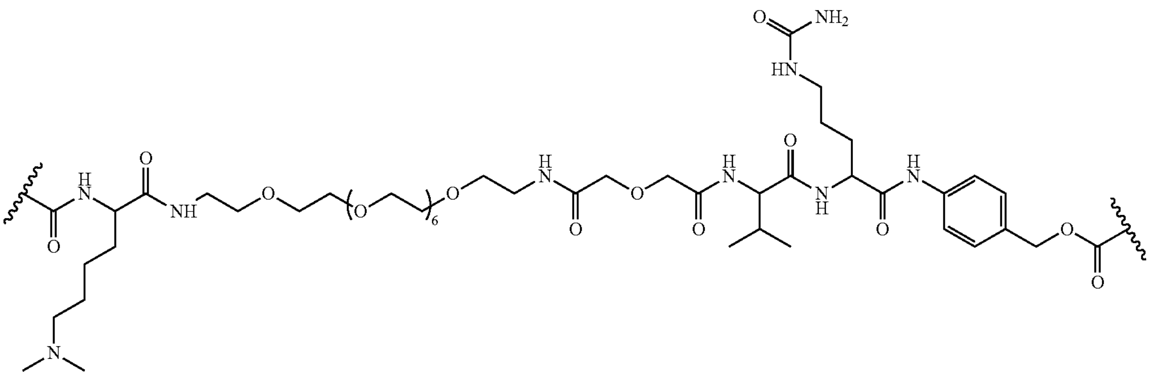
C
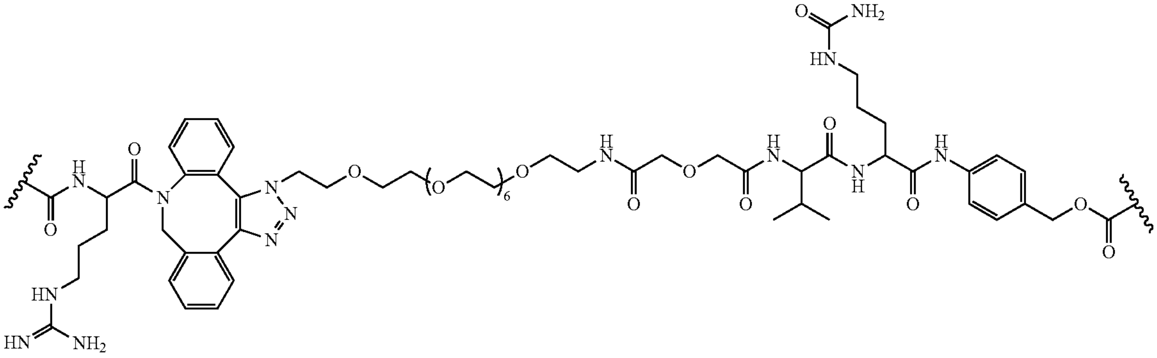
CI
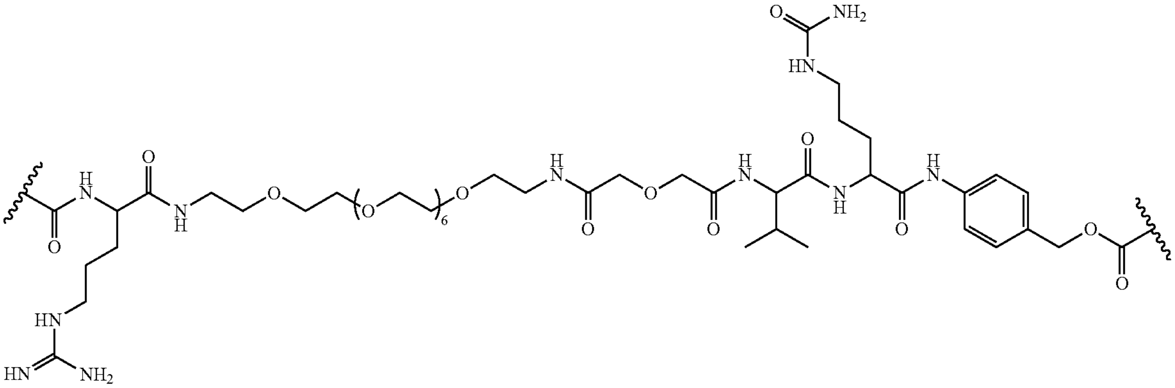
CII
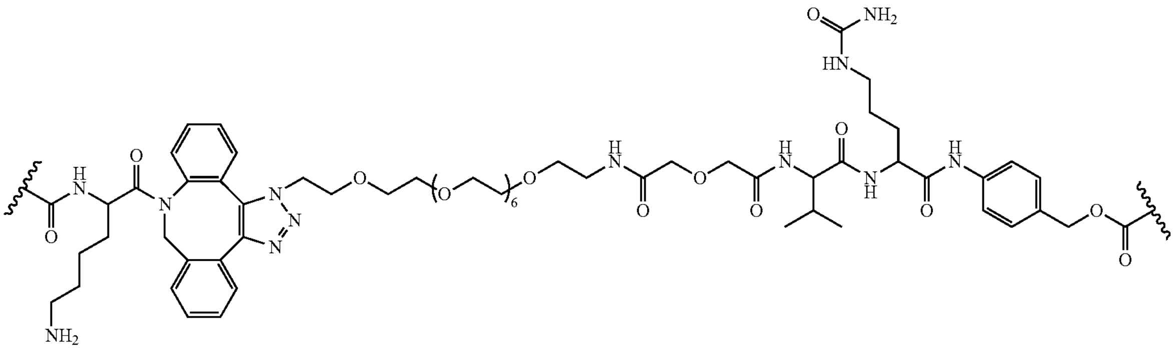

-continued
CIII
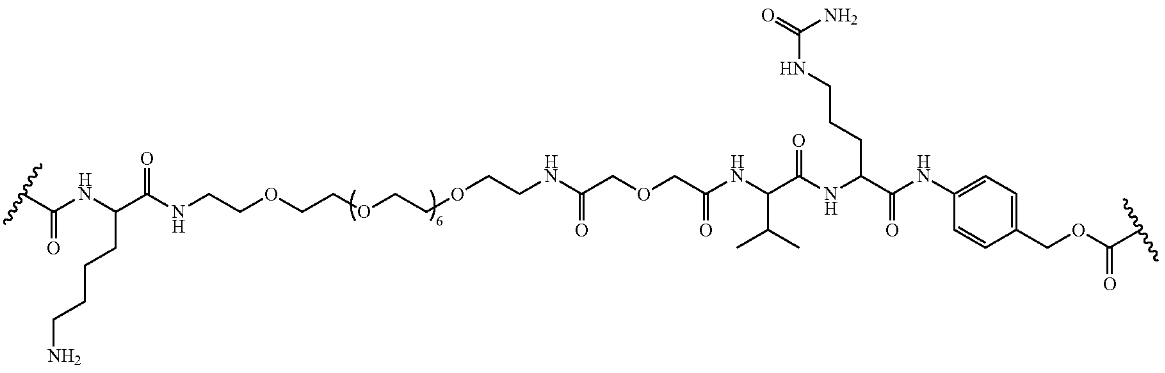
CIV
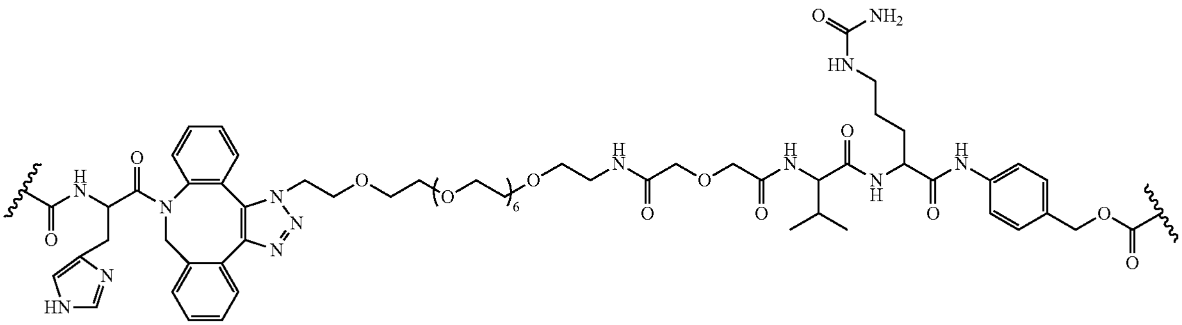
CV
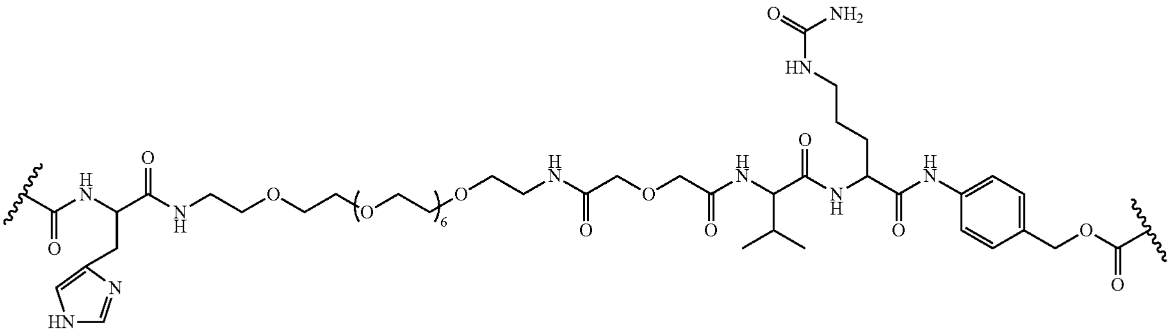
CVI
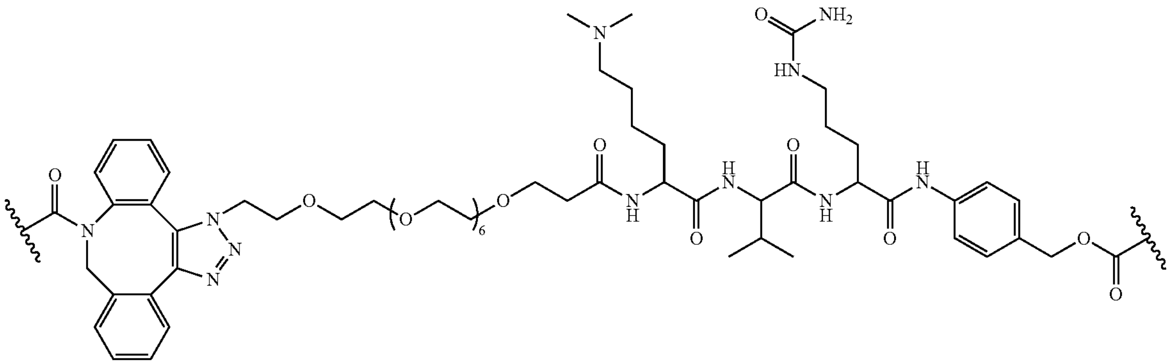

-continued
CVII
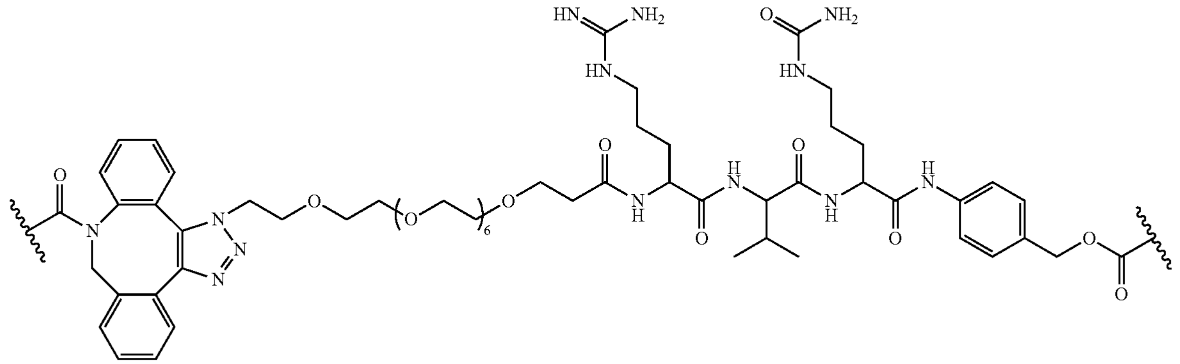
CVIII
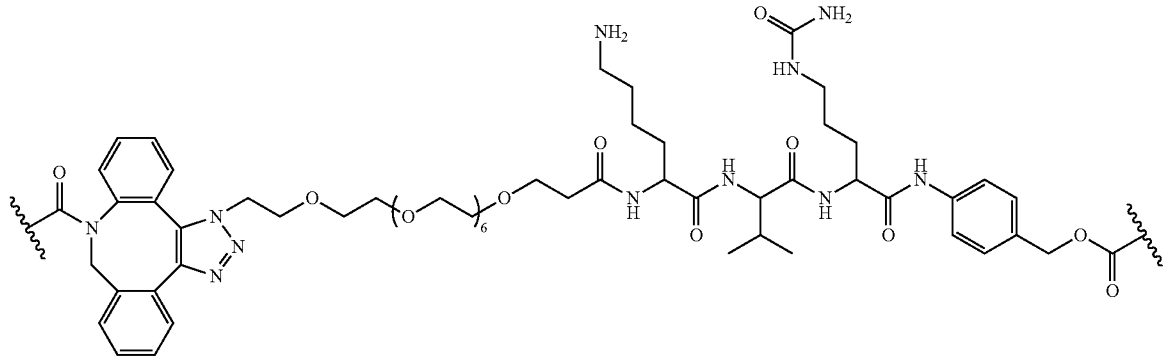
Exemplary conjugates comprising a tumor-targeting NIR dye, a linker having (i) a basic functional group and specifically, the linker shown in Formula XCVIII, and (ii) a cleavable peptide portion coupled to a chemotherapeutic agent which may be useful with the present invention are shown in Formulas CIX and CX.
CIX
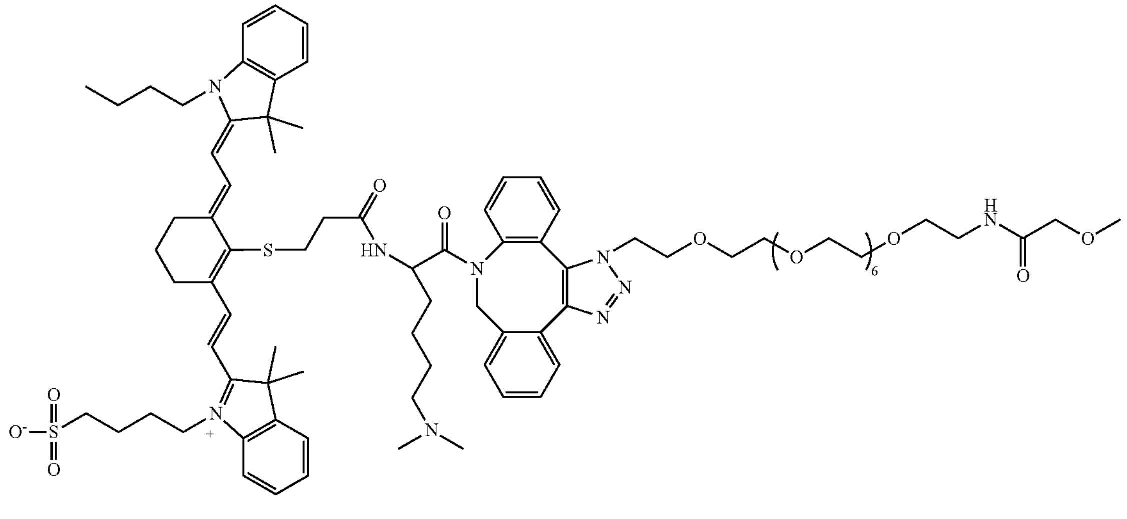

-continued
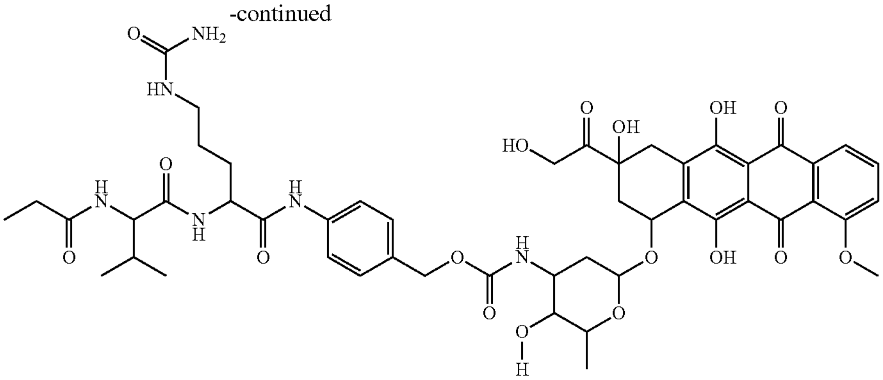
CX
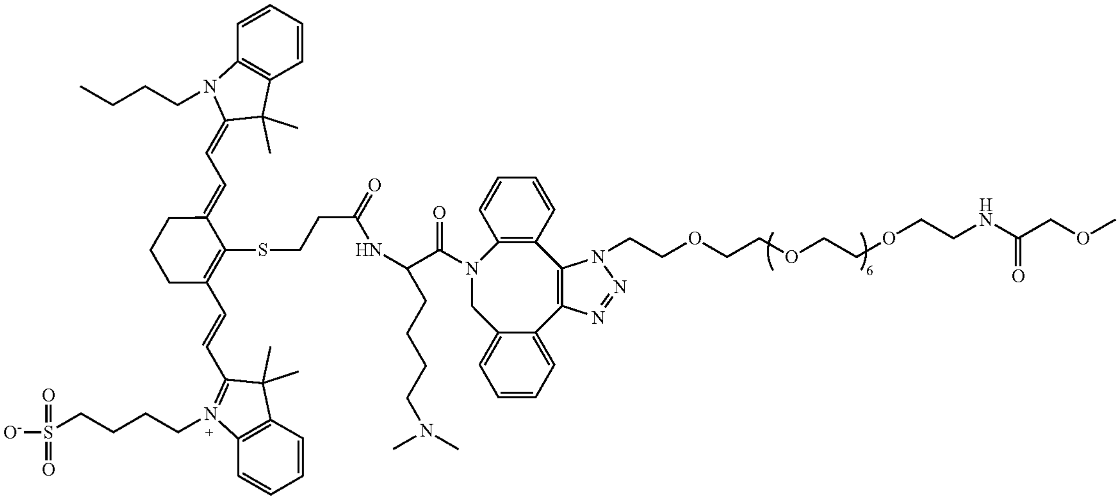
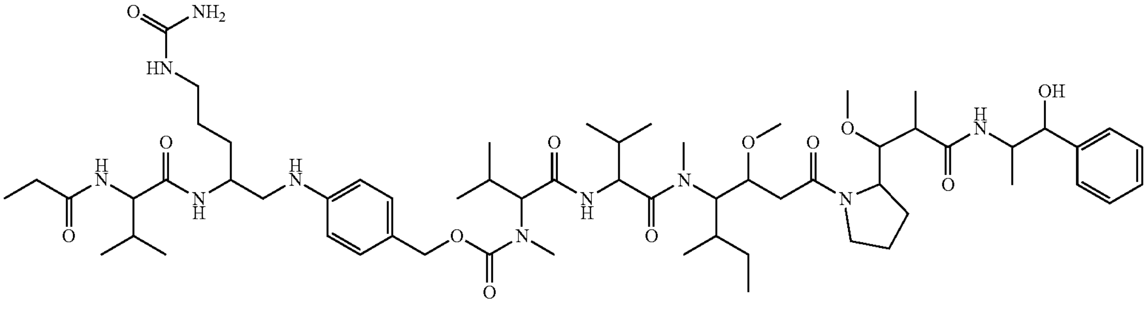
An exemplary conjugate comprising a tumor-targeting NIR dye, a linker having (i) a basic functional group and specifically, the linker shown in Formula C, and (ii) a cleavable peptide portion coupled to a chemotherapeutic agent which may be useful with the present invention is shown in Formula CXI.

CXI
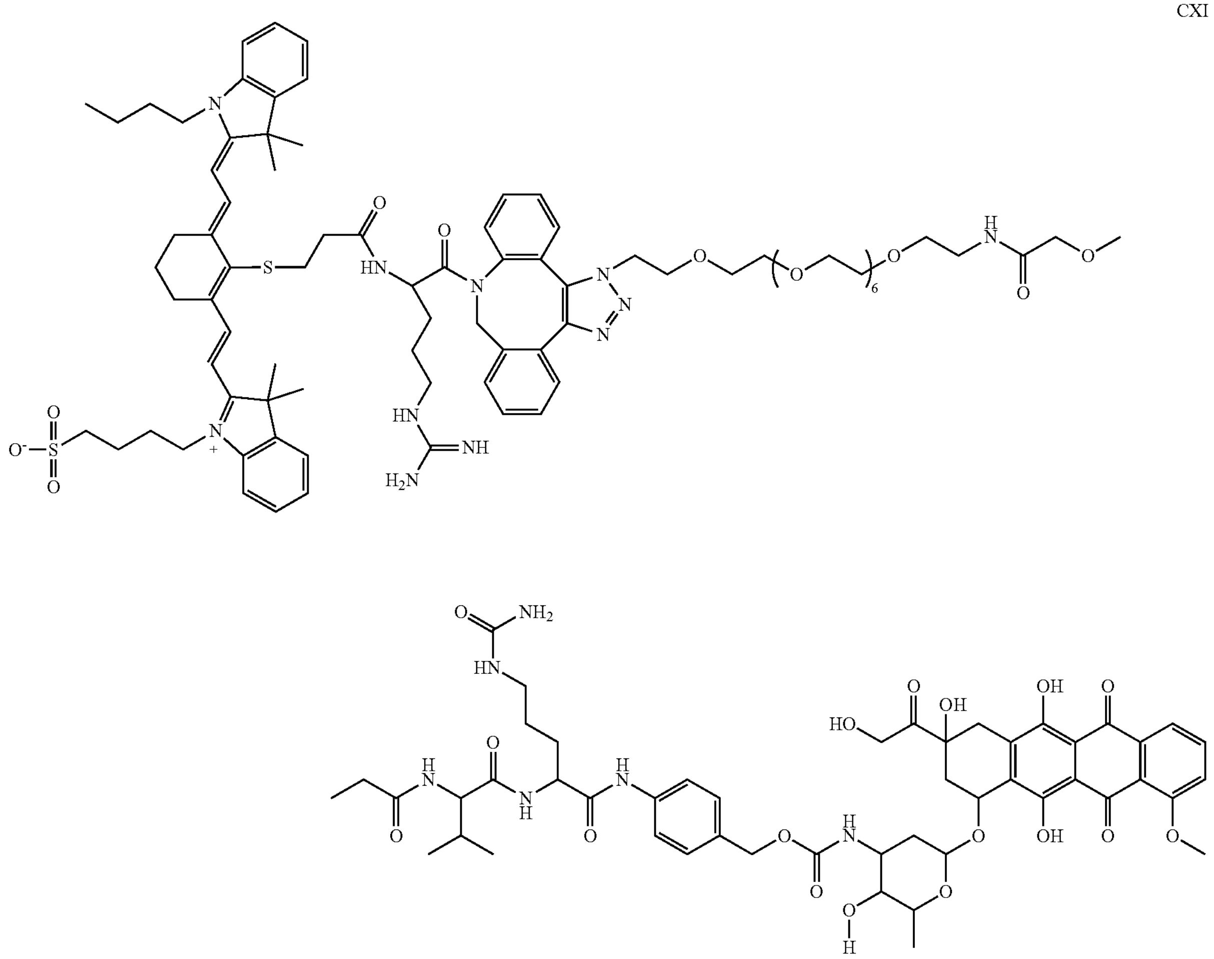
An exemplary conjugate comprising a tumor-targeting NIR dye, a linker having (i) a basic functional group and specifically, the linker shown in Formula CII, and (ii) a cleavable peptide portion coupled to a chemotherapeutic agent which may be useful with the present invention is shown in Formula CXII.
CXII
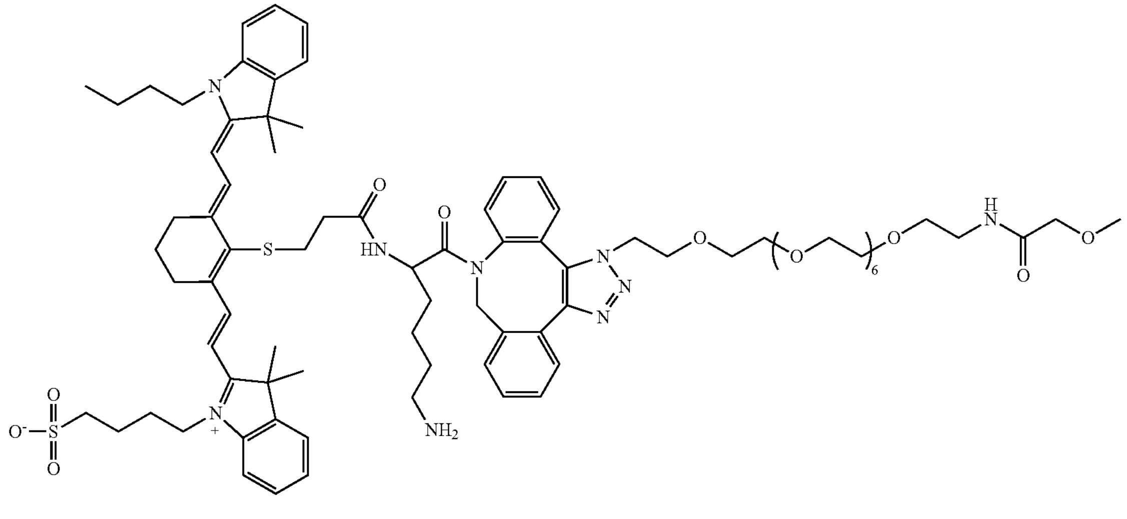

-continued
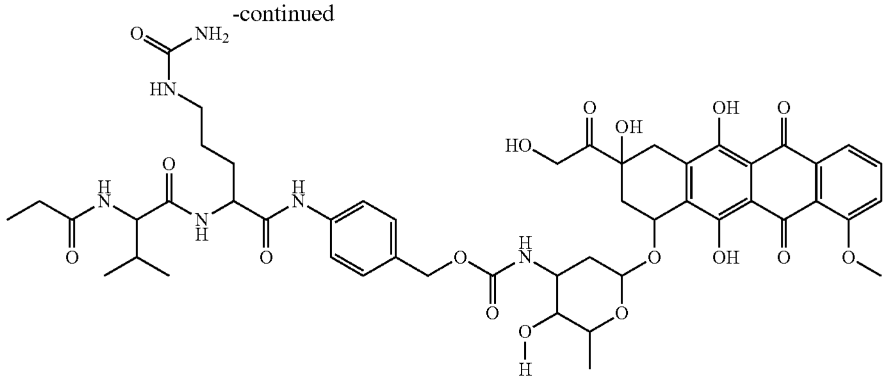
Exemplary conjugates comprising a tumor-targeting NIR dye, a linker having (i) a basic functional group and specifically, the linker shown in Formula CVI, and (ii) a cleavable peptide portion coupled to a chemotherapeutic agent which may be useful with the present invention are shown in Formulas CXIII through CXV.
CXIII
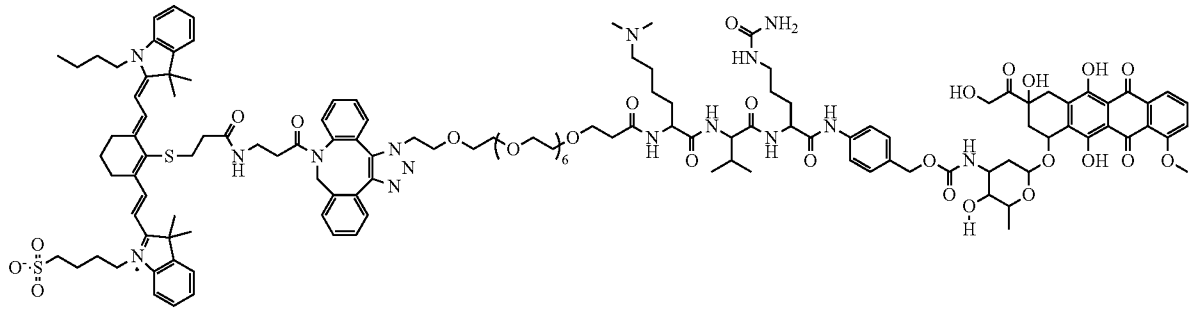
CXIV
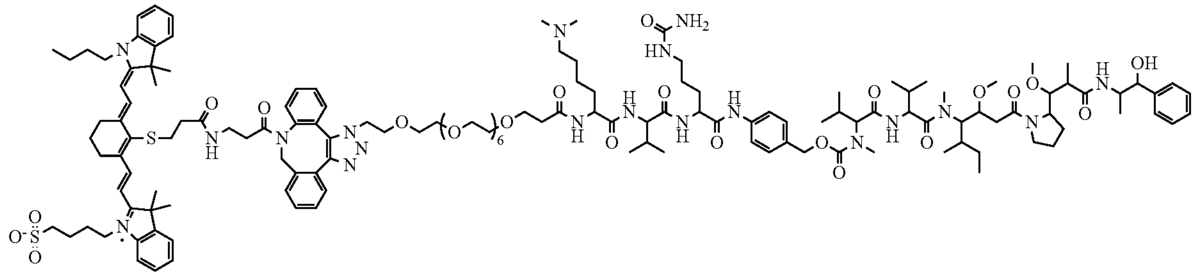
CXV
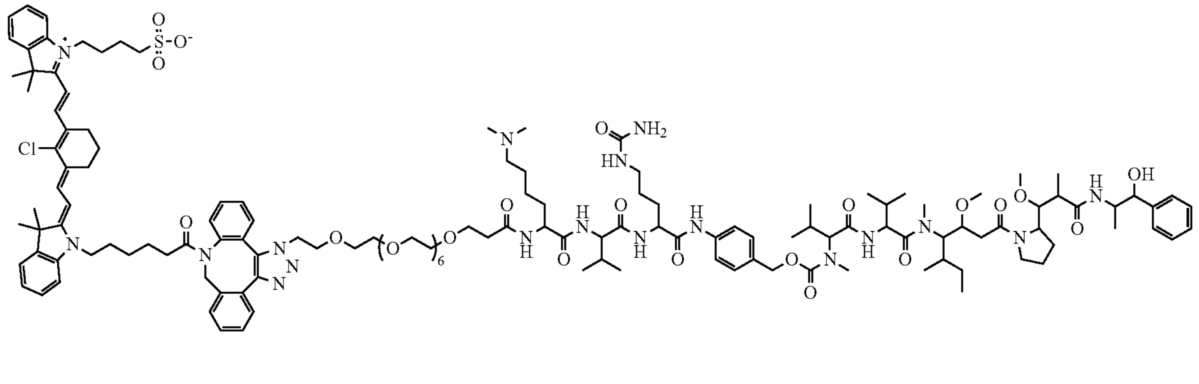

An exemplary conjugate comprising a tumor-targeting NIR dye, a linker having (i) a basic functional group and specifically, the linker shown in Formula CVII, and (ii) a cleavable peptide portion coupled to a chemotherapeutic agent which may be useful with the present invention is shown in Formula CXVI.

CXVI

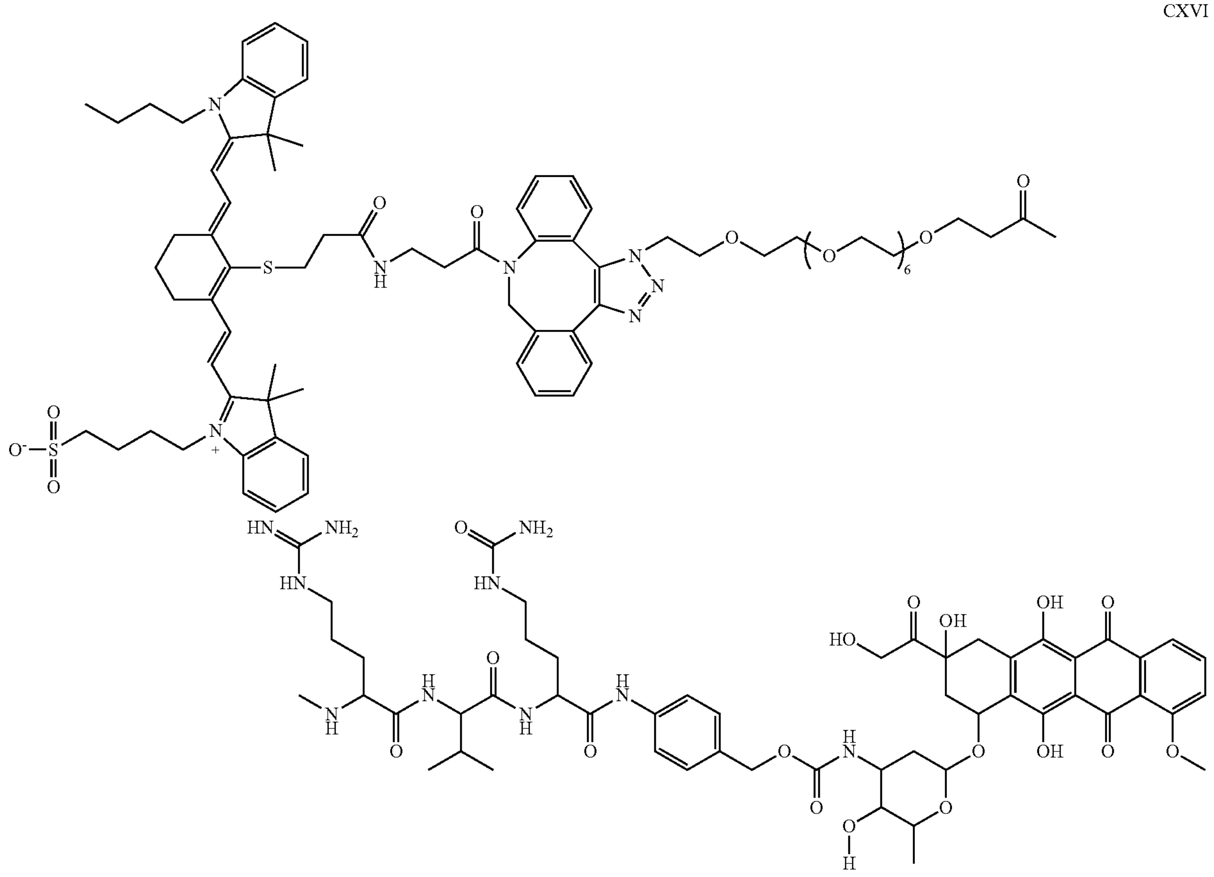

An exemplary conjugate comprising a tumor-targeting NIR dye, a linker having (i) a basic functional group and specifically, the linker shown in Formula CVIII, and (ii) a cleavable peptide portion coupled to a chemotherapeutic agent which may be useful with the present invention is shown in Formula CXVII.

CXVII

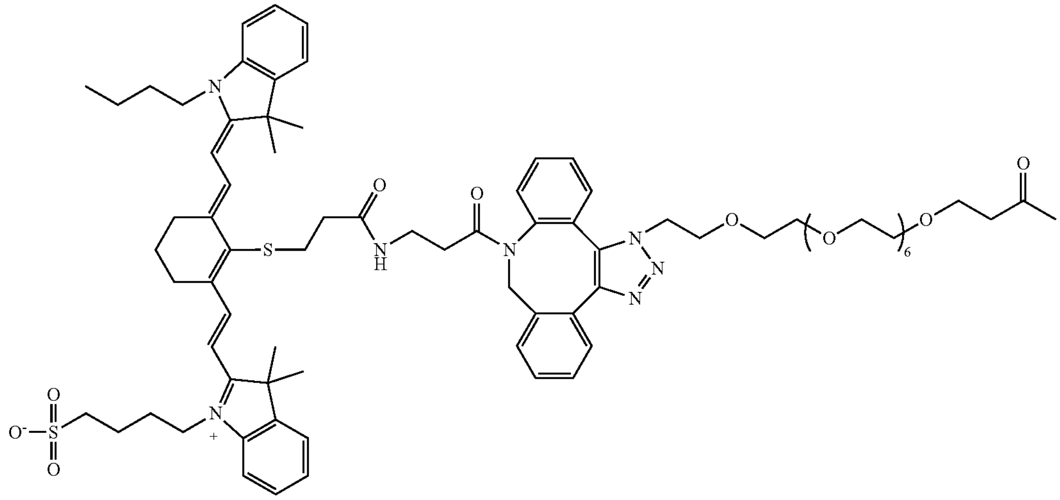

-continued

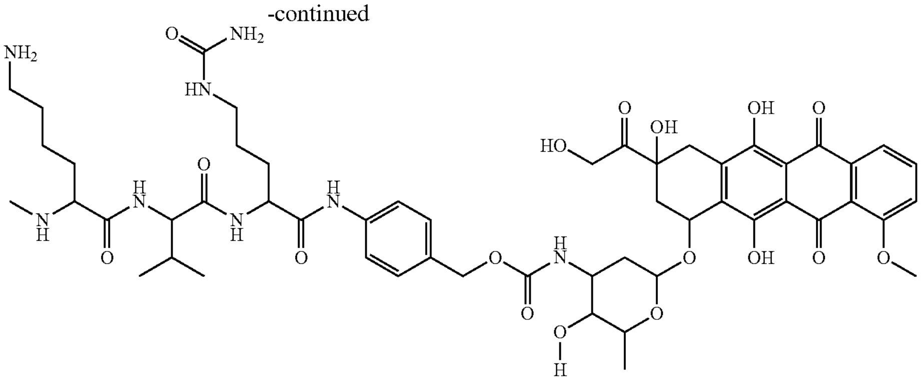

An exemplary conjugate comprising a tumor-targeting NIR dye, a linker having (i) two basic functional groups and (ii) a cleavable peptide portion coupled to a chemotherapeutic agent which may be useful with the present invention is shown in Formula CXVIII.

CXVIII

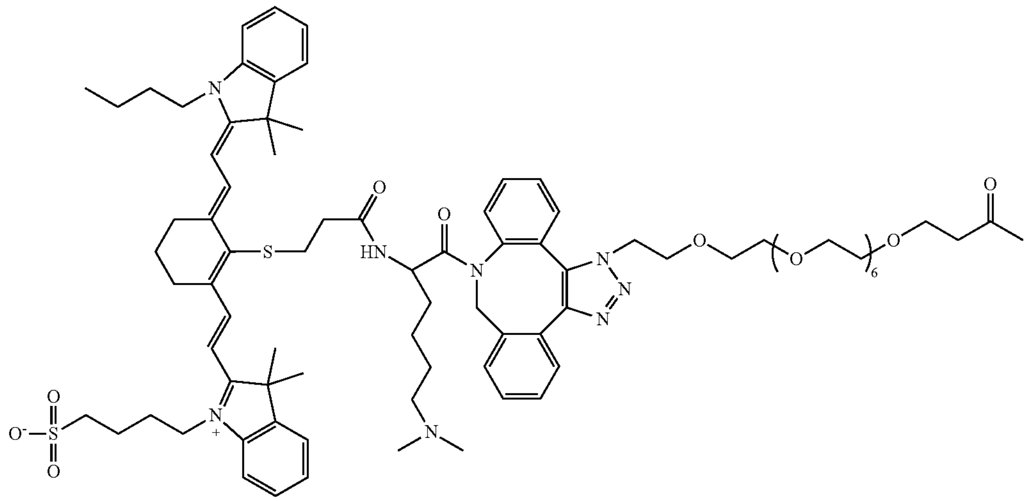

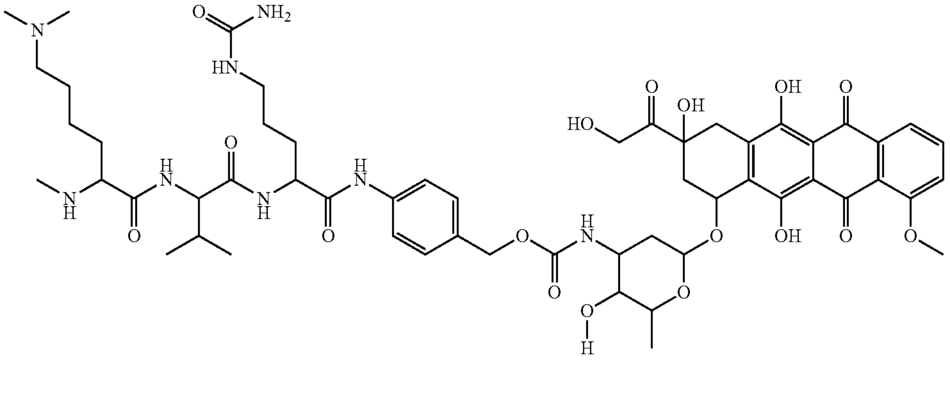

An exemplary conjugate comprising (i) a tumor-targeting NIR dye having a basic functional group and specifically, the dye shown in Formula LXXXVII, and (ii) a linker having two basic functional groups and a cleavable peptide portion coupled to a chemotherapeutic agent which may be useful with the present invention is shown in Formulas CXIX.

CXIX

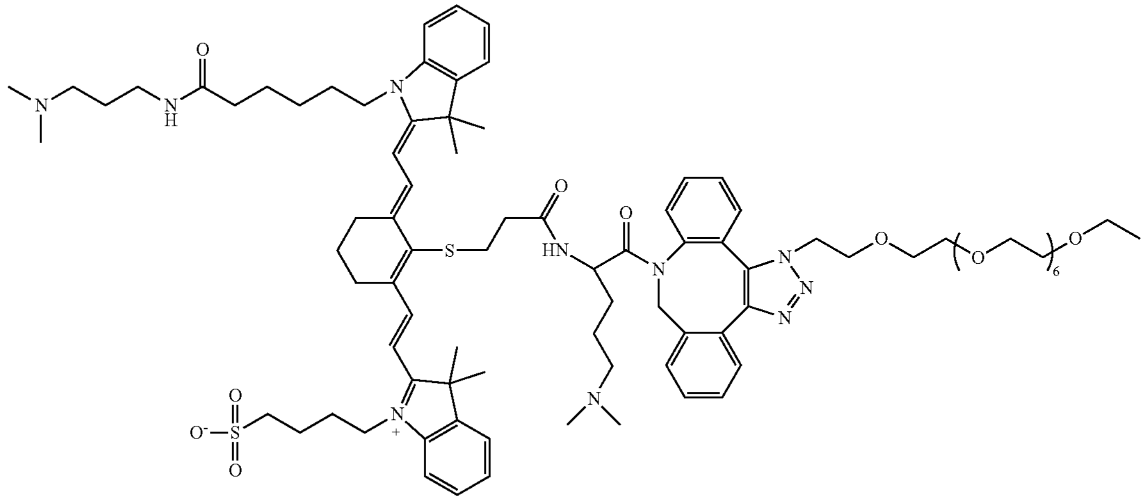

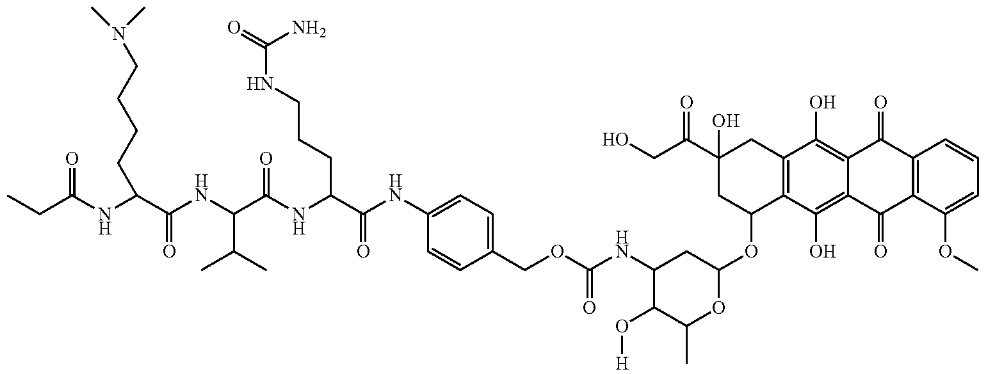

As to particular embodiments, the tumor-targeting NIR dye or the linker can be modified to have a functional group which targets tumor cell mitochondria, whereby such a modification may include the attachment of one or more lipophilic moieties and/or cationic moieties to the dye or the linker or the incorporation of one or more lipophilic moieties and/or cationic moieties into the dye or the linker, whereby the lipophilic moieties can readily cross the cell and mitochondrial membranes and the cationic moieties (such as with a delocalized positive charge) may be attracted by the negative charge within the mitochondrial matrix. As to particular embodiments, the mitochondria-targeting functional group can be both lipophilic and cationic.

As illustrative examples, mitochondria-targeting functional groups which may be useful with the present invention can include those shown in FIGS. 18A through 18D.

Exemplary dyes having a mitochondria-targeting functional group which may be useful with the present invention are shown in Formulas CXX through CXXV.

-continued
CXX
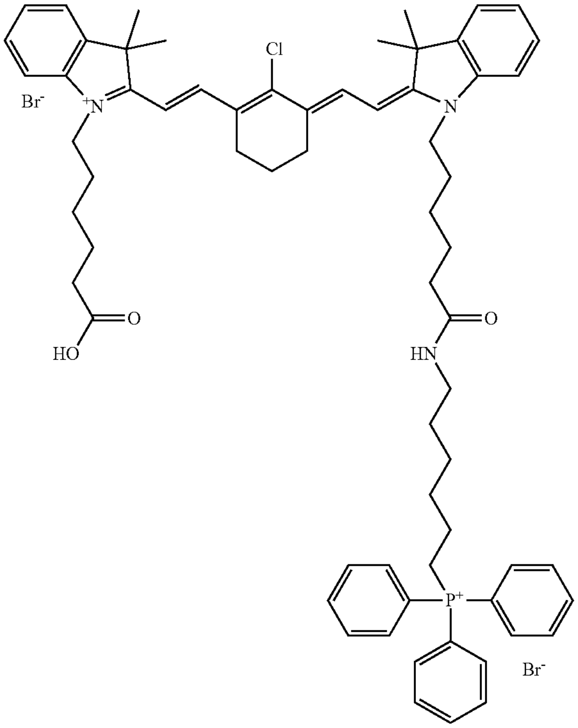
CXXI
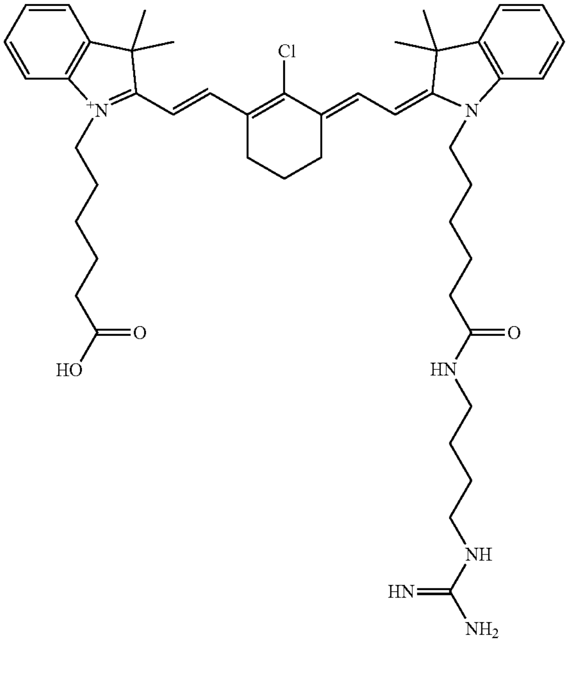
CXXII
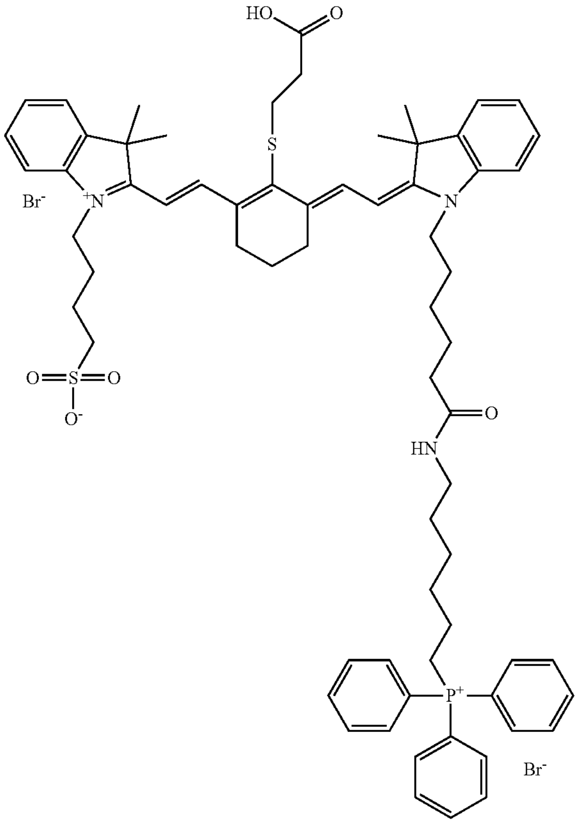
CXXIII
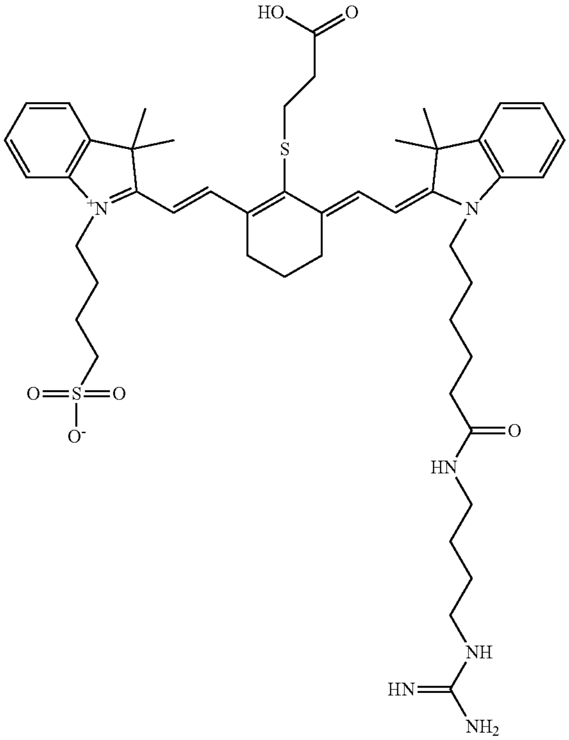

-continued
CXXIV
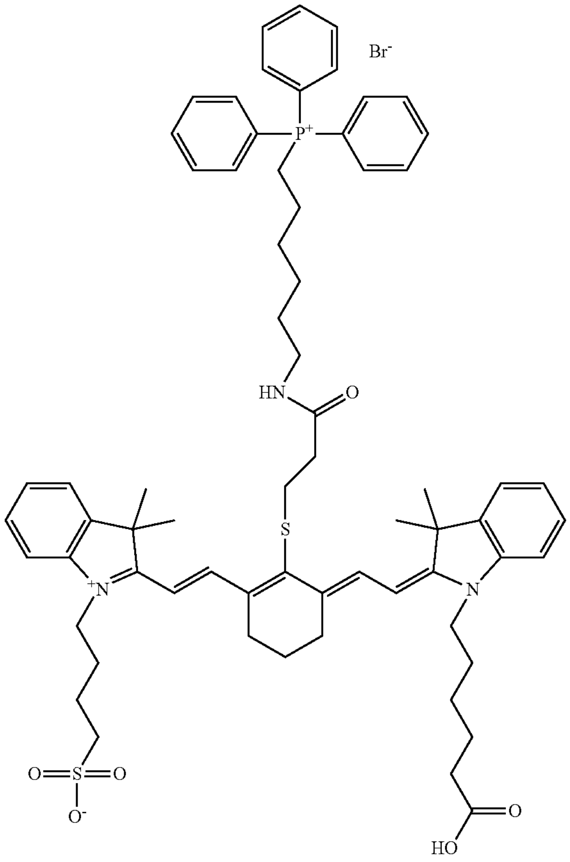
-continued
CXXV
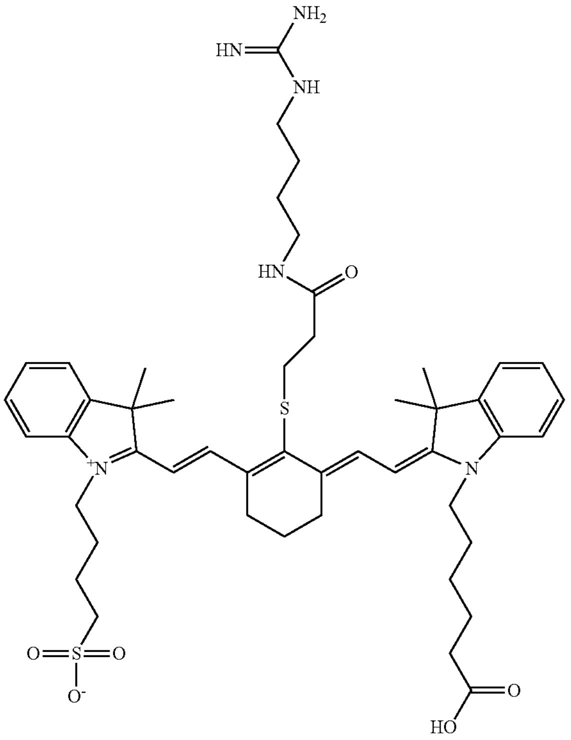
An exemplary conjugate comprising a tumor-targeting NIR dye having a mitochondria-targeting functional group and specifically, the dye shown in Formula CXX, coupled to a chemotherapeutic agent via a linker including a cleavable peptide portion which may be useful with the present invention is shown in Formula CXXVI.
CXXVI
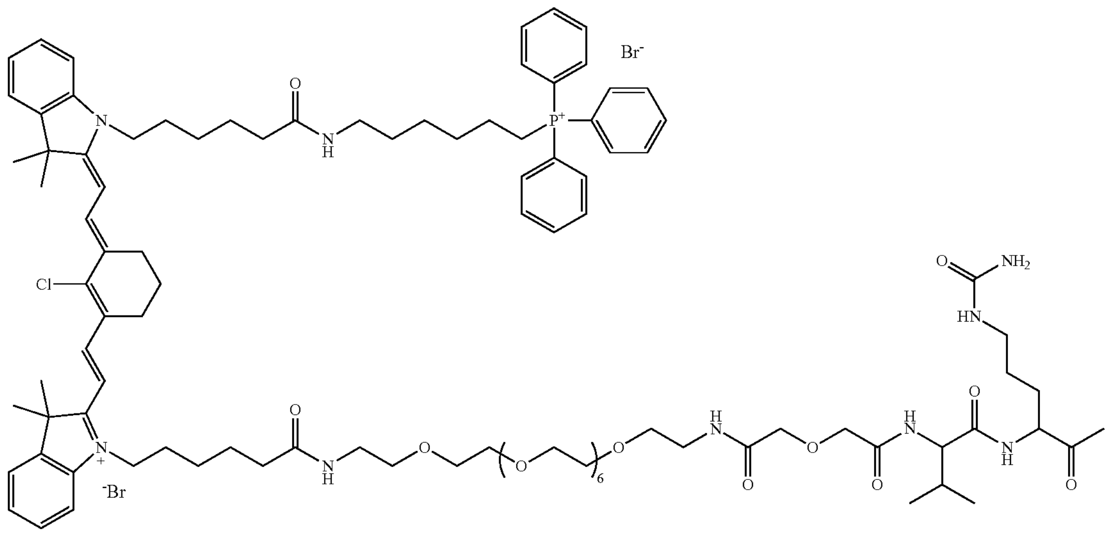

-continued

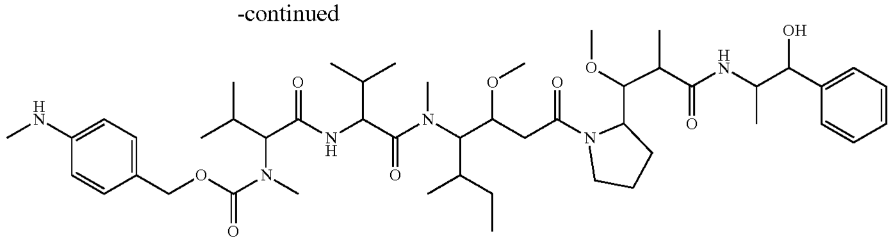

An exemplary conjugate comprising a tumor-targeting NIR dye having a mitochondria-targeting functional group and specifically, the dye shown in Formula CXXII, coupled to a chemotherapeutic agent via a linker including a cleavable peptide portion which may be useful with the present invention is shown in Formula CXXVII.

CXXVII

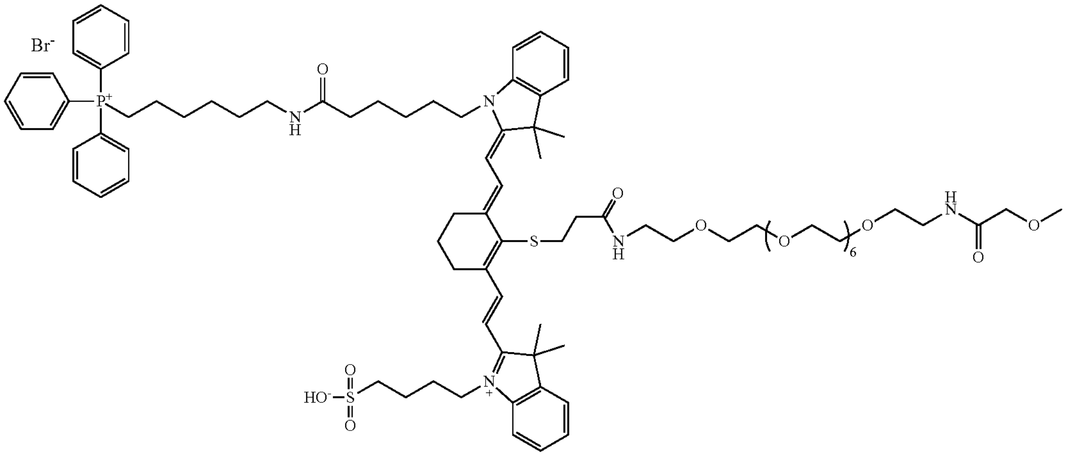

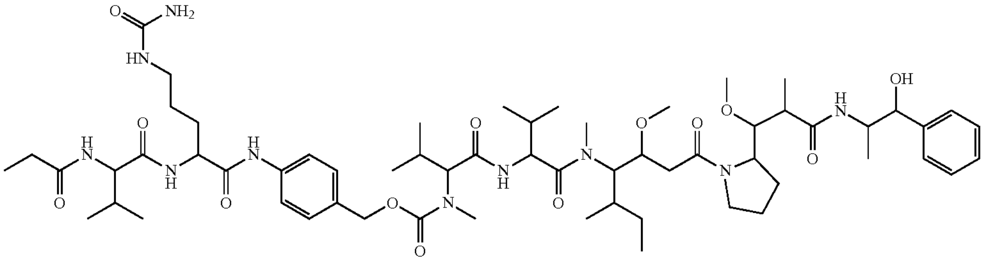

Exemplary conjugates comprising a tumor-targeting NIR dye having a mitochondria-targeting functional group and specifically, the dye shown in Formula CXXIV, coupled to a chemotherapeutic agent via a linker including a cleavable peptide portion which may be useful with the present invention are shown in Formulas CXXVIII and CXXIX.

CXXVIII
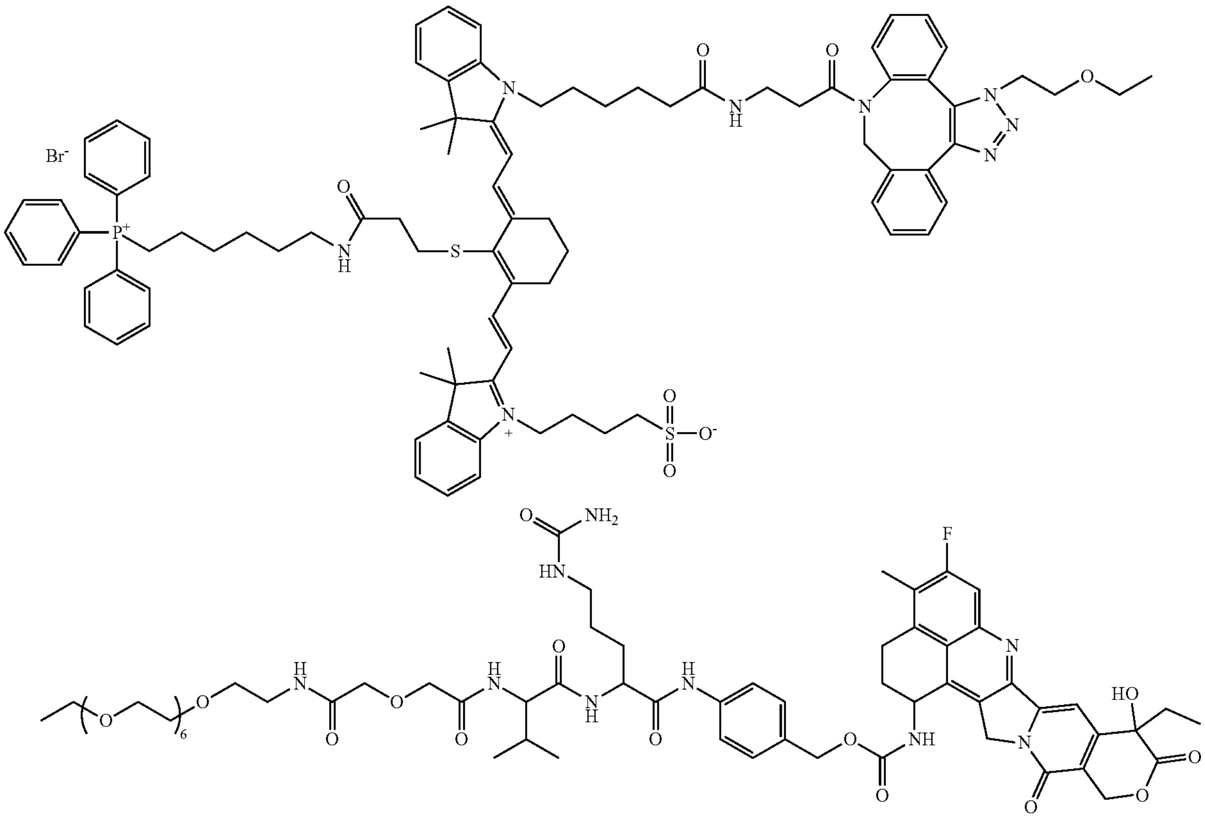
CXXIX
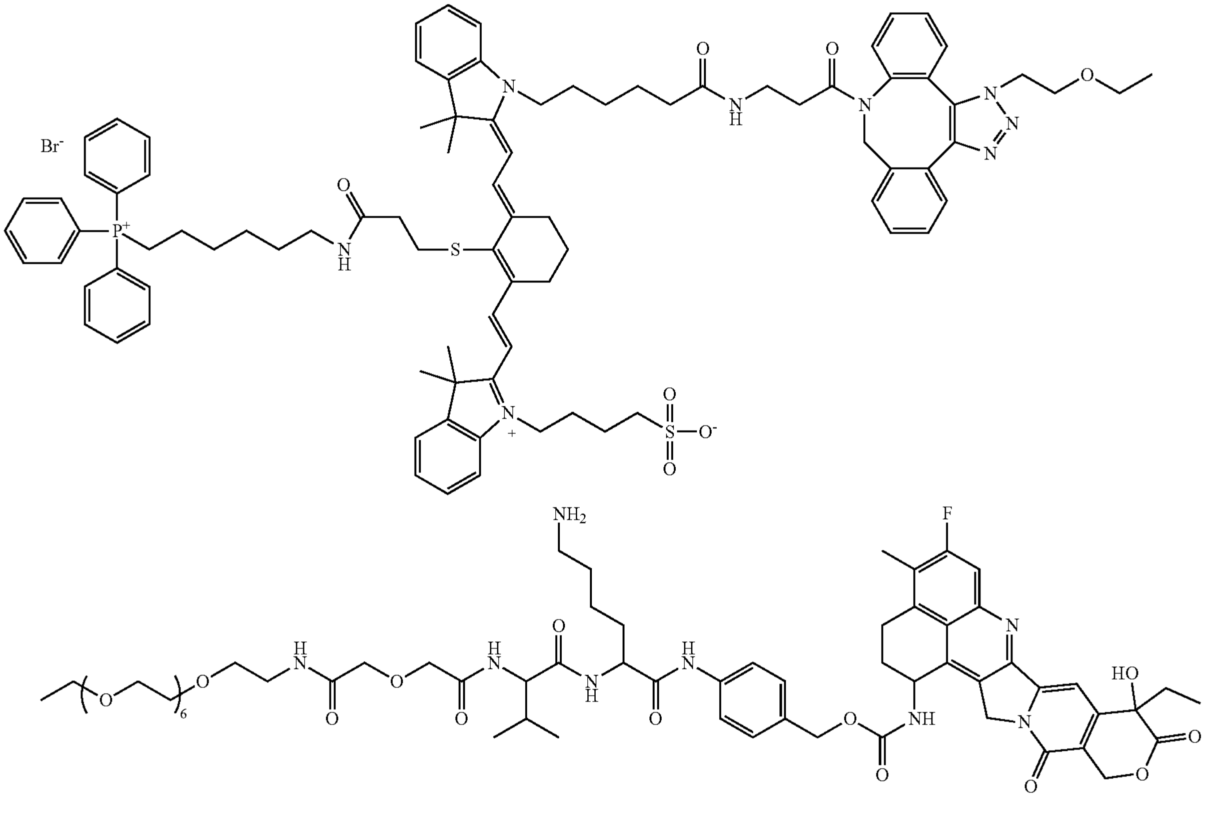

As to particular embodiments, as stated above, the linker can also be modified to have a mitochondria-targeting functionality, whereby such a modification may include the attachment of one or more lipophilic moieties and/or cationic moieties to the linker or the incorporation of one or more lipophilic moieties and/or cationic moieties into the linker.

Exemplary linkers having a mitochondria-targeting functional group and a cleavable peptide portion which may be useful with the present invention are shown in Formulas CXXX through CXXXII.

CXXX

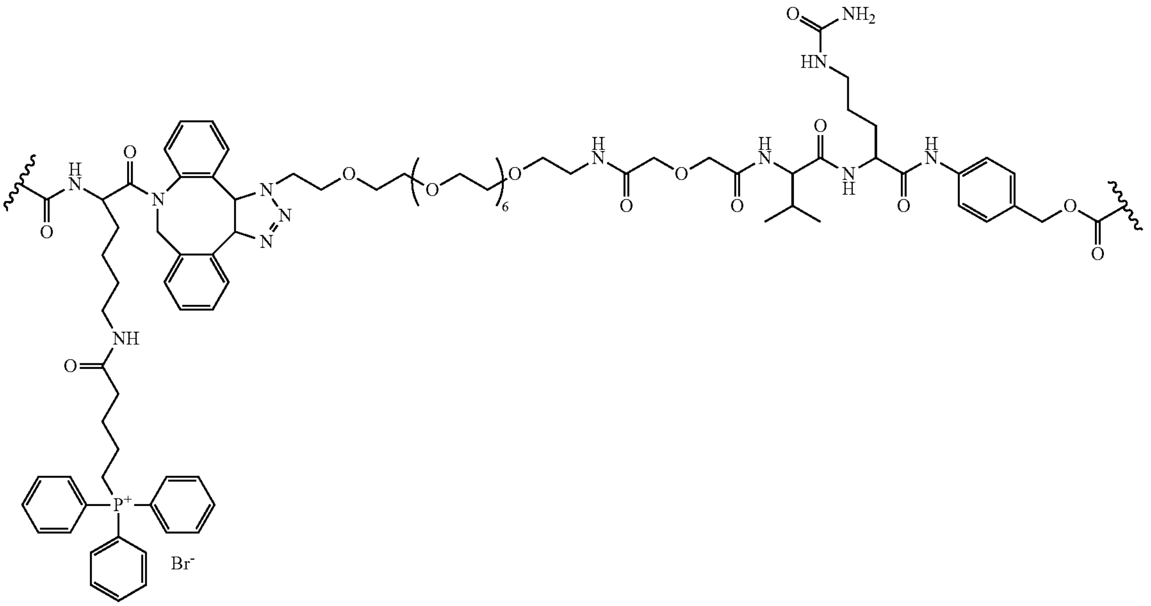

CXXXI

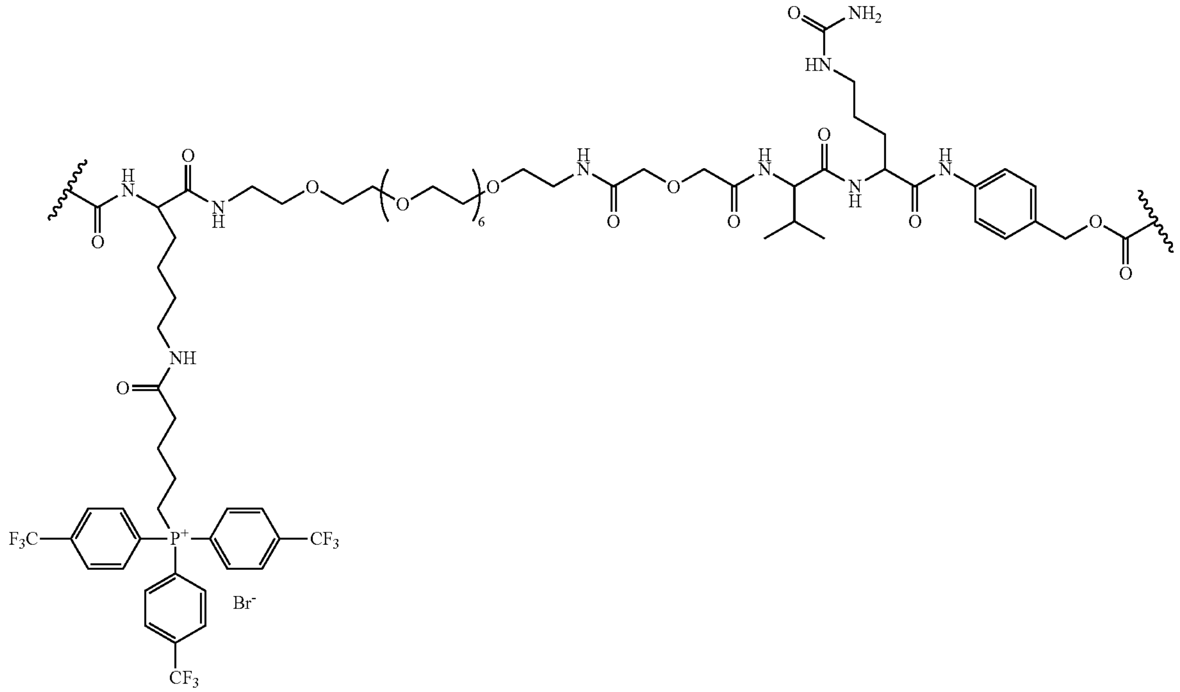

-continued
CXXXII
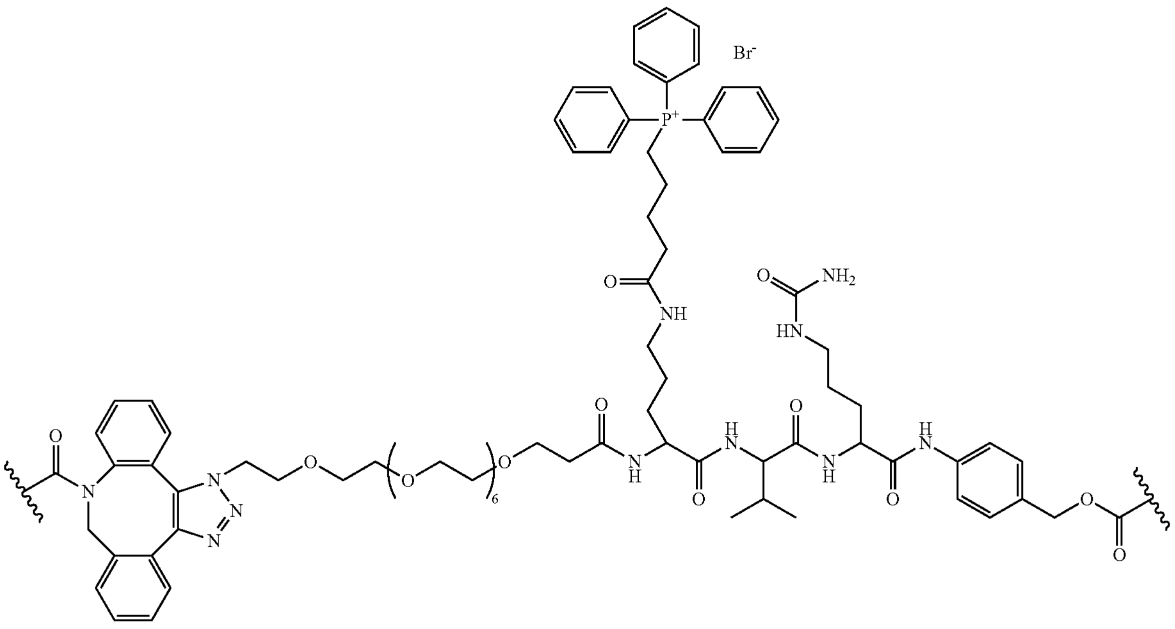
An exemplary conjugate comprising a tumor-targeting NIR dye, a linker having (i) a mitochondria-targeting functional group and specifically, the linker shown in Formula CXXXII, and (ii) a cleavable peptide portion coupled to a chemotherapeutic agent which may be useful with the present invention is shown in Formulas CXXXIII.
CXXXIII
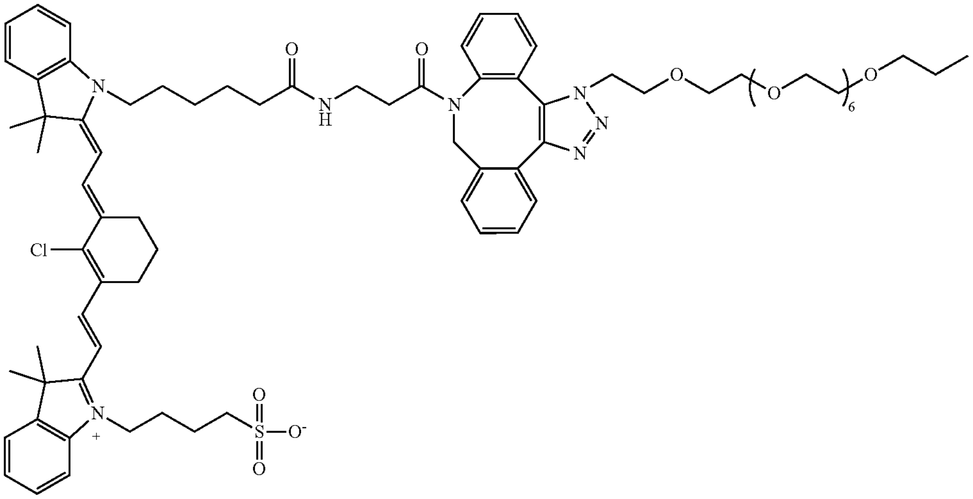

-continued

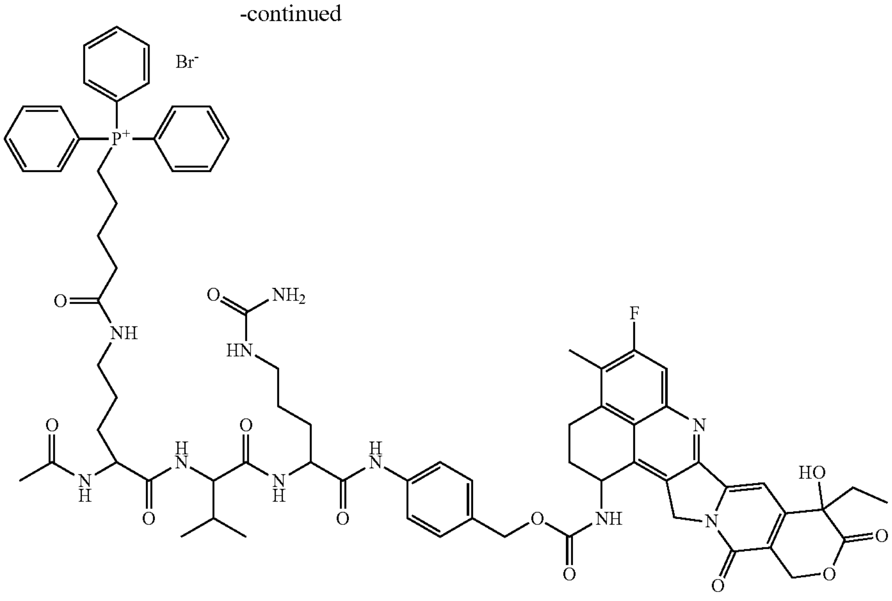

As to particular embodiments, the tumor-targeting NIR dye can form a complex with albumin and such conjugates may be useful for NIR bioimaging, as albumin binding can enhance the brightness, photostability, and biosafety of the dye and correspondingly, enable long-term, high resolution imaging in the NIR window.

As to particular embodiments, the dye can covalently interact with albumin via a meso-chloride which may form a covalent adduct with albumin's free thiol.

Exemplary conjugates comprising a tumor-targeting NIR dye having a meso-chloride coupled to a chemotherapeutic agent via a linker including a cleavable peptide portion which may be useful with the present invention are shown in Formulas CXXXIV and CXXXV.

CXXXIV

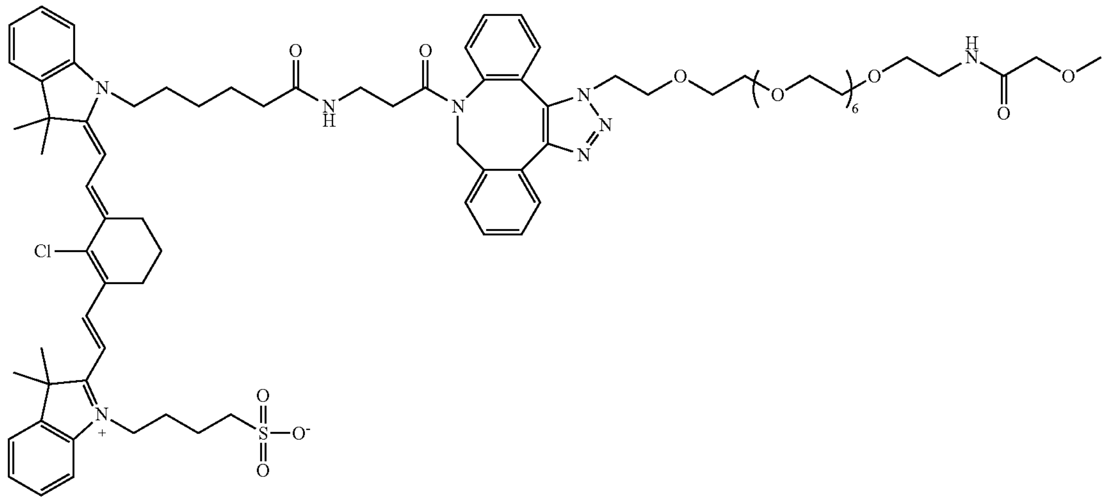

-continued

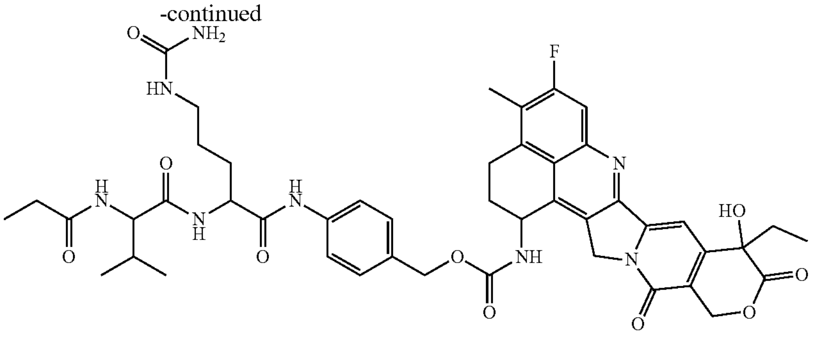

CXXXV

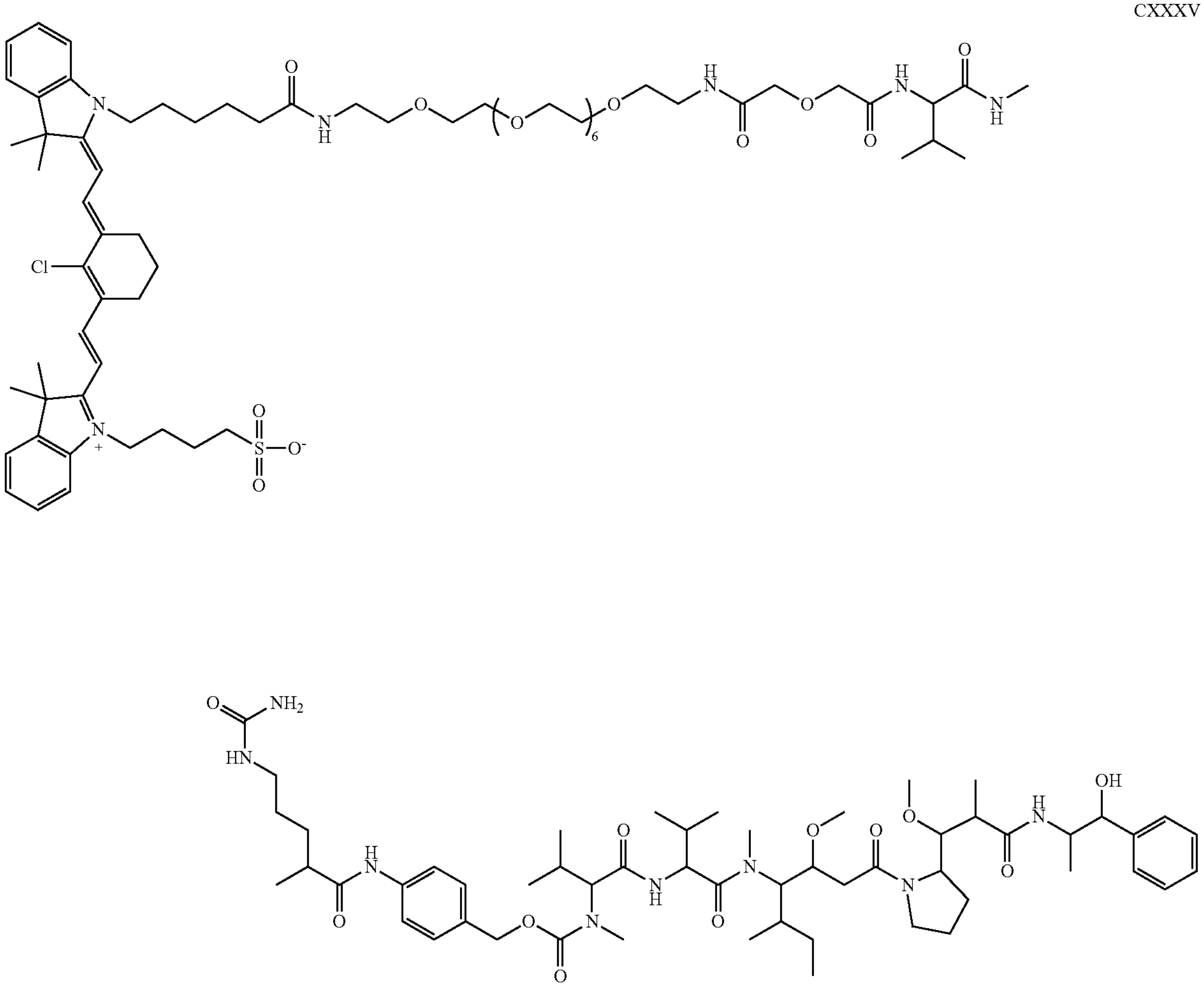

As to other particular embodiments, the dye can noncovalently interact with albumin, such as via electrostatic interactions, hydrophobic interactions, or hydrogen bonding.

Figure 19A:
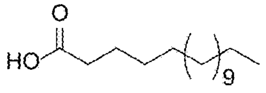
FIG. 19A shows an illustrative example of a functional group which can facilitate noncovalent interactions between a tumor-targeting NIR dye and albumin and thus may be useful with the present invention.
Figure 19B:
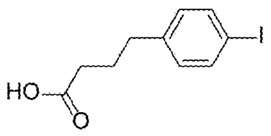
FIG. 19B shows an illustrative example of a functional group which can facilitate noncovalent interactions between a tumor-targeting NIR dye and albumin and thus may be useful with the present invention.
Figure 21A:
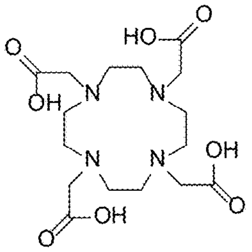
FIG. 21A shows an illustrative example of a chelator which may be useful with the present invention.
Figure 21B:
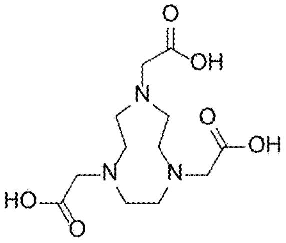
FIG. 21B shows an illustrative example of a chelator which may be useful with the present invention.
Figure 21C:
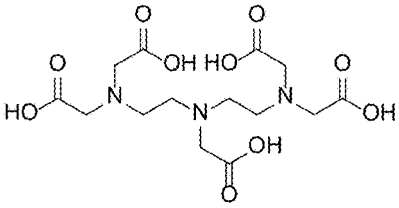
FIG. 21C shows an illustrative example of a chelator which may be useful with the present invention.
Figure 21D:
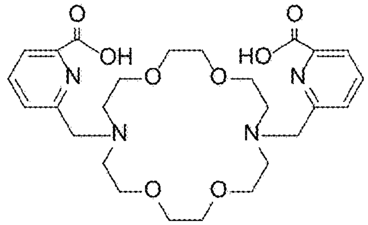
FIG. 21D shows an illustrative example of a chelator which may be useful with the present invention.

As illustrative examples, functional groups which may facilitate noncovalent interactions between the dye and albumin and thus can be useful with the present invention may include those shown in FIGS. 19A and 19B.

An exemplary conjugate comprising a tumor-targeting NIR dye having a fatty acid functional group coupled to a chemotherapeutic agent via a linker including a cleavable peptide portion which may be useful with the present invention is shown in Formula CXXXVI.

CXXXVI
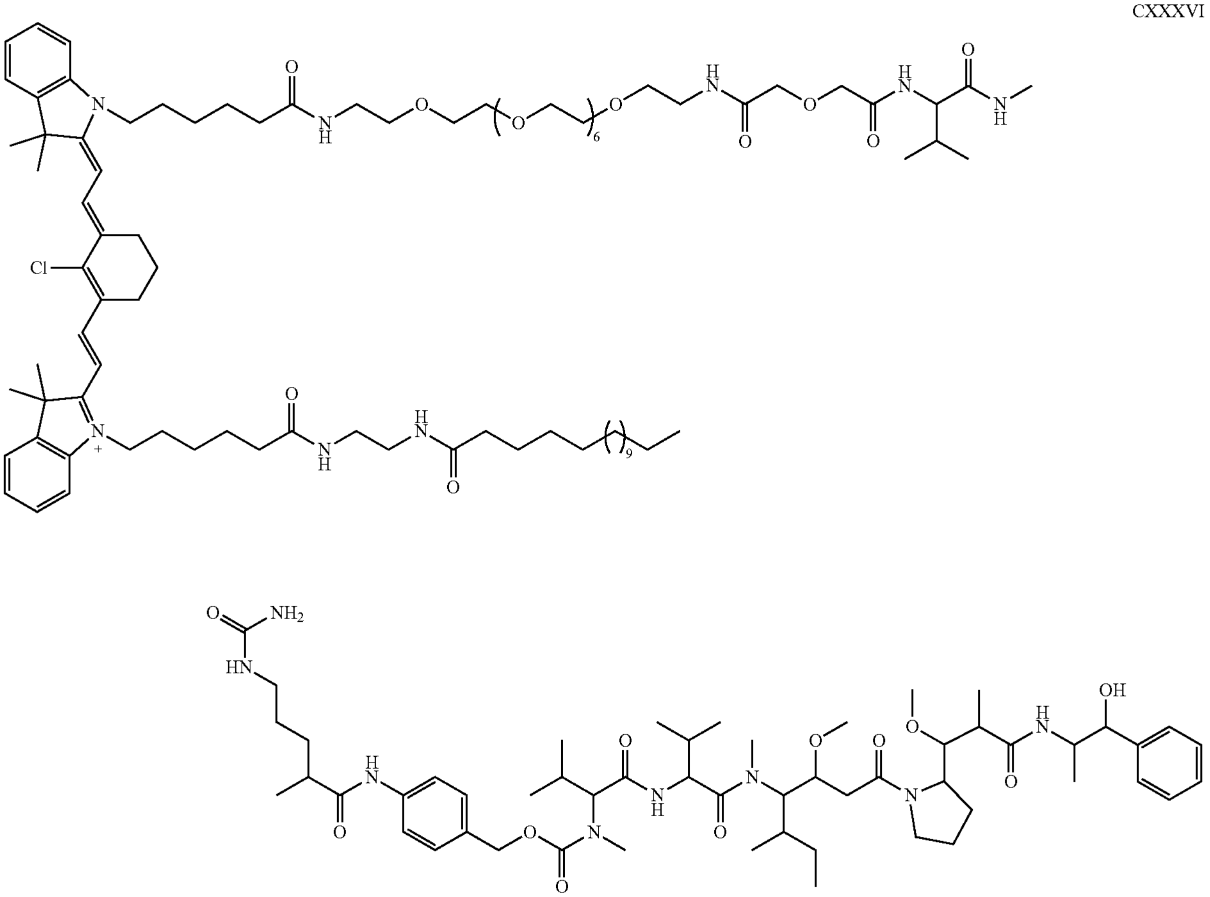
Exemplary conjugates comprising a tumor-targeting NIR dye having a p-iodophenyl butyric acid functional group coupled to a chemotherapeutic agent via a linker including a cleavable peptide portion which may be useful with the present invention are shown in Formulas CXXXVII and CXXXVIII.
CXXXVII
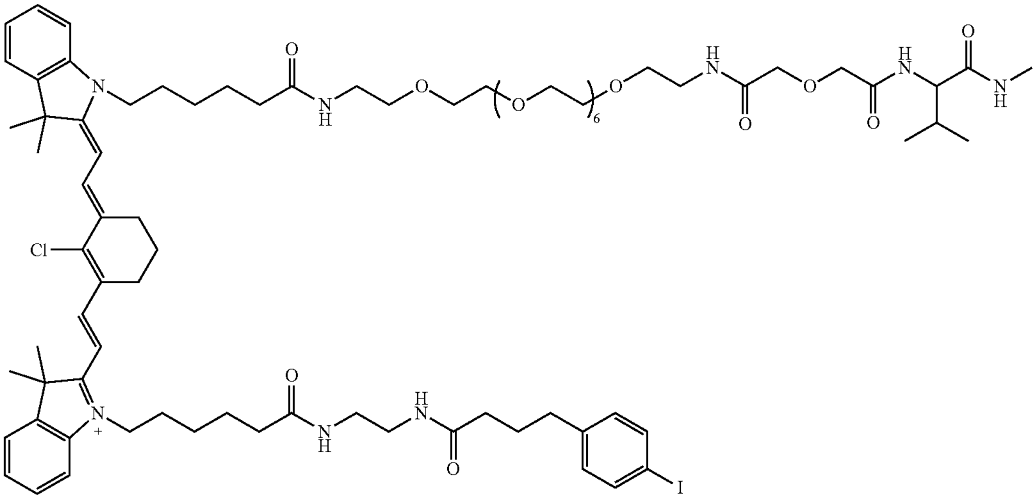

-continued

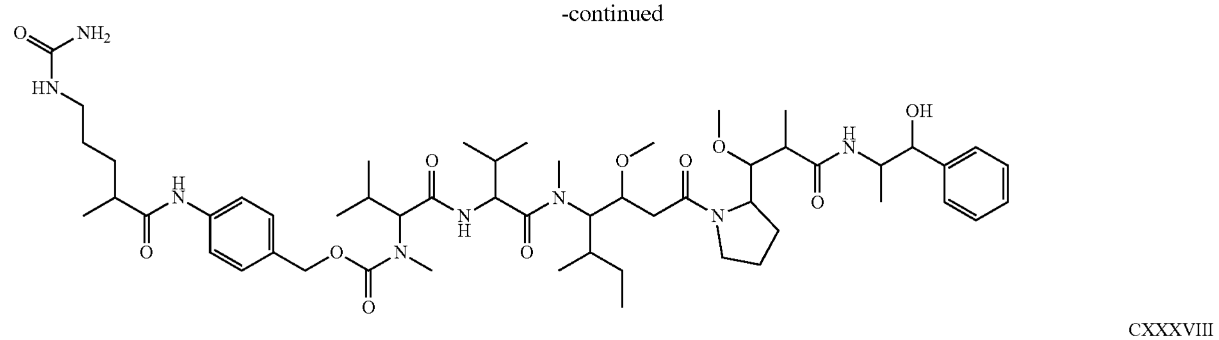

CXXXVIII

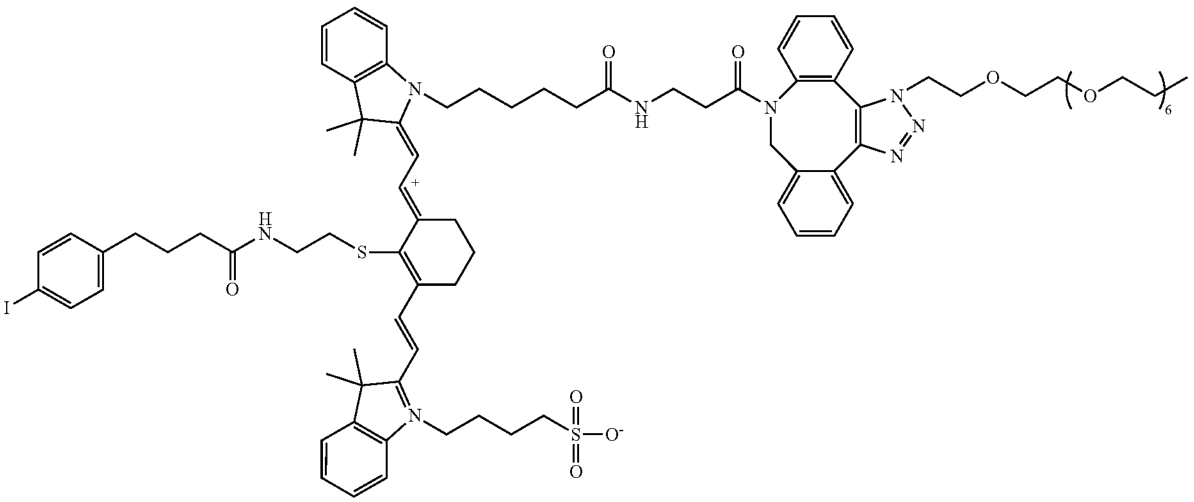

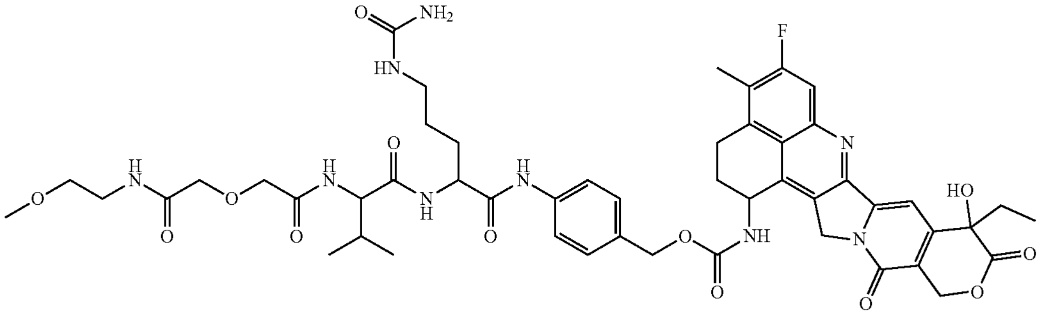

Figure 20:
FIG. 20 shows an embodiment of the inventive conjugate.

Now referring primarily to FIG. 20, as stated above, the present invention can combine a tumor-targeting NIR dye with various therapeutic agents to create conjugates for the treatment of different cancers, whereby these conjugates may be delivered directly to a target tumor cell population. As to particular embodiments, a dye can be coupled to (for example via conjugation) a payload comprising a radioisotope which may release alpha particles, beta particles, or gamma rays, whereby the dye functions to direct the conjugate and correspondingly, the radioisotope, to a target tumor cell population; this may be in contrast to conventional radiation therapy which can cause significant adverse side effects.

Exemplary radioisotopes which may be useful with the present invention include iodine-131 ($^{131}I$), lutetium-177 ($^{177}Lu$), yttrium-90 ($^{90}Y$), radium-223 ($^{223}Ra$), actinium-225 ($^{225}Ac$), strontium-89 ($^{89}Sr$), samarium-153 ($^{153}Sm$), rhenium-186 ($^{186}Re$), rhenium-188 ($^{188}Re$), copper-67 ($^{67}Cu$), astatine-211 ($^{211}At$), terbium-161 ($^{161}Tb$), gallium-68 ($^{68}Ga$), americium-241 ($^{241}Am$), and plutonium-239 ($^{239}Pu$).

As to particular embodiments, a chelator can be coupled to the radioisotope to form a stable complex; following, the dye can be coupled to the chelator to form the present conjugate including the radioisotope. In practice, due to the short lifespan of radioisotopes, the dye can typically be coupled to the chelator first followed by coupling of the radioisotope to form the present conjugate.

Exemplary chelators which may be useful with the present invention include those shown in FIGS. 21A through 21D, whereby DOTA can be used with $^{225}Ac$ and $^{177}Lu$, NOTA can be used with $^{68}Ga$ and $^{90}Y$, DTPA can be used with $^{241}Am$ and $^{239}Pu$, and macropa can be used with $^{225}Ac$ and $^{223}Ra$.

The dye can be coupled to the chelator to form the present conjugate including the radioisotope via a linker, whereby the linker need not be cleavable. As to particular embodiments, the linker can include a solubility-modifying portion. As to particular embodiments, the linker can include a hydrophilic portion. As to particular embodiments, an illustrative example of a linker including a hydrophilic portion which may be useful with the present invention includes PEG with various chain lengths.

Exemplary conjugates comprising a tumor-targeting NIR dye coupled to a radioisotope via a linker which may be useful with the present invention are shown in Formulas CXXXIX through CXLIV.
CXXXIX
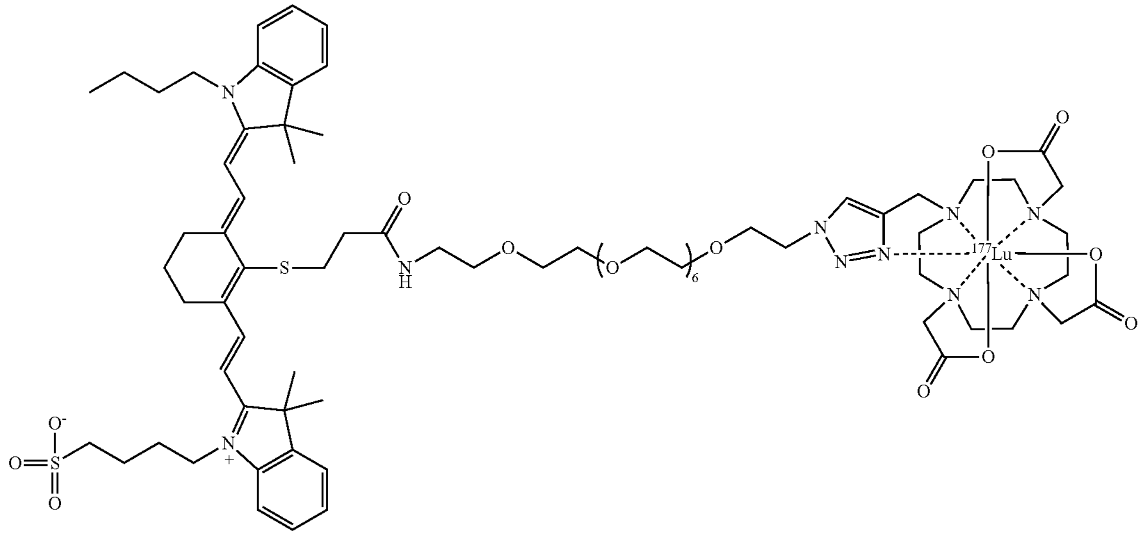
CXL
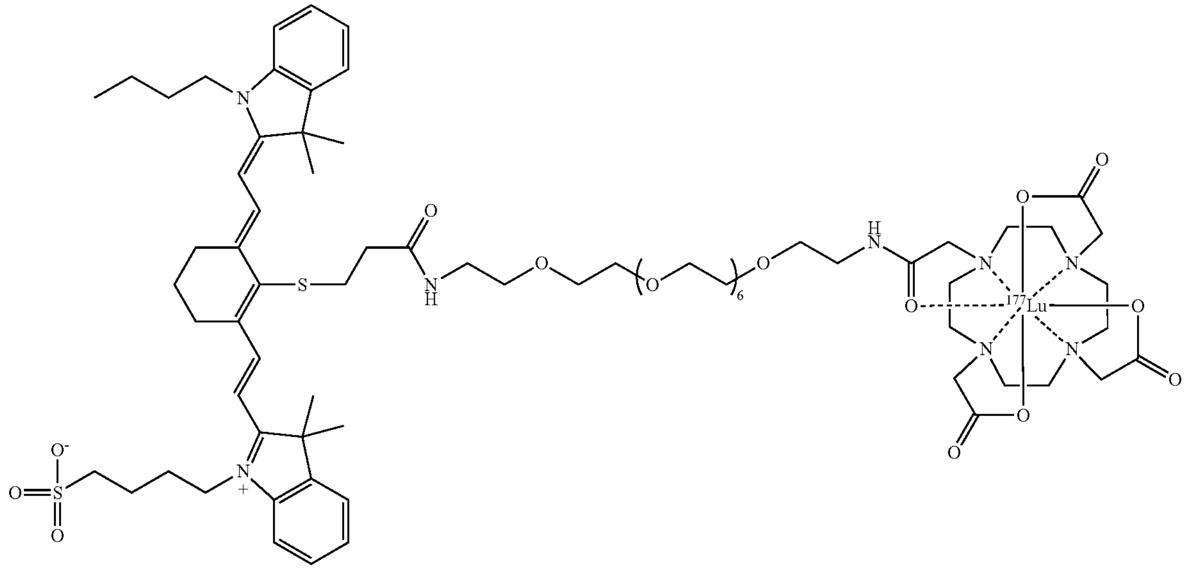

-continued
CXLI
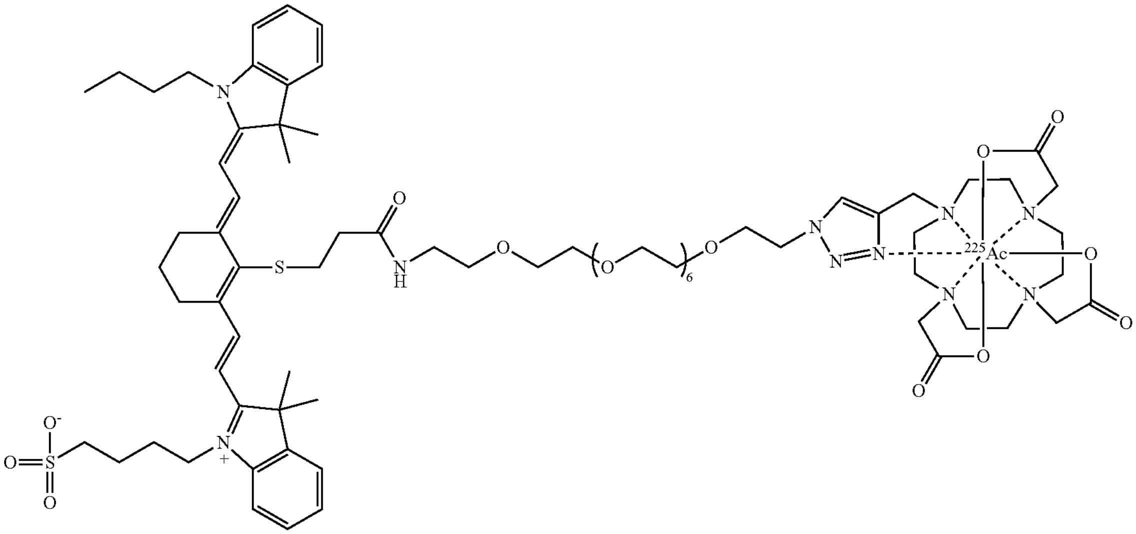
CXLII
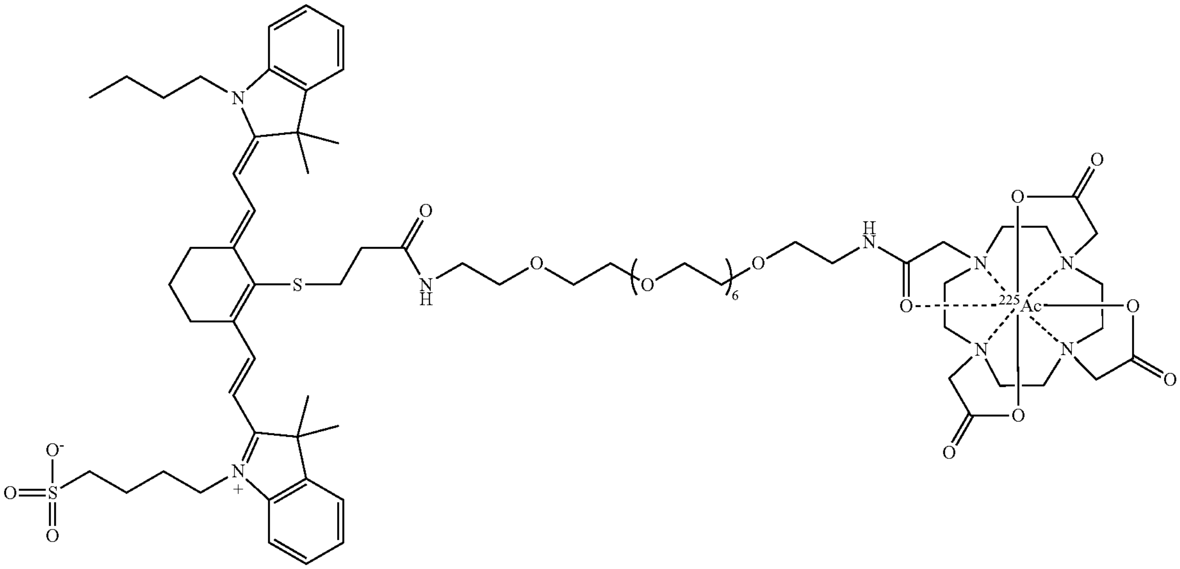
CXLIII
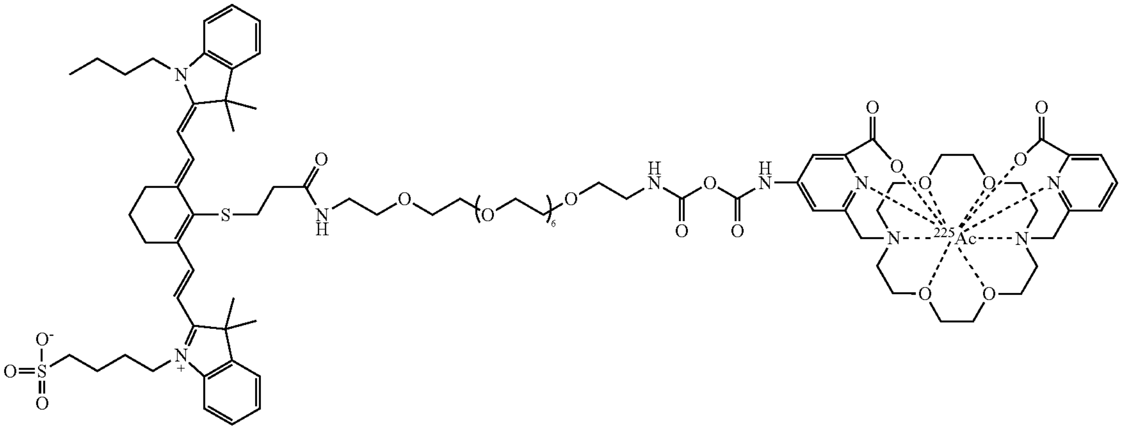

-continued
CXLIV
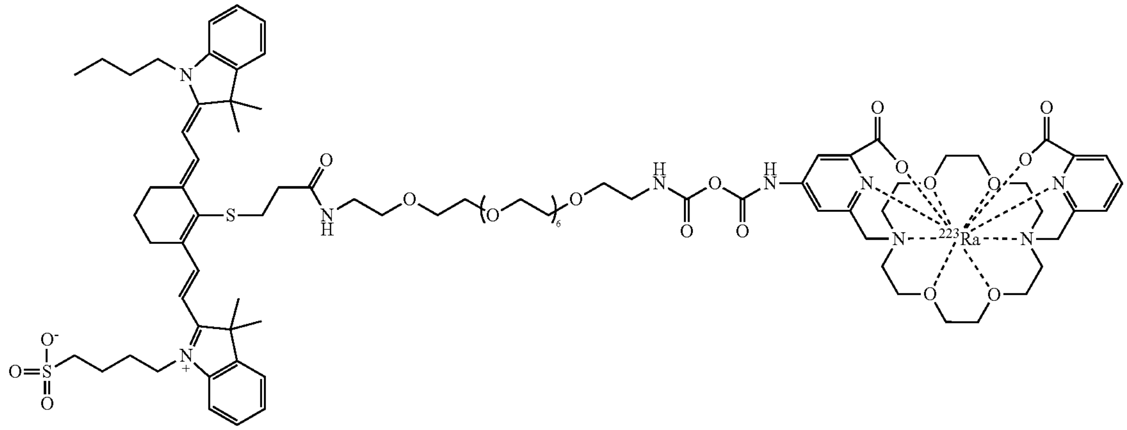
Exemplary conjugates comprising a tumor-targeting NIR dye coupled to (i) a radioisotope via a linker and (ii) a chemotherapeutic agent via a linker including a cleavable peptide portion which may be useful with the present invention are shown in Formulas CXLV and CXLVI.
CXLV
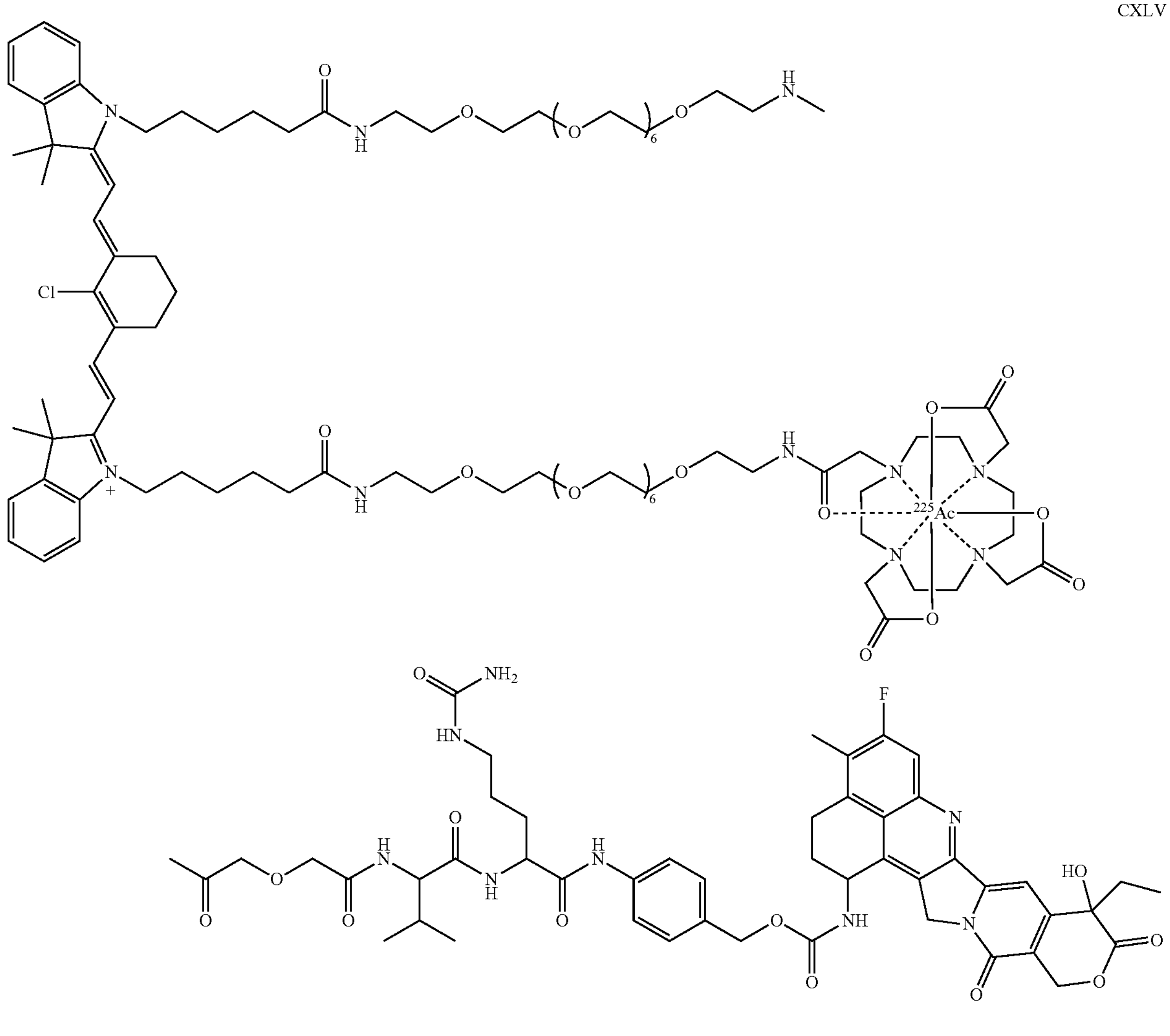

-continued

CXLVI

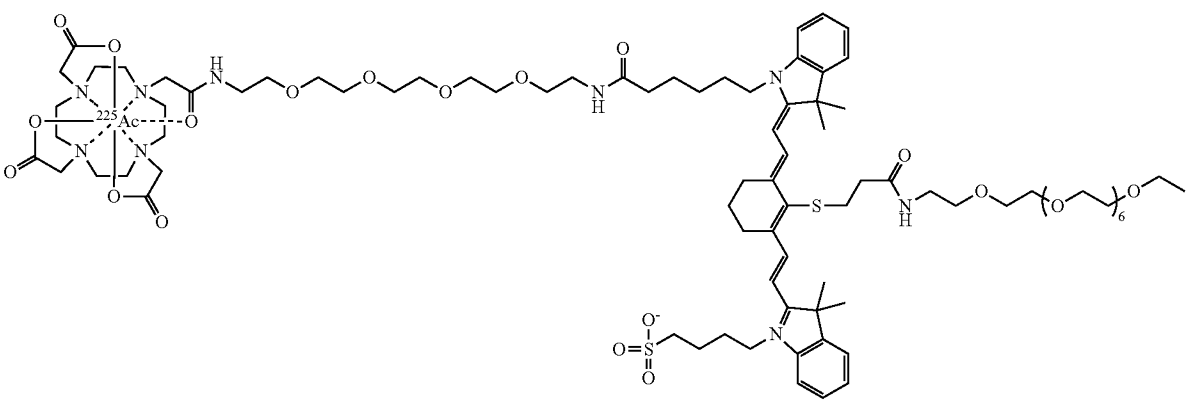

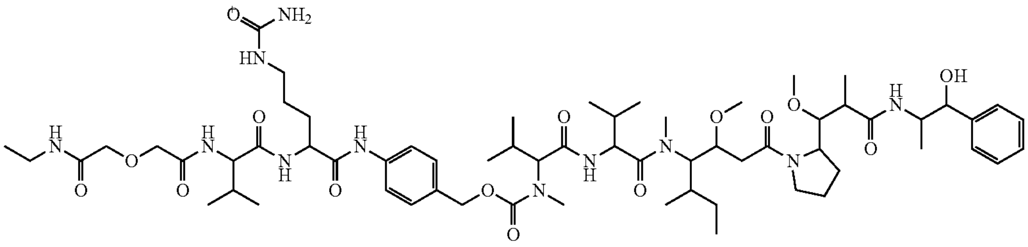

Figure 22:
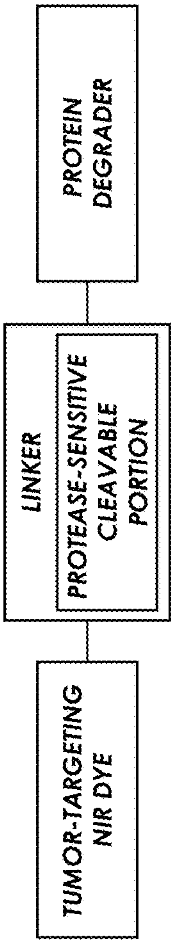
FIG. 22 shows an embodiment of the inventive conjugate.

Now referring primarily to FIG. 22, as stated above, the present invention can combine a tumor-targeting NIR dye with various therapeutic agents to create conjugates for the treatment of different cancers, whereby these conjugates may be delivered directly to a target tumor cell population. As to particular embodiments, a dye can be coupled to (for example via conjugation) a payload comprising a small molecule protein degrader, whereby the dye functions to direct the conjugate and correspondingly, the protein degrader, to a target tumor cell population; this may be in contrast to conventional protein degraders which can cause significant adverse side effects.

A protein degrader can induce degradation of a target disease-causing protein, such as by locating said protein proximate E3 ubiquitin ligase which tags said protein with ubiquitin. Upon ubiquitination, the protein can be recognized by a proteasome for degradation into small peptides and amino acids.

Figure 23A:
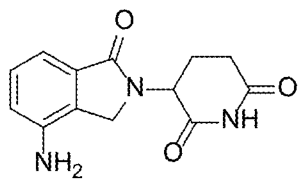
FIG. 23A shows an illustrative example of a molecular glue which may be useful with the present invention.
Figure 23B:
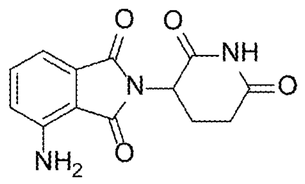
FIG. 23B shows an illustrative example of a molecular glue which may be useful with the present invention.
Figure 23C:
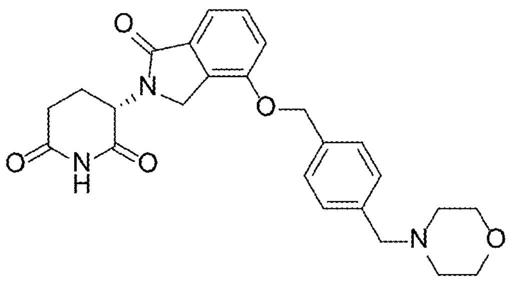
FIG. 23C shows an illustrative example of a molecular glue which may be useful with the present invention.

Exemplary small molecule protein degraders which may be useful with the present invention include proteolysis-targeting chimeras (PROTACs) and molecular glues, whereby examples of the latter can include lenalidomide, pomalidomide, and iberdomide as shown in FIGS. 23A through 23C.

Exemplary conjugates comprising a tumor-targeting NIR dye coupled to a molecular glue via a linker including a cleavable peptide portion which may be useful with the present invention are shown in Formulas CXL VII through CL.

CXLVII

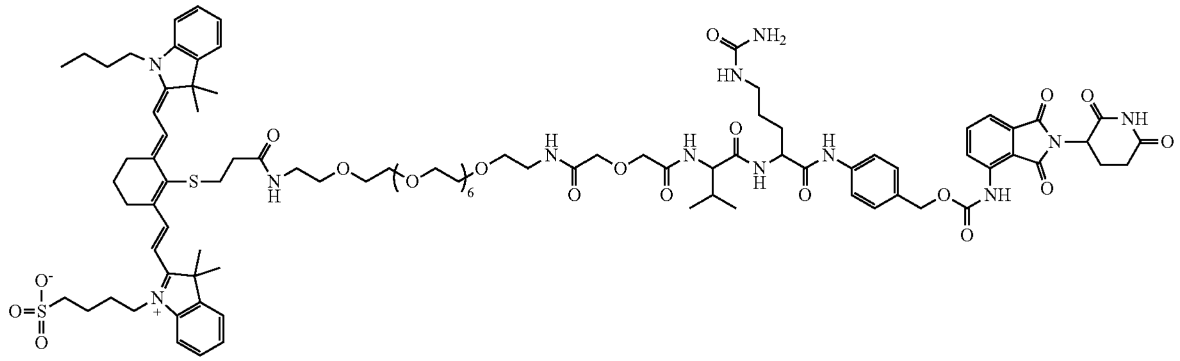

-continued

CXLVIII

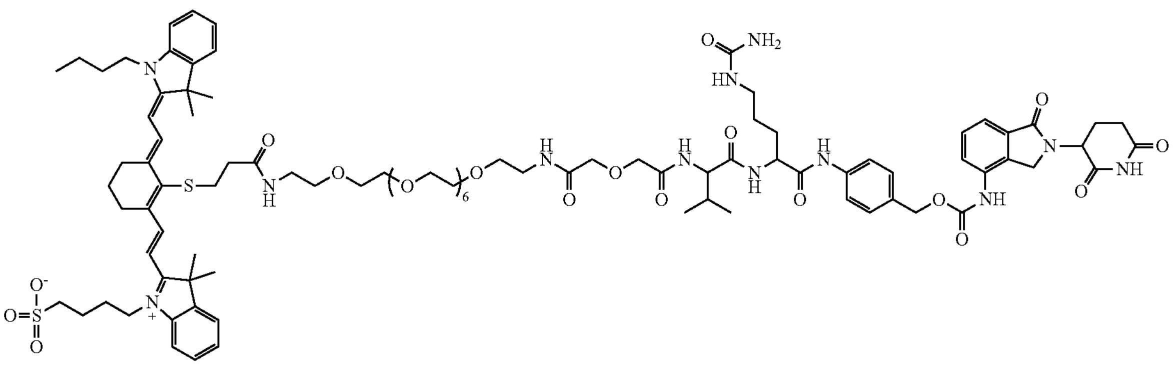

CXLIX

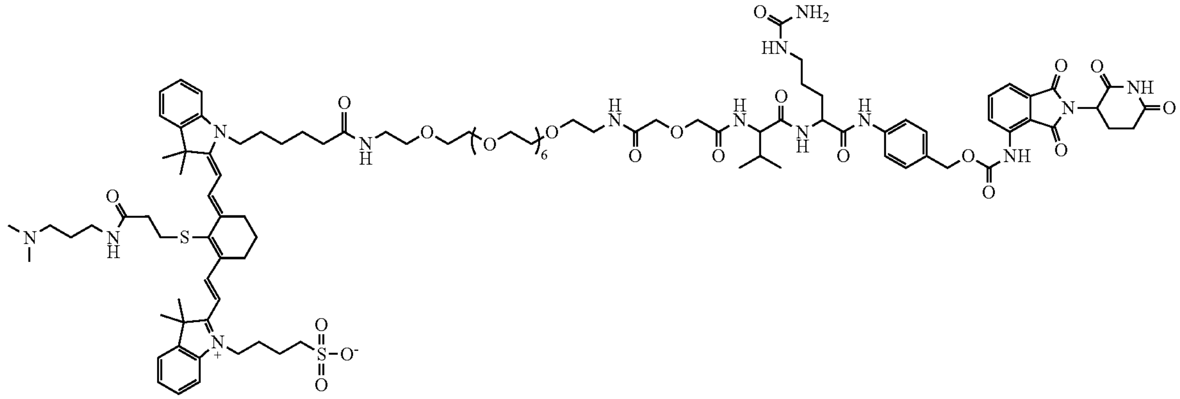

CL

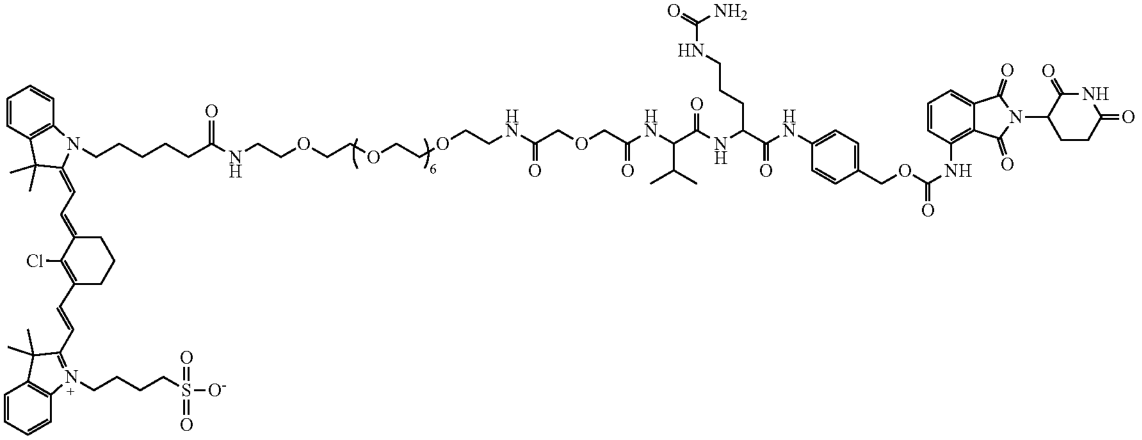

The inventive conjugate structures are shown, described, and claimed without specifying the three-dimensional arrangement at any stereocenter and are intended to be construed as covering all stereoisomers, conformational isomers, and tautomers. Without sacrificing the breadth of the foregoing, particular embodiments of the inventive conjugate structures shown, described, and claimed can include steric features, and specifically can include one or more of the steric features of (i) the protease-sensitive cleavable portions shown in FIGS. 8A through 8N, (ii) the chemotherapeutic agents shown in FIGS. 2A through 4M, and/or (iii) the molecular glues shown in FIGS. 23A through 23C, whereby each of these steric features shown in the Figures is hereby incorporated by reference into each conjugate structure in the description and the claims herein.

Synthesis

Now referring primarily to FIG. 24, the tumor-targeting NIR dye can be conjugated to DBCO as follows: 1-hydroxybenzotriazole (HOBt) hydrate (2 eq.), 1-ethyl-3-(3-dimethylaminopropyl) carbodiimide hydrochloride (EDC·HCl) (1.6 eq.), and DBCO amine (1.0 eq.) can be added to a solution of dye (1 eq.) in dry dimethylformamide (DMF), such as the dye shown in Formula VI, and the mixture may be stirred for 20 hours (h) at room temperature. The mixture can be concentrated in a vacuum, and the residue may be suspended in dichloromethane (DCM). The mixture can be washed with saturated ammonium chloride ($NH_4Cl$) and brine, dried over sodium sulfate ($Na_2SO_4$), and concentrated. The crude product can be purified with a silicon dioxide ($SiO_2$) column (using a mixture of DCM and methanol (MeOH)) to yield the final product.

Now referring primarily to FIG. 25, the tumor-targeting NIR dye can be conjugated to PEG as follows.

Step 1: HOBt hydrate (1.2 eq.) and EDC·HCl (1.2 eq.) can be added to a solution of dye (1 eq.) in dry DMF, such as the dye shown in Formula VI. Azido-PEG12-amine (1 eq.) can be added and the mixture may be stirred for 20 h at room temperature. The mixture can be concentrated in a vacuum, and the residue may be suspended in DCM. The mixture can be washed with saturated $NH_4Cl$ and brine, dried over $Na_2SO_4$, and concentrated. The crude product can be purified with a $SiO_2$ column (using a mixture of DCM and methanol MeOH) to yield azide-functionalized NIR dye.

Step 2: the product obtained from Step 1 (1 eq.) in tetrahydrofuran (THF), triphenylphosphine (2 eq.), and water (10 eq.) can be combined, and the mixture may be gently heated for a few hours. The reaction can be monitored via thin layer chromatography (TLC). After cooling the mixture to room temperature, DCM can be added and the organic layer may be washed with saline and dried over $Na_2SO_4$. The crude product can be purified with a $SiO_2$ column to yield the final product.

Figure 26:
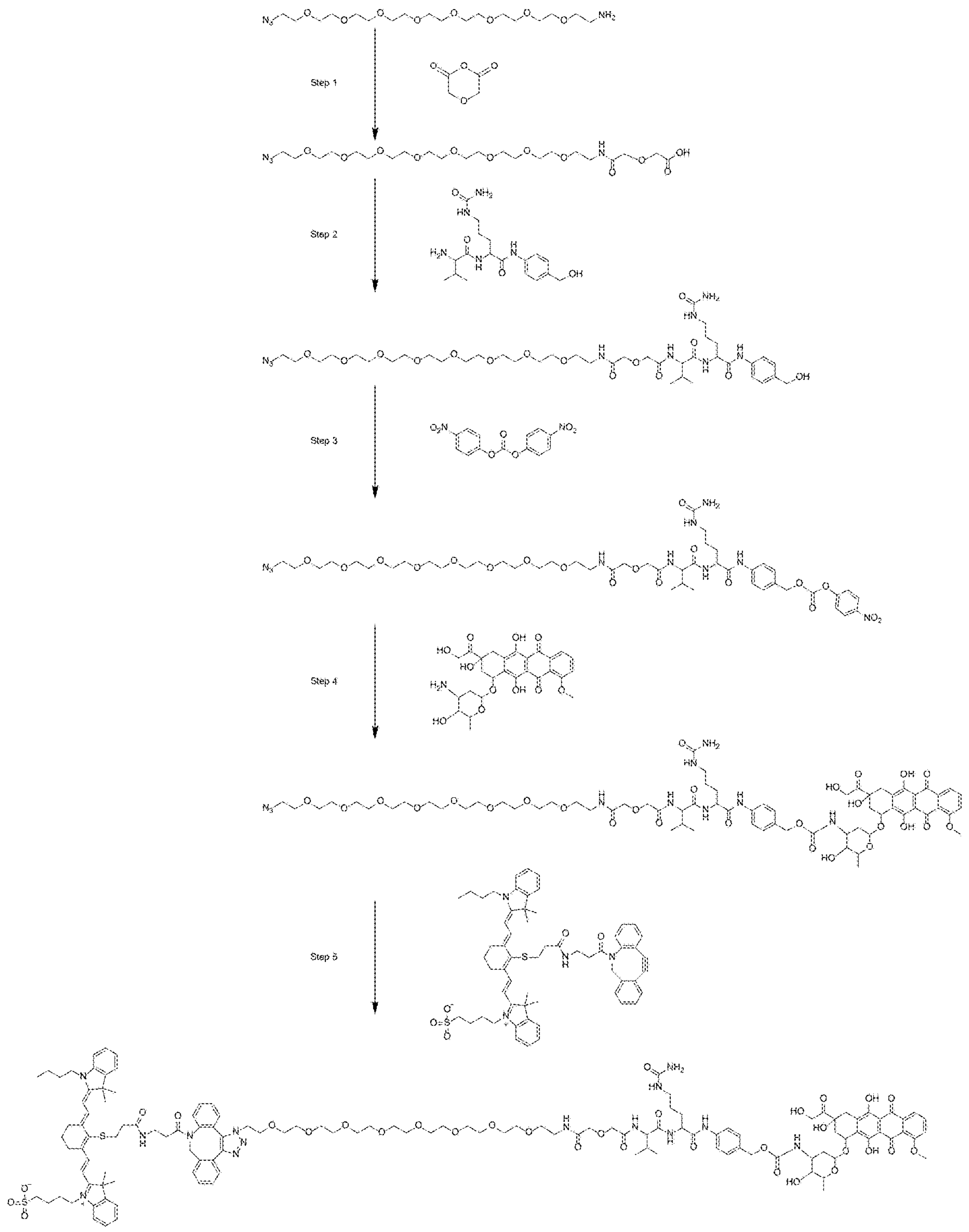
FIG. 26 shows an exemplary synthesis of the conjugate shown in Formula XXII.

Now referring primarily to FIG. 26, the conjugate shown in Formula XXII can be synthesized as follows.

Step 1: a solution of $N_3$-$(PEG)_8$-$NH_2$ (1 eq) in DCM and diglycolic anhydride (1.5 eq) can be combined, and the mixture may be stirred overnight. The mixture can be concentrated to provide a yellowish residue which may be dissolved in water. The product can be isolated from the aqueous phase by continuous extraction with DCM overnight.

Step 2: the product obtained from Step 1 (1.1 eq), valine-citrulline-PABA (1,000 mg, 2.635 mmol, 1 eq) dissolved in DMF, N,N-diisopropylethylamine (DIPEA) (1.1 eq), and hexafluorophosphate benzotriazole tetramethyl uronium (HBTU) (1.1 eq) can be combined, and the mixture may be stirred overnight. The crude product can be purified with a $SiO_2$ column (using a mixture of DCM and MeOH) to yield the product.

Step 3: the product obtained from Step 2 (1.0 eq.), bis(4-nitrophenyl) carbonate (1.0 eq.), and DIPEA (4.0 eq.) in DMF can be combined, and the mixture may be stirred for 1 h at room temperature. The mixture can be poured into ice-cold ether, and the filtrate may be collected via centrifugation and dried under vacuum to yield the product (a yellowish powder).

Step 4: the product obtained from Step 3 (1.2 eq.) in dimethyl sulfoxide (DMSO), doxorubicin (1.0 eq.) in DMSO, and HOBt hydrate in DMSO (1.0 eq.) can be combined. DIPEA (3.0 eq.) can be added, and the mixture may be stirred for 3 h at room temperature. After consumption of the doxorubicin starting material (monitored via TLC), a mixture of acetonitrile and water can be added. The crude product can be purified via preparative high-performance liquid chromatography (HPLC) to yield the product.

Figure 24:
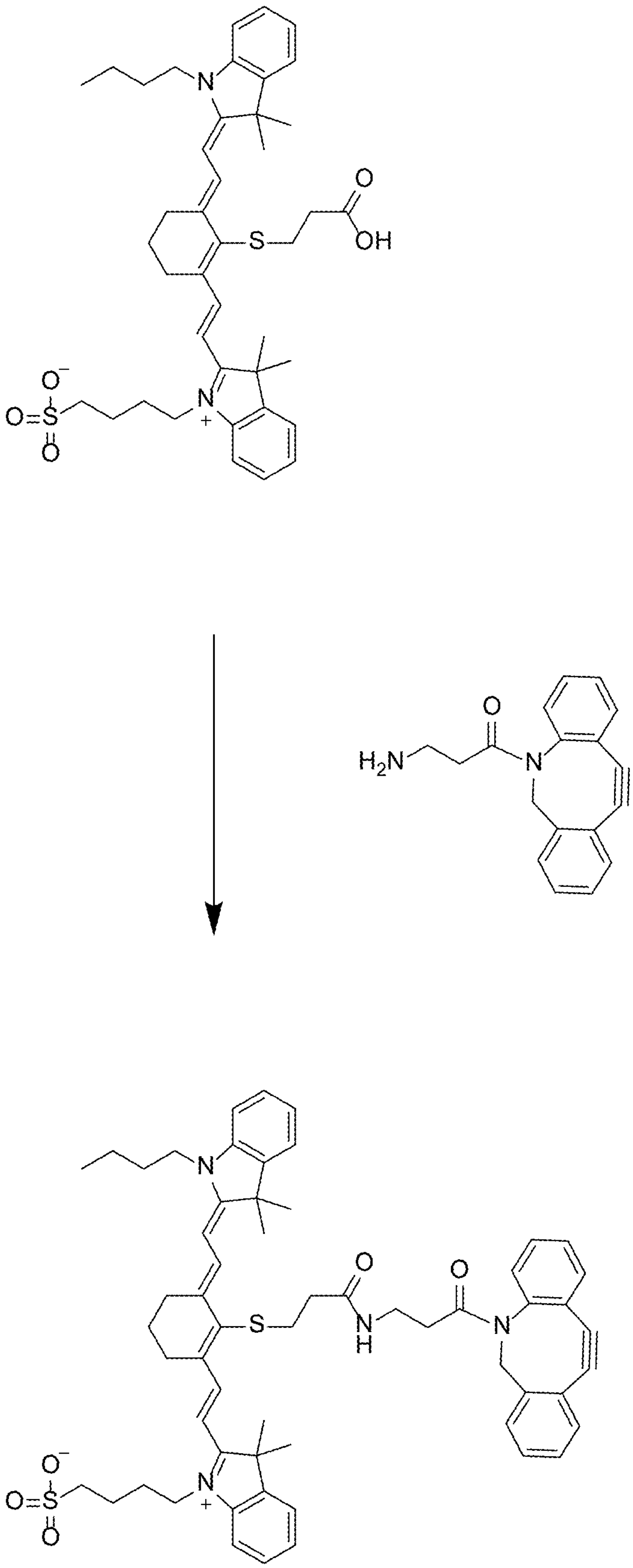
FIG. 24 shows conjugation of a tumor-targeting NIR dye to DBCO.

Step 5: the product obtained from Step 4 (1.5 eq.) in a mixture of acetonitrile and water and DBCO-functionalized NIR dye (1 eq.), such as that synthesized in FIG. 24, can be combined, and the mixture may be stirred overnight at 4° C. The mixture can be concentrated in a vacuum, and the crude product may be purified with a $SiO_2$ column (using a mixture of DCM and MeOH) to yield the conjugate shown in Formula XXII.

Figure 27:
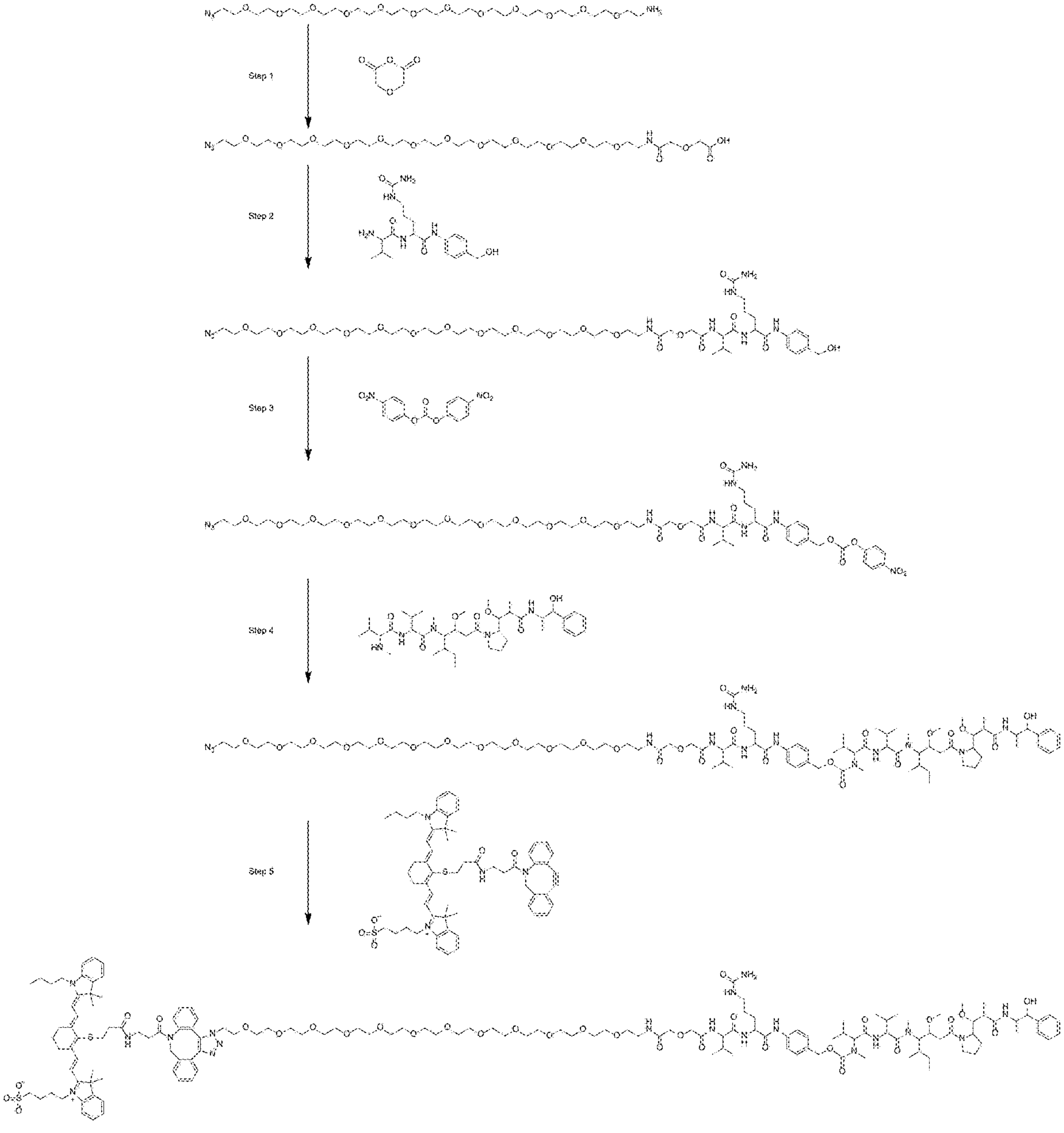
FIG. 27 shows an exemplary synthesis of the conjugate shown in Formula XXXIV.

Now referring primarily to FIG. 27, the conjugate shown in Formula XXXIV can be synthesized as follows.

Figure 25:
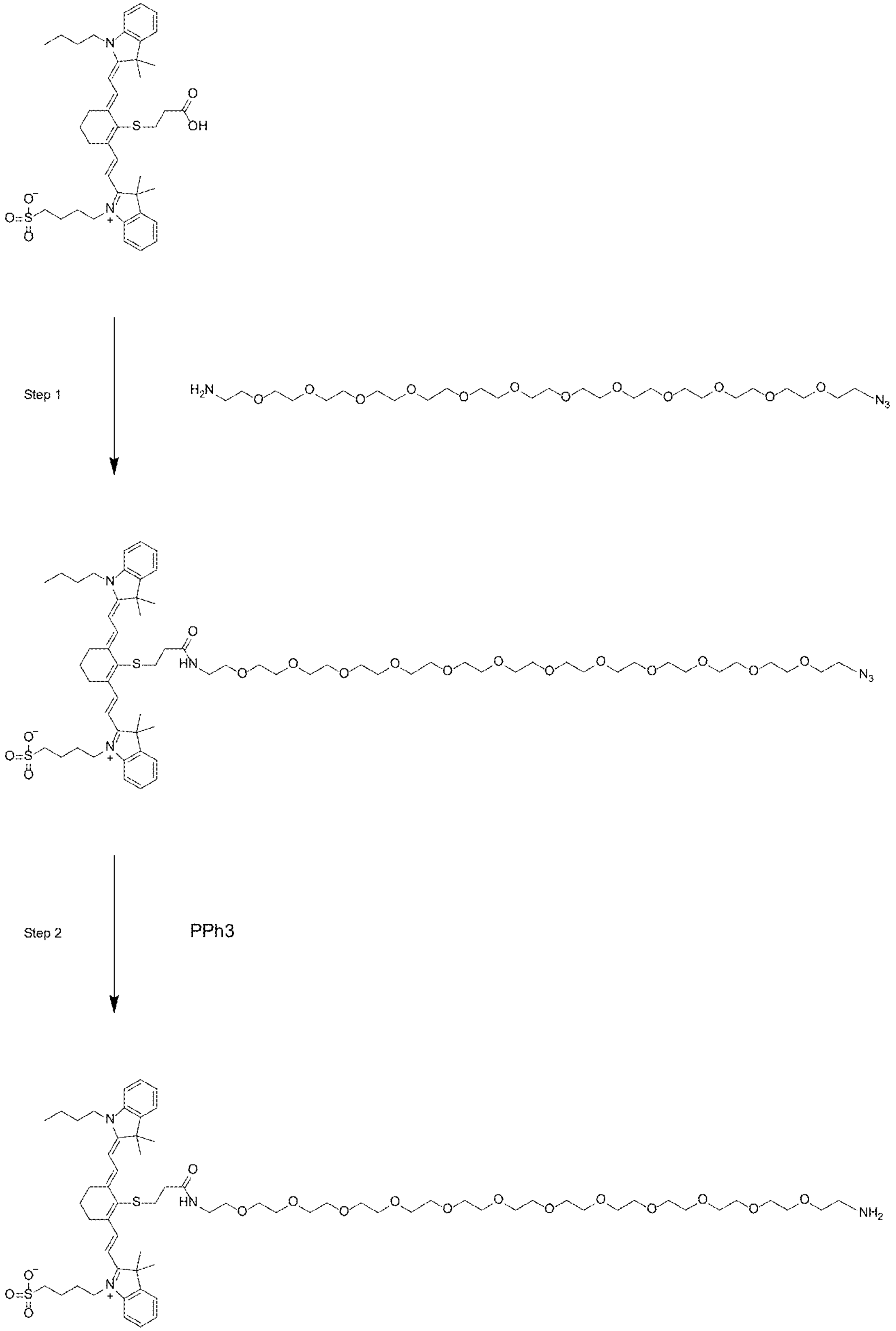
FIG. 25 shows conjugation of a tumor-targeting NIR dye to PEG.

Step 1: a solution of $N_3$-$(PEG)_{12}$-$NH_2$ (1 eq), such as that synthesized in FIG. 25, in DCM and diglycolic anhydride (1.5 eq) can be combined, and the mixture may be stirred overnight. The mixture can be concentrated to provide a yellowish residue. The product can be isolated from the aqueous phase by continuous extraction with DCM overnight.

Step 2: the product obtained from Step 1 (1.1 eq), valine-citrulline-PABA (1,000 mg, 2.635 mmol, 1 eq) dissolved in DMF, DIPEA (1.1 eq), and HBTU (1.1 eq) can be combined, and the mixture may be stirred overnight. The crude product can be purified with a $SiO_2$ column (using a mixture of DCM and MeOH) to yield the product.

Step 3: the product obtained from Step 2 (1.0 eq.), bis(4-nitrophenyl) carbonate (1.0 eq.), and DIPEA (4.0 eq.) in DMF can be combined, and the mixture may be stirred for 1 h at room temperature. The mixture can be poured into ice-cold ether, and the filtrate may be collected via centrifugation and dried under vacuum to yield the product (a yellowish powder).

Step 4: the product obtained from Step 3 (1.2 eq.) in DMSO, MMAE (1.0 eq.) in DMSO, and HOBt hydrate in DMSO (1.0 eq.) can be combined. DIPEA (3.0 eq.) can be added, and the mixture may be stirred for 3 h at room temperature. After consumption of the MMAE starting material (monitored via TLC), a mixture of acetonitrile and water can be added. The crude product can be purified via preparative HPLC to yield the product.

Step 5: the product obtained from Step 4 (1.5 eq.) in a mixture of acetonitrile and water and DBCO-functionalized NIR dye (1 eq.), such as that synthesized in FIG. 24, can be combined, and the mixture may be stirred overnight at 4° C. The mixture can be concentrated in a vacuum, and the crude product may be purified with a $SiO_2$ column (using a mixture of DCM and MeOH) to yield the conjugate shown in Formula XXXIV.

Figure 28:
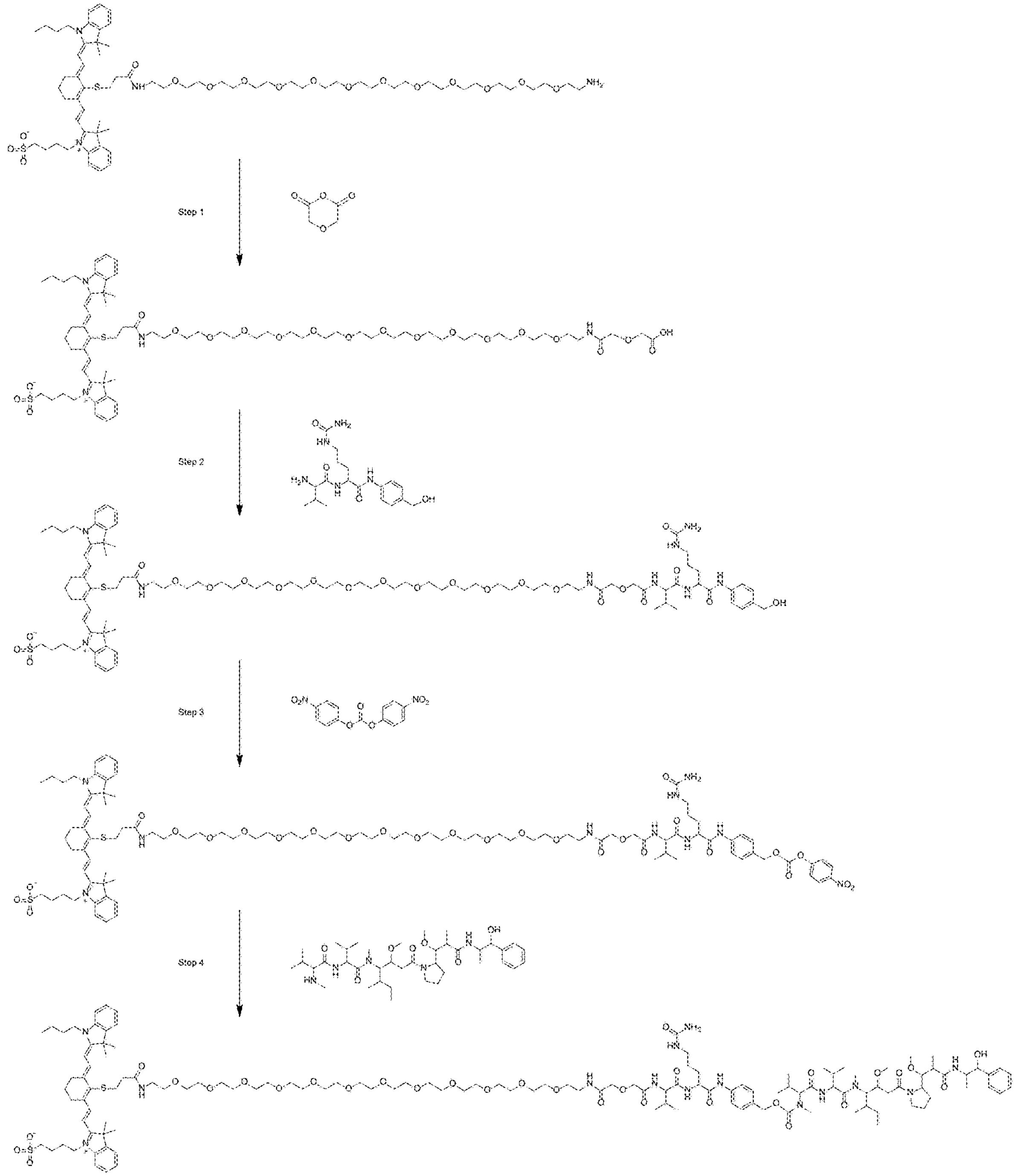
FIG. 28 shows an exemplary synthesis of the conjugate shown in Formula LXXII.

Now referring primarily to FIG. 28, the conjugate shown in Formula LXXII can be synthesized as follows.

Step 1: a solution of dye-$(PEG)_{12}$-$NH_2$ (1 eq) in DCM and diglycolic anhydride (1.5 eq) can be combined, and the mixture may be stirred overnight. The crude product can be purified with a $SiO_2$ column (using a mixture of DCM and MeOH) to yield the product.

Step 2: the product obtained from Step 1 (1.1 eq), valine-citrulline-PABA (1,000 mg, 2.635 mmol, 1 eq) dissolved in DMF, DIPEA (1.1 eq), and HBTU (1.1 eq) can be combined, and the mixture may be stirred overnight. The crude product can be purified with a $SiO_2$ column (using a mixture of DCM and MeOH) to yield the product.

Step 3: the product obtained from Step 2 (1.0 eq.), bis(4-nitrophenyl) carbonate (1.0 eq.), and DIPEA (4.0 eq.) in DMF can be combined, and the mixture may be stirred for 1 h at room temperature. The mixture can be poured into ice-cold ether, and the filtrate may be collected via centrifugation and dried under vacuum to yield the product.

Step 4: the product obtained from Step 3 (1.2 eq.) in DMSO, MMAE (1.0 eq.) in DMSO, and HOBt hydrate in DMSO (1.0 eq.) can be combined. DIPEA (3.0 eq.) can be added, and the mixture may be stirred for 3 h at room temperature. After consumption of the MMAE starting material (monitored via TLC), a mixture of acetonitrile and water can be added. The crude product can be purified via preparative HPLC to yield the conjugate shown in Formula LXXII.

Example 1

Figure 29A:
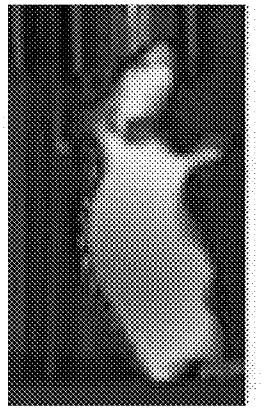
FIG. 29A shows NIR imaging of a mouse bearing a SW620 tumor on its right flank at 24 hours post dose of the conjugate shown in Formula XXII.
Figure 29B:
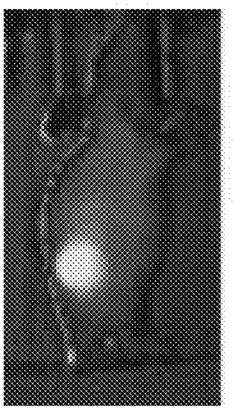
FIG. 29B shows NIR imaging of the mouse shown in FIG. 29A 4 days post conjugate dose.
Figure 29C:
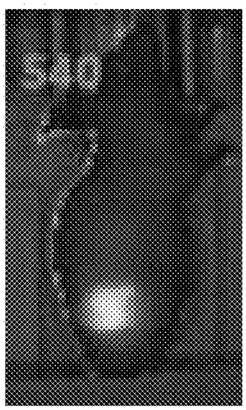
FIG. 29C shows NIR imaging of the mouse shown in FIG. 29A 9 days post conjugate dose.

The tumor-targeting ability of the conjugate shown in Formula XXII is presented in FIGS. 29A through 29C, whereby mice bearing tumors derived from the injection of SW620 colon cancer cells into their right flank were subjected to NIR imaging at 24 hours post conjugate dose (via intravenous tail vein injection) (FIG. 29A), 4 days post conjugate dose (FIG. 29B), and 9 days post conjugate dose (FIG. 29C). The results indicate that the conjugate was distributed throughout the body at 24 h post dose, and then was localized to the tumor at 4 and 9 days post dose.

Example 2

Figure 30A:
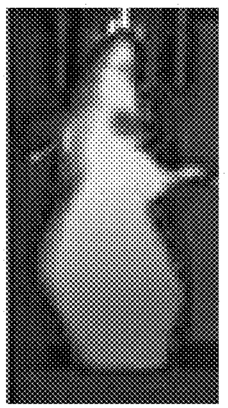
FIG. 30A shows NIR imaging of a mouse bearing a SW620 tumor on its right flank at 24 hours post dose of the conjugate shown in Formula XLVI.
Figure 30B:
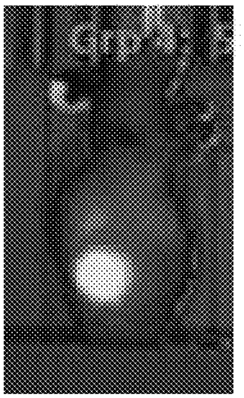
FIG. 30B shows NIR imaging of the mouse shown in FIG. 30A 4 days post conjugate dose.
Figure 30C:
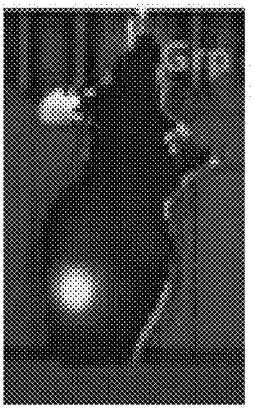
FIG. 30C shows NIR imaging of the mouse shown in FIG. 30A 9 days post conjugate dose.

The tumor-targeting ability of the conjugate shown in Formula XLVI is presented in FIGS. 30A through 30C, whereby mice bearing tumors derived from the injection of SW620 colon cancer cells into their right flank were subjected to NIR imaging at 24 hours post conjugate dose (via intravenous tail vein injection) (FIG. 30A), 4 days post conjugate dose (FIG. 30B), and 9 days post conjugate dose (FIG. 30C). The results indicate that the conjugate was distributed throughout the body at 24 h post dose, and then was localized to the tumor at 4 and 9 days post dose.

Example 3

Figure 31:
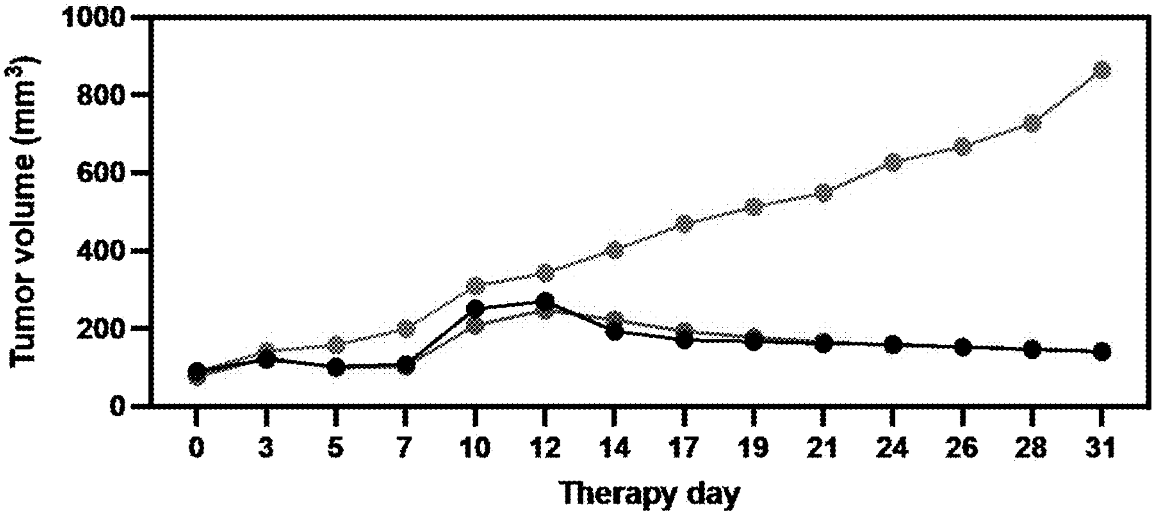
FIG. 31 shows the efficacy of (i) doxorubicin HCl and (ii) the conjugate shown in Formula XXII in mice bearing A549 tumors on their right flanks.

The efficacy of the conjugate shown in Formula XXII is presented in FIG. 31, whereby 3 randomized groups of mice bearing tumors derived from the injection of A549 lung cancer cells into their right flank were dosed (via intravenous tail vein injection) twice a week for 5 weeks with (i) vehicle at 4 mL/kg (Group 1, n=10), (ii) doxorubicin HCl at 3.9 mg/kg (Group 2, n=9), or (iii) the conjugate shown in Formula XXII at 30 mg/kg (Group 3, n=7). Tumor size was measured with digital calipers 3 times a week. In FIG. 31, (i) the average tumor volume of Group 1 is shown in blue, (i) the average tumor volume of Group 2 is shown in black, and (iii) the average tumor volume of Group 3 is shown in red. The results indicate that tumor growth was inhibited in both Groups 2 and 3, particularly after day 12, while tumor growth progressed in Group 1.

Example 4

Figure 32A:
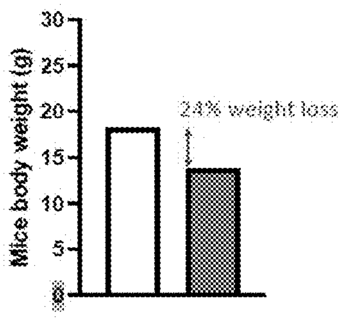
FIG. 32A shows the toxicity of doxorubicin in the mice of FIG. 31.
Figure 32B:
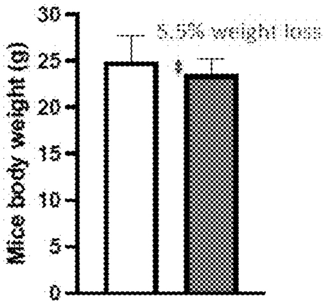
FIG. 32B shows the toxicity of the conjugate shown in Formula XXII in the mice of FIG. 31.

The toxicity of the conjugate shown in Formula XXII relative to doxorubicin HCl is presented in FIGS. 32A and 32B in terms of percent body weight loss, whereby during the study of Example 3, the body weight of the mice was recorded at (i) 22 days (when the cumulative dose of doxorubicin was 240 mg) for Group 2, and (ii) 28 days (when the cumulative dose of doxorubicin was 240 mg) for Group 3. The results indicate that toxicity in terms of body weight loss was 4.4 fold less in Group 3 relative to Group 2.

As can be easily understood from the foregoing, the basic concepts of the present invention may be embodied in a variety of ways. The invention involves numerous and varied embodiments of tumor-targeting NIR dyes and associated conjugates and methods for making and using such dyes and associated conjugates.

As such, the particular embodiments or elements of the invention disclosed by the description or shown in the figures or tables accompanying this application are not intended to be limiting, but rather exemplary of the numerous and varied embodiments generically encompassed by the invention or equivalents encompassed with respect to any particular element thereof. In addition, the specific description of a single embodiment or element of the invention may not explicitly describe all embodiments or elements possible; many alternatives are implicitly disclosed by the description and figures.

It should be understood that each element of an apparatus or each step of a method may be described by an apparatus term or method term. Such terms can be substituted where desired to make explicit the implicitly broad coverage to which this invention is entitled. As but one example, it should be understood that all steps of a method may be disclosed as an action, a means for taking that action, or as an element which causes that action. Similarly, each element of an apparatus may be disclosed as the physical element or the action which that physical element facilitates. As but one example, the disclosure of a "therapeutic" should be understood to encompass disclosure of the act of "providing therapy"—whether explicitly discussed or not—and, conversely, were there effectively disclosure of the act of "providing therapy", such a disclosure should be understood to encompass disclosure of an "therapeutic" and even a "means for providing therapy." Such alternative terms for each element or step are to be understood to be explicitly included in the description.

In addition, as to each term used it should be understood that unless its utilization in this application is inconsistent with such interpretation, common dictionary definitions should be understood to be included in the description for each term as contained in the Random House Webster's Unabridged Dictionary, second edition, each definition hereby incorporated by reference.

All numeric values herein are assumed to be modified by the term "about", whether or not explicitly indicated. For the purposes of the present invention, ranges may be expressed as from "about" one particular value to "about" another particular value. When such a range is expressed, another embodiment includes from the one particular value to the other particular value. The recitation of numerical ranges by endpoints includes all the numeric values subsumed within that range. A numerical range of one to five includes for example the numeric values 1, 1.5, 2, 2.75, 3, 3.80, 4, 5, and so forth. It will be further understood that the endpoints of each of the ranges are significant both in relation to the other endpoint, and independently of the other endpoint. When a value is expressed as an approximation by use of the antecedent "about," it will be understood that the particular value forms another embodiment. The term "about" generally refers to a range of numeric values that one of skill in the art would consider equivalent to the recited numeric value or having the same function or result. Similarly, the antecedent "substantially" means largely, but not wholly, the same form, manner or degree and the particular element will have a range of configurations as a person of ordinary skill in the art would consider as having the same function or result. When a particular element is expressed as an approximation by use of the antecedent "substantially," it will be understood that the particular element forms another embodiment.

Moreover, for the purposes of the present invention, the term "a" or "an" entity refers to one or more of that entity unless otherwise limited. As such, the terms "a" or "an", "one or more" and "at least one" can be used interchangeably herein.

Thus, the applicant(s) should be understood to claim at least: i) each of the NIR dyes and associated conjugates herein disclosed and described, ii) the related methods disclosed and described, iii) similar, equivalent, and even implicit variations of each of these devices and methods, iv) those alternative embodiments which accomplish each of the functions shown, disclosed, or described, v) those alternative designs and methods which accomplish each of the functions shown as are implicit to accomplish that which is disclosed and described, vi) each feature, component, and step shown as separate and independent inventions, vii) the applications enhanced by the various systems or components disclosed, viii) the resulting products produced by such systems or components, ix) methods and apparatuses substantially as described hereinbefore and with reference to any of the accompanying examples, x) the various combinations and permutations of each of the previous elements disclosed.

The background section of this patent application, if any, provides a statement of the field of endeavor to which the invention pertains. This section may also incorporate or contain paraphrasing of certain United States patents, patent applications, publications, or subject matter of the claimed invention useful in relating information, problems, or concerns about the state of technology to which the invention is drawn toward. It is not intended that any United States patent, patent application, publication, statement or other information cited or incorporated herein be interpreted, construed or deemed to be admitted as prior art with respect to the invention.

The claims set forth in this specification, if any, are hereby incorporated by reference as part of this description of the invention, and the applicant expressly reserves the right to use all of or a portion of such incorporated content of such claims as additional description to support any of or all of the claims or any element or component thereof, and the applicant further expressly reserves the right to move any portion of or all of the incorporated content of such claims or any element or component thereof from the description into the claims or vice-versa as necessary to define the matter for which protection is sought by this application or by any subsequent application or continuation, division, or continuation-in-part application thereof, or to obtain any benefit of, reduction in fees pursuant to, or to comply with the patent laws, rules, or regulations of any country or treaty, and such content incorporated by reference shall survive during the entire pendency of this application including any subsequent continuation, division, or continuation-in-part application thereof or any reissue or extension thereon.

Additionally, the claims set forth in this specification, if any, are further intended to describe the metes and bounds of a limited number of the preferred embodiments of the invention and are not to be construed as the broadest embodiment of the invention or a complete listing of embodiments of the invention that may be claimed. The applicant does not waive any right to develop further claims based upon the description set forth above as a part of any continuation, division, or continuation-in-part, or similar application.

The invention claimed is:

1. A method of killing tumor cells, comprising:

administering a conjugate to a subject, said conjugate comprising:

a tumor-targeting near-infrared dye; and a therapeutic agent coupled to said dye via a linker comprising a cleavable portion comprising protease sensitivity;

wherein said dye targets said therapeutic agent to tumor cells; and wherein said conjugate comprises one of:

Formula XX

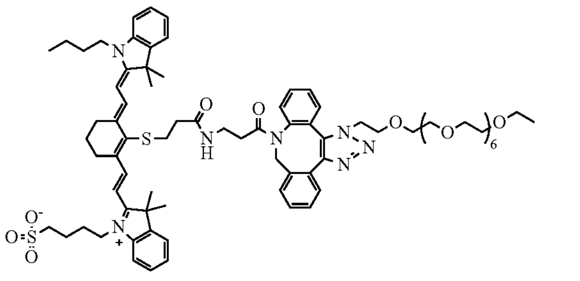

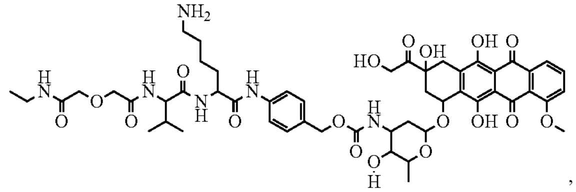

,

Formula XXII

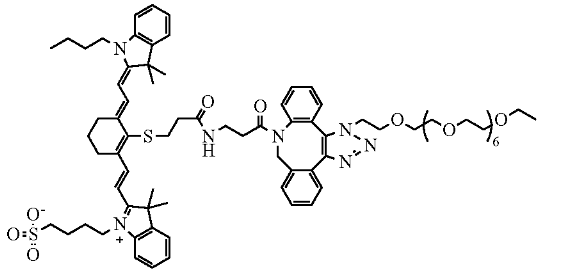

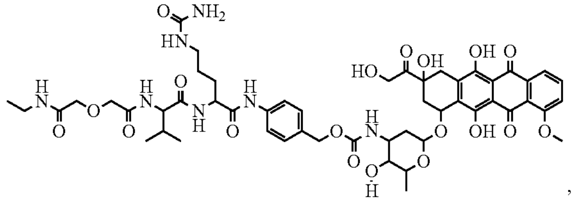

,

Formula XXV

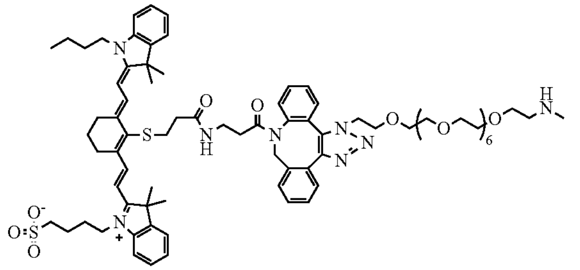

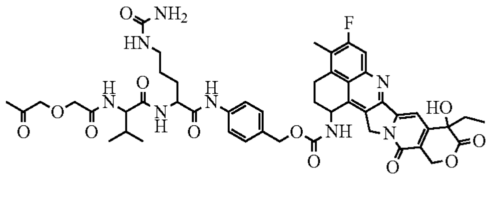

,

-continued
Formula XXVII
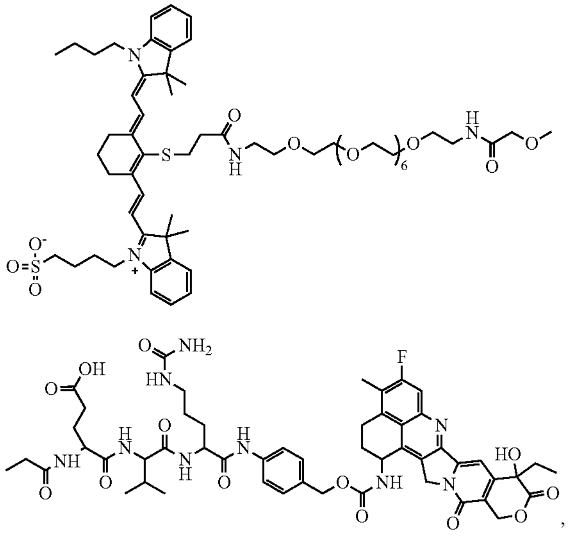
,
Formula XXXIII
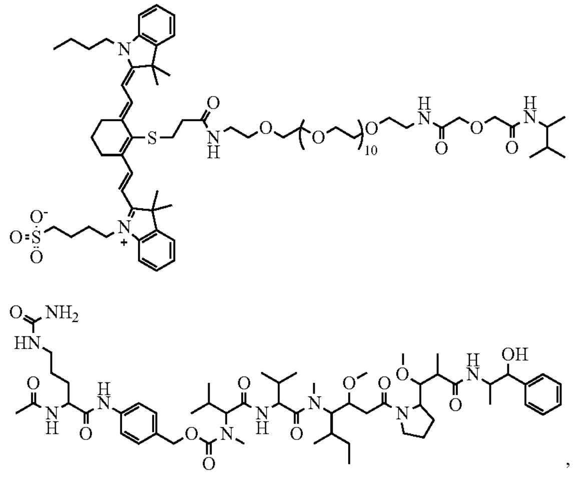
,
Formula XXXIV
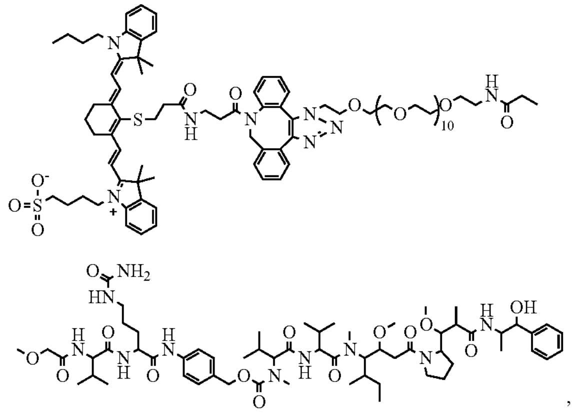
,
-continued
Formula XXXV
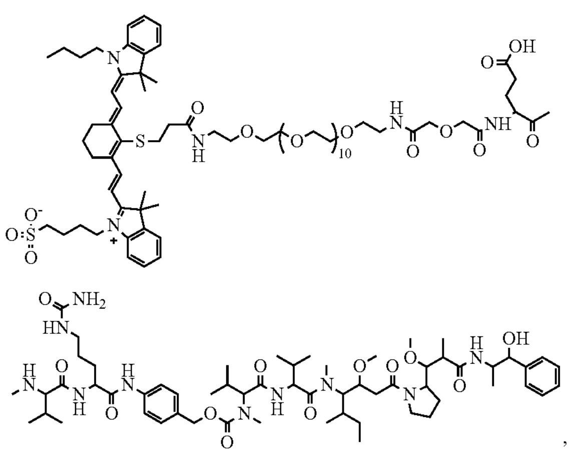
,
Formula XLVI
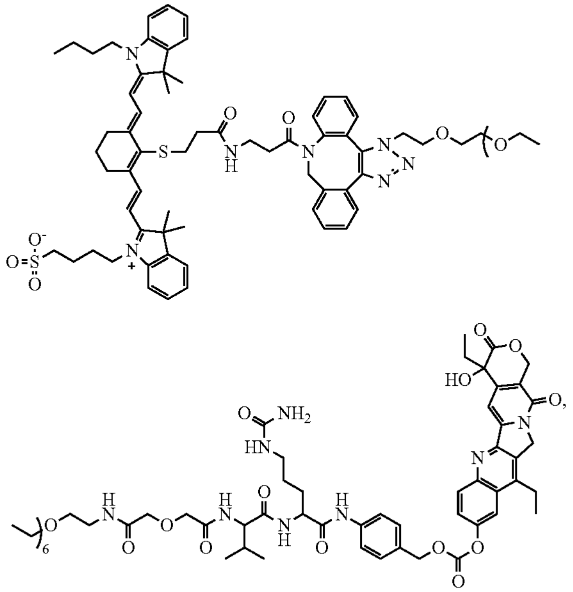
,
Formula LVII
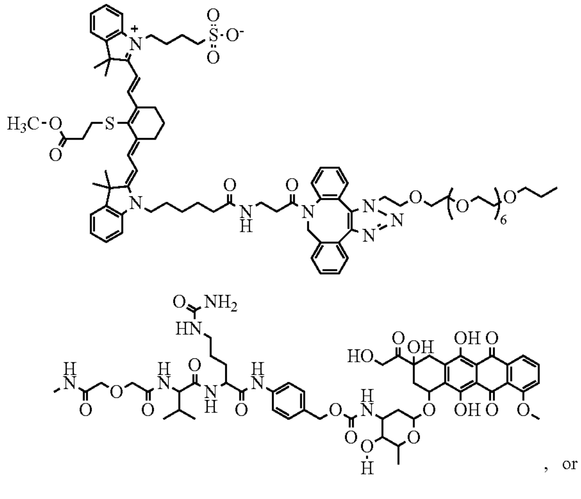
, or -continued Formula LXIX

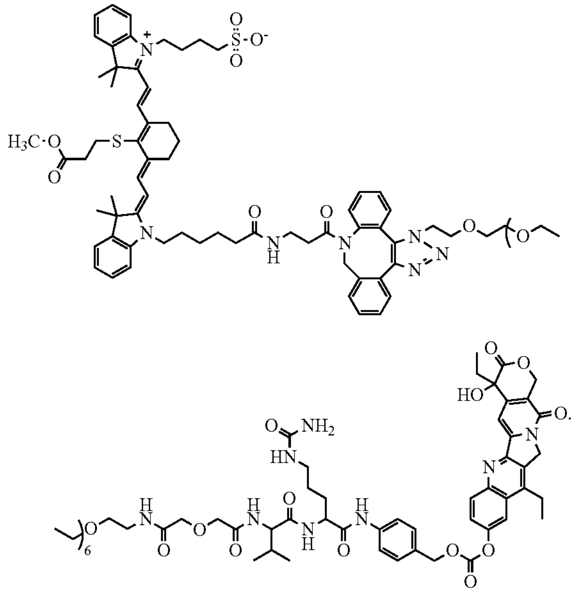

2. A method of killing tumor cells, comprising:

administering a conjugate to a subject, said conjugate comprising:

a tumor-targeting near-infrared dye; and a therapeutic agent coupled to said dye via a linker comprising a cleavable portion comprising protease sensitivity:

wherein said dye targets said therapeutic agent to tumor cells; and wherein said conjugate is selected from the group consisting of:

Formula XX

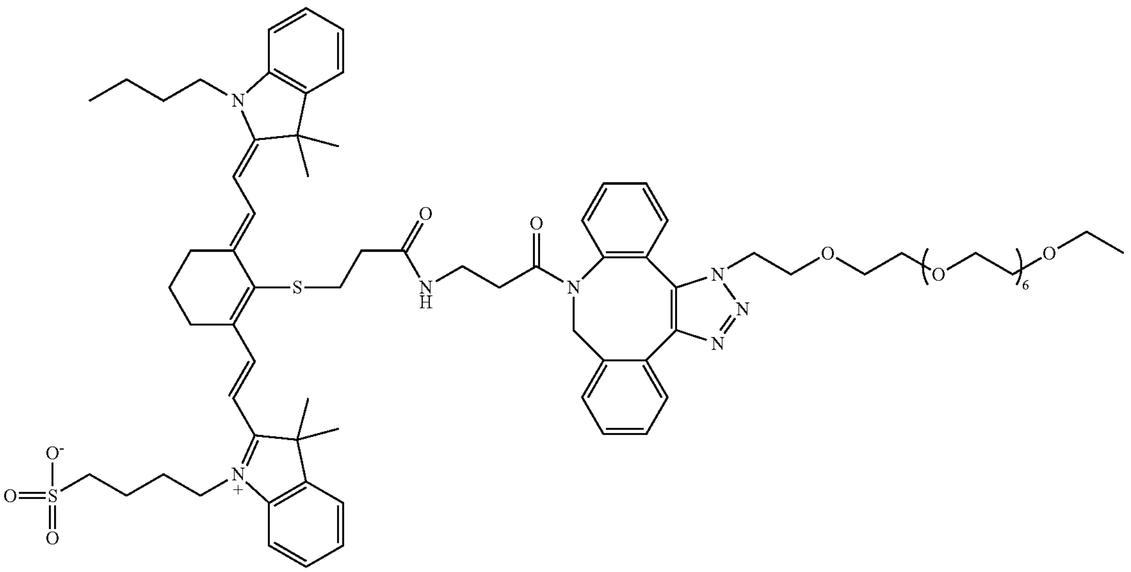

-continued
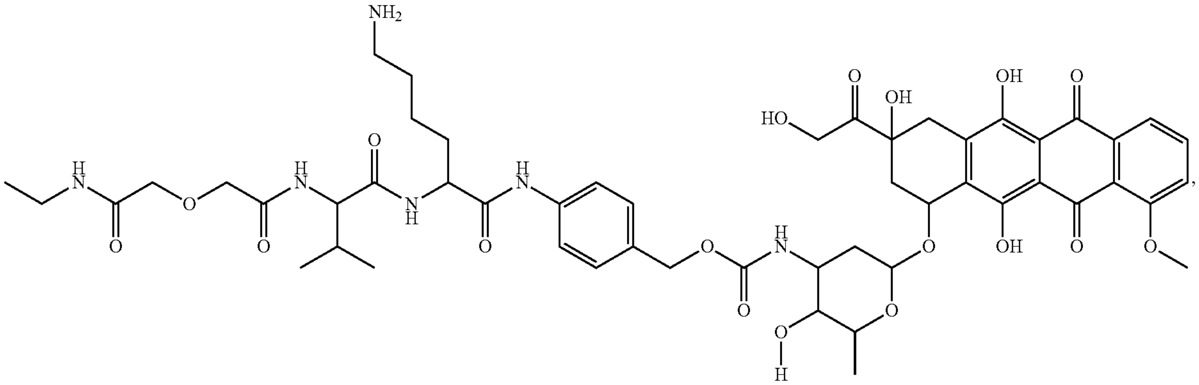
Formula XXII
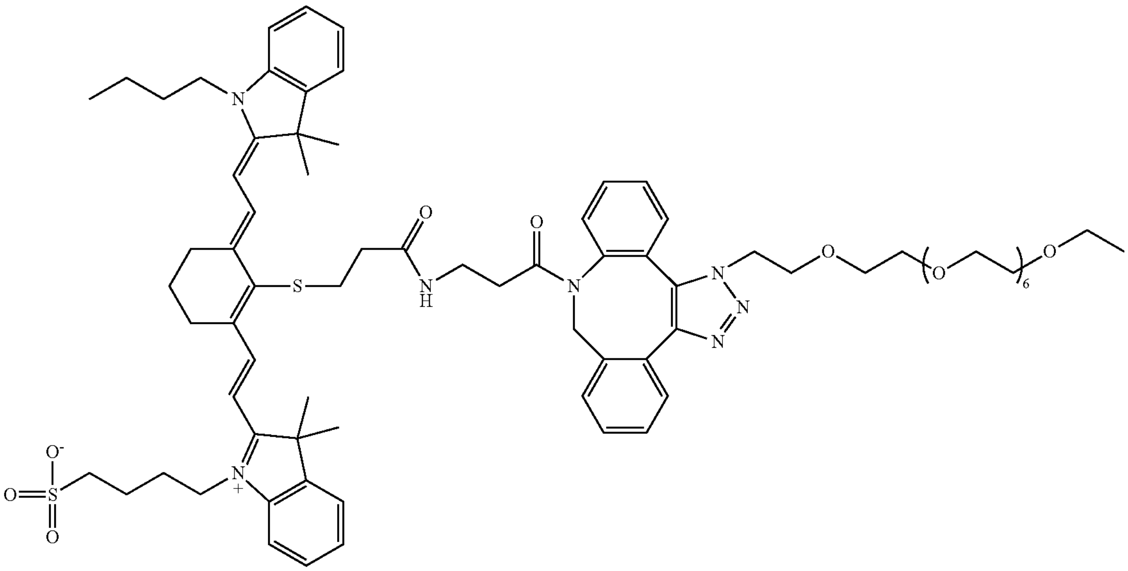
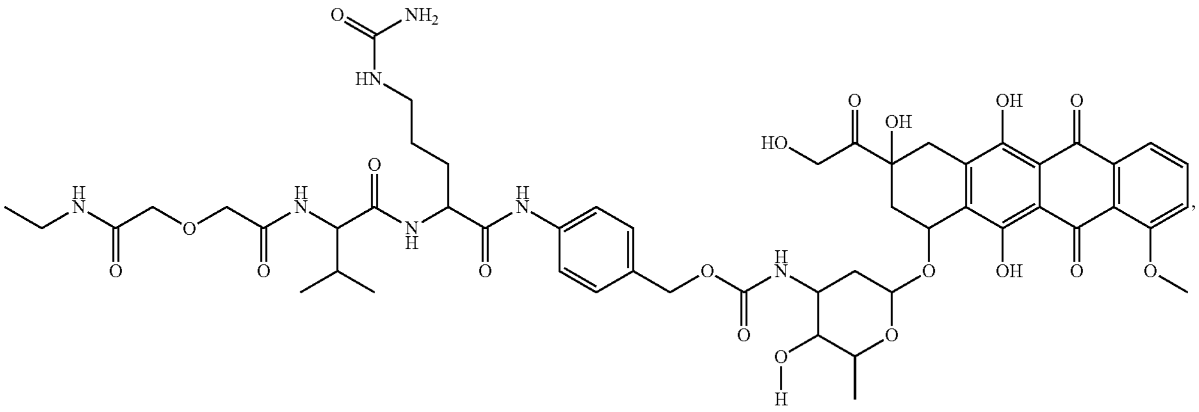

-continued
Formula XXV
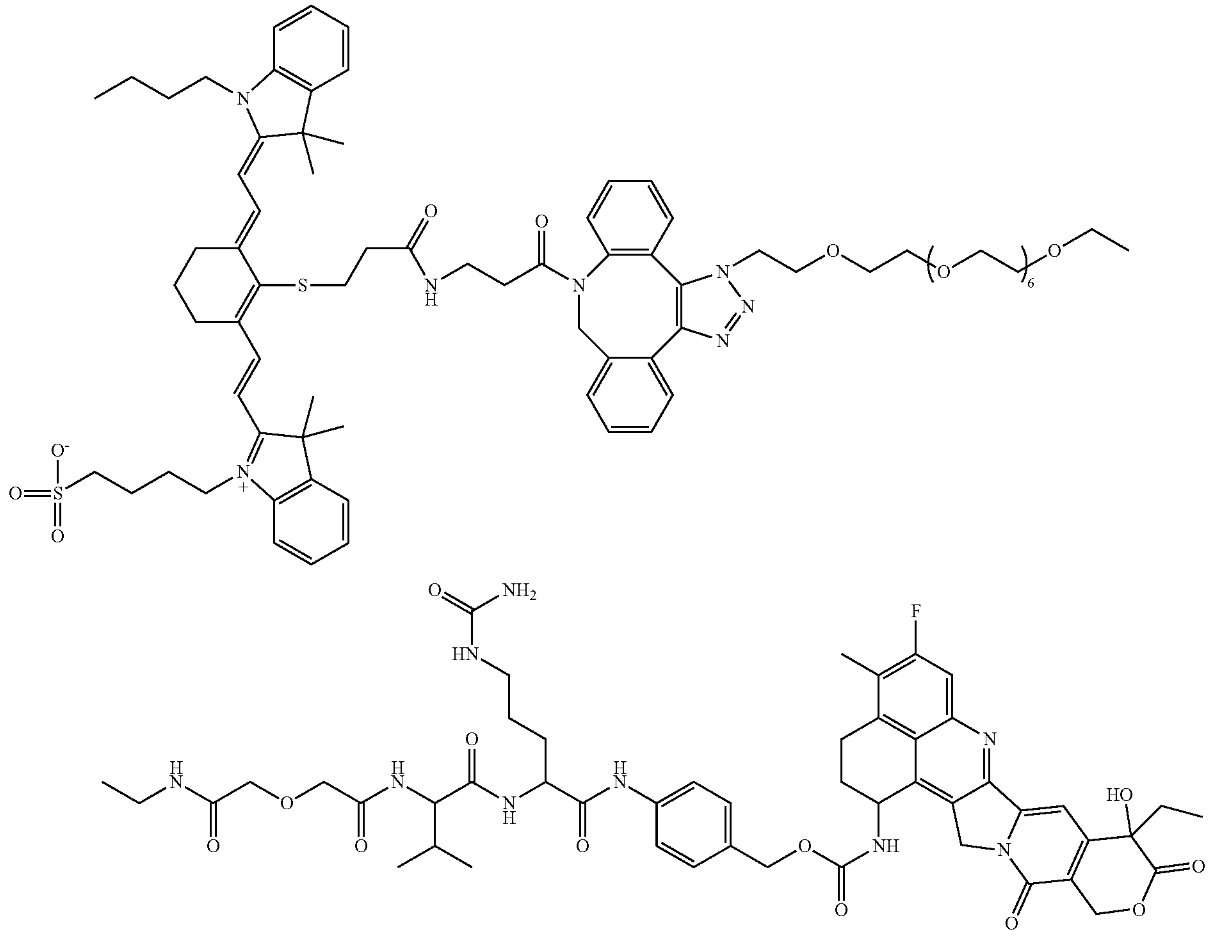
Formula XXVII
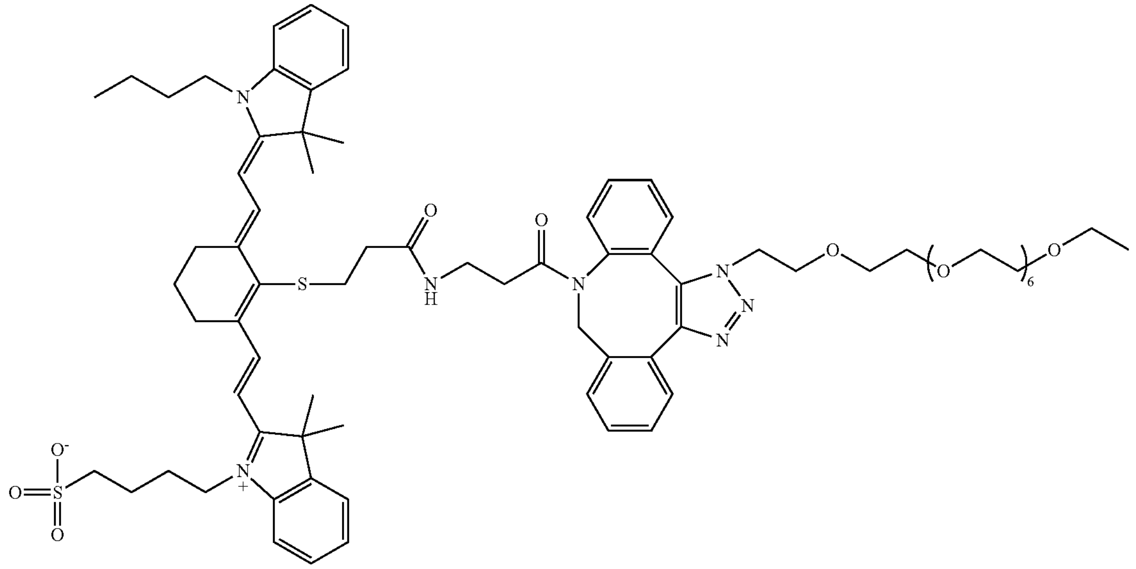

-continued
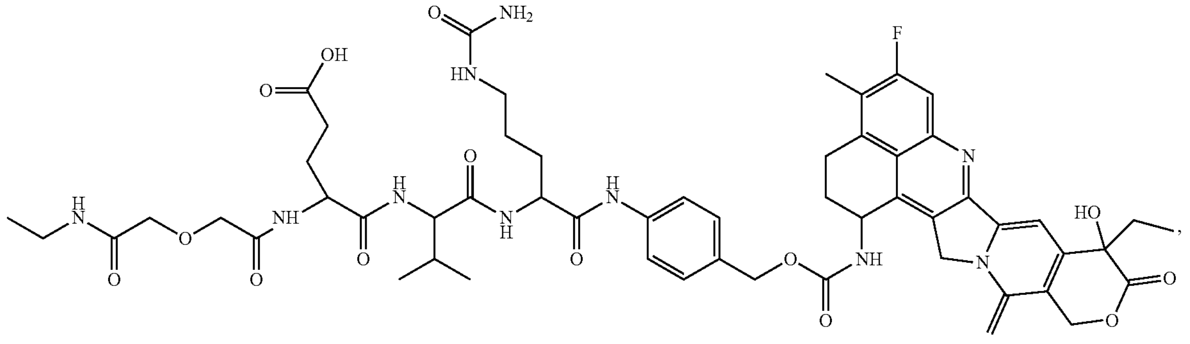
Formula XXXIII
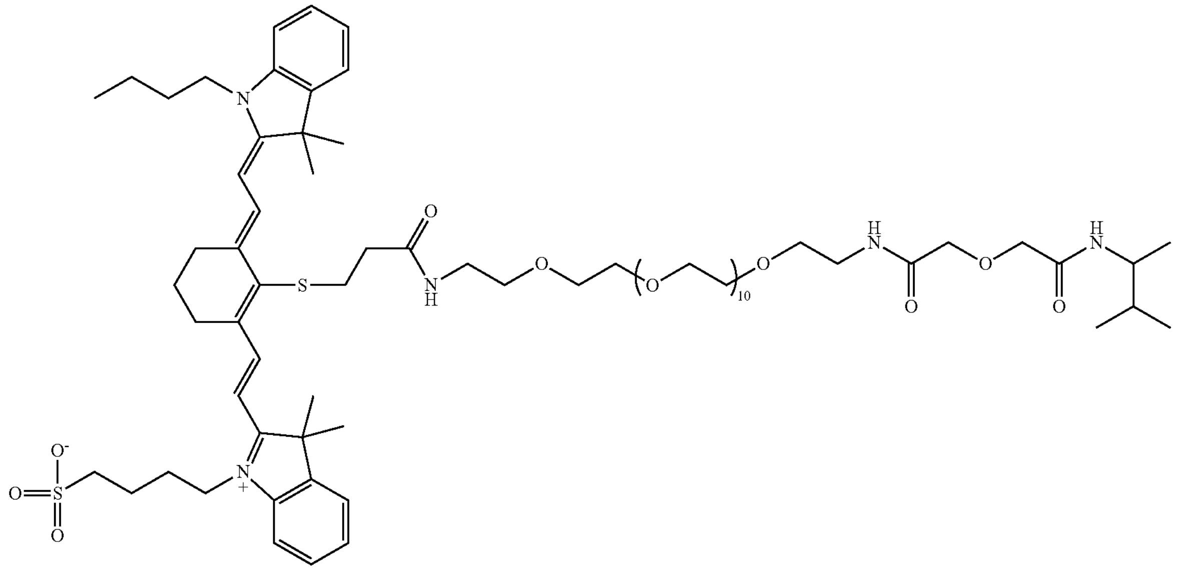
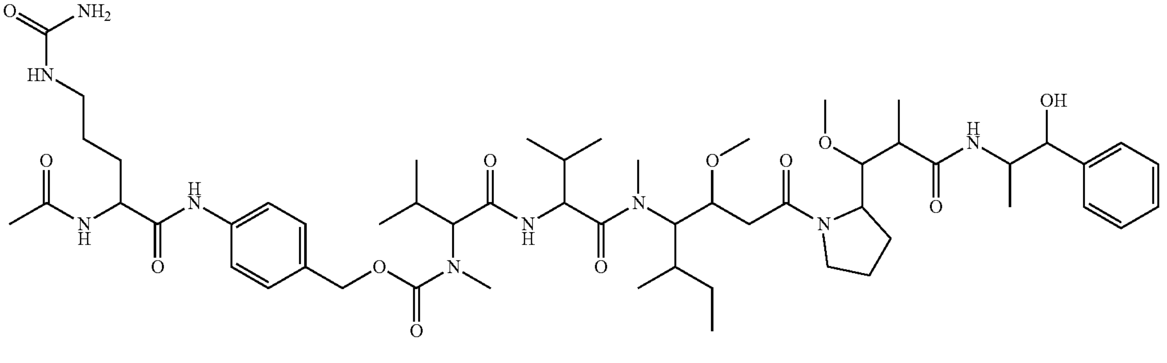

-continued
Formula XXXIV
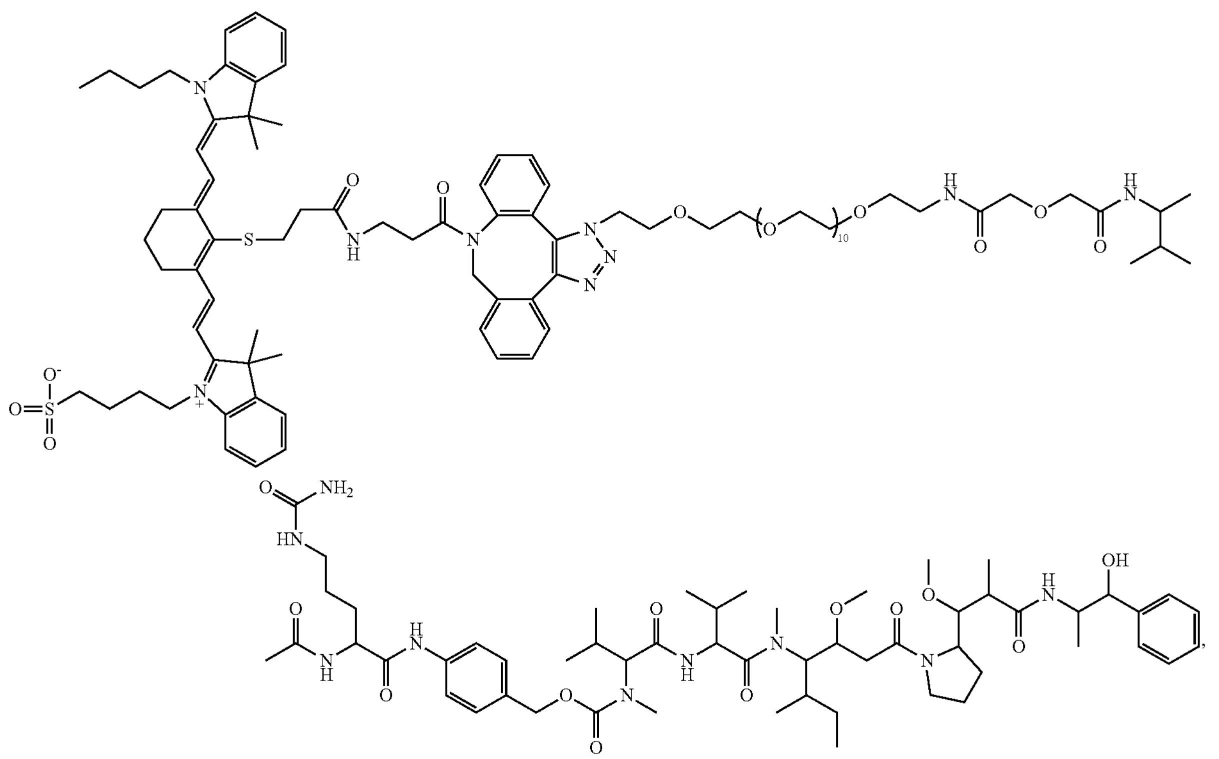
Formula XXXV
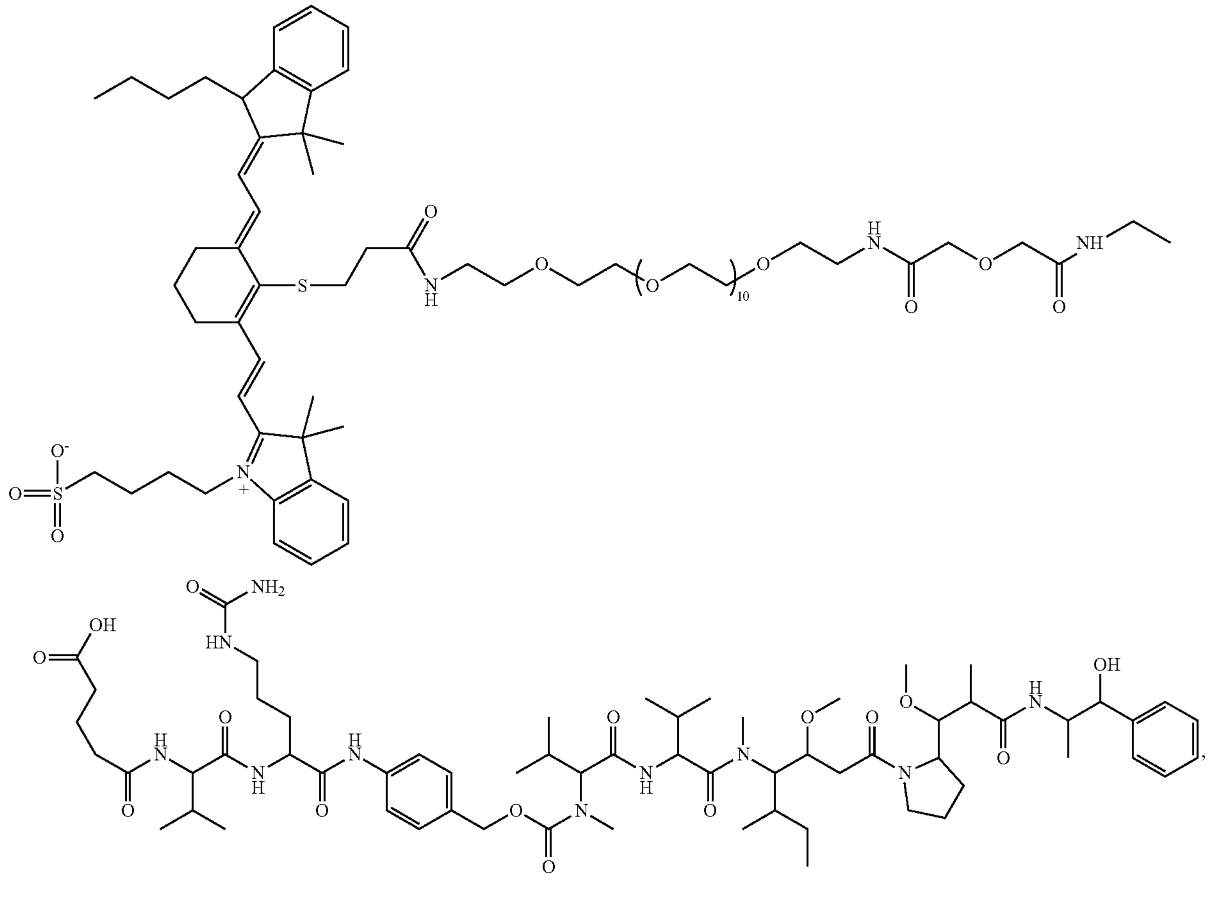

-continued
Formula XLVI
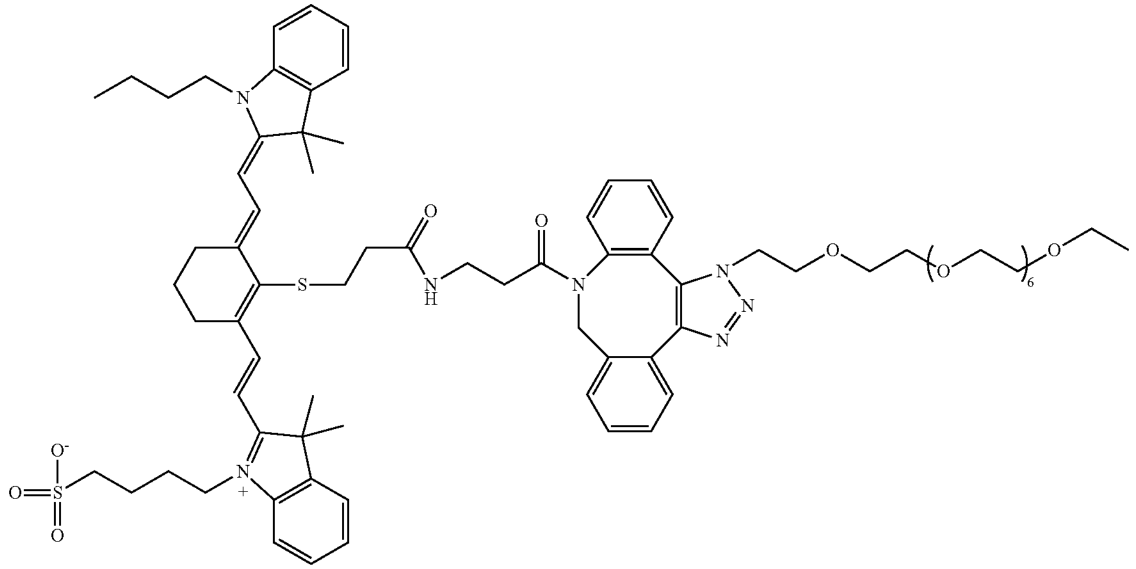
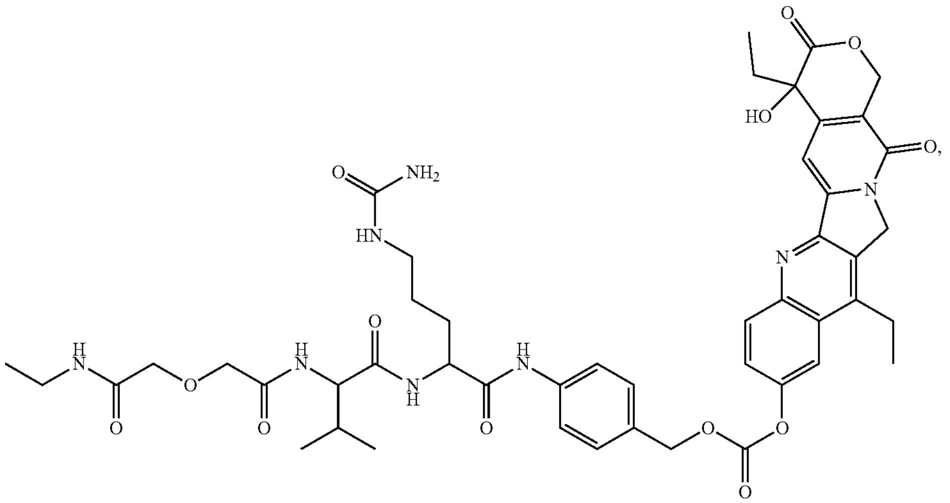
Formula LVII
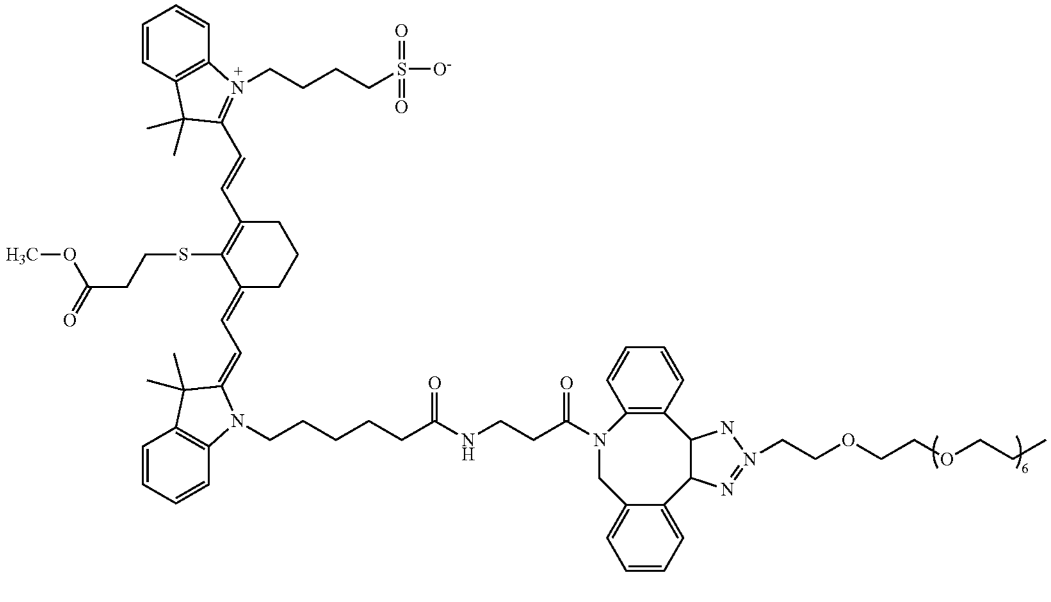

-continued
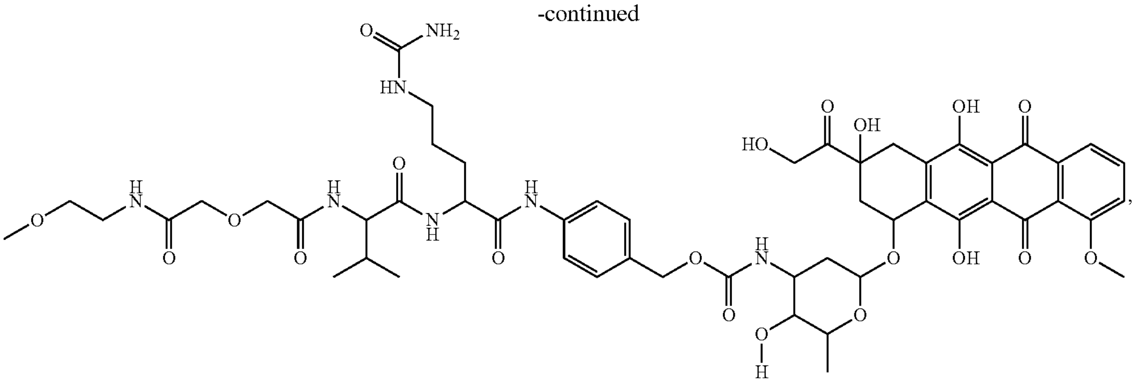
, and
Formula LXIX
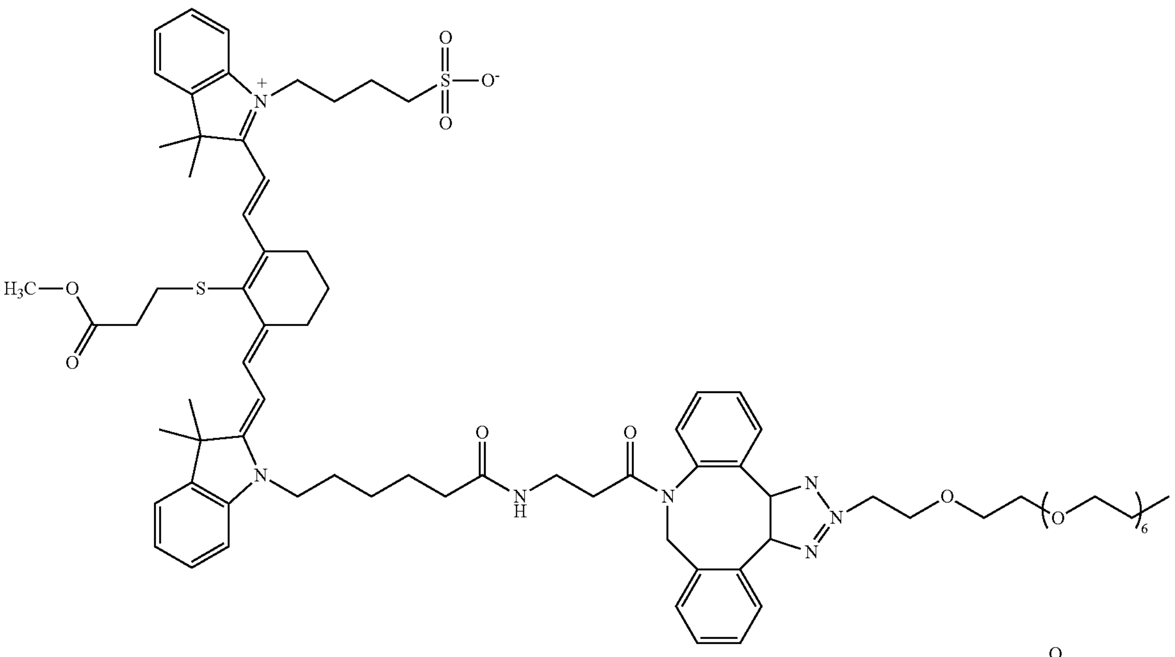
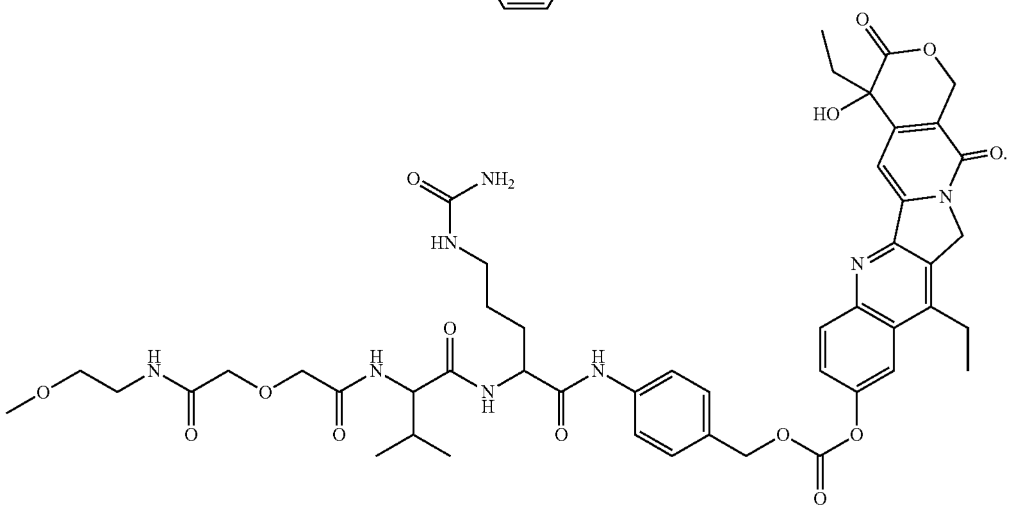
* * * * *